US008232081B2

(12) United States Patent
Yocum et al.

(10) Patent No.: US 8,232,081 B2
(45) Date of Patent: *Jul. 31, 2012

(54) METHODS AND MICROORGANISMS FOR PRODUCTION OF PANTO-COMPOUNDS

(75) Inventors: R. Rogers Yocum, Lexington, MA (US); Thomas A. Patterson, North Attleboro, MA (US); Theron Hermann, Kinnelon, NJ (US); Janice G. Pero, Lexington, MA (US)

(73) Assignee: BASF SE, Ludwigshafen (DE)

( * ) Notice: Subject to any disclaimer, the term of this patent is extended or adjusted under 35 U.S.C. 154(b) by 868 days.

This patent is subject to a terminal disclaimer.

(21) Appl. No.: 10/984,449

(22) Filed: Nov. 8, 2004

(65) Prior Publication Data

US 2005/0089973 A1    Apr. 28, 2005

Related U.S. Application Data

(63) Continuation of application No. 09/667,569, filed on Sep. 21, 2000, now abandoned, which is a continuation-in-part of application No. 09/400,494, filed on Sep. 21, 1999, now abandoned.

(60) Provisional application No. 60/227,860, filed on Aug. 24, 2000, provisional application No. 60/210,072, filed on Jun. 7, 2000, provisional application No. 60/221,836, filed on Jul. 28, 2000.

(51) Int. Cl.
| C12P 13/04 | (2006.01) |
| C12P 13/02 | (2006.01) |
| C12P 7/42 | (2006.01) |
| C12P 7/18 | (2006.01) |

(52) U.S. Cl. ......... 435/106; 435/158; 435/129; 435/146
(58) Field of Classification Search .......... None
See application file for complete search history.

(56) References Cited

U.S. PATENT DOCUMENTS

| 5,089,276 A | 2/1992 | Yamashita et al. |
| 5,294,542 A | 3/1994 | Sloma et al. |
| 5,518,906 A | 5/1996 | Hikichi et al. |
| 5,529,908 A | 6/1996 | Palva et al. |
| 5,534,420 A | 7/1996 | Debono et al. |
| 5,599,689 A | 2/1997 | Haynie et al. |
| 5,721,137 A | 2/1998 | Frascotti et al. |
| 5,756,536 A | 5/1998 | Chen et al. |
| 5,856,165 A | 1/1999 | Van Solingen |
| 5,912,164 A | 6/1999 | Warneck et al. |
| 5,925,538 A | 7/1999 | Perkins et al. |
| 5,932,457 A | 8/1999 | Moriya et al. |
| 6,171,845 B1 | 1/2001 | Elischweski et al. |
| 6,177,264 B1 | 1/2001 | Eggeling et al. |
| 6,184,006 B1 | 2/2001 | Rieping et al. |
| 6,184,007 B1 | 2/2001 | Dusch et al. |
| 6,322,995 B1 * | 11/2001 | Hohmann et al. ............. 435/66 |
| 6,682,915 B2 * | 1/2004 | Hermann et al. ............. 435/146 |
| 6,686,183 B2 * | 2/2004 | Rieping et al. ............... 435/146 |
| 6,689,592 B2 * | 2/2004 | Rieping et al. ............... 435/146 |
| 6,913,912 B2 * | 7/2005 | Hermann et al. ............. 435/146 |
| 7,220,561 B2 * | 5/2007 | Hermann et al. ............. 435/128 |
| 7,244,593 B2 * | 7/2007 | Yocum et al. ............... 435/106 |
| 7,989,187 B2 * | 8/2011 | Yocum et al. ............... 435/106 |

FOREIGN PATENT DOCUMENTS

| EP | 0 224 294 A1 | 6/1987 |
| EP | 0 493 060 A2 | 7/1992 |
| EP | 0 590 857 A2 | 4/1994 |
| EP | 1 001 027 A2 | 5/2000 |
| EP | 1 001 189 A2 | 5/2000 |
| EP | 1 001 192 A2 | 5/2000 |
| EP | 1 001 193 A2 | 5/2000 |
| EP | 1006189 A2 | 6/2000 |
| EP | 1006192 A2 | 6/2000 |
| WO | WO 97/10340 A1 | 3/1997 |
| WO | WO 98/18954 A1 | 5/1998 |
| WO | WO 01/83799 A1 | 11/2001 |

OTHER PUBLICATIONS

Leigh, Appl. Environmen. Microbiol. 45:800-803, 1983.*
Earl et al., Trends Microbiol. 16:269-275, 2008.*
Dickinson et al., Appl. Environmen. Microbiol. 70:475-482, 2004.*
Baigori, et al. Isolation and characterization of *Bacillus subtilis* mutants blocked in the synthesis of pantothenic acid. J Bacteriol. Jul. 1991;173(13):4240-2.
Downs, et al. Evidence for a new, oxygen-regulated biosynthetic pathway for the pyrimidine moiety of thiamine in *Salmonella typhimurium*. J Bacteriol. Mar. 1992;174(5):1515-21.
Downs, et al. apbA; a new genetic locus involved in thiamine biosynthesis in *Salmonella typhimurium*. J Bacteriol. Aug. 1994;176(16):4858-64.

(Continued)

*Primary Examiner* — David J Steadman
(74) *Attorney, Agent, or Firm* — Connolly Bove Lodge & Hutz, LLP

(57) ABSTRACT

The present invention features methods of producing panto-compounds (e.g., pantothenate) using microorganisms in which the pantothenate biosynthetic pathway and/or the iso-leucine-valine biosynthetic pathway and/or the coenzymeA biosynthetic pathway has been manipulated. Methods featuring ketopantoate reductase overexpressing microorganisms as well as aspartate α-decarboxylase overexpressing microorganisms are provided. Methods of producing panto-compounds in a precursor-independent manner and in high yield are described. Recombinant microorganisms, vectors, isolated nucleic acid molecules, genes and gene products useful in practicing the above methodologies are also provided. The present invention also features a previously unidentified microbial pantothenate kinase gene, coaX, as well as methods of producing panto-compounds utilizing microorganisms having modified pantothenate kinase activity. Recombinant microorganisms, vectors, isolated coaX nucleic acid molecules and purified CoaX proteins are featured. Also featured are methods for identifying pantothenate kinase modulators utilizing the recombinant microorganisms and/or purified CoaX proteins of the present invention.

13 Claims, 31 Drawing Sheets

OTHER PUBLICATIONS

Dusch, et al. Cloning and characterization of the *C. glutamicum* ATCC13032 panD igene coding for L-aspartate-?-decarboxylase. 1999, No. P-L 06.

Dusch, et al. Expression of the *Corynebacterium glutamicum* panD gene encoding L-aspartate-alpha-decarboxylase leads to pantothenate overproduction in *Escherichia coli*. Appl Environ Microbiol. Apr. 1999;65(4):1530-9.

Elischewski, et al. Pantothenate production in *Escherichia coli* K12 by enhanced expression of the panE gene encoding ketopantoate reductase. J Biotechnol. Oct. 8, 1999;75(2-3):135-46.

Elischewski, et al. Identification and analysis of the pan# gene involved in panto-thenate biosynthesis in *Escherichia coli* K12. Mar. 1999, Abstract No. P-L 29.

EMBL L47709 *Bacillus subtilis* (clone YAC15-6B) ypiABF genes, qcrABC genes, ypjABCDEFGHI DE genes, birA gene, panBCD genes, dinG gene, ypmB gene, aspB gene, asnS gene, DE dnaD gene, nth gene and ypoC gene, complete cds. Jan. 23, 1996.

Frodyma, et al. ApbA, the ketopantoate reductase enzyme of *Salmonella typhimurium* is required for the synthesis of thiamine via the alternative pyrimidine biosynthetic pathway. J Biol Chem. Mar. 6, 1998;273(10):5572-6.

Frodyma, et al. The panE gene, encoding ketopantoate reductase, maps at 10 minutes and is allelic to apbA in *Salmonella typhimurium*. J Bacteriol. Sep. 1998;180(17):4757-9.

GenBank U09529 *Salmonella typhimurium* LT2 ApbA protein (apbA) gene, complete cds. Dec. 7, 1994.

GenBank P37402 2-dehydropantoate 2-reductase (Ketopantoate reductase) (KPA reductase) (KPR) Dec. 15, 1998.

GenBank AAA56681 ApbA protein [*Salmonella typhimurium*] Dec. 7, 1994.

GenBank Z99111 AL009126 *Bacillus subtilis* complete genome (section 8 of 21): from 1394791 Nov. 26, 1997.

GenBank P52996 3-Methyl-2-Oxobutanoate Hydroxymethyltransferase (Ketopantoate Hydroxymethyltransferase) Oct. 1, 1996.

GenBank Z98682 *Bacillus subtilis* genomic DNA 23.9kB fragment Aug. 19, 1997.

GenBank O34661 Probable 2-Dehydropantoate 2-Reductase (Ketopantoate Reductase) (Kpa Reductase) Nov. 1, 1998.

GenBank CAB13317 similar to thiamin biosynthesis [*Bacillus subtilis*] Nov. 26, 1997.

GenBank CAB11364 YlbQ protein [*Bacillus subtilis*] Aug. 19, 1997.

GenBank P52999 Aspartate 1-decarboxylase precursor (Aspartate alpha-decarboxylase) 1-decarboxylase precursor (Aspartate alpha-decarboxylase) Dec. 15, 1998.

GenBank P77728 2-dehydropantoate 2-reductase (Ketopantoate reductase) (KPA reductase) (KPR) Dec. 15, 1998.

GenBank U09529 *Salmonella typhimurium* LT2 ApbA protein (apbA) gene, complete cds Dec. 7, 1994.

GenBank P372053 Ketol-acid reductoisomerase (Acetohydroxy-acid isomeroreductase) (Alpha-keto-beta-hydroxylacil reductoisomerase) Dec. 15, 1998.

GenBank P37252 Acetolactate synthase small subunit (AHAS) (Acetohydroxy-acid synthase small subunit) (ALS) Dec. 15, 1998.

GenBank P37251 Acetolactate synthase large subunit (AHAS) (Acetohydroxy-acid synthase large subunit) (ALS) (Vegetative protein 105) (VEG105) Jul. 15, 1998.

GenBank P52998 Pantoate—beta-alanine ligase (Pantothenate synthetase) (Pantoate activating enzyme) Dec. 15, 1998.

GenBank P51785 Dihydroxy-acid dehydratase (DAD) (Vegetative protein 110) (VEG110) Dec. 15, 1998.

GenBank F69875 pyrimidine-thiamin biosynthesis homolog ylbQ— *Bacillus subtilis*. Nov. 5, 1999.

Hoch, et al. Panspermia, spores and the *Bacillus subtilis* genome. Nature. Nov. 20, 1997;390(6657):237-8.

Jackowski, S. Biosynthesis of Pantothenic Acid and Coenzyme A. *Escherichia coli and Salmonella typhimurium: Cellular and Molecular Biology*. Second Edition, 1995, American Society of Microbiology, Washington DC, pp. 687-695.

Kunst, et al. The complete genome sequence of the gram-positive bacterium *Bacillus subtilis*. Nature. Nov. 20, 1997; 390(6657):249-56.

Merkel, et al. Characterization and sequence of the *Escherichia coli* panBCD gene cluster. FEMS Microbiol Lett. Oct. 1, 1996;143(2-3):247-52.

Ramjee, et al. *Escherichia coli* L-aspartate-alpha-decarboxylase: preprotein processing and observation of reaction intermediates by electrospray mass spectrometry. Biochem J. May 1, 1997;323 ( Pt 3):661-9.

Sahm, et al. D-Pantothenate synthesis in *Corynebacterium glutamicum* and use of panBC genes encoding L-valine synthesis for D-pantothenate overproduction. Appl Environ Microbiol. May 1999;65(5):1973-9.

Shimizu, et al. Ketopantoic acid reductase of *Pseudomonas maltophilia* 845. Purification, characterization, and role in pantothenate biosynthesis. J Biol Chem. Aug. 25, 1988;263(24):12077-84.

Sorokin, et al. Sequence analysis of the *Bacillus subtilis* chromosome region between the serA and kdg loci cloned in a yeast artificial chromosome. Microbiology. Aug. 1996 ;142 ( Pt 8):2005-16.

Vandamme, EJ. Production of vitamins, coenzymes and related biochemicals by biotechnological processes. J Chem Technol Biotechnol. 1992;53(4):313-27.

Vandamme, EJ. The search for novel microbial fine chemicals, agrochemicals and biopharmaceuticals. J Biotechnol. Sep. 30, 1994;37(2):89-108.

Office Communication Issued in EP Application No. 00966799.9, Feb. 17, 2010.

* cited by examiner

FIG. 20A

```
CLUSTAL W (1.7) Multiple Sequence Alignments
Sequence type explicitly set to Protein
Sequence format is Pearson Sequence 1: sp|Q9X795|M.leprae          312 aa (SEQ ID NO: 4)
Sequence 2: sp|O86779|S.coelicolor      329 aa (SEQ ID NO: 6)
Sequence 3: sp|O53440|M.tuberculosis    312 aa (SEQ ID NO: 5)
Sequence 4: sp|P54556|B.subtilis        319 aa (SEQ ID NO: 3)
Sequence 5: sp|P44793|H.influenzae      311 aa (SEQ ID NO: 1)
Sequence 6: sp|P15044|E.coli            316 aa (SEQ ID NO: 2)

sp|Q9X795|M.leprae           ------MPRLSE---P--SPYVEFDRKQWRALRMSTPLALTEEELIGLR
sp|O53440|M.tuberculosis     ------MSRLSE---P--SPYVEFDRRQWRALRMSTPLALTEEELVGLR
sp|O86779|S.coelicolor       MISPVPSIPRSAHRQRPEATPYVDLTRPEWSALRDKTPLPLTAEEVEKLR
sp|P44793|H.influenzae       ------MEFSTQ------QTPFLSFNREQWAELRKSVPLKLTEQDLKPLL
sp|P15044|E.coli             ------MSIKEQTL----MTPYLQFDRNQWAALRDSVPMTLSEDEIARLK
sp|P54556|B.subtilis         -----MKNKELN---LHTLYTQHNRESWSGFGGHLSIAVSEEEAKAVE
                                    :.  :   :   .  ::   :     :  :

sp|Q9X795|M.leprae           GLGEQIDLLEVEEVYLPLARLIHLQVAARQRLFAATAEFLGEPQQNPGRP
sp|O53440|M.tuberculosis     GLGEQIDLLEVEEVYLPLARLIHLQVAARQRLFAATAEFLGEPQQNPDRP
sp|O86779|S.coelicolor       GLGDVIDLDEVRDIYLPLSRLLNLYVGATDGLRGALNTFLGE--QGSQSG
sp|P44793|H.influenzae       GFNEDLSLDEVSTIYLPLTRLINYYIDENLHRQTVLHRFLGR-----NNAK
sp|P15044|E.coli             GINEDLSLEEVAEIYLPLSRLLNFYISSNLRRQAVLEQFLGT------NGQR
sp|P54556|B.subtilis         GLNDYLSVEEVETIYIPLVRLLHLHVKSAAERNKHVNVFLKHP---HSAK
                             *   :   ** ::** :**  **:

sp|Q9X795|M.leprae           VPFIIGVAGSVAVGKSTTARVLQALLARWDHHTRVDLVTTDGFLYPNAEL
sp|O53440|M.tuberculosis     VPFIIGVAGSVAVGKSTTARVLQALLARWDHHTRVDLVTTDGFLYPNAEL
sp|O86779|S.coelicolor       TPFVIGVAGSVAVGKSTVARLLQALLSRWPEHPRVELVTTDGFLLPTREL
sp|P44793|H.influenzae       TPYIISIAGSVAVGKSTSARILQSLLSHWPTERKVDLITTDGFLYPLNKL
sp|P15044|E.coli             IPYIISIAGSVAVGKSTTARVLQALLSRWPEHRRVELITTDGFLHPNQVL
sp|P54556|B.subtilis         IPFIGIGVAGSVAVGKSTTARILQKLLSRLPDRPKVSLITTDGFLFPTAEL
                             * :  :**********  **:**  **:         *:******  * 
```

FIG. 20B

```
sp|Q9X795|M.leprae         GRRNLMHRKGFPESYNRRALMRFVTSVKSGADYACAPVYSHLRYDTIPGA
sp|O53440|M.tuberculosis   QRRNLMHRKGFPESYNRRALMRFVTSVKSGSDYACAPVYSHLH?DIIPGA
sp|O86779|S.coelicolor     EARGLMSRKGFPESYDRRALTRFVADIKAGKAEVTAPVYSHLIYDIVPDQ
sp|P44793|H.influenzae     KQDNLLQKKGFPVSYDTTPKLIRFLADVKSGKSNVTAPIYSHLTYDIIPDK
sp|P15044|E.coli           KERGLMKKGFPESYDMHRLVKFVSDLKSGVPNVTAPVYSHLIYDVIPDG
sp|P54556|B.subtilis       KKKNMMSRKGFPESYDVKALLEFLNDLKSGKDSVKAPVYSHLTYDREEGV
                           ::  :****:**:         *  * ::*:  .   **:*****:**  .

sp|Q9X795|M.leprae         KHVVRHPDILILEGLNVLQTGP-------TLMVSDLFDFSLYVDARIQD
sp|O53440|M.tuberculosis   EQVVRHPDILILEGLNVLQTGP-------TLMVSDLFDFSLYVDARIED
sp|O86779|S.coelicolor     RLVVRRPDILIVEGLNVLQPALPGKDGRT-RVGLADYFDFSVYVDARTED
sp|P44793|H.influenzae     FDVDKPDILILEGLNVLQTGNNK---TD-QTFVSDFVDFSIYVDAEEKL
sp|P15044|E.coli           DKTVQPDILILEGLNVLQSGMDYPHDPH-HVFVSDFVDFSIYVDAPEDL
sp|P54556|B.subtilis       FEVVEQADIVIIEGINVLQSPTLEDDRENPRIFVSDFFDFSIYVDAEESR
                              : ***:*:**:*****    .         . .**:* :** **     .

sp|Q9X795|M.leprae         IEQWYVSRFLAMRGTAFADPESHFHHYSALTDSKAIIAAREIWRSINRPN
sp|O53440|M.tuberculosis   IEQWYVSRFLAMRTTAFADPESHFHHYAAFSDSQAVVAAREIWRTINRPN
sp|O86779|S.coelicolor     IERWYLNRFRKLRATAFQNPSSYFRKYTQVSEEEALDYARTTWRTINKPN
sp|P44793|H.influenzae     LKEWYIKRFLKFRESAFNDPNSYFKHYASLSKEEAIATASKIWDEINGLN
sp|P15044|E.coli           LQTWYINRFLKFREGAFTDPDSYFHNYAKLTKEEAIKTAMTLWKEINWLN
sp|P54556|B.subtilis       IFTWYLERFRLLRETAFQNPDSYFHKFKDLSDQEADEMAASIWESVNRPN
                           :      :  :** :* *:* :: :   :: .*      :*  :* * sp|Q9X795|M.leprae         LVENILPTRPRATLVLRKDADHSINRLRLRKL
sp|O53440|M.tuberculosis   LVENILPTRPRATLVLRKDADHSINRLRLRKL
sp|O86779|S.coelicolor     LVENVAPTRGRATLVLRKGPDHKVQRLSLRKL
sp|P44793|H.influenzae     LNQNILPTRERANLILKKGHNHQVELIKLRK-
sp|P15044|E.coli           LKQNILPTRERASLILTKSANHAVEEVRLRK-
sp|P54556|B.subtilis       LYENILPTKFRSDLILRKGDGHKVEEVLVRRV
                           *  *:  **:   *::  *. .*:    : *:
```

FIG. 23A

CLUSTAL W (1.7) Multiple Sequence Alignments

Sequence type explicitly set to Protein
Sequence format is Pearson

```
B.subtilis|CoaX|                       258 aa (SEQ ID NO:9)      sp|O51477|B.burgdorferi         262 aa (SEQ ID NO: 14)
dbj|BAA21476.1|D.vulgaris              212 aa (SEQ ID NO:11)     sp|P74045|Synechocystis         257 aa (SEQ ID NO: 16)
gb|AAD35964.1|T.maritima               246 aa (SEQ ID NO:12)     sp|O25533|H.pylori              223 aa (SEQ ID NO: 17)
pir|T36391|S.coelicolor                265 aa (SEQ ID NO: 7)     sp|O67753|A.aeolicus            229 aa (SEQ ID NO: 15)
sp|Q45338|B.pertussis                  267 aa (SEQ ID NO: 18)    sp|Q9RX54|D.radiodurans         262 aa (SEQ ID NO: 10)
sp|O06282|M.tuberculosis               272 aa (SEQ ID NO: 8)     WIT|RCA03301|C.acetobutylicum   250 aa (SEQ ID NO: 74)
sp|O83446|T.pallidum                   273 aa (SEQ ID NO: 13)    WIT|RRC02473|R.capsulatus       258 aa (SEQ ID NO: 75)

B.subtilis|CoaX|                   ------------------NKRAAFMLLLFLRSVLKVILVLDVGNTNIVLGIYNDT----KLTAEWRLS
WIT|RCA03301|C.acetobutylicum      ---------------------------------MLLVIDVGNTNTVLGVYHDG----KLEYHWRIE
pir|T36391|S.coelicolor            ----------------------------------MLLTIDVGNTHTVLGLFDGE----DIVEHWRIS
sp|O06282|M.tuberculosis           ----------------------------------MLLAIDVRNTHTVVGLLSGMKEHAKVVQQWRIR
WIT|RRC02473|R.capsulatus          -----------------------------------MLICIDCGNTNTVFSVWDGT----DFAATWRIA
dbj|BAA21476.1|D.vulgaris          ----------------------------------------MTQHFLLFDIGNTNVKIGIAVET----AVLTSYVLP
sp|Q9RX54|D.radiodurans            ------------------------------------MPAFPLLAVDIGNTTTVLGLADASG----ALTHTWRIR
gb|AAD35964.1|T.maritima           -----------------------------------MYLLVDVGNTHSVFSITEDG----KTFRRWRLS
sp|O83446|T.pallidum               ----------------------------MLLIDVGNSHVVFGIQGENGGRVCVRELFRLA
sp|O51477|B.burgdorferi            -------------------------MNKPLLSELIIDIGNTSIAFALFKDN----QVNLFIKMK
sp|O67753|A.aeolicus               ---------------------------------MRFLTVDVGNSSVDIALWEGK-------KVK
sp|P74045|Synechocystis            -----------------------METSKPGCGLALDNDKQKPWLGLMIGN----SRLBWAYC
sp|O25533|H.pylori                 ---------------------------------MPARQSFTDLKN---LVLCDIGN---------TR
sp|Q45338|B.pertussis              ------------------------------------MIILIDSGNSRLKVGWFDPDAP--QAAREPAPV
                                                                                        *         :
```

FIG. 23B

```
B.subtilis|CoaX|              TSRHKTEDEFGMILRSLFDHS-----GLMFEQIDGIIISSVVPPIMFALER
WIT|RCA03301|C.acetobutylicum TDVLRSADEYGIQVMNLFQQD-----KLDPTLVEGVIISSVVPNIMYSLEH
pir|T36391|S.coelicolor       TDSRRTADELAVLLQGLMGMHPLLGDELGDGIDGIAICATVPSVLHELRE
sp|O06282|M.tuberculosis      TESEVTADELALTIDGLIG-------EDSERLTGTAALSTVPSVLHEVRI
WIT|RRC02473|R.capsulatus     TDHRRTADEYFVWLNTLMQLK-----GLQGRISEAIISSTAPRVVFNLRV
dbj|BAA21476.1|D.vulgaris     TDPGQTTDSIGLRLLEVLRHAG----LGPADVGACVASSVVPGVNPLIRR
sp|Q9RX54|D.radiodurans       TNREMLPDDLALQLHGLFTLA-----GAP-IPRAAVLSSVAPPVGENYAL
gb|AAD35964.1|T.maritima      TGVFQTEDELFSHLRPLLG-------DAMREIKGIGVASVVPTQNTVIER
sp|O83446|T.pallidum          PDARKTQDEYSLLIHALCERAG----VGRASLRDAFISSVVPVLTKTIAD
sp|O51477|B.burgdorferi       TNLMLRYDEVYSFFEENFDFN-----VN---K-VFISSVVPILNETFKN
sp|O67753|A.aeolicus          DFLKLSHEEFLKEEFPKLK-------------ALGISVKQSFSEKVRG
sp|P74045|Synechocystis       SGNAPLQTWVTDYNPKSAQLP------------VLLGKVPLMLASVVPE
sp|O25533|H.pylori            IHFAQNYQLFSSAKEDLKR---------------LGIQKEIFYISVNEE
sp|Q45338|B.pertussis         AFDNLDLDALGRWLATLPRRP---------Q----RALGVNVAGLARGEAIA
                                                                         *  *

B.subtilis|CoaX|              MCTKYFHIEPQIVG-PG-MKTGLNIKYDNPKEVGADRIVNAVAAIHLYG-
WIT|RCA03301|C.acetobutylicum MIRKYFKINPLVVG-PG-IKTGINIKYDNPKEVGADRIVNAVAAHEIYK-
pir|T36391|S.coelicolor       VTRRYYGDVPAVLVEPG-VKTGVPILTDHPKEVGADRIINAVAAVELYG-
sp|O06282|M.tuberculosis      MLDQYWPSVPHVLIEPG-VRTGIPLLVDNPKEVGADRIVNCLAAYDRFR-
WIT|RRC02473|R.capsulatus     LCNRYFDCRPYVVGKPG-CELPVAPRVDPGTTVGPDRLVNTVAGYDRHG-
dbj|BAA21476.1|D.vulgaris     ACERYL--YRKLLFAPGDIAIPLDNRYERPAEVGADRLVAAYAARRLYP-
sp|Q9RX54|D.radiodurans       ALKRHFMIDAFAVSAEN--LPDVTVELDTPGSVGADRLCNLFGAEKYLG-
gb|AAD35964.1|T.maritima      FSQKYFHISPIWVKARN---GCVKWNVKNPSEVGADRVANVVAFVKEYG-
sp|O83446|T.pallidum          AVAQISGVQPVVFGPWAYEHLPVRIPEPVRAEIGTDLVANAVAAYVHFR-
sp|O51477|B.burgdorferi       VIFSFFKIKPLFIGFDLNYDLTFNPYKSDKFLLGSDVFANLVAAIENYS-
sp|O67753|A.aeolicus          KIPKIK-----FLRKEN----FPIQVDYKTPETLGTDRVALAYSARKFYG-
sp|P74045|Synechocystis       QTEVWRVYQPKILTLKN----LPLVNLYP---SFGIDRALAGLGTGLTYG-
sp|O25533|H.pylori            NEKALLNCYPNAKNIAG--FFHLETDYVG---LGIDRQMACLA---VN--
sp|Q45338|B.pertussis         ATLRAGGCDIRWLRAQP-LAMGLRNGYRNPDQLGADRWACMVGVLARQPS
```

B.subtilis|CoaX|
WIT|RCA03301|C.acetobutylicum
pir|T36391|S.coelicolor
sp|O06282|M.tuberculosis
WIT|RRC02473|R.capsulatus
dbj|BAA21476.1|D.vulgaris
sp|Q9RX54|D.radiodurans
gb|AAD35964.1|T.maritima
sp|O83446|T.pallidum
sp|O51477|B.burgdorferi
sp|O67753|A.aeolicus
sp|P74045|Synechocystis
sp|O25533|H.pylori
sp|Q45338|B.pertussis

FIG. 23C

```
B.subtilis|CoaX|              NP--LIVVDFGTATTYCYIDENKQYMGGAIAPGITISTEALYSRAAKLPR
WIT|RCA03301|C.acetobutylicum RS--LIIIDFGTATTFCAVRENGDYLGGAICPGIKVSSEALFEKAAKLPR
pir|T36391|S.coelicolor       GP--AIVVDFGTATTFDAVSARGEYIGGVIAPGIEISVEALGVKGAQLRK
sp|O06282|M.tuberculosis      KA--AIVVDFGSSICVDVVSAKGEFLGGAIAPGVQVSSDAAAARSAALRR
WIT|RRC02473|R.capsulatus     GD--LIVVDFGTATTFDVVAPDGAYIGGVIAPGVNLSLEALHMAAAALPH
dbj|BAA21476.1|D.vulgaris     GPRSLVSVDFGTATTFDCVEG-GAYLGGLICPGVLSSAGALSSRTAKLPR
sp|Q9RX54|D.radiodurans       GLDYAVVVDFGTSTNFDVVGRGRRFLGGILATGAQVSADALFARAAKLPR
gb|AAD35964.1|T.maritima      KN--GIIIDMGTATTVDLVVN-GSYEGGAILPGFFMVHSLFRGTAKLPL
sp|O83446|T.pallidum          SA--CVVVDCGTALTFTAVDGTGLIQGVAIAPGLRTAVQSLHTGTAQLPL
sp|O51477|B.burgdorferi       FEN-VLVVDLGTACTIFAVSRQDGILGGIINSGPLINFNSLLDNAYLIKK
sp|O67753|A.aeolicus          KN--VVVISAGTALVIDLVLE-GKFKGGFITLGLGKKLKILSDLAEGIPE
sp|P74045|Synechocystis       FP--CLVVDGGTALTITGFDQDKKLVGGAILPGLGLQLATLGDRLAALPK
sp|O25533|H.pylori            NG--VVVDAGSAITIDLIKE-GKHLGGCILPGLAQYIHAYKKSAKILEQ
sp|Q45338|B.pertussis         VHPPLLVASFGTATTLDTIGPDNVFPGGLILPGPAMMRGALAYGTAHLPL
                                  :  .  *:::         .     *          *

B.subtilis|CoaX|              IEITRPDN---IIGKNTVSAMQSGILFGYVGQVEGIVKRMKWQAKQDLK-
WIT|RCA03301|C.acetobutylicum VELIKPAY---AICKNTISSIQSGIVYRYLRQVKYLFEKLKENLPDGRRT
pir|T36391|S.coelicolor       IEVARPRS---VIGKNTVEAMQSGIVYGFAGQVDGVVNRMARELADD--P
sp|O06282|M.tuberculosis      VELARPRS---VVGKNTVECMQAGAVFGFAGLVDGLVGRIREDVSGFSVD
WIT|RRC02473|R.capsulatus     VDVTKPQG---VIGTNTVACIQSGVYWGYIGLVEGIVRQIRMERDRP---
dbj|BAA21476.1|D.vulgaris     ISLEVEEDS-PVIGRSTTTSLNHGFIFGFAAMTEGVLAA-----------
sp|Q9RX54|D.radiodurans       ITLQAPET---AIGKNTVHALQSGLVFGYAEMVDGLLRRIRAELPGE---
gb|AAD35964.1|T.maritima      VEVKPADF---VVGKDTEENIRLGVVNGSVYALEGIIGRIKEVYGDLP--
sp|O83446|T.pallidum          VPLALPDS---VLGKDTTHAVQAGVVRGTLFVIRAMIAQCQKELGCR---
sp|O51477|B.burgdorferi       FPISTPNN---LLERTTSGSVNSGLFYQYKYLIEGVYRDIKQMYKKK---
sp|O67753|A.aeolicus          FFPEEVEI---FLGRSTRECVLGGAYRESTEFIKSTLKLWRKVFKRK---
sp|P74045|Synechocystis       LEMDQLTELPDRWALDTPSAIFSGVVYGVLGALQSYLQDWQKLFPGA---
sp|O25533|H.pylori            PFKALDSL-EVLPKSTRDAVNYGMVLSVIACIQHLAK--NQK-------
sp|Q45338|B.pertussis         ADGLVADY------PIDTHQAIASGIAAAQAGAIVRQWLAGRQRYGQAP--
                                              :       .                *
```

FIG. 23D

```
B.subtilis|CoaX|                    ----VIATGG-------LAPLIANES-----DCIDIVDPFLTLKGLELI
WIT|RCA03301|C.acetobutylicum       RTSLVLATGG-------LARLIN-----------------------
pir|T36391|S.coelicolor             DDVTVIATGG-------LAPMVLGES-----SVIDEHEPWLTLMGLRLV
sp|O06282|M.tuberculosis            HDVAIVATGH-------TAPLLLPEL-----HTVDHYDQHLTLQGLRLV
WIT|RRC02473|R.capsulatus           --MRVIATGG-------LASLFDLGF-----DLFDRKVEDDLTMBGLRLI
dbj|BAA21476.1|D.vulgaris           ----------------------------------------------
sp|Q9RX54|D.radiodurans             --AVAVATGG-------FSRTVQGIC-----QEIDYYDETLTLRGLVEL
gb|AAD35964.1|T.maritima            ---VVLTGG--------QSKIVR-DM-----IKHEIFDEDLTIKGVYHF
sp|O83446|T.pallidum                --CAAVITGG-------LSRLFS-SE-----VDFPPIDAQLTLSGLAHI
sp|O51477|B.burgdorferi             --FNLIITGG-------NADLILSLI-----EIEFIFNIHLTVEGVRIL
sp|O67753|A.aeolicus                --FKVVITGG-------EGKYFS--------KFGIYDPLLVHRGMRNL
sp|P74045|Synechocystis             ---AMVITGG-------DGKILHGFLKEHSPNLSVAWDDNLIFLGMAAI
sp|O25533|H.pylori                  ---IYLCGG--------DAKYLSAFL-----PHSVCKERLVFDGMEIA
sp|Q45338|B.pertussis               ----EIYVAGGGWPEVRQEAERLLAVTGAAFGATPQPTYLDSPVLDGLAAL B.subtilis|CoaX|                    YERNRVGSV---------
WIT|RCA03301|C.acetobutylicum       ------------------
pir|T36391|S.coelicolor             YERNVSRM----------
sp|O06282|M.tuberculosis            FERNLEVQRGRLKTAR--
WIT|RRC02473|R.capsulatus           FDYNKGLGA---------
dbj|BAA21476.1|D.vulgaris           ------------------
sp|Q9RX54|D.radiodurans             WASRSEVR----------
gb|AAD35964.1|T.maritima            CFGD--------------
sp|O83446|T.pallidum                ARLVPTSLLPPATVSGSSGN
sp|O51477|B.burgdorferi             GNSIDFKFVN--------
sp|O67753|A.aeolicus                LYLYHRI-----------
sp|P74045|Synechocystis             HHGDRPIC----------
sp|O25533|H.pylori                  LKKAGILECK--------
sp|Q45338|B.pertussis               AAQGAPTA----------
```

FIG. 24

|   | K | D | N | V | T | A | P | V | Y | S | H | L | I | Y | D | I | I | P | G | A | |
|---|---|---|---|---|---|---|---|---|---|---|---|---|---|---|---|---|---|---|---|---|---|
| 168 | K | D | S | V | K | A | P | V | Y | S | H | L | T | Y | D | R | E | E | G | V | B. subtilis CoaA1 |
| 167 | V | P | N | V | T | A | P | V | Y | S | H | L | – | Y | D | V | I | P | D | G | E. coli CoaA |
| 165 | K | S | N | V | T | A | P | V | Y | S | H | L | T | Y | D | I | I | P | D | K | H. influenzae CoaA |
| 169 | A | D | Y | A | C | A | P | V | I | Y | S | H | L | R | Y | D | T | – | P | G | A | M. leprae CoaA |
| 169 | S | D | Y | A | C | A | P | V | Y | S | H | L | H | Y | D | – | – | P | G | A | M. tuberculosis CoaA |
| 179 | K | A | E | V | T | A | P | V | Y | S | H | L | – | Y | D | I | V | P | D | Q | S. coelecolor CoaA |

Majority

SEQUENCE LISTING

<160> NUMBER OF SEQ ID NOS: 98

<210> SEQ ID NO 1
<211> LENGTH: 311
<212> TYPE: PRT
<213> ORGANISM: Haemophilus influenzae

<400> SEQUENCE: 1

```
Met Glu Phe Ser Thr Gln Gln Thr Pro Phe Leu Ser Phe Asn Arg Glu
 1               5                  10                  15

Gln Trp Ala Glu Leu Arg Lys Ser Val Pro Leu Lys Leu Thr Glu Gln
            20                  25                  30

Asp Leu Lys Pro Leu Leu Gly Phe Asn Glu Asp Leu Ser Leu Asp Glu
        35                  40                  45

Val Ser Thr Ile Tyr Leu Pro Leu Thr Arg Leu Ile Asn Tyr Tyr Ile
    50                  55                  60

Asp Glu Asn Leu His Arg Gln Thr Val Leu His Arg Phe Leu Gly Arg
65                  70                  75                  80

Asn Asn Ala Lys Thr Pro Tyr Ile Ile Ser Ile Ala Gly Ser Val Ala
                85                  90                  95

Val Gly Lys Ser Thr Ser Ala Arg Ile Leu Gln Ser Leu Leu Ser His
            100                 105                 110

Trp Pro Thr Glu Arg Lys Val Asp Leu Ile Thr Thr Asp Gly Phe Leu
        115                 120                 125

Tyr Pro Leu Asn Lys Leu Lys Gln Asp Asn Leu Leu Gln Lys Lys Gly
    130                 135                 140

Phe Pro Val Ser Tyr Asp Thr Pro Lys Leu Ile Arg Phe Leu Ala Asp
145                 150                 155                 160

Val Lys Ser Gly Lys Ser Asn Val Thr Ala Pro Ile Tyr Ser His Leu
                165                 170                 175
```

Thr Tyr Asp Ile Ile Pro Asp Lys Phe Asp Val Asp Lys Pro Asp
            180                 185                 190
Ile Leu Ile Leu Glu Gly Leu Asn Val Leu Gln Thr Gly Asn Asn Lys
        195                 200                 205
Thr Asp Gln Thr Phe Val Ser Asp Phe Val Asp Phe Ser Ile Tyr Val
210                 215                 220
Asp Ala Glu Glu Lys Leu Leu Lys Glu Trp Tyr Ile Lys Arg Phe Leu
225                 230                 235                 240
Lys Phe Arg Glu Ser Ala Phe Asn Asp Pro Asn Ser Tyr Phe Lys His
                245                 250                 255
Tyr Ala Ser Leu Ser Lys Glu Glu Ala Ile Ala Thr Ala Ser Lys Ile
            260                 265                 270
Trp Asp Glu Ile Asn Gly Leu Asn Leu Asn Gln Asn Ile Leu Pro Thr
        275                 280                 285
Arg Glu Arg Ala Asn Leu Ile Leu Lys Lys Gly His Asn His Gln Val
290                 295                 300
Glu Leu Ile Lys Leu Arg Lys
305                 310

<210> SEQ ID NO 2
<211> LENGTH: 316
<212> TYPE: PRT
<213> ORGANISM: Escherichia coli

<400> SEQUENCE: 2

Met Ser Ile Lys Glu Gln Thr Leu Met Thr Pro Tyr Leu Gln Phe Asp
1               5                   10                  15
Arg Asn Gln Trp Ala Ala Leu Arg Asp Ser Val Pro Met Thr Leu Ser
            20                  25                  30
Glu Asp Glu Ile Ala Arg Leu Lys Gly Ile Asn Glu Asp Leu Ser Leu
        35                  40                  45
Glu Glu Val Ala Glu Ile Tyr Leu Pro Leu Ser Arg Leu Leu Asn Phe
    50                  55                  60
Tyr Ile Ser Ser Asn Leu Arg Arg Gln Ala Val Leu Glu Gln Phe Leu
65                  70                  75                  80
Gly Thr Asn Gly Gln Arg Ile Pro Tyr Ile Ile Ser Ile Ala Gly Ser
                85                  90                  95
Val Ala Val Gly Lys Ser Thr Thr Ala Arg Val Leu Gln Ala Leu Leu
            100                 105                 110
Ser Arg Trp Pro Glu His Arg Arg Val Glu Leu Ile Thr Thr Asp Gly
        115                 120                 125
Phe Leu His Pro Asn Gln Val Leu Lys Glu Arg Gly Leu Met Lys Lys
    130                 135                 140
Lys Gly Phe Pro Glu Ser Tyr Asp Met His Arg Leu Val Lys Phe Val
145                 150                 155                 160
Ser Asp Leu Lys Ser Gly Val Pro Asn Val Thr Ala Pro Val Tyr Ser
                165                 170                 175
His Leu Ile Tyr Asp Val Ile Pro Asp Gly Asp Lys Thr Val Val Gln
            180                 185                 190
Pro Asp Ile Leu Ile Leu Glu Gly Leu Asn Val Leu Gln Ser Gly Met
        195                 200                 205
Asp Tyr Pro His Asp Pro His His Val Phe Val Ser Asp Phe Val Asp
    210                 215                 220
Phe Ser Ile Tyr Val Asp Ala Pro Glu Asp Leu Leu Gln Thr Trp Tyr
225                 230                 235                 240

```
Ile Asn Arg Phe Leu Lys Phe Arg Glu Gly Ala Phe Thr Asp Pro Asp
            245                 250                 255

Ser Tyr Phe His Asn Tyr Ala Lys Leu Thr Lys Glu Glu Ala Ile Lys
        260                 265                 270

Thr Ala Met Thr Leu Trp Lys Glu Ile Asn Trp Leu Asn Leu Lys Gln
    275                 280                 285

Asn Ile Leu Pro Thr Arg Glu Arg Ala Ser Leu Ile Leu Thr Lys Ser
290                 295                 300

Ala Asn His Ala Val Glu Glu Val Arg Leu Arg Lys
305                 310                 315

<210> SEQ ID NO 3
<211> LENGTH: 319
<212> TYPE: PRT
<213> ORGANISM: Bacillus subtilis

<400> SEQUENCE: 3

Met Lys Asn Lys Glu Leu Asn Leu His Thr Leu Tyr Thr Gln His Asn
  1               5                  10                  15

Arg Glu Ser Trp Ser Gly Phe Gly Gly His Leu Ser Ile Ala Val Ser
             20                  25                  30

Glu Glu Glu Ala Lys Ala Val Glu Gly Leu Asn Asp Tyr Leu Ser Val
         35                  40                  45

Glu Glu Val Glu Thr Ile Tyr Ile Pro Leu Val Arg Leu Leu His Leu
     50                  55                  60

His Val Lys Ser Ala Ala Glu Arg Asn Lys His Val Asn Val Phe Leu
 65                  70                  75                  80

Lys His Pro His Ser Ala Lys Ile Pro Phe Ile Ile Gly Ile Ala Gly
                 85                  90                  95

Ser Val Ala Val Gly Lys Ser Thr Thr Ala Arg Ile Leu Gln Lys Leu
            100                 105                 110

Leu Ser Arg Leu Pro Asp Arg Pro Lys Val Ser Leu Ile Thr Thr Asp
        115                 120                 125

Gly Phe Leu Phe Pro Thr Ala Glu Leu Lys Lys Lys Asn Met Met Ser
    130                 135                 140

Arg Lys Gly Phe Pro Glu Ser Tyr Asp Val Lys Ala Leu Leu Glu Phe
145                 150                 155                 160

Leu Asn Asp Leu Lys Ser Gly Lys Asp Ser Val Lys Ala Pro Val Tyr
                165                 170                 175

Ser His Leu Thr Tyr Asp Arg Glu Glu Gly Val Phe Glu Val Val Glu
            180                 185                 190

Gln Ala Asp Ile Val Ile Ile Glu Gly Ile Asn Val Leu Gln Ser Pro
        195                 200                 205

Thr Leu Glu Asp Asp Arg Glu Asn Pro Arg Ile Phe Val Ser Asp Phe
    210                 215                 220

Phe Asp Phe Ser Ile Tyr Val Asp Ala Glu Glu Ser Arg Ile Phe Thr
225                 230                 235                 240

Trp Tyr Leu Glu Arg Phe Arg Leu Leu Arg Glu Thr Ala Phe Gln Asn
                245                 250                 255

Pro Asp Ser Tyr Phe His Lys Phe Lys Asp Leu Ser Asp Gln Glu Ala
            260                 265                 270

Asp Glu Met Ala Ala Ser Ile Trp Glu Ser Val Asn Arg Pro Asn Leu
        275                 280                 285

Tyr Glu Asn Ile Leu Pro Thr Lys Phe Arg Ser Asp Leu Ile Leu Arg
    290                 295                 300
```

Lys Gly Asp Gly His Lys Val Glu Glu Val Leu Val Arg Arg Val
305                 310                 315

<210> SEQ ID NO 4
<211> LENGTH: 312
<212> TYPE: PRT
<213> ORGANISM: Mycobacterium leprae

<400> SEQUENCE: 4

Met Pro Arg Leu Ser Glu Pro Ser Tyr Val Glu Phe Asp Arg Lys
1               5                   10                  15

Gln Trp Arg Ala Leu Arg Met Ser Thr Pro Leu Ala Leu Thr Glu Glu
                20                  25                  30

Glu Leu Ile Gly Leu Arg Gly Leu Gly Glu Gln Ile Asp Leu Leu Glu
                35                  40                  45

Val Glu Glu Val Tyr Leu Pro Leu Ala Arg Leu Ile His Leu Gln Val
            50                  55                      60

Ala Ala Arg Gln Arg Leu Phe Ala Ala Thr Ala Glu Phe Leu Gly Glu
65              70                  75                      80

Pro Gln Gln Asn Pro Gly Arg Pro Val Pro Phe Ile Ile Gly Val Ala
                    85                  90                  95

Gly Ser Val Ala Val Gly Lys Ser Thr Thr Ala Arg Val Leu Gln Ala
                100                 105                 110

Leu Leu Ala Arg Trp Asp His His Thr Arg Val Asp Leu Val Thr Thr
            115                 120                 125

Asp Gly Phe Leu Tyr Pro Asn Ala Glu Leu Gly Arg Arg Asn Leu Met
130                 135                 140

His Arg Lys Gly Phe Pro Glu Ser Tyr Asn Arg Ala Leu Met Arg
145                 150                 155                 160

Phe Val Thr Ser Val Lys Ser Gly Ala Asp Tyr Ala Cys Ala Pro Val
                165                 170                 175

Tyr Ser His Leu Arg Tyr Asp Thr Ile Pro Gly Ala Lys His Val Val
            180                 185                 190

Arg His Pro Asp Ile Leu Ile Leu Glu Gly Leu Asn Val Leu Gln Thr
            195                 200                 205

Gly Pro Thr Leu Met Val Ser Asp Leu Phe Asp Phe Ser Leu Tyr Val
210                 215                 220

Asp Ala Arg Ile Gln Asp Ile Glu Gln Trp Tyr Val Ser Arg Phe Leu
225                 230                 235                 240

Ala Met Arg Gly Thr Ala Phe Ala Asp Pro Glu Ser His Phe His His
                245                 250                 255

Tyr Ser Ala Leu Thr Asp Ser Lys Ala Ile Ile Ala Ala Arg Glu Ile
            260                 265                 270

Trp Arg Ser Ile Asn Arg Pro Asn Leu Val Glu Asn Ile Leu Pro Thr
        275                 280                 285

Arg Pro Arg Ala Thr Leu Val Leu Arg Lys Asp Ala Asp His Ser Ile
    290                 295                 300

Asn Arg Leu Arg Leu Arg Lys Leu
305                 310

<210> SEQ ID NO 5
<211> LENGTH: 312
<212> TYPE: PRT
<213> ORGANISM: Mycobacterium tuberculosis

<400> SEQUENCE: 5

Met Ser Arg Leu Ser Glu Pro Ser Pro Tyr Val Glu Phe Asp Arg Arg
1               5                   10                  15

Gln Trp Arg Ala Leu Arg Met Ser Thr Pro Leu Ala Leu Thr Glu Glu
            20                  25                  30

Glu Leu Val Gly Leu Arg Gly Leu Gly Glu Gln Ile Asp Leu Leu Glu
        35                  40                  45

Val Glu Glu Val Tyr Leu Pro Leu Ala Arg Leu Ile His Leu Gln Val
    50                  55                  60

Ala Ala Arg Gln Arg Leu Phe Ala Ala Thr Ala Glu Phe Leu Gly Glu
65                  70                  75                  80

Pro Gln Gln Asn Pro Asp Arg Pro Val Pro Phe Ile Ile Gly Val Ala
                85                  90                  95

Gly Ser Val Ala Val Gly Lys Ser Thr Thr Ala Arg Val Leu Gln Ala
            100                 105                 110

Leu Leu Ala Arg Trp Asp His His Pro Arg Val Asp Leu Val Thr Thr
        115                 120                 125

Asp Gly Phe Leu Tyr Pro Asn Ala Glu Leu Gln Arg Arg Asn Leu Met
    130                 135                 140

His Arg Lys Gly Phe Pro Glu Ser Tyr Asn Arg Ala Leu Met Arg
145                 150                 155                 160

Phe Val Thr Ser Val Lys Ser Gly Ser Asp Tyr Ala Cys Ala Pro Val
                165                 170                 175

Tyr Ser His Leu His Tyr Asp Ile Ile Pro Gly Ala Glu Gln Val Val
            180                 185                 190

Arg His Pro Asp Ile Leu Ile Leu Glu Gly Leu Asn Val Leu Gln Thr
        195                 200                 205

Gly Pro Thr Leu Met Val Ser Asp Leu Phe Asp Phe Ser Leu Tyr Val
    210                 215                 220

Asp Ala Arg Ile Glu Asp Ile Glu Gln Trp Tyr Val Ser Arg Phe Leu
225                 230                 235                 240

Ala Met Arg Thr Thr Ala Phe Ala Asp Pro Glu Ser His Phe His His
                245                 250                 255

Tyr Ala Ala Phe Ser Asp Ser Gln Ala Val Val Ala Ala Arg Glu Ile
            260                 265                 270

Trp Arg Thr Ile Asn Arg Pro Asn Leu Val Glu Asn Ile Leu Pro Thr
        275                 280                 285

Arg Pro Arg Ala Thr Leu Val Leu Arg Lys Asp Ala Asp His Ser Ile
    290                 295                 300

Asn Arg Leu Arg Leu Arg Lys Leu
305                 310

<210> SEQ ID NO 6
<211> LENGTH: 329
<212> TYPE: PRT
<213> ORGANISM: Streptomyces coelicolor

<400> SEQUENCE: 6

Met Ile Ser Pro Val Pro Ser Ile Pro Arg Ser Ala His Arg Gln Arg
1               5                   10                  15

Pro Glu Ala Thr Pro Tyr Val Asp Leu Thr Arg Pro Glu Trp Ser Ala
            20                  25                  30

Leu Arg Asp Lys Thr Pro Leu Pro Leu Thr Ala Glu Glu Val Glu Lys
        35                  40                  45

Leu Arg Gly Leu Gly Asp Val Ile Asp Leu Asp Glu Val Arg Asp Ile
    50                  55                  60

```
Tyr Leu Pro Leu Ser Arg Leu Leu Asn Leu Tyr Val Gly Ala Thr Asp
 65                  70                  75                  80

Gly Leu Arg Gly Ala Leu Asn Thr Phe Leu Gly Glu Gln Gly Ser Gln
                 85                  90                  95

Ser Gly Thr Pro Phe Val Ile Gly Val Ala Gly Ser Val Ala Val Gly
            100                 105                 110

Lys Ser Thr Val Ala Arg Leu Leu Gln Ala Leu Leu Ser Arg Trp Pro
        115                 120                 125

Glu His Pro Arg Val Glu Leu Val Thr Thr Asp Gly Phe Leu Leu Pro
    130                 135                 140

Thr Arg Glu Leu Glu Ala Arg Gly Leu Met Ser Arg Lys Gly Phe Pro
145                 150                 155                 160

Glu Ser Tyr Asp Arg Arg Ala Leu Thr Arg Phe Val Ala Asp Ile Lys
                165                 170                 175

Ala Gly Lys Ala Glu Val Thr Ala Pro Val Tyr Ser His Leu Ile Tyr
            180                 185                 190

Asp Ile Val Pro Asp Gln Arg Leu Val Val Arg Arg Pro Asp Ile Leu
        195                 200                 205

Ile Val Glu Gly Leu Asn Val Leu Gln Pro Ala Leu Pro Gly Lys Asp
    210                 215                 220

Gly Arg Thr Arg Val Gly Leu Ala Asp Tyr Phe Asp Phe Ser Val Tyr
225                 230                 235                 240

Val Asp Ala Arg Thr Glu Asp Ile Glu Arg Trp Tyr Leu Asn Arg Phe
                245                 250                 255

Arg Lys Leu Arg Ala Thr Ala Phe Gln Asn Pro Ser Ser Tyr Phe Arg
            260                 265                 270

Lys Tyr Thr Gln Val Ser Glu Glu Ala Leu Asp Tyr Ala Arg Thr
        275                 280                 285

Thr Trp Arg Thr Ile Asn Lys Pro Asn Leu Val Glu Asn Val Ala Pro
    290                 295                 300

Thr Arg Gly Arg Ala Thr Leu Val Leu Arg Lys Gly Pro Asp His Lys
305                 310                 315                 320

Val Gln Arg Leu Ser Leu Arg Lys Leu
                325

<210> SEQ ID NO 7
<211> LENGTH: 265
<212> TYPE: PRT
<213> ORGANISM: Streptomyces coelicolor

<400> SEQUENCE: 7

Met Leu Leu Thr Ile Asp Val Gly Asn Thr His Thr Val Leu Gly Leu
  1               5                  10                  15

Phe Asp Gly Glu Asp Ile Val Glu His Trp Arg Ile Ser Thr Asp Ser
                 20                  25                  30

Arg Arg Thr Ala Asp Glu Leu Ala Val Leu Leu Gln Gly Leu Met Gly
             35                  40                  45

Met His Pro Leu Leu Gly Asp Glu Leu Gly Asp Gly Ile Asp Gly Ile
         50                  55                  60

Ala Ile Cys Ala Thr Val Pro Ser Val Leu His Glu Leu Arg Glu Val
 65                  70                  75                  80

Thr Arg Arg Tyr Tyr Gly Asp Val Pro Ala Val Leu Val Glu Pro Gly
                 85                  90                  95

Val Lys Thr Gly Val Pro Ile Leu Thr Asp His Pro Lys Glu Val Gly
            100                 105                 110
```

Ala Asp Arg Ile Ile Asn Ala Val Ala Val Glu Leu Tyr Gly Gly
            115                 120                 125

Pro Ala Ile Val Val Asp Phe Gly Thr Ala Thr Phe Asp Ala Val
        130                 135                 140

Ser Ala Arg Gly Glu Tyr Ile Gly Gly Val Ile Ala Pro Gly Ile Glu
145                 150                 155                 160

Ile Ser Val Glu Ala Leu Gly Val Lys Gly Ala Gln Leu Arg Lys Ile
                165                 170                 175

Glu Val Ala Arg Pro Arg Ser Val Ile Gly Lys Asn Thr Val Glu Ala
                180                 185                 190

Met Gln Ser Gly Ile Val Tyr Gly Phe Ala Gly Gln Val Asp Gly Val
                195                 200                 205

Val Asn Arg Met Ala Arg Glu Leu Ala Asp Asp Pro Asp Val Thr
210                 215                 220

Val Ile Ala Thr Gly Gly Leu Ala Pro Met Val Leu Gly Glu Ser Ser
225                 230                 235                 240

Val Ile Asp Glu His Glu Pro Trp Leu Thr Leu Met Gly Leu Arg Leu
                245                 250                 255

Val Tyr Glu Arg Asn Val Ser Arg Met
                260                 265

<210> SEQ ID NO 8
<211> LENGTH: 272
<212> TYPE: PRT
<213> ORGANISM: Mycobacterium tuberculosis

<400> SEQUENCE: 8

Met Leu Leu Ala Ile Asp Val Arg Asn Thr His Thr Val Val Gly Leu
1               5                   10                  15

Leu Ser Gly Met Lys Glu His Ala Lys Val Val Gln Gln Trp Arg Ile
                20                  25                  30

Arg Thr Glu Ser Glu Val Thr Ala Asp Glu Leu Ala Leu Thr Ile Asp
            35                  40                  45

Gly Leu Ile Gly Glu Asp Ser Glu Arg Leu Thr Gly Thr Ala Ala Leu
        50                  55                  60

Ser Thr Val Pro Ser Val Leu His Glu Val Arg Ile Met Leu Asp Gln
65              70                  75                  80

Tyr Trp Pro Ser Val Pro His Val Leu Ile Glu Pro Gly Val Arg Thr
                85                  90                  95

Gly Ile Pro Leu Leu Val Asp Asn Pro Lys Glu Val Gly Ala Asp Arg
            100                 105                 110

Ile Val Asn Cys Leu Ala Ala Tyr Asp Arg Phe Arg Lys Ala Ala Ile
        115                 120                 125

Val Val Asp Phe Gly Ser Ser Ile Cys Val Asp Val Val Ser Ala Lys
    130                 135                 140

Gly Glu Phe Leu Gly Gly Ala Ile Ala Pro Gly Val Gln Val Ser Ser
145                 150                 155                 160

Asp Ala Ala Ala Ala Arg Ser Ala Ala Leu Arg Arg Val Glu Leu Ala
                165                 170                 175

Arg Pro Arg Ser Val Val Gly Lys Asn Thr Val Glu Cys Met Gln Ala
                180                 185                 190

Gly Ala Val Phe Gly Phe Ala Gly Leu Val Asp Gly Leu Val Gly Arg
            195                 200                 205

Ile Arg Glu Asp Val Ser Gly Phe Ser Val Asp His Asp Val Ala Ile
        210                 215                 220

```
Val Ala Thr Gly His Thr Ala Pro Leu Leu Leu Pro Glu Leu His Thr
225                 230                 235                 240

Val Asp His Tyr Asp Gln His Leu Thr Leu Gln Gly Leu Arg Leu Val
                245                 250                 255

Phe Glu Arg Asn Leu Glu Val Gln Arg Gly Arg Leu Lys Thr Ala Arg
            260                 265                 270

<210> SEQ ID NO 9
<211> LENGTH: 258
<212> TYPE: PRT
<213> ORGANISM: Bacillus subtilis

<400> SEQUENCE: 9

Leu Leu Leu Val Ile Asp Val Gly Asn Thr Asn Thr Val Leu Gly Val
1               5                   10                  15

Tyr His Asp Gly Lys Leu Glu Tyr His Trp Arg Ile Glu Thr Ser Arg
                20                  25                  30

His Lys Thr Glu Asp Glu Phe Gly Met Ile Leu Arg Ser Leu Phe Asp
            35                  40                  45

His Ser Gly Leu Met Phe Glu Gln Ile Asp Gly Ile Ile Ser Ser
     50                  55                  60

Val Val Pro Pro Ile Met Phe Ala Leu Glu Arg Met Cys Thr Lys Tyr
65                  70                  75                  80

Phe His Ile Glu Pro Gln Ile Val Gly Pro Gly Met Lys Thr Gly Leu
                85                  90                  95

Asn Ile Lys Tyr Asp Asn Pro Lys Glu Val Gly Ala Asp Arg Ile Val
            100                 105                 110

Asn Ala Val Ala Ala Ile His Leu Tyr Gly Asn Pro Leu Ile Val Val
        115                 120                 125

Asp Phe Gly Thr Ala Thr Thr Tyr Cys Tyr Ile Asp Glu Asn Lys Gln
130                 135                 140

Tyr Met Gly Gly Ala Ile Ala Pro Gly Ile Thr Ile Ser Thr Glu Ala
145                 150                 155                 160

Leu Tyr Ser Arg Ala Ala Lys Leu Pro Arg Ile Glu Ile Thr Arg Pro
                165                 170                 175

Asp Asn Ile Ile Gly Lys Asn Thr Val Ser Ala Met Gln Ser Gly Ile
            180                 185                 190

Leu Phe Gly Tyr Val Gly Gln Val Glu Gly Ile Val Lys Arg Met Lys
        195                 200                 205

Trp Gln Ala Lys Gln Asp Leu Lys Val Ile Ala Thr Gly Gly Leu Ala
210                 215                 220

Pro Leu Ile Ala Asn Glu Ser Asp Cys Ile Asp Ile Val Asp Pro Phe
225                 230                 235                 240

Leu Thr Leu Lys Gly Leu Glu Leu Ile Tyr Glu Arg Asn Arg Val Gly
                245                 250                 255

Ser Val

<210> SEQ ID NO 10
<211> LENGTH: 262
<212> TYPE: PRT
<213> ORGANISM: Deinococcus radiopugnans

<400> SEQUENCE: 10

Met Pro Ala Phe Pro Leu Leu Ala Val Asp Ile Gly Asn Thr Thr Thr
1               5                   10                  15

Val Leu Gly Leu Ala Asp Ala Ser Gly Ala Leu Thr His Thr Trp Arg
                20                  25                  30
```

```
Ile Arg Thr Asn Arg Glu Met Leu Pro Asp Asp Leu Ala Leu Gln Leu
            35                  40                  45

His Gly Leu Phe Thr Leu Ala Gly Ala Pro Ile Pro Arg Ala Ala Val
        50                  55                  60

Leu Ser Ser Val Ala Pro Pro Val Gly Glu Asn Tyr Ala Leu Ala Leu
65                  70                  75                  80

Lys Arg His Phe Met Ile Asp Ala Phe Ala Val Ser Ala Glu Asn Leu
                85                  90                  95

Pro Asp Val Thr Val Glu Leu Asp Thr Pro Gly Ser Val Gly Ala Asp
            100                 105                 110

Arg Leu Cys Asn Leu Phe Gly Ala Glu Lys Tyr Leu Gly Gly Leu Asp
        115                 120                 125

Tyr Ala Val Val Val Asp Phe Gly Thr Ser Thr Asn Phe Asp Val Val
130                 135                 140

Gly Arg Gly Arg Arg Phe Leu Gly Gly Ile Leu Ala Thr Gly Ala Gln
145                 150                 155                 160

Val Ser Ala Asp Ala Leu Phe Ala Arg Ala Ala Lys Leu Pro Arg Ile
                165                 170                 175

Thr Leu Gln Ala Pro Glu Thr Ala Ile Gly Lys Asn Thr Val His Ala
            180                 185                 190

Leu Gln Ser Gly Leu Val Phe Gly Tyr Ala Glu Met Val Asp Gly Leu
        195                 200                 205

Leu Arg Arg Ile Arg Ala Glu Leu Pro Gly Glu Ala Val Ala Val Ala
210                 215                 220

Thr Gly Gly Phe Ser Arg Thr Val Gln Gly Ile Cys Gln Glu Ile Asp
225                 230                 235                 240

Tyr Tyr Asp Glu Thr Leu Thr Leu Arg Gly Leu Val Glu Leu Trp Ala
                245                 250                 255

Ser Arg Ser Glu Val Arg
            260

<210> SEQ ID NO 11
<211> LENGTH: 212
<212> TYPE: PRT
<213> ORGANISM: Desulfovibrio vulgaris

<400> SEQUENCE: 11

Met Thr Gln His Phe Leu Leu Phe Asp Ile Gly Asn Thr Asn Val Lys
1               5                   10                  15

Ile Gly Ile Ala Val Glu Thr Ala Val Leu Thr Ser Tyr Val Leu Pro
            20                  25                  30

Thr Asp Pro Gly Gln Thr Thr Asp Ser Ile Gly Leu Arg Leu Leu Glu
        35                  40                  45

Val Leu Arg His Ala Gly Leu Gly Pro Ala Asp Val Gly Ala Cys Val
    50                  55                  60

Ala Ser Ser Val Val Pro Gly Val Asn Pro Leu Ile Arg Arg Ala Cys
65                  70                  75                  80

Glu Arg Tyr Leu Tyr Arg Lys Leu Leu Phe Ala Pro Gly Asp Ile Ala
                85                  90                  95

Ile Pro Leu Asp Asn Arg Tyr Glu Arg Pro Ala Glu Val Gly Ala Asp
            100                 105                 110

Arg Leu Val Ala Ala Tyr Ala Ala Arg Arg Leu Tyr Pro Gly Pro Arg
        115                 120                 125

Ser Leu Val Ser Val Asp Phe Gly Thr Ala Thr Thr Phe Asp Cys Val
    130                 135                 140
```

Glu Gly Gly Ala Tyr Leu Gly Leu Ile Cys Pro Gly Val Leu Ser
145                 150                 155                 160

Ser Ala Gly Ala Leu Ser Ser Arg Thr Ala Lys Leu Pro Arg Ile Ser
            165                 170                 175

Leu Glu Val Glu Glu Asp Ser Pro Val Ile Gly Arg Ser Thr Thr Thr
        180                 185                 190

Ser Leu Asn His Gly Phe Ile Phe Gly Phe Ala Ala Met Thr Glu Gly
            195                 200                 205

Val Leu Ala Ala
        210

<210> SEQ ID NO 12
<211> LENGTH: 246
<212> TYPE: PRT
<213> ORGANISM: Thermotoga maritima

<400> SEQUENCE: 12

Met Tyr Leu Leu Val Asp Val Gly Asn Thr His Ser Val Phe Ser Ile
 1               5                  10                  15

Thr Glu Asp Gly Lys Thr Phe Arg Arg Trp Arg Leu Ser Thr Gly Val
            20                  25                  30

Phe Gln Thr Glu Asp Glu Leu Phe Ser His Leu His Pro Leu Leu Gly
        35                  40                  45

Asp Ala Met Arg Glu Ile Lys Gly Ile Gly Val Ala Ser Val Val Pro
    50                  55                  60

Thr Gln Asn Thr Val Ile Glu Arg Phe Ser Gln Lys Tyr Phe His Ile
65                  70                  75                  80

Ser Pro Ile Trp Val Lys Ala Lys Asn Gly Cys Val Lys Trp Asn Val
                85                  90                  95

Lys Asn Pro Ser Glu Val Gly Ala Asp Arg Val Ala Asn Val Val Ala
            100                 105                 110

Phe Val Lys Glu Tyr Gly Lys Asn Gly Ile Ile Ile Asp Met Gly Thr
        115                 120                 125

Ala Thr Thr Val Asp Leu Val Val Asn Gly Ser Tyr Glu Gly Gly Ala
    130                 135                 140

Ile Leu Pro Gly Phe Phe Met Met Val His Ser Leu Phe Arg Gly Thr
145                 150                 155                 160

Ala Lys Leu Pro Leu Val Glu Val Lys Pro Ala Asp Phe Val Val Gly
                165                 170                 175

Lys Asp Thr Glu Glu Asn Ile Arg Leu Gly Val Val Asn Gly Ser Val
            180                 185                 190

Tyr Ala Leu Glu Gly Ile Ile Gly Arg Ile Lys Glu Val Tyr Gly Asp
        195                 200                 205

Leu Pro Val Val Leu Thr Gly Gly Gln Ser Lys Ile Val Lys Asp Met
    210                 215                 220

Ile Lys His Glu Ile Phe Asp Glu Asp Leu Thr Ile Lys Gly Val Tyr
225                 230                 235                 240

His Phe Cys Phe Gly Asp
                245

<210> SEQ ID NO 13
<211> LENGTH: 273
<212> TYPE: PRT
<213> ORGANISM: Treponema pallidum

<400> SEQUENCE: 13

```
Met Leu Leu Ile Asp Val Gly Asn Ser His Val Val Phe Gly Ile Gln
  1               5                  10                  15

Gly Glu Asn Gly Gly Arg Val Cys Val Arg Glu Leu Phe Arg Leu Ala
             20                  25                  30

Pro Asp Ala Arg Lys Thr Gln Asp Glu Tyr Ser Leu Leu Ile His Ala
         35                  40                  45

Leu Cys Glu Arg Ala Gly Val Gly Arg Ala Ser Leu Arg Asp Ala Phe
     50                  55                  60

Ile Ser Ser Val Val Pro Val Leu Thr Lys Thr Ile Ala Asp Ala Val
 65                  70                  75                  80

Ala Gln Ile Ser Gly Val Gln Pro Val Val Phe Gly Pro Trp Ala Tyr
                 85                  90                  95

Glu His Leu Pro Val Arg Ile Pro Glu Pro Val Arg Ala Glu Ile Gly
            100                 105                 110

Thr Asp Leu Val Ala Asn Ala Val Ala Ala Tyr Val His Phe Arg Ser
        115                 120                 125

Ala Cys Val Val Val Asp Cys Gly Thr Ala Leu Thr Phe Thr Ala Val
    130                 135                 140

Asp Gly Thr Gly Leu Ile Gln Gly Val Ala Ile Ala Pro Gly Leu Arg
145                 150                 155                 160

Thr Ala Val Gln Ser Leu His Thr Gly Thr Ala Gln Leu Pro Leu Val
                165                 170                 175

Pro Leu Ala Leu Pro Asp Ser Val Leu Gly Lys Asp Thr Thr His Ala
            180                 185                 190

Val Gln Ala Gly Val Val Arg Gly Thr Leu Phe Val Ile Arg Ala Met
        195                 200                 205

Ile Ala Gln Cys Gln Lys Glu Leu Gly Cys Arg Cys Ala Ala Val Ile
    210                 215                 220

Thr Gly Gly Leu Ser Arg Leu Phe Ser Ser Glu Val Asp Phe Pro Pro
225                 230                 235                 240

Ile Asp Ala Gln Leu Thr Leu Ser Gly Leu Ala His Ile Ala Arg Leu
                245                 250                 255

Val Pro Thr Ser Leu Leu Pro Pro Ala Thr Val Ser Gly Ser Ser Gly
            260                 265                 270

Asn

<210> SEQ ID NO 14
<211> LENGTH: 262
<212> TYPE: PRT
<213> ORGANISM: Borrelia burgdorferi

<400> SEQUENCE: 14

Met Asn Lys Pro Leu Leu Ser Glu Leu Ile Ile Asp Ile Gly Asn Thr
  1               5                  10                  15

Ser Ile Ala Phe Ala Leu Phe Lys Asp Asn Gln Val Asn Leu Phe Ile
             20                  25                  30

Lys Met Lys Thr Asn Leu Met Leu Arg Tyr Asp Glu Val Tyr Ser Phe
         35                  40                  45

Phe Glu Glu Asn Phe Asp Phe Asn Val Asn Lys Val Phe Ile Ser Ser
     50                  55                  60

Val Val Pro Ile Leu Asn Glu Thr Phe Lys Asn Val Ile Phe Ser Phe
 65                  70                  75                  80

Phe Lys Ile Lys Pro Leu Phe Ile Gly Phe Asp Leu Asn Tyr Asp Leu
                 85                  90                  95

Thr Phe Asn Pro Tyr Lys Ser Asp Lys Phe Leu Leu Gly Ser Asp Val
```

```
                     100                 105                 110
Phe Ala Asn Leu Val Ala Ala Ile Glu Asn Tyr Ser Phe Glu Asn Val
            115                 120                 125

Leu Val Val Asp Leu Gly Thr Ala Cys Thr Ile Phe Ala Val Ser Arg
130                 135                 140

Gln Asp Gly Ile Leu Gly Gly Ile Ile Asn Ser Gly Pro Leu Ile Asn
145                 150                 155                 160

Phe Asn Ser Leu Leu Asp Asn Ala Tyr Leu Ile Lys Lys Phe Pro Ile
            165                 170                 175

Ser Thr Pro Asn Asn Leu Leu Glu Arg Thr Thr Ser Gly Ser Val Asn
            180                 185                 190

Ser Gly Leu Phe Tyr Gln Tyr Lys Tyr Leu Ile Glu Gly Val Tyr Arg
            195                 200                 205

Asp Ile Lys Gln Met Tyr Lys Lys Phe Asn Leu Ile Ile Thr Gly
            210                 215                 220

Gly Asn Ala Asp Leu Ile Leu Ser Leu Ile Glu Ile Glu Phe Ile Phe
225                 230                 235                 240

Asn Ile His Leu Thr Val Glu Gly Val Arg Ile Leu Gly Asn Ser Ile
            245                 250                 255

Asp Phe Lys Phe Val Asn
            260

<210> SEQ ID NO 15
<211> LENGTH: 229
<212> TYPE: PRT
<213> ORGANISM: Aquifex aeolicus

<400> SEQUENCE: 15

Met Arg Phe Leu Thr Val Asp Val Gly Asn Ser Ser Val Asp Ile Ala
1               5                   10                  15

Leu Trp Glu Gly Lys Lys Val Lys Asp Phe Leu Lys Leu Ser His Glu
            20                  25                  30

Glu Phe Leu Lys Glu Glu Phe Pro Lys Leu Lys Ala Leu Gly Ile Ser
        35                  40                  45

Val Lys Gln Ser Phe Ser Glu Lys Val Arg Gly Lys Ile Pro Lys Ile
    50                  55                  60

Lys Phe Leu Lys Lys Glu Asn Phe Pro Ile Gln Val Asp Tyr Lys Thr
65              70                  75                  80

Pro Glu Thr Leu Gly Thr Asp Arg Val Ala Leu Ala Tyr Ser Ala Lys
            85                  90                  95

Lys Phe Tyr Gly Lys Asn Val Val Ile Ser Ala Gly Thr Ala Leu
            100                 105                 110

Val Ile Asp Leu Val Leu Glu Gly Lys Phe Lys Gly Phe Ile Thr
            115                 120                 125

Leu Gly Leu Gly Lys Lys Leu Lys Ile Leu Ser Asp Leu Ala Glu Gly
130                 135                 140

Ile Pro Glu Phe Phe Pro Glu Val Glu Ile Phe Leu Gly Arg Ser
145                 150                 155                 160

Thr Arg Glu Cys Val Leu Gly Gly Ala Tyr Arg Glu Ser Thr Glu Phe
            165                 170                 175

Ile Lys Ser Thr Leu Lys Leu Trp Arg Lys Val Phe Lys Arg Lys Phe
            180                 185                 190

Lys Val Val Ile Thr Gly Gly Glu Gly Lys Tyr Phe Ser Lys Phe Gly
            195                 200                 205

Ile Tyr Asp Pro Leu Leu Val His Arg Gly Met Arg Asn Leu Leu Tyr
```

```
                 210                 215                 220

Leu Tyr His Arg Ile
225

<210> SEQ ID NO 16
<211> LENGTH: 257
<212> TYPE: PRT
<213> ORGANISM: Synechocystis sp.

<400> SEQUENCE: 16

Met Glu Thr Ser Lys Pro Gly Cys Gly Leu Ala Leu Asp Asn Asp Lys
  1               5                  10                  15

Gln Lys Pro Trp Leu Gly Leu Met Ile Gly Asn Ser Arg Leu His Trp
             20                  25                  30

Ala Tyr Cys Ser Gly Asn Ala Pro Leu Gln Thr Trp Val Thr Asp Tyr
         35                  40                  45

Asn Pro Lys Ser Ala Gln Leu Pro Val Leu Gly Lys Val Pro Leu
     50                  55                  60

Met Leu Ala Ser Val Val Pro Glu Gln Thr Glu Val Trp Arg Val Tyr
 65                  70                  75                  80

Gln Pro Lys Ile Leu Thr Leu Lys Asn Leu Pro Val Asn Leu Tyr
             85                  90                  95

Pro Ser Phe Gly Ile Asp Arg Ala Leu Ala Gly Leu Gly Thr Gly Leu
            100                 105                 110

Thr Tyr Gly Phe Pro Cys Leu Val Val Asp Gly Gly Thr Ala Leu Thr
            115                 120                 125

Ile Thr Gly Phe Asp Gln Asp Lys Lys Leu Val Gly Gly Ala Ile Leu
        130                 135                 140

Pro Gly Leu Gly Leu Gln Leu Ala Thr Leu Gly Asp Arg Leu Ala Ala
145                 150                 155                 160

Leu Pro Lys Leu Glu Met Asp Gln Leu Thr Glu Leu Pro Asp Arg Trp
                165                 170                 175

Ala Leu Asp Thr Pro Ser Ala Ile Phe Ser Gly Val Val Tyr Gly Val
            180                 185                 190

Leu Gly Ala Leu Gln Ser Tyr Leu Gln Asp Trp Gln Lys Leu Phe Pro
        195                 200                 205

Gly Ala Ala Met Val Ile Thr Gly Gly Asp Gly Lys Ile Leu His Gly
    210                 215                 220

Phe Leu Lys Glu His Ser Pro Asn Leu Ser Val Ala Trp Asp Asp Asn
225                 230                 235                 240

Leu Ile Phe Leu Gly Met Ala Ala Ile His His Gly Asp Arg Pro Ile
                245                 250                 255

Cys

<210> SEQ ID NO 17
<211> LENGTH: 223
<212> TYPE: PRT
<213> ORGANISM: Helicobacter pylori

<400> SEQUENCE: 17

Met Pro Ala Arg Gln Ser Phe Thr Asp Leu Lys Asn Leu Val Leu Cys
  1               5                  10                  15

Asp Ile Gly Asn Thr Arg Ile His Phe Ala Gln Asn Tyr Gln Leu Phe
             20                  25                  30

Ser Ser Ala Lys Glu Asp Leu Lys Arg Leu Gly Ile Gln Lys Glu Ile
         35                  40                  45
```

```
Phe Tyr Ile Ser Val Asn Glu Glu Asn Glu Lys Ala Leu Leu Asn Cys
 50                  55                  60

Tyr Pro Asn Ala Lys Asn Ile Ala Gly Phe His Leu Glu Thr Asp
 65                  70                  75                  80

Tyr Val Gly Leu Gly Ile Asp Arg Gln Met Ala Cys Leu Ala Val Asn
                 85                  90                  95

Asn Gly Val Val Val Asp Ala Gly Ser Ala Ile Thr Ile Asp Leu Ile
                100                 105                 110

Lys Glu Gly Lys His Leu Gly Gly Cys Ile Leu Pro Gly Leu Ala Gln
                115                 120                 125

Tyr Ile His Ala Tyr Lys Lys Ser Ala Lys Ile Leu Glu Gln Pro Phe
130                 135                 140

Lys Ala Leu Asp Ser Leu Glu Val Leu Pro Lys Ser Thr Arg Asp Ala
145                 150                 155                 160

Val Asn Tyr Gly Met Val Leu Ser Val Ile Ala Cys Ile Gln His Leu
                165                 170                 175

Ala Lys Asn Gln Lys Ile Tyr Leu Cys Gly Gly Asp Ala Lys Tyr Leu
                180                 185                 190

Ser Ala Phe Leu Pro His Ser Val Cys Lys Glu Arg Leu Val Phe Asp
195                 200                 205

Gly Met Glu Ile Ala Leu Lys Lys Ala Gly Ile Leu Glu Cys Lys
210                 215                 220

<210> SEQ ID NO 18
<211> LENGTH: 267
<212> TYPE: PRT
<213> ORGANISM: Bordetella pertussis

<400> SEQUENCE: 18

Met Ile Ile Leu Ile Asp Ser Gly Asn Ser Arg Leu Lys Val Gly Trp
 1               5                  10                  15

Phe Asp Pro Asp Ala Pro Gln Ala Ala Arg Glu Pro Ala Pro Val Ala
                20                  25                  30

Phe Asp Asn Leu Asp Leu Asp Ala Leu Gly Arg Trp Leu Ala Thr Leu
             35                  40                  45

Pro Arg Arg Pro Gln Arg Ala Leu Gly Val Asn Val Ala Gly Leu Ala
 50                  55                  60

Arg Gly Glu Ala Ile Ala Ala Thr Leu Arg Ala Gly Gly Cys Asp Ile
 65                  70                  75                  80

Arg Trp Leu Arg Ala Gln Pro Leu Ala Met Gly Leu Arg Asn Gly Tyr
                 85                  90                  95

Arg Asn Pro Asp Gln Leu Gly Ala Asp Arg Trp Ala Cys Met Val Gly
                100                 105                 110

Val Leu Ala Arg Gln Pro Ser Val His Pro Leu Leu Val Ala Ser
                115                 120                 125

Phe Gly Thr Ala Thr Thr Leu Asp Thr Ile Gly Pro Asp Asn Val Phe
130                 135                 140

Pro Gly Gly Leu Ile Leu Pro Gly Pro Ala Met Met Arg Gly Ala Leu
145                 150                 155                 160

Ala Tyr Gly Thr Ala His Leu Pro Leu Ala Asp Gly Leu Val Ala Asp
                165                 170                 175

Tyr Pro Ile Asp Thr His Gln Ala Ile Ala Ser Gly Ile Ala Ala Ala
                180                 185                 190

Gln Ala Gly Ala Ile Val Arg Gln Trp Leu Ala Gly Arg Gln Arg Tyr
195                 200                 205
```

```
Gly Gln Ala Pro Glu Ile Tyr Val Ala Gly Gly Trp Pro Glu Val
    210                 215                 220

Arg Gln Glu Ala Glu Arg Leu Leu Ala Val Thr Gly Ala Ala Phe Gly
225                 230                 235                 240

Ala Thr Pro Gln Pro Thr Tyr Leu Asp Ser Pro Val Leu Asp Gly Leu
                245                 250                 255

Ala Ala Leu Ala Ala Gln Gly Ala Pro Thr Ala
            260                 265

<210> SEQ ID NO 19
<211> LENGTH: 777
<212> TYPE: DNA
<213> ORGANISM: Bacillus subtilis
<220> FEATURE:
<221> NAME/KEY: CDS
<222> LOCATION: (1)..(774)

<400> SEQUENCE: 19 ttg tta ctg gtt atc gat gtg ggg aac acc aat act gta ctt ggt gta      48
Leu Leu Leu Val Ile Asp Val Gly Asn Thr Asn Thr Val Leu Gly Val
 1               5                  10                  15 tat cat gat gga aaa tta gaa tat cac tgg cgt ata gaa aca agc agg      96
Tyr His Asp Gly Lys Leu Glu Tyr His Trp Arg Ile Glu Thr Ser Arg
                20                  25                  30 cat aaa aca gaa gat gag ttt ggg atg att ttg cgc tcc tta ttt gat     144
His Lys Thr Glu Asp Glu Phe Gly Met Ile Leu Arg Ser Leu Phe Asp
            35                  40                  45 cac tcc ggg ctt atg ttt gaa cag ata gat ggc att att att tcg tca     192
His Ser Gly Leu Met Phe Glu Gln Ile Asp Gly Ile Ile Ile Ser Ser
        50                  55                  60 gta gtg ccg cca atc atg ttt gcg tta gaa aga atg tgc aca aaa tac     240
Val Val Pro Pro Ile Met Phe Ala Leu Glu Arg Met Cys Thr Lys Tyr
 65                 70                  75                  80 ttt cat atc gag cct caa att gtt ggt cca ggt atg aaa acc ggt tta     288
Phe His Ile Glu Pro Gln Ile Val Gly Pro Gly Met Lys Thr Gly Leu
                85                  90                  95 aat ata aaa tat gac aat ccg aaa gaa gta ggg gca gac aga atc gta     336
Asn Ile Lys Tyr Asp Asn Pro Lys Glu Val Gly Ala Asp Arg Ile Val
            100                 105                 110 aat gct gtc gct gcg ata cac ttg tac ggc aat cca tta att gtt gtc     384
Asn Ala Val Ala Ala Ile His Leu Tyr Gly Asn Pro Leu Ile Val Val
        115                 120                 125 gat ttc gga acc gcc aca acg tac tgc tat att gat gaa aac aaa caa     432
Asp Phe Gly Thr Ala Thr Thr Tyr Cys Tyr Ile Asp Glu Asn Lys Gln
130                 135                 140 tac atg ggc ggg gcg att gcc cct ggg att aca att tcg aca gag gcg     480
Tyr Met Gly Gly Ala Ile Ala Pro Gly Ile Thr Ile Ser Thr Glu Ala
145                 150                 155                 160 ctt tac tcg cgt gca gca aag ctt cct cgt atc gaa atc acc cgg ccc     528
Leu Tyr Ser Arg Ala Ala Lys Leu Pro Arg Ile Glu Ile Thr Arg Pro
                165                 170                 175 gac aat att atc gga aaa aac act gtt agc gcg atg caa tct gga att     576
Asp Asn Ile Ile Gly Lys Asn Thr Val Ser Ala Met Gln Ser Gly Ile
            180                 185                 190 tta ttt ggc tat gtc ggc caa gtg gaa gga atc gtt aag cga atg aaa     624
Leu Phe Gly Tyr Val Gly Gln Val Glu Gly Ile Val Lys Arg Met Lys
        195                 200                 205 tgg cag gca aaa cag gac ctc aag gtc att gcg aca gga ggc ctg gcg     672
Trp Gln Ala Lys Gln Asp Leu Lys Val Ile Ala Thr Gly Gly Leu Ala
    210                 215                 220 ccg ctc att gcg aac gaa tca gat tgt ata gac atc gtt gat cca ttc     720
```

```
Pro Leu Ile Ala Asn Glu Ser Asp Cys Ile Asp Ile Val Asp Pro Phe
225                 230                 235                 240 tta acc cta aaa ggg ctg gaa ttg att tat gaa aga aac cgc gta gga      768
Leu Thr Leu Lys Gly Leu Glu Leu Ile Tyr Glu Arg Asn Arg Val Gly
                245                 250                 255 agt gta tag                                                          777
Ser Val <210> SEQ ID NO 20
<211> LENGTH: 960
<212> TYPE: DNA
<213> ORGANISM: Bacillus subtilis
<220> FEATURE:
<221> NAME/KEY: CDS
<222> LOCATION: (1)..(957)

<400> SEQUENCE: 20 gtg aaa aat aaa gaa ctt aac cta cat act tta tat aca cag cac aat       48
Met Lys Asn Lys Glu Leu Asn Leu His Thr Leu Tyr Thr Gln His Asn
 1               5                  10                  15 cgg gag tct tgg tct ggt ttt ggg ggg cat ttg tcg att gct gta tct       96
Arg Glu Ser Trp Ser Gly Phe Gly Gly His Leu Ser Ile Ala Val Ser
             20                  25                  30 gaa gaa gag gca aaa gct gtg gaa gga ttg aat gat tat cta tct gtt      144
Glu Glu Glu Ala Lys Ala Val Glu Gly Leu Asn Asp Tyr Leu Ser Val
         35                  40                  45 gaa gaa gtg gag acg atc tat att ccg ctt gtt cgc ttg ctt cat tta      192
Glu Glu Val Glu Thr Ile Tyr Ile Pro Leu Val Arg Leu Leu His Leu
     50                  55                  60 cat gtc aag tct gcg gct gaa cgc aat aag cat gtc aat gtt ttt ttg      240
His Val Lys Ser Ala Ala Glu Arg Asn Lys His Val Asn Val Phe Leu
 65                  70                  75                  80 aag cac cca cat tca gcc aaa att ccg ttt att atc ggc att gcc ggc      288
Lys His Pro His Ser Ala Lys Ile Pro Phe Ile Ile Gly Ile Ala Gly
                 85                  90                  95 agt gtc gca gtc gga aaa agc acg acg gcg cgg atc ttg cag aag ctg      336
Ser Val Ala Val Gly Lys Ser Thr Thr Ala Arg Ile Leu Gln Lys Leu
            100                 105                 110 ctt tcg cgt ttg cct gac cgt cca aaa gtg agc ctt atc acg aca gat      384
Leu Ser Arg Leu Pro Asp Arg Pro Lys Val Ser Leu Ile Thr Thr Asp
        115                 120                 125 ggt ttt tta ttt cct act gcc gag ctg aaa aag aaa aat atg atg tca      432
Gly Phe Leu Phe Pro Thr Ala Glu Leu Lys Lys Lys Asn Met Met Ser
    130                 135                 140 aga aaa gga ttt cct gaa agc tat gat gta aag gcg ctc ctc gaa ttt      480
Arg Lys Gly Phe Pro Glu Ser Tyr Asp Val Lys Ala Leu Leu Glu Phe
145                 150                 155                 160 ttg aat gac tta aaa tca gga aag gac agc gta aag gcc ccg gtg tat      528
Leu Asn Asp Leu Lys Ser Gly Lys Asp Ser Val Lys Ala Pro Val Tyr
                165                 170                 175 tcc cat cta acc tat gac cgc gag gaa ggt gtg ttc gag gtt gta gaa      576
Ser His Leu Thr Tyr Asp Arg Glu Glu Gly Val Phe Glu Val Val Glu
            180                 185                 190 cag gcg gat att gtg att att gaa ggc att aat gtt ctt cag tcg ccc      624
Gln Ala Asp Ile Val Ile Ile Glu Gly Ile Asn Val Leu Gln Ser Pro
        195                 200                 205 acc ttg gag gat gac cgg gaa aac ccg cgt att ttt gtt tcc gat ttc      672
Thr Leu Glu Asp Asp Arg Glu Asn Pro Arg Ile Phe Val Ser Asp Phe
    210                 215                 220 ttt gat ttt tcg att tat gtg gat gcg gag gaa agc cgg att ttc act      720
Phe Asp Phe Ser Ile Tyr Val Asp Ala Glu Glu Ser Arg Ile Phe Thr
225                 230                 235                 240
```

```
tgg tat tta gag cgt ttt cgc ctg ctt cgg gaa aca gct ttt caa aat      768
Trp Tyr Leu Glu Arg Phe Arg Leu Leu Arg Glu Thr Ala Phe Gln Asn
            245                 250                 255 cct gat tca tat ttt cat aaa ttt aaa gac ttg tcc gat cag gag gct      816
Pro Asp Ser Tyr Phe His Lys Phe Lys Asp Leu Ser Asp Gln Glu Ala
            260                 265                 270 gac gag atg gca gcc tcg att tgg gag agt gtc aac cgg ccg aat tta      864
Asp Glu Met Ala Ala Ser Ile Trp Glu Ser Val Asn Arg Pro Asn Leu
        275                 280                 285 tat gaa aat att ttg cca act aaa ttc agg tca gat ctc att ttg cgt      912
Tyr Glu Asn Ile Leu Pro Thr Lys Phe Arg Ser Asp Leu Ile Leu Arg
        290                 295                 300 aag gga gac ggg cat aag gtc gag gaa gtg ttg gta agg agg gta tga      960
Lys Gly Asp Gly His Lys Val Glu Glu Val Leu Val Arg Arg Val
305                 310                 315

<210> SEQ ID NO 21
<211> LENGTH: 882
<212> TYPE: DNA
<213> ORGANISM: Bacillus subtilis
<220> FEATURE:
<221> NAME/KEY: CDS
<222> LOCATION: (1)..(879)

<400> SEQUENCE: 21 ttg tcg att gct gta tct gaa gag gag gca aaa gct gtg gaa gga ttg       48
Met Ser Ile Ala Val Ser Glu Glu Glu Ala Lys Ala Val Glu Gly Leu
1               5                   10                  15 aat gat tat cta tct gtt gaa gaa gtg gag acg atc tat att ccg ctt       96
Asn Asp Tyr Leu Ser Val Glu Glu Val Glu Thr Ile Tyr Ile Pro Leu
            20                  25                  30 gtt cgc ttg ctt cat tta cat gtc aag tct gcg gct gaa cgc aat aag      144
Val Arg Leu Leu His Leu His Val Lys Ser Ala Ala Glu Arg Asn Lys
        35                  40                  45 cat gtc aat gtt ttt ttg aag cac cca cat tca gcc aaa att ccg ttt      192
His Val Asn Val Phe Leu Lys His Pro His Ser Ala Lys Ile Pro Phe
    50                  55                  60 att atc ggc att gcc ggc agt gtc gca gtc gga aaa agc acg acg gcg      240
Ile Ile Gly Ile Ala Gly Ser Val Ala Val Gly Lys Ser Thr Thr Ala
65                  70                  75                  80 cgg atc ttg cag aag ctg ctt tcg cgt ttg cct gac cgt cca aaa gtg      288
Arg Ile Leu Gln Lys Leu Leu Ser Arg Leu Pro Asp Arg Pro Lys Val
                85                  90                  95 agc ctt atc acg aca gat ggt ttt tta ttt cct act gcc gag ctg aaa      336
Ser Leu Ile Thr Thr Asp Gly Phe Leu Phe Pro Thr Ala Glu Leu Lys
            100                 105                 110 aag aaa aat atg atg tca aga aaa gga ttt cct gaa agc tat gat gta      384
Lys Lys Asn Met Met Ser Arg Lys Gly Phe Pro Glu Ser Tyr Asp Val
        115                 120                 125 aag gcg ctg ctc gaa ttt ttg aat gac tta aaa tca gga aag gac agc      432
Lys Ala Leu Leu Glu Phe Leu Asn Asp Leu Lys Ser Gly Lys Asp Ser
    130                 135                 140 gta aag gcc ccg gtg tat tcc cat cta acc tat gac cgc gag gaa ggt      480
Val Lys Ala Pro Val Tyr Ser His Leu Thr Tyr Asp Arg Glu Glu Gly
145                 150                 155                 160 gtg ttc gag gtt gta gaa cag gcg gat att gtg att att gaa ggc att      528
Val Phe Glu Val Val Glu Gln Ala Asp Ile Val Ile Ile Glu Gly Ile
                165                 170                 175 aat gtt ctt cag tcg ccc acc ttg gag gat gac cgg gaa aac ccg cgt      576
Asn Val Leu Gln Ser Pro Thr Leu Glu Asp Asp Arg Glu Asn Pro Arg
            180                 185                 190
```

```
att ttt gtt tcc gat ttc ttt gat ttt tcg att tat gtg gat gcg gag     624
Ile Phe Val Ser Asp Phe Phe Asp Phe Ser Ile Tyr Val Asp Ala Glu
        195                 200                 205 gaa agc cgg att ttc act tgg tat tta gag cgt ttt cgc ctg ctt cgg     672
Glu Ser Arg Ile Phe Thr Trp Tyr Leu Glu Arg Phe Arg Leu Leu Arg
    210                 215                 220 gaa aca gct ttt caa aat cct gat tca tat ttt cat aaa ttt aaa gac     720
Glu Thr Ala Phe Gln Asn Pro Asp Ser Tyr Phe His Lys Phe Lys Asp
225                 230                 235                 240 ttg tcc gat cag gag gct gac gag atg gca gcc tcg att tgg gag agt     768
Leu Ser Asp Gln Glu Ala Asp Glu Met Ala Ala Ser Ile Trp Glu Ser
            245                 250                 255 gtc aac cgg ccg aat tta tat gaa aat att ttg cca act aaa ttc agg     816
Val Asn Arg Pro Asn Leu Tyr Glu Asn Ile Leu Pro Thr Lys Phe Arg
        260                 265                 270 tca gat ctc att ttg cgt aag gga gac ggg cat aag gtc gag gaa gtg     864
Ser Asp Leu Ile Leu Arg Lys Gly Asp Gly His Lys Val Glu Glu Val
    275                 280                 285 ttg gta agg agg gta tga                                              882
Leu Val Arg Arg Val
        290
```

<210> SEQ ID NO 22
<211> LENGTH: 846
<212> TYPE: DNA
<213> ORGANISM: Bacillus subtilis
<220> FEATURE:
<221> NAME/KEY: CDS
<222> LOCATION: (1)..(843)

<400> SEQUENCE: 22

```
gtg gaa gga ttg aat gat tat cta tct gtt gaa gaa gtg gag acg atc      48
Met Glu Gly Leu Asn Asp Tyr Leu Ser Val Glu Glu Val Glu Thr Ile
  1               5                  10                  15 tat att ccg ctt gtt cgc ttg ctt cat tta cat gtc aag tct gcg gct      96
Tyr Ile Pro Leu Val Arg Leu Leu His Leu His Val Lys Ser Ala Ala
                 20                  25                  30 gaa cgc aat aag cat gtc aat gtt ttt ttg aag cac cca cat tca gcc     144
Glu Arg Asn Lys His Val Asn Val Phe Leu Lys His Pro His Ser Ala
             35                  40                  45 aaa att ccg ttt att atc ggc att gcc ggc agt gtc gca gtc gga aaa     192
Lys Ile Pro Phe Ile Ile Gly Ile Ala Gly Ser Val Ala Val Gly Lys
         50                  55                  60 agc acg acg gcg cgg atc ttg cag aag ctg ctt tcg cgt ttg cct gac     240
Ser Thr Thr Ala Arg Ile Leu Gln Lys Leu Leu Ser Arg Leu Pro Asp
 65                  70                  75                  80 cgt cca aaa gtg agc ctt atc acg aca gat ggt ttt tta ttt cct act     288
Arg Pro Lys Val Ser Leu Ile Thr Thr Asp Gly Phe Leu Phe Pro Thr
                 85                  90                  95 gcc gag ctg aaa aag aaa aat atg atg tca aga aaa gga ttt cct gaa     336
Ala Glu Leu Lys Lys Lys Asn Met Met Ser Arg Lys Gly Phe Pro Glu
            100                 105                 110 agc tat gat gta aag gcg ctg ctc gaa ttt ttg aat gac tta aaa tca     384
Ser Tyr Asp Val Lys Ala Leu Leu Glu Phe Leu Asn Asp Leu Lys Ser
        115                 120                 125 gga aag gac agc gta aag gcc ccg gtg tat tcc cat cta acc tat gac     432
Gly Lys Asp Ser Val Lys Ala Pro Val Tyr Ser His Leu Thr Tyr Asp
    130                 135                 140 cgc gag gaa ggt gtg ttc gag gtt gta gaa cag gcg gat att gtg att     480
Arg Glu Glu Gly Val Phe Glu Val Val Glu Gln Ala Asp Ile Val Ile
145                 150                 155                 160 att gaa ggc att aat gtt ctt cag tcg ccc acc ttg gag gat gac cgg     528
```

```
Ile Glu Gly Ile Asn Val Leu Gln Ser Pro Thr Leu Glu Asp Asp Arg
              165                 170                 175 gaa aac ccg cgt att ttt gtt tcc gat ttc ttt gat ttc tcg att tat       576
Glu Asn Pro Arg Ile Phe Val Ser Asp Phe Phe Asp Phe Ser Ile Tyr
            180                 185                 190 gtg gat gcg gag gaa agc cgg att ttc act tgg tat tta gag cgt ttt       624
Val Asp Ala Glu Glu Ser Arg Ile Phe Thr Trp Tyr Leu Glu Arg Phe
        195                 200                 205 cgc ctg ctt cgg gaa aca gct ttt caa aat cct gat tca tat ttt cat       672
Arg Leu Leu Arg Glu Thr Ala Phe Gln Asn Pro Asp Ser Tyr Phe His
    210                 215                 220 aaa ttt aaa gac ttg tcc gat cag gag gct gac gag atg gca gcc tcg       720
Lys Phe Lys Asp Leu Ser Asp Gln Glu Ala Asp Glu Met Ala Ala Ser
225                 230                 235                 240 att tgg gag agt gtc aac cgg ccg aat tta tat gaa aat att ttg cca       768
Ile Trp Glu Ser Val Asn Arg Pro Asn Leu Tyr Glu Asn Ile Leu Pro
                245                 250                 255 act aaa ttc agg tca gat ctc att ttg cgt aag gga gac ggg cat aag       816
Thr Lys Phe Arg Ser Asp Leu Ile Leu Arg Lys Gly Asp Gly His Lys
            260                 265                 270 gtc gag gaa gtg ttg gta agg agg gta tga                               846
Val Glu Glu Val Leu Val Arg Arg Val
        275                 280

<210> SEQ ID NO 23
<211> LENGTH: 831
<212> TYPE: DNA
<213> ORGANISM: Bacillus subtilis
<220> FEATURE:
<221> NAME/KEY: CDS
<222> LOCATION: (1)..(831)

<400> SEQUENCE: 23 atg aca aca aaa ctg gat ttt cta aaa atg aag gag tct gaa gaa ccg        48
Met Lys Thr Lys Leu Asp Phe Leu Lys Met Lys Glu Ser Glu Glu Pro
1               5                   10                  15 att gtc atg ctg acc gct tat gat tat ccg gca gct aaa ctt gct gaa        96
Ile Val Met Leu Thr Ala Tyr Asp Tyr Pro Ala Ala Lys Leu Ala Glu
            20                  25                  30 caa gcg gga gtt gac atg att tta gtc ggt gat tca ctt gga atg gtc       144
Gln Ala Gly Val Asp Met Ile Leu Val Gly Asp Ser Leu Gly Met Val
        35                  40                  45 gtc ctc ggc ctt gat tca act gtc ggt gtg aca gtt gcg gac atg atc       192
Val Leu Gly Leu Asp Ser Thr Val Gly Val Thr Val Ala Asp Met Ile
    50                  55                  60 cat cat aca aaa gcc gtt aaa agg ggt gcg ccg aat acc ttt att gtg       240
His His Thr Lys Ala Val Lys Arg Gly Ala Pro Asn Thr Phe Ile Val
65                  70                  75                  80 aca gat atg ccg ttt atg tct tat cac ctg tct aag gaa gat acg ctg       288
Thr Asp Met Pro Phe Met Ser Tyr His Leu Ser Lys Glu Asp Thr Leu
                85                  90                  95 aaa aat gca gcg gct atc gtt cag gaa agc gga gct gac gca ctg aag       336
Lys Asn Ala Ala Ala Ile Val Gln Glu Ser Gly Ala Asp Ala Leu Lys
            100                 105                 110 ctt gag ggc gga gaa ggc gtg ttt gaa tcc att cgc gca ttg acg ctt       384
Leu Glu Gly Gly Glu Gly Val Phe Glu Ser Ile Arg Ala Leu Thr Leu
        115                 120                 125 gga ggc att cca gta gtc agt cac tta ggt ttg aca ccg cag tca gtc       432
Gly Gly Ile Pro Val Val Ser His Leu Gly Leu Thr Pro Gln Ser Val
    130                 135                 140 ggc gta ctg ggc ggc tat aaa gta cag ggc aaa gac gaa caa agc gcc       480
Gly Val Leu Gly Gly Tyr Lys Val Gln Gly Lys Asp Glu Gln Ser Ala
```

```
                145                 150                 155                 160
aaa aaa tta ata gaa gac agt ata aaa tgc gaa gaa gca gga gct atg              528
Lys Lys Leu Ile Glu Asp Ser Ile Lys Cys Glu Glu Ala Gly Ala Met
                    165                 170                 175 atg ctt gtg ctg gaa tgt gtg ccg gca gaa ctc aca gcc aaa att gcc              576
Met Leu Val Leu Glu Cys Val Pro Ala Glu Leu Thr Ala Lys Ile Ala
                180                 185                 190 gag acg cta agc ata ccg gtc att gga atc ggg gct ggt gtg aaa gcg              624
Glu Thr Leu Ser Ile Pro Val Ile Gly Ile Gly Ala Gly Val Lys Ala
            195                 200                 205 gac gga caa gtt ctc gtt tat cat gat att atc ggc cac ggt gtt gag              672
Asp Gly Gln Val Leu Val Tyr His Asp Ile Ile Gly His Gly Val Glu
        210                 215                 220 aga aca cct aaa ttt gta aag caa tat acg cgc att gat gaa acc atc              720
Arg Thr Pro Lys Phe Val Lys Gln Tyr Thr Arg Ile Asp Glu Thr Ile
225                 230                 235                 240 gaa aca gca atc agc gga tat gtt cag gat gta aga cat cgt gct ttc              768
Glu Thr Ala Ile Ser Gly Tyr Val Gln Asp Val Arg His Arg Ala Phe
                245                 250                 255 cct gaa caa aag cat tcc ttt caa atg aac cag aca gtg ctt gac ggc              816
Pro Glu Gln Lys His Ser Phe Gln Met Asn Gln Thr Val Leu Asp Gly
            260                 265                 270 ttg tac ggg gga aaa                                                          831
Leu Tyr Gly Gly Lys
        275

<210> SEQ ID NO 24
<211> LENGTH: 277
<212> TYPE: PRT
<213> ORGANISM: Bacillus subtilis

<400> SEQUENCE: 24

Met Lys Thr Lys Leu Asp Phe Leu Lys Met Lys Glu Ser Glu Glu Pro
 1               5                  10                  15

Ile Val Met Leu Thr Ala Tyr Asp Tyr Pro Ala Ala Lys Leu Ala Glu
            20                  25                  30

Gln Ala Gly Val Asp Met Ile Leu Val Gly Asp Ser Leu Gly Met Val
        35                  40                  45

Val Leu Gly Leu Asp Ser Thr Val Gly Val Thr Val Ala Asp Met Ile
    50                  55                  60

His His Thr Lys Ala Val Lys Arg Gly Ala Pro Asn Thr Phe Ile Val
65                  70                  75                  80

Thr Asp Met Pro Phe Met Ser Tyr His Leu Ser Lys Glu Asp Thr Leu
                85                  90                  95

Lys Asn Ala Ala Ala Ile Val Gln Glu Ser Gly Ala Asp Ala Leu Lys
            100                 105                 110

Leu Glu Gly Gly Glu Gly Val Phe Glu Ser Ile Arg Ala Leu Thr Leu
        115                 120                 125

Gly Gly Ile Pro Val Val Ser His Leu Gly Leu Thr Pro Gln Ser Val
    130                 135                 140

Gly Val Leu Gly Gly Tyr Lys Val Gln Gly Lys Asp Glu Gln Ser Ala
145                 150                 155                 160

Lys Lys Leu Ile Glu Asp Ser Ile Lys Cys Glu Glu Ala Gly Ala Met
                165                 170                 175

Met Leu Val Leu Glu Cys Val Pro Ala Glu Leu Thr Ala Lys Ile Ala
            180                 185                 190

Glu Thr Leu Ser Ile Pro Val Ile Gly Ile Gly Ala Gly Val Lys Ala
        195                 200                 205
```

```
Asp Gly Gln Val Leu Val Tyr His Asp Ile Ile Gly His Gly Val Glu
    210                 215                 220

Arg Thr Pro Lys Phe Val Lys Gln Tyr Thr Arg Ile Asp Glu Thr Ile
225                 230                 235                 240

Glu Thr Ala Ile Ser Gly Tyr Val Gln Asp Val Arg His Arg Ala Phe
                245                 250                 255

Pro Glu Gln Lys His Ser Phe Gln Met Asn Gln Thr Val Leu Asp Gly
            260                 265                 270

Leu Tyr Gly Gly Lys
        275

<210> SEQ ID NO 25
<211> LENGTH: 858
<212> TYPE: DNA
<213> ORGANISM: Bacillus subtilis
<220> FEATURE:
<221> NAME/KEY: CDS
<222> LOCATION: (1)..(858)

<400> SEQUENCE: 25
```

| | | |
|---|---|---|
| atg aga cag att act gat att tca cag ctg aaa gaa gcc ata aaa caa<br>Met Arg Gln Ile Thr Asp Ile Ser Gln Leu Lys Glu Ala Ile Lys Gln<br>1               5                   10                  15 | | 48 |
| tac cat tca gag ggc aag tca atc gga ttt gtt ccg acg atg ggg ttt<br>Tyr His Ser Glu Gly Lys Ser Ile Gly Phe Val Pro Thr Met Gly Phe<br>            20                  25                  30 | | 96 |
| ctg cat gag ggg cat tta acc tta gca gac aaa gca aga caa gaa aac<br>Leu His Glu Gly His Leu Thr Leu Ala Asp Lys Ala Arg Gln Glu Asn<br>        35                  40                  45 | | 144 |
| gac gcc gtt att atg agt att ttt gtg aat cct gca caa ttc ggc cct<br>Asp Ala Val Ile Met Ser Ile Phe Val Asn Pro Ala Gln Phe Gly Pro<br>    50                  55                  60 | | 192 |
| aat gaa gat ttt gaa gca tat ccg cgc gat att gag cgg gat gca gct<br>Asn Glu Asp Phe Glu Ala Tyr Pro Arg Asp Ile Glu Arg Asp Ala Ala<br>65                  70                  75                  80 | | 240 |
| ctt gca gaa aac gcc gga gtc gat att ctt ttt acg cca gat gct cat<br>Leu Ala Glu Asn Ala Gly Val Asp Ile Leu Phe Thr Pro Asp Ala His<br>                85                  90                  95 | | 288 |
| gat atg tat ccc ggt gaa aag aat gtc acg att cat gta gaa aga cgc<br>Asp Met Tyr Pro Gly Glu Lys Asn Val Thr Ile His Val Glu Arg Arg<br>            100                 105                 110 | | 336 |
| aca gac gtg tta tgc ggg cgc tca aga gaa gga cat ttt gac ggg gtc<br>Thr Asp Val Leu Cys Gly Arg Ser Arg Glu Gly His Phe Asp Gly Val<br>        115                 120                 125 | | 384 |
| gcg atc gta ctg acg aag ctt ttc aat cta gtc aag ccg act cgt gcc<br>Ala Ile Val Leu Thr Lys Leu Phe Asn Leu Val Lys Pro Thr Arg Ala<br>    130                 135                 140 | | 432 |
| tat ttc ggt tta aaa gat gcg cag cag gta gct gtt gtt gat ggg tta<br>Tyr Phe Gly Leu Lys Asp Ala Gln Gln Val Ala Val Val Asp Gly Leu<br>145                 150                 155                 160 | | 480 |
| atc agc gac ttc ttc atg gat att gaa ttg gtt cct gtc gat acg gtc<br>Ile Ser Asp Phe Phe Met Asp Ile Glu Leu Val Pro Val Asp Thr Val<br>                165                 170                 175 | | 528 |
| aga gag gaa gac ggc tta gcc aaa agc tct cgc aat gta tac tta aca<br>Arg Glu Glu Asp Gly Leu Ala Lys Ser Ser Arg Asn Val Tyr Leu Thr<br>            180                 185                 190 | | 576 |
| gct gag gaa aga aaa gaa gcg cct aag ctg tat cgg gcc ctt caa aca<br>Ala Glu Glu Arg Lys Glu Ala Pro Lys Leu Tyr Arg Ala Leu Gln Thr<br>        195                 200                 205 | | 624 |
| agt gcg gaa ctt gtc caa gcc ggt gaa aga gat cct gaa gcg gtg ata<br> | | 672 |

```
Ser Ala Glu Leu Val Gln Ala Gly Glu Arg Asp Pro Glu Ala Val Ile
    210                 215                 220 aaa gct gca aaa gat atc att gaa acg act agc gga acc ata gac tat      720
Lys Ala Ala Lys Asp Ile Ile Glu Thr Thr Ser Gly Thr Ile Asp Tyr
225                 230                 235                 240 gta gag ctt tat tcc tat ccg gaa ctc gag cct gtg aat gaa att gct      768
Val Glu Leu Tyr Ser Tyr Pro Glu Leu Glu Pro Val Asn Glu Ile Ala
                245                 250                 255 gga aag atg att ctc gct gtt gca gtt gct ttt tca aaa gcg cgt tta      816
Gly Lys Met Ile Leu Ala Val Ala Val Ala Phe Ser Lys Ala Arg Leu
            260                 265                 270 ata gat aat atc att att gat att cga gaa atg gag aga ata              858
Ile Asp Asn Ile Ile Ile Asp Ile Arg Glu Met Glu Arg Ile
        275                 280                 285
```

<210> SEQ ID NO 26
<211> LENGTH: 286
<212> TYPE: PRT
<213> ORGANISM: Bacillus subtilis

<400> SEQUENCE: 26

```
Met Arg Gln Ile Thr Asp Ile Ser Gln Leu Lys Glu Ala Ile Lys Gln
1               5                   10                  15

Tyr His Ser Glu Gly Lys Ser Ile Gly Phe Val Pro Thr Met Gly Phe
                20                  25                  30

Leu His Glu Gly His Leu Thr Leu Ala Asp Lys Ala Arg Gln Glu Asn
            35                  40                  45

Asp Ala Val Ile Met Ser Ile Phe Val Asn Pro Ala Gln Phe Gly Pro
        50                  55                  60

Asn Glu Asp Phe Glu Ala Tyr Pro Arg Asp Ile Glu Arg Asp Ala Ala
65                  70                  75                  80

Leu Ala Glu Asn Ala Gly Val Asp Ile Leu Phe Thr Pro Asp Ala His
                85                  90                  95

Asp Met Tyr Pro Gly Glu Lys Asn Val Thr Ile His Val Glu Arg Arg
            100                 105                 110

Thr Asp Val Leu Cys Gly Arg Ser Arg Glu Gly His Phe Asp Gly Val
        115                 120                 125

Ala Ile Val Leu Thr Lys Leu Phe Asn Leu Val Lys Pro Thr Arg Ala
130                 135                 140

Tyr Phe Gly Leu Lys Asp Ala Gln Gln Val Ala Val Val Asp Gly Leu
145                 150                 155                 160

Ile Ser Asp Phe Phe Met Asp Ile Glu Leu Val Pro Val Asp Thr Val
                165                 170                 175

Arg Glu Glu Asp Gly Leu Ala Lys Ser Ser Arg Asn Val Tyr Leu Thr
            180                 185                 190

Ala Glu Glu Arg Lys Glu Ala Pro Lys Leu Tyr Arg Ala Leu Gln Thr
        195                 200                 205

Ser Ala Glu Leu Val Gln Ala Gly Glu Arg Asp Pro Glu Ala Val Ile
210                 215                 220

Lys Ala Ala Lys Asp Ile Ile Glu Thr Thr Ser Gly Thr Ile Asp Tyr
225                 230                 235                 240

Val Glu Leu Tyr Ser Tyr Pro Glu Leu Glu Pro Val Asn Glu Ile Ala
                245                 250                 255

Gly Lys Met Ile Leu Ala Val Ala Val Ala Phe Ser Lys Ala Arg Leu
            260                 265                 270

Ile Asp Asn Ile Ile Ile Asp Ile Arg Glu Met Glu Arg Ile
        275                 280                 285
```

<210> SEQ ID NO 27
<211> LENGTH: 381
<212> TYPE: DNA
<213> ORGANISM: Bacillus subtilis
<220> FEATURE:
<221> NAME/KEY: CDS
<222> LOCATION: (1)..(381)

<400> SEQUENCE: 27

```
atg tat cga aca atg atg agc ggc aaa ctt cac agg gca act gtt acg      48
Met Tyr Arg Thr Met Met Ser Gly Lys Leu His Arg Ala Thr Val Thr
 1               5                  10                  15 gaa gca aac ctg aac tat gtg gga agc att aca att gat gaa gat ctc      96
Glu Ala Asn Leu Asn Tyr Val Gly Ser Ile Thr Ile Asp Glu Asp Leu
             20                  25                  30 att gat gct gtg gga atg ctt cct aat gaa aaa gta caa att gtg aat     144
Ile Asp Ala Val Gly Met Leu Pro Asn Glu Lys Val Gln Ile Val Asn
         35                  40                  45 aat aat aat gga gca cgt ctt gaa acg tat att att cct ggt aaa cgg     192
Asn Asn Asn Gly Ala Arg Leu Glu Thr Tyr Ile Ile Pro Gly Lys Arg
     50                  55                  60 gga agc ggc gtc ata tgc tta aac ggt gca gcc gca cgc ctt gtg cag     240
Gly Ser Gly Val Ile Cys Leu Asn Gly Ala Ala Ala Arg Leu Val Gln
 65                  70                  75                  80 gaa gga gat aag gtc att att att tcc tac aaa atg atg tct gat caa     288
Glu Gly Asp Lys Val Ile Ile Ile Ser Tyr Lys Met Met Ser Asp Gln
                 85                  90                  95 gaa gcg gca agc cat gag ccg aaa gtg gct gtt ctg aat gat caa aac     336
Glu Ala Ala Ser His Glu Pro Lys Val Ala Val Leu Asn Asp Gln Asn
            100                 105                 110 aaa att gaa caa atg ctg ggg aac gaa cca gcc cgt aca att ttg         381
Lys Ile Glu Gln Met Leu Gly Asn Glu Pro Ala Arg Thr Ile Leu
        115                 120                 125
```

<210> SEQ ID NO 28
<211> LENGTH: 127
<212> TYPE: PRT
<213> ORGANISM: Bacillus subtilis

<400> SEQUENCE: 28

```
Met Tyr Arg Thr Met Met Ser Gly Lys Leu His Arg Ala Thr Val Thr
 1               5                  10                  15

Glu Ala Asn Leu Asn Tyr Val Gly Ser Ile Thr Ile Asp Glu Asp Leu
             20                  25                  30

Ile Asp Ala Val Gly Met Leu Pro Asn Glu Lys Val Gln Ile Val Asn
         35                  40                  45

Asn Asn Asn Gly Ala Arg Leu Glu Thr Tyr Ile Ile Pro Gly Lys Arg
     50                  55                  60

Gly Ser Gly Val Ile Cys Leu Asn Gly Ala Ala Ala Arg Leu Val Gln
 65                  70                  75                  80

Glu Gly Asp Lys Val Ile Ile Ile Ser Tyr Lys Met Met Ser Asp Gln
                 85                  90                  95

Glu Ala Ala Ser His Glu Pro Lys Val Ala Val Leu Asn Asp Gln Asn
            100                 105                 110

Lys Ile Glu Gln Met Leu Gly Asn Glu Pro Ala Arg Thr Ile Leu
        115                 120                 125
```

<210> SEQ ID NO 29
<211> LENGTH: 894
<212> TYPE: DNA

```
<213> ORGANISM: Bacillus subtilis
<220> FEATURE:
<221> NAME/KEY: CDS
<222> LOCATION: (1)..(894)

<400> SEQUENCE: 29 atg aaa att gga att atc ggc gga ggc tcc gtt ggt ctt tta tgc gcc      48
Met Lys Ile Gly Ile Ile Gly Gly Gly Ser Val Gly Leu Leu Cys Ala
 1               5                  10                  15 tat tat ttg tca ctt tat cac gac gtg act gtt gtg acg agg cgg caa      96
Tyr Tyr Leu Ser Leu Tyr His Asp Val Thr Val Val Thr Arg Arg Gln
             20                  25                  30 gaa cag gct gcg gcc att cag tct gaa gga atc cgg ctt tat aaa ggc     144
Glu Gln Ala Ala Ala Ile Gln Ser Glu Gly Ile Arg Leu Tyr Lys Gly
         35                  40                  45 ggg gag gaa ttc agg gct gat tgc agt gcg gac acg agt atc aat tcg     192
Gly Glu Glu Phe Arg Ala Asp Cys Ser Ala Asp Thr Ser Ile Asn Ser
 50                  55                  60 gac ttt gac ctg ctt gtc gtg aca gtg aag cag cat cag ctt caa tct     240
Asp Phe Asp Leu Leu Val Val Thr Val Lys Gln His Gln Leu Gln Ser
 65                  70                  75                  80 gtt ttt tcg tcg ctt gaa cga atc ggg aag acg aat ata tta ttt ttg     288
Val Phe Ser Ser Leu Glu Arg Ile Gly Lys Thr Asn Ile Leu Phe Leu
                 85                  90                  95 caa aac ggc atg ggg cat atc cac gac cta aaa gac tgg cac gtt ggc     336
Gln Asn Gly Met Gly His Ile His Asp Leu Lys Asp Trp His Val Gly
            100                 105                 110 cat tcc att tat gtt gga atc gtt gag cac gga gct gta aga aaa tcg     384
His Ser Ile Tyr Val Gly Ile Val Glu His Gly Ala Val Arg Lys Ser
        115                 120                 125 gat aca gct gtt gat cat aca ggc cta ggt gcg ata aaa tgg agc gcg     432
Asp Thr Ala Val Asp His Thr Gly Leu Gly Ala Ile Lys Trp Ser Ala
    130                 135                 140 ttc gac gat gct gaa cca gac cgg ctg aac atc ttg ttt cag cat aac     480
Phe Asp Asp Ala Glu Pro Asp Arg Leu Asn Ile Leu Phe Gln His Asn
145                 150                 155                 160 cat tcg gat ttt ccg att tat tat gag acg gat tgg tac cgt ctg ctg     528
His Ser Asp Phe Pro Ile Tyr Tyr Glu Thr Asp Trp Tyr Arg Leu Leu
                165                 170                 175 acg ggc aag ctg att gta aat gcg tgt att aat cct tta act gcg tta     576
Thr Gly Lys Leu Ile Val Asn Ala Cys Ile Asn Pro Leu Thr Ala Leu
            180                 185                 190 ttg caa gtg aaa aat gga gaa ctg ctg aca acg cca gct tat ctg gct     624
Leu Gln Val Lys Asn Gly Glu Leu Leu Thr Thr Pro Ala Tyr Leu Ala
        195                 200                 205 ttt atg aag ctg gta ttt cag gag gca tgc cgc att tta aaa ctt gaa     672
Phe Met Lys Leu Val Phe Gln Glu Ala Cys Arg Ile Leu Lys Leu Glu
    210                 215                 220 aat gaa gaa aag gct tgg gag cgg gtt cag gcc gtt tgt ggg caa acg     720
Asn Glu Glu Lys Ala Trp Glu Arg Val Gln Ala Val Cys Gly Gln Thr
225                 230                 235                 240 aaa gag aat cgt tca tca atg ctg gtt gac gtc att gga ggc cgg cag     768
Lys Glu Asn Arg Ser Ser Met Leu Val Asp Val Ile Gly Gly Arg Gln
                245                 250                 255 acg gaa gct gac gcc att atc gga tac tta ttg aag gaa gca agt ctt     816
Thr Glu Ala Asp Ala Ile Ile Gly Tyr Leu Leu Lys Glu Ala Ser Leu
            260                 265                 270 caa ggt ctt gat gcc gtc cac cta gag ttt tta tat ggc agc atc aaa     864
Gln Gly Leu Asp Ala Val His Leu Glu Phe Leu Tyr Gly Ser Ile Lys
        275                 280                 285 gca ttg gag cga aat aca aac aaa gtc ttt                             894
```

```
Ala Leu Glu Arg Asn Thr Asn Lys Val Phe
    290                 295
```

<210> SEQ ID NO 30
<211> LENGTH: 298
<212> TYPE: PRT
<213> ORGANISM: Bacillus subtilis

<400> SEQUENCE: 30

```
Met Lys Ile Gly Ile Ile Gly Gly Ser Val Gly Leu Leu Cys Ala
 1               5                  10                  15

Tyr Tyr Leu Ser Leu Tyr His Asp Val Thr Val Thr Arg Arg Gln
            20                  25                  30

Glu Gln Ala Ala Ala Ile Gln Ser Glu Gly Ile Arg Leu Tyr Lys Gly
        35                  40                  45

Gly Glu Glu Phe Arg Ala Asp Cys Ser Ala Asp Thr Ser Ile Asn Ser
    50                  55                  60

Asp Phe Asp Leu Leu Val Val Thr Val Lys Gln His Gln Leu Gln Ser
 65                 70                  75                  80

Val Phe Ser Ser Leu Glu Arg Ile Gly Lys Thr Asn Ile Leu Phe Leu
            85                  90                  95

Gln Asn Gly Met Gly His Ile His Asp Leu Lys Asp Trp His Val Gly
            100                 105                 110

His Ser Ile Tyr Val Gly Ile Val Glu His Gly Ala Val Arg Lys Ser
            115                 120                 125

Asp Thr Ala Val Asp His Thr Gly Leu Gly Ala Ile Lys Trp Ser Ala
    130                 135                 140

Phe Asp Asp Ala Glu Pro Asp Arg Leu Asn Ile Leu Phe Gln His Asn
145                 150                 155                 160

His Ser Asp Phe Pro Ile Tyr Tyr Glu Thr Asp Trp Tyr Arg Leu Leu
                165                 170                 175

Thr Gly Lys Leu Ile Val Asn Ala Cys Ile Asn Pro Leu Thr Ala Leu
            180                 185                 190

Leu Gln Val Lys Asn Gly Glu Leu Leu Thr Thr Pro Ala Tyr Leu Ala
        195                 200                 205

Phe Met Lys Leu Val Phe Gln Glu Ala Cys Arg Ile Leu Lys Leu Glu
    210                 215                 220

Asn Glu Glu Lys Ala Trp Glu Arg Val Gln Ala Val Cys Gly Gln Thr
225                 230                 235                 240

Lys Glu Asn Arg Ser Ser Met Leu Val Asp Val Ile Gly Gly Arg Gln
                245                 250                 255

Thr Glu Ala Asp Ala Ile Ile Gly Tyr Leu Leu Lys Glu Ala Ser Leu
            260                 265                 270

Gln Gly Leu Asp Ala Val His Leu Glu Phe Leu Tyr Gly Ser Ile Lys
        275                 280                 285

Ala Leu Glu Arg Asn Thr Asn Lys Val Phe
    290                 295
```

<210> SEQ ID NO 31
<211> LENGTH: 1725
<212> TYPE: DNA
<213> ORGANISM: Bacillus subtilis
<220> FEATURE:
<221> NAME/KEY: CDS
<222> LOCATION: (1)..(1722)

<400> SEQUENCE: 31

```
atg ggg act aat gta cag gtg gat tca gca tct gcc gaa tgt aca cag        48
```

```
                Met Gly Thr Asn Val Gln Val Asp Ser Ala Ser Ala Glu Cys Thr Gln
                  1               5                  10                 15 acg atg agc gga gca tta atg ctg att gaa tca tta aaa aaa gag aaa          96
Thr Met Ser Gly Ala Leu Met Leu Ile Glu Ser Leu Lys Lys Glu Lys
             20                  25                  30 gta gaa atg atc ttc ggt tat ccg ggc ggg gct gtg ctt ccg att tac         144
Val Glu Met Ile Phe Gly Tyr Pro Gly Gly Ala Val Leu Pro Ile Tyr
         35                  40                  45 gat aag cta tac aat tca ggg ttg gta cat atc ctt ccc cgt cac gaa         192
Asp Lys Leu Tyr Asn Ser Gly Leu Val His Ile Leu Pro Arg His Glu
     50                  55                  60 caa gga gca att cat gca gcg gag gga tac gca agg gtc tcc gga aaa         240
Gln Gly Ala Ile His Ala Ala Glu Gly Tyr Ala Arg Val Ser Gly Lys
 65                  70                  75                  80 ccg ggt gtc gtc att gcc acg tca ggg ccg gga gcg aca aac ctt gtt         288
Pro Gly Val Val Ile Ala Thr Ser Gly Pro Gly Ala Thr Asn Leu Val
                 85                  90                  95 aca ggc ctt gct gat gcc atg att gat tca ttg ccg tta gtc gtc ttt         336
Thr Gly Leu Ala Asp Ala Met Ile Asp Ser Leu Pro Leu Val Val Phe
             100                 105                 110 aca ggg cag gta gca acc tct gta atc ggg agc gat gca ttt cag gaa         384
Thr Gly Gln Val Ala Thr Ser Val Ile Gly Ser Asp Ala Phe Gln Glu
         115                 120                 125 gca gac att tta ggg att acg atg cca gta aca aaa cac agc tac cag         432
Ala Asp Ile Leu Gly Ile Thr Met Pro Val Thr Lys His Ser Tyr Gln
     130                 135                 140 gtt cgc cag ccg gaa gat ctg ccg cgc atc att aaa gaa gcg ttc cat         480
Val Arg Gln Pro Glu Asp Leu Pro Arg Ile Ile Lys Glu Ala Phe His
145                 150                 155                 160 att gca aca act gga aga ccc gga cct gta ttg att gat att ccg aaa         528
Ile Ala Thr Thr Gly Arg Pro Gly Pro Val Leu Ile Asp Ile Pro Lys
                 165                 170                 175 gat gta gca aca att gaa gga gaa ttc agc tac gat cat gag atg aat         576
Asp Val Ala Thr Ile Glu Gly Glu Phe Ser Tyr Asp His Glu Met Asn
             180                 185                 190 ctc ccg gga tac cag ccg aca aca gag ccg aat tat ttg cag atc cgc         624
Leu Pro Gly Tyr Gln Pro Thr Thr Glu Pro Asn Tyr Leu Gln Ile Arg
         195                 200                 205 aag ctt gtg gaa gcc gtg agc agt gcg aaa aaa ccg gtg atc ctg gcg         672
Lys Leu Val Glu Ala Val Ser Ser Ala Lys Lys Pro Val Ile Leu Ala
     210                 215                 220 ggt gcg ggc gta ctg cac gga aaa gcg tca gaa gaa tta aaa aat tat         720
Gly Ala Gly Val Leu His Gly Lys Ala Ser Glu Glu Leu Lys Asn Tyr
225                 230                 235                 240 gct gaa cag cag caa atc cct gtg gca cac acc ctt ttg ggg ctc gga         768
Ala Glu Gln Gln Gln Ile Pro Val Ala His Thr Leu Leu Gly Leu Gly
                 245                 250                 255 ggc ttc ccg gct gac cat ccg ctt ttc cta ggg atg gcg gga atg cac         816
Gly Phe Pro Ala Asp His Pro Leu Phe Leu Gly Met Ala Gly Met His
             260                 265                 270 ggt act tat aca gcc aat atg gcc ctt cat gaa tgt gat cta tta atc         864
Gly Thr Tyr Thr Ala Asn Met Ala Leu His Glu Cys Asp Leu Leu Ile
         275                 280                 285 agt atc ggc gcc cgt ttt gat gac cgt gtc aca gga aac ctg aaa cac         912
Ser Ile Gly Ala Arg Phe Asp Asp Arg Val Thr Gly Asn Leu Lys His
     290                 295                 300 ttt gcc aga aac gca aag ata gcc cac atc gat att gat cca gct gaa         960
Phe Ala Arg Asn Ala Lys Ile Ala His Ile Asp Ile Asp Pro Ala Glu
305                 310                 315                 320 atc gga aaa atc atg aaa aca cag att cct gta gtc gga gac agc aaa        1008
```

```
        Ile Gly Lys Ile Met Lys Thr Gln Ile Pro Val Val Asp Ser Lys
                        325                 330                 335 att gtc ctg cag gag ctg atc aaa caa gac ggc aaa caa agc gat tca    1056
Ile Val Leu Gln Glu Leu Ile Lys Gln Asp Gly Lys Gln Ser Asp Ser
                340                 345                 350 agc gaa tgg aaa aaa cag ctc gca gaa tgg aaa gaa gag tat ccg ctc    1104
Ser Glu Trp Lys Lys Gln Leu Ala Glu Trp Lys Glu Glu Tyr Pro Leu
            355                 360                 365 tgg tat gta gat aat gaa gaa gaa ggt ttt aaa cct cag aaa ttg att    1152
Trp Tyr Val Asp Asn Glu Glu Glu Gly Phe Lys Pro Gln Lys Leu Ile
        370                 375                 380 gaa tat att cat caa ttt aca aaa gga gag gcc att gtc gca acg gat    1200
Glu Tyr Ile His Gln Phe Thr Lys Gly Glu Ala Ile Val Ala Thr Asp
385                 390                 395                 400 gta ggc cag cat caa atg tgg tca gcg caa ttt tat ccg ttc caa aaa    1248
Val Gly Gln His Gln Met Trp Ser Ala Gln Phe Tyr Pro Phe Gln Lys
                405                 410                 415 gca gat aaa tgg gtc acg tca ggc gga ctt gga acg atg gga ttc ggt    1296
Ala Asp Lys Trp Val Thr Ser Gly Gly Leu Gly Thr Met Gly Phe Gly
            420                 425                 430 ctt ccg gcg gcg atc ggc gca cag ctg gcc gaa aaa gat gct act gtt    1344
Leu Pro Ala Ala Ile Gly Ala Gln Leu Ala Glu Lys Asp Ala Thr Val
        435                 440                 445 gtc gcg gtt gtc gga gac ggc gga ttc caa atg acg ctt caa gaa ctc    1392
Val Ala Val Val Gly Asp Gly Gly Phe Gln Met Thr Leu Gln Glu Leu
    450                 455                 460 gat gtt att cgc gaa tta aat ctt ccg gtc aag gta gtg att tta aat    1440
Asp Val Ile Arg Glu Leu Asn Leu Pro Val Lys Val Val Ile Leu Asn
465                 470                 475                 480 aac gct tgt ctc gga atg gtc aga cag tgg cag gaa att ttc tat gaa    1488
Asn Ala Cys Leu Gly Met Val Arg Gln Trp Gln Glu Ile Phe Tyr Glu
                485                 490                 495 gaa cgt tat tca gaa tct aaa ttc gct tct cag cct gac ttc gtc aaa    1536
Glu Arg Tyr Ser Glu Ser Lys Phe Ala Ser Gln Pro Asp Phe Val Lys
            500                 505                 510 ttg tcc gaa gca tac ggc att aaa ggc atc aga att tca tca gaa gcg    1584
Leu Ser Glu Ala Tyr Gly Ile Lys Gly Ile Arg Ile Ser Ser Glu Ala
        515                 520                 525 gaa gca aag gaa aag ctg gaa gag gca tta aca tca aga gaa cct gtt    1632
Glu Ala Lys Glu Lys Leu Glu Glu Ala Leu Thr Ser Arg Glu Pro Val
    530                 535                 540 gtc att gac gtg cgg gtt gcc agc gaa gaa aaa gta ttc ccg atg gtg    1680
Val Ile Asp Val Arg Val Ala Ser Glu Glu Lys Val Phe Pro Met Val
545                 550                 555                 560 gct ccg ggg aaa ggg ctg cat gaa atg gtg ggg gtg aaa cct tga        1725
Ala Pro Gly Lys Gly Leu His Glu Met Val Gly Val Lys Pro
                565                 570

<210> SEQ ID NO 32
<211> LENGTH: 574
<212> TYPE: PRT
<213> ORGANISM: Bacillus subtilis

<400> SEQUENCE: 32

Met Gly Thr Asn Val Gln Val Asp Ser Ala Ser Ala Glu Cys Thr Gln
 1               5                  10                  15

Thr Met Ser Gly Ala Leu Met Leu Ile Glu Ser Leu Lys Lys Glu Lys
                20                  25                  30

Val Glu Met Ile Phe Gly Tyr Pro Gly Gly Ala Val Leu Pro Ile Tyr
            35                  40                  45
```

```
Asp Lys Leu Tyr Asn Ser Gly Leu Val His Ile Leu Pro Arg His Glu
     50                  55                  60

Gln Gly Ala Ile His Ala Glu Gly Tyr Ala Arg Val Ser Gly Lys
 65                  70                  75                  80

Pro Gly Val Val Ile Ala Thr Ser Gly Pro Gly Ala Thr Asn Leu Val
                 85                  90                  95

Thr Gly Leu Ala Asp Ala Met Ile Asp Ser Leu Pro Leu Val Val Phe
            100                 105                 110

Thr Gly Gln Val Ala Thr Ser Val Ile Gly Ser Asp Ala Phe Gln Glu
            115                 120                 125

Ala Asp Ile Leu Gly Ile Thr Met Pro Val Thr Lys His Ser Tyr Gln
        130                 135                 140

Val Arg Gln Pro Glu Asp Leu Pro Arg Ile Ile Lys Glu Ala Phe His
145                 150                 155                 160

Ile Ala Thr Thr Gly Arg Pro Gly Pro Val Leu Ile Asp Ile Pro Lys
                165                 170                 175

Asp Val Ala Thr Ile Glu Gly Glu Phe Ser Tyr Asp His Glu Met Asn
            180                 185                 190

Leu Pro Gly Tyr Gln Pro Thr Thr Glu Pro Asn Tyr Leu Gln Ile Arg
        195                 200                 205

Lys Leu Val Glu Ala Val Ser Ser Ala Lys Lys Pro Val Ile Leu Ala
    210                 215                 220

Gly Ala Gly Val Leu His Gly Lys Ala Ser Glu Glu Leu Lys Asn Tyr
225                 230                 235                 240

Ala Glu Gln Gln Gln Ile Pro Val Ala His Thr Leu Leu Gly Leu Gly
                245                 250                 255

Gly Phe Pro Ala Asp His Pro Leu Phe Leu Gly Met Ala Gly Met His
            260                 265                 270

Gly Thr Tyr Thr Ala Asn Met Ala Leu His Glu Cys Asp Leu Leu Ile
        275                 280                 285

Ser Ile Gly Ala Arg Phe Asp Asp Arg Val Thr Gly Asn Leu Lys His
    290                 295                 300

Phe Ala Arg Asn Ala Lys Ile Ala His Ile Asp Ile Asp Pro Ala Glu
305                 310                 315                 320

Ile Gly Lys Ile Met Lys Thr Gln Ile Pro Val Val Gly Asp Ser Lys
                325                 330                 335

Ile Val Leu Gln Glu Leu Ile Lys Gln Asp Gly Lys Gln Ser Asp Ser
            340                 345                 350

Ser Glu Trp Lys Lys Gln Leu Ala Glu Trp Lys Glu Glu Tyr Pro Leu
        355                 360                 365

Trp Tyr Val Asp Asn Glu Glu Glu Gly Phe Lys Pro Gln Lys Leu Ile
    370                 375                 380

Glu Tyr Ile His Gln Phe Thr Lys Gly Glu Ala Ile Val Ala Thr Asp
385                 390                 395                 400

Val Gly Gln His Gln Met Trp Ser Ala Gln Phe Tyr Pro Phe Gln Lys
                405                 410                 415

Ala Asp Lys Trp Val Thr Ser Gly Gly Leu Gly Thr Met Gly Phe Gly
            420                 425                 430

Leu Pro Ala Ala Ile Gly Ala Gln Leu Ala Glu Lys Asp Ala Thr Val
        435                 440                 445

Val Ala Val Val Gly Asp Gly Gly Phe Gln Met Thr Leu Gln Glu Leu
    450                 455                 460

Asp Val Ile Arg Glu Leu Asn Leu Pro Val Lys Val Val Ile Leu Asn
465                 470                 475                 480
```

```
Asn Ala Cys Leu Gly Met Val Arg Gln Trp Gln Glu Ile Phe Tyr Glu
                485                 490                 495

Glu Arg Tyr Ser Glu Ser Lys Phe Ala Ser Gln Pro Asp Phe Val Lys
            500                 505                 510

Leu Ser Glu Ala Tyr Gly Ile Lys Gly Ile Arg Ile Ser Ser Glu Ala
            515                 520                 525

Glu Ala Lys Glu Lys Leu Glu Glu Ala Leu Thr Ser Arg Glu Pro Val
        530                 535                 540

Val Ile Asp Val Arg Val Ala Ser Glu Glu Lys Val Phe Pro Met Val
545                 550                 555                 560

Ala Pro Gly Lys Gly Leu His Glu Met Val Gly Val Lys Pro
                565                 570

<210> SEQ ID NO 33
<211> LENGTH: 525
<212> TYPE: DNA
<213> ORGANISM: Bacillus subtilis
<220> FEATURE:
<221> NAME/KEY: CDS
<222> LOCATION: (1)..(522)

<400> SEQUENCE: 33 ttg aaa aga att atc aca ttg act gtg gtg aac cgc tcc ggg gtg tta        48
Met Lys Arg Ile Ile Thr Leu Thr Val Val Asn Arg Ser Gly Val Leu
 1               5                  10                  15 aac cgg atc acc ggt cta ttc aca aaa agg cat tac aac att gaa agc        96
Asn Arg Ile Thr Gly Leu Phe Thr Lys Arg His Tyr Asn Ile Glu Ser
                20                  25                  30 att aca gtt gga cac aca gaa aca gcc ggc gtt tcc aga atc acc ttc       144
Ile Thr Val Gly His Thr Glu Thr Ala Gly Val Ser Arg Ile Thr Phe
            35                  40                  45 gtc gtt cat gtt gaa ggt gaa aat gat gtt gaa cag tta acg aaa cag       192
Val Val His Val Glu Gly Glu Asn Asp Val Glu Gln Leu Thr Lys Gln
        50                  55                  60 ctc aac aaa cag att gat gtg ctg aaa gtc aca gac atc aca aat caa       240
Leu Asn Lys Gln Ile Asp Val Leu Lys Val Thr Asp Ile Thr Asn Gln
    65                  70                  75                  80 tcg att gtc cag agg gag ctg gcc tta atc aag gtt gtc tcc gca cct       288
Ser Ile Val Gln Arg Glu Leu Ala Leu Ile Lys Val Val Ser Ala Pro
                85                  90                  95 tca aca aga aca gag att aat gga atc ata gaa ccg ttt aga gcc tct       336
Ser Thr Arg Thr Glu Ile Asn Gly Ile Ile Glu Pro Phe Arg Ala Ser
            100                 105                 110 gtc gtt gat gtc agc aga gac agc atc gtt gtt cag gtg aca ggt gaa       384
Val Val Asp Val Ser Arg Asp Ser Ile Val Val Gln Val Thr Gly Glu
        115                 120                 125 tct aac aaa att gaa gcg ctt att gag tta tta aaa cct tat ggc att       432
Ser Asn Lys Ile Glu Ala Leu Ile Glu Leu Leu Lys Pro Tyr Gly Ile
    130                 135                 140 aaa gaa atc gcg aga aca ggt aca acg gct ttt gcg agg gga acc agc       480
Lys Glu Ile Ala Arg Thr Gly Thr Thr Ala Phe Ala Arg Gly Thr Ser
145                 150                 155                 160 aaa agg cgt cat cca ata aaa caa tat cta ttg tat aaa aca taa           525
Lys Arg Arg His Pro Ile Lys Gln Tyr Leu Leu Tyr Lys Thr
                165                 170

<210> SEQ ID NO 34
<211> LENGTH: 174
<212> TYPE: PRT
<213> ORGANISM: Bacillus subtilis
```

-continued

```
<400> SEQUENCE: 34

Met Lys Arg Ile Ile Thr Leu Thr Val Val Asn Arg Ser Gly Val Leu
 1               5                  10                  15

Asn Arg Ile Thr Gly Leu Phe Thr Lys Arg His Tyr Asn Ile Glu Ser
             20                  25                  30

Ile Thr Val Gly His Thr Glu Thr Ala Gly Val Ser Arg Ile Thr Phe
         35                  40                  45

Val Val His Val Glu Gly Glu Asn Asp Val Gln Leu Thr Lys Gln
     50                  55                  60

Leu Asn Lys Gln Ile Asp Val Leu Lys Val Thr Asp Ile Thr Asn Gln
 65                  70                  75                  80

Ser Ile Val Gln Arg Glu Leu Ala Leu Ile Lys Val Val Ser Ala Pro
                 85                  90                  95

Ser Thr Arg Thr Glu Ile Asn Gly Ile Ile Glu Pro Phe Arg Ala Ser
                100                 105                 110

Val Val Asp Val Ser Arg Asp Ser Ile Val Val Gln Val Thr Gly Glu
            115                 120                 125

Ser Asn Lys Ile Glu Ala Leu Ile Glu Leu Leu Lys Pro Tyr Gly Ile
        130                 135                 140

Lys Glu Ile Ala Arg Thr Gly Thr Thr Ala Phe Ala Arg Gly Thr Ser
145                 150                 155                 160

Lys Arg Arg His Pro Ile Lys Gln Tyr Leu Leu Tyr Lys Thr
                165                 170

<210> SEQ ID NO 35
<211> LENGTH: 1029
<212> TYPE: DNA
<213> ORGANISM: Bacillus subtilis
<220> FEATURE:
<221> NAME/KEY: CDS
<222> LOCATION: (1)..(1026)

<400> SEQUENCE: 35 atg gta aaa gta tat tat aac ggt gat atc aaa gag aac gta ttg gct      48
Met Val Lys Val Tyr Tyr Asn Gly Asp Ile Lys Glu Asn Val Leu Ala
 1               5                  10                  15 gga aaa aca gta gcg gtt atc ggg tac ggt tcg caa ggc cac gca cat      96
Gly Lys Thr Val Ala Val Ile Gly Tyr Gly Ser Gln Gly His Ala His
             20                  25                  30 gcc ctg aac ctt aaa gaa agc gga gta gac gtg atc gtc ggt gtt aga     144
Ala Leu Asn Leu Lys Glu Ser Gly Val Asp Val Ile Val Gly Val Arg
         35                  40                  45 caa gga aaa tct ttc act caa gcc caa gaa gac gga cat aaa gta ttt     192
Gln Gly Lys Ser Phe Thr Gln Ala Gln Glu Asp Gly His Lys Val Phe
     50                  55                  60 tca gta aaa gaa gcg gca gcc caa gcc gaa atc atc atg gtt ctg ctt     240
Ser Val Lys Glu Ala Ala Ala Gln Ala Glu Ile Ile Met Val Leu Leu
 65                  70                  75                  80 ccg gat gag cag cag caa aaa gta tac gaa gct gaa atc aaa gat gaa     288
Pro Asp Glu Gln Gln Gln Lys Val Tyr Glu Ala Glu Ile Lys Asp Glu
                 85                  90                  95 ttg aca gca gga aaa tca tta gta ttc gct cat gga ttt aac gtg cat     336
Leu Thr Ala Gly Lys Ser Leu Val Phe Ala His Gly Phe Asn Val His
                100                 105                 110 ttc cat caa att gtt cct ccg gcg gat gta gat gta ttc tta gtg gcc     384
Phe His Gln Ile Val Pro Pro Ala Asp Val Asp Val Phe Leu Val Ala
            115                 120                 125 cct aaa ggc ccg gga cac ttg gta aga aga aca tat gag caa gga gct     432
Pro Lys Gly Pro Gly His Leu Val Arg Arg Thr Tyr Glu Gln Gly Ala
```

```
ggc gta cct gca ttg ttc gca atc tat caa gat gtg act gga gaa gca    480
Gly Val Pro Ala Leu Phe Ala Ile Tyr Gln Asp Val Thr Gly Glu Ala
145                 150                 155                 160 aga gac aaa gcc ctc gct tat gct aaa gga atc ggc ggc gca aga gcg    528
Arg Asp Lys Ala Leu Ala Tyr Ala Lys Gly Ile Gly Gly Ala Arg Ala
                165                 170                 175 ggc gta tta gaa acg aca ttt aaa gaa gaa aca gaa aca gat ttg ttc    576
Gly Val Leu Glu Thr Thr Phe Lys Glu Glu Thr Glu Thr Asp Leu Phe
            180                 185                 190 ggt gag caa gca gtt ctt tgc ggc gga tta agc gcg ctt gtc aaa gcc    624
Gly Glu Gln Ala Val Leu Cys Gly Gly Leu Ser Ala Leu Val Lys Ala
        195                 200                 205 gga ttt gaa acc tta act gaa gca ggt tat cag cct gaa ctt gca tac    672
Gly Phe Glu Thr Leu Thr Glu Ala Gly Tyr Gln Pro Glu Leu Ala Tyr
    210                 215                 220 ttc gag tgt ctt cat gag ctg aaa tta atc gta gac ctt atg tac gaa    720
Phe Glu Cys Leu His Glu Leu Lys Leu Ile Val Asp Leu Met Tyr Glu
225                 230                 235                 240 gaa gga ctt gca gga atg aga tat tca atc tct gac aca gca cag tgg    768
Glu Gly Leu Ala Gly Met Arg Tyr Ser Ile Ser Asp Thr Ala Gln Trp
                245                 250                 255 gga gat ttc gta tca ggc cct cgc gtt gtg gac gcc aaa gta aaa gaa    816
Gly Asp Phe Val Ser Gly Pro Arg Val Val Asp Ala Lys Val Lys Glu
            260                 265                 270 tct atg aaa gaa gta tta aaa gat atc caa aac ggt aca ttc gca aaa    864
Ser Met Lys Glu Val Leu Lys Asp Ile Gln Asn Gly Thr Phe Ala Lys
        275                 280                 285 gag tgg atc gtc gaa aac caa gta aac cgt cct cgt ttc aac gct atc    912
Glu Trp Ile Val Glu Asn Gln Val Asn Arg Pro Arg Phe Asn Ala Ile
    290                 295                 300 aat gca agc gag aac gaa cat caa atc gaa gta gtg gga aga aag ctt    960
Asn Ala Ser Glu Asn Glu His Gln Ile Glu Val Val Gly Arg Lys Leu
305                 310                 315                 320 cgt gaa atg atg ccg ttt gtg aaa caa ggc aag aag aag gaa gcg gtg    1008
Arg Glu Met Met Pro Phe Val Lys Gln Gly Lys Lys Lys Glu Ala Val
                325                 330                 335 gtc tcc gtt gcg caa aat taa                                        1029
Val Ser Val Ala Gln Asn
            340

<210> SEQ ID NO 36
<211> LENGTH: 342
<212> TYPE: PRT
<213> ORGANISM: Bacillus subtilis

<400> SEQUENCE: 36

Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
                20                  25                  30

Ala Leu Asn Leu Lys Glu Ser Gly Val Asp Val Ile Gly Val Arg
            35                  40                  45

Gln Gly Lys Ser Phe Thr Gln Ala Gln Glu Asp Gly His Lys Val Phe
        50                  55                  60

Ser Val Lys Glu Ala Ala Ala Gln Ala Glu Ile Ile Met Val Leu Leu
65                  70                  75                  80

Pro Asp Glu Gln Gln Lys Val Tyr Glu Ala Glu Ile Lys Asp Glu
                85                  90                  95
```

```
Leu Thr Ala Gly Lys Ser Leu Val Phe Ala His Gly Phe Asn Val His
                100                 105                 110

Phe His Gln Ile Val Pro Pro Ala Asp Val Asp Val Phe Leu Val Ala
            115                 120                 125

Pro Lys Gly Pro Gly His Leu Val Arg Arg Thr Tyr Glu Gln Gly Ala
130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Thr Glu Thr Asp Leu Phe
            180                 185                 190

Gly Glu Gln Ala Val Leu Cys Gly Gly Leu Ser Ala Leu Val Lys Ala
            195                 200                 205

Gly Phe Glu Thr Leu Thr Glu Ala Gly Tyr Gln Pro Glu Leu Ala Tyr
            210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
    290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Glu Ala Val
                325                 330                 335

Val Ser Val Ala Gln Asn
            340

<210> SEQ ID NO 37
<211> LENGTH: 1674
<212> TYPE: DNA
<213> ORGANISM: Bacillus subtilis
<220> FEATURE:
<221> NAME/KEY: CDS
<222> LOCATION: (1)..(1674)

<400> SEQUENCE: 37 atg gca gaa tta cgc agt aat atg atc aca caa gga atc gat aga gct    48
Met Ala Glu Leu Arg Ser Asn Met Ile Thr Gln Gly Ile Asp Arg Ala
1               5                   10                  15 ccg cac cgc agt ttg ctt cgt gca gca ggg gta aaa gaa gag gat ttc    96
Pro His Arg Ser Leu Leu Arg Ala Ala Gly Val Lys Glu Glu Asp Phe
                20                  25                  30 ggc aag ccg ttt att gcg gtg tgt aat tca tac att gat atc gtt ccc   144
Gly Lys Pro Phe Ile Ala Val Cys Asn Ser Tyr Ile Asp Ile Val Pro
            35                  40                  45 ggt cat gtt cac ttg cag gag ttt ggg aaa atc gta aaa gaa gca atc   192
Gly His Val His Leu Gln Glu Phe Gly Lys Ile Val Lys Glu Ala Ile
        50                  55                  60 aga gaa gca ggg ggc gtt ccg ttt gaa ttt aat acc att ggg gta gat   240
Arg Glu Ala Gly Gly Val Pro Phe Glu Phe Asn Thr Ile Gly Val Asp
65                  70                  75                  80 gat ggc atc gca atg ggg cat atc ggt atg aga tat tcg ctg cca agc   288
```

-continued

```
                Asp Gly Ile Ala Met Gly His Ile Gly Met Arg Tyr Ser Leu Pro Ser
                                 85                  90                  95 cgt gaa att atc gca gac tct gtg gaa acg gtt gta tcc gca cac tgg         336
Arg Glu Ile Ile Ala Asp Ser Val Glu Thr Val Val Ser Ala His Trp
                100                 105                 110 ttt gac gga atg gtc tgt att ccg aac tgc gac aaa atc aca ccg gga         384
Phe Asp Gly Met Val Cys Ile Pro Asn Cys Asp Lys Ile Thr Pro Gly
            115                 120                 125 atg ctt atg gcg gca atg cgc atc aac att ccg acg att ttt gtc agc         432
Met Leu Met Ala Ala Met Arg Ile Asn Ile Pro Thr Ile Phe Val Ser
        130                 135                 140 ggc gga ccg atg gcg gca gga aga aca agt tac ggg cga aaa atc tcc         480
Gly Gly Pro Met Ala Ala Gly Arg Thr Ser Tyr Gly Arg Lys Ile Ser
145                 150                 155                 160 ctt tcc tca gta ttc gaa ggg gta ggc gcc tac caa gca ggg aaa atc         528
Leu Ser Ser Val Phe Glu Gly Val Gly Ala Tyr Gln Ala Gly Lys Ile
                165                 170                 175 aac gaa aac gag ctt caa gaa cta gag cag ttc gga tgc cca acg tgc         576
Asn Glu Asn Glu Leu Gln Glu Leu Glu Gln Phe Gly Cys Pro Thr Cys
            180                 185                 190 ggg tct tgc tca ggc atg ttt acg gcg aac tca atg aac tgt ctg tca         624
Gly Ser Cys Ser Gly Met Phe Thr Ala Asn Ser Met Asn Cys Leu Ser
        195                 200                 205 gaa gca ctt ggt ctt gct ttg ccg ggt aat gga acc att ctg gca aca         672
Glu Ala Leu Gly Leu Ala Leu Pro Gly Asn Gly Thr Ile Leu Ala Thr
    210                 215                 220 tct ccg gaa cgc aaa gag ttt gtg aga aaa tcg gct gcg caa tta atg         720
Ser Pro Glu Arg Lys Glu Phe Val Arg Lys Ser Ala Ala Gln Leu Met
225                 230                 235                 240 gaa acg att cgc aaa gat atc aaa ccg cgt gat att gtt aca gta aaa         768
Glu Thr Ile Arg Lys Asp Ile Lys Pro Arg Asp Ile Val Thr Val Lys
                245                 250                 255 gcg att gat aac gcg ttt gca ctc gat atg gcg ctc gga ggt tct aca         816
Ala Ile Asp Asn Ala Phe Ala Leu Asp Met Ala Leu Gly Gly Ser Thr
            260                 265                 270 aat acc gtt ctt cat acc ctt gcc ctt gca aac gaa gcc ggc gtt gaa         864
Asn Thr Val Leu His Thr Leu Ala Leu Ala Asn Glu Ala Gly Val Glu
        275                 280                 285 tac tct tta gaa cgc att aac gaa gtc gct gag cgc gtg ccg cac ttg         912
Tyr Ser Leu Glu Arg Ile Asn Glu Val Ala Glu Arg Val Pro His Leu
    290                 295                 300 gct aag ctg gcg cct gca tcg gat gtg ttt att gaa gat ctt cac gaa         960
Ala Lys Leu Ala Pro Ala Ser Asp Val Phe Ile Glu Asp Leu His Glu
305                 310                 315                 320 gcg ggc ggc gtt tca gcg gct ctg aat gag ctt tcg aag aaa gaa gga        1008
Ala Gly Gly Val Ser Ala Ala Leu Asn Glu Leu Ser Lys Lys Glu Gly
                325                 330                 335 gcg ctt cat tta gat gcg ctg act gtt aca gga aaa act ctt gga gaa        1056
Ala Leu His Leu Asp Ala Leu Thr Val Thr Gly Lys Thr Leu Gly Glu
            340                 345                 350 acc att gcc gga cat gaa gta aag gat tat gac gtc att cac ccg ctg        1104
Thr Ile Ala Gly His Glu Val Lys Asp Tyr Asp Val Ile His Pro Leu
        355                 360                 365 gat caa cca ttc act gaa aag gga ggc ctt gct gtt tta ttc ggt aat        1152
Asp Gln Pro Phe Thr Glu Lys Gly Gly Leu Ala Val Leu Phe Gly Asn
    370                 375                 380 cta gct ccg gac ggc gct atc att aaa aca ggc ggc gta cag aat ggg        1200
Leu Ala Pro Asp Gly Ala Ile Ile Lys Thr Gly Gly Val Gln Asn Gly
385                 390                 395                 400 att aca aga cac gaa ggg ccg gct gtc gta ttc gat tct cag gac gag        1248
```

```
Ile Thr Arg His Glu Gly Pro Ala Val Val Phe Asp Ser Gln Asp Glu
            405                 410                 415 gcg ctt gac ggc att atc aac cga aaa gta aaa gaa ggc gac gtt gtc     1296
Ala Leu Asp Gly Ile Ile Asn Arg Lys Val Lys Glu Gly Asp Val Val
            420                 425                 430 atc atc aga tac gaa ggg cca aaa ggc gga cct ggc atg ccg gaa atg     1344
Ile Ile Arg Tyr Glu Gly Pro Lys Gly Gly Pro Gly Met Pro Glu Met
            435                 440                 445 ctg gcg cca aca tcc caa atc gtt gga atg gga ctc ggg cca aaa gtg     1392
Leu Ala Pro Thr Ser Gln Ile Val Gly Met Gly Leu Gly Pro Lys Val
            450                 455                 460 gca ttg att acg gac gga cgt ttt tcc gga gcc tcc cgt ggc ctc tca     1440
Ala Leu Ile Thr Asp Gly Arg Phe Ser Gly Ala Ser Arg Gly Leu Ser
465                 470                 475                 480 atc ggc cac gta tca cct gag gcc gct gag ggc ggg ccg ctt gcc ttt     1488
Ile Gly His Val Ser Pro Glu Ala Ala Glu Gly Gly Pro Leu Ala Phe
                485                 490                 495 gtt gaa aac gga gac cat att atc gtt gat att gaa aaa cgc atc ttg     1536
Val Glu Asn Gly Asp His Ile Ile Val Asp Ile Glu Lys Arg Ile Leu
                500                 505                 510 gat gta caa gtg cca gaa gaa gag tgg gaa aaa cga aaa gcg aac tgg     1584
Asp Val Gln Val Pro Glu Glu Glu Trp Glu Lys Arg Lys Ala Asn Trp
            515                 520                 525 aaa ggt ttt gaa ccg aaa gtg aaa acc ggc tac ctg gca cgt tat tct     1632
Lys Gly Phe Glu Pro Lys Val Lys Thr Gly Tyr Leu Ala Arg Tyr Ser
530                 535                 540 aaa ctt gtg aca agt gcc aac acc ggc ggt att atg aaa atc                 1674
Lys Leu Val Thr Ser Ala Asn Thr Gly Gly Ile Met Lys Ile
545                 550                 555

<210> SEQ ID NO 38
<211> LENGTH: 558
<212> TYPE: PRT
<213> ORGANISM: Bacillus subtilis

<400> SEQUENCE: 38

Met Ala Glu Leu Arg Ser Asn Met Ile Thr Gln Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
65                  70                  75                  80

Asp Gly Ile Ala Met Gly His Ile Gly Met Arg Tyr Ser Leu Pro Ser
                85                  90                  95

Arg Glu Ile Ile Ala Asp Ser Val Glu Thr Val Val Ser Ala His Trp
            100                 105                 110

Phe Asp Gly Met Val Cys Ile Pro Asn Cys Asp Lys Ile Thr Pro Gly
        115                 120                 125

Met Leu Met Ala Ala Met Arg Ile Asn Ile Pro Thr Ile Phe Val Ser
    130                 135                 140

Gly Gly Pro Met Ala Ala Gly Arg Thr Ser Tyr Gly Arg Lys Ile Ser
145                 150                 155                 160

Leu Ser Ser Val Phe Glu Gly Val Gly Ala Tyr Gln Ala Gly Lys Ile
                165                 170                 175
```

Asn Glu Asn Glu Leu Gln Glu Leu Glu Gln Phe Gly Cys Pro Thr Cys
                180                 185                 190

Gly Ser Cys Ser Gly Met Phe Thr Ala Asn Ser Met Asn Cys Leu Ser
            195                 200                 205

Glu Ala Leu Gly Leu Ala Leu Pro Gly Asn Gly Thr Ile Leu Ala Thr
210                 215                 220

Ser Pro Glu Arg Lys Glu Phe Val Arg Lys Ser Ala Ala Gln Leu Met
225                 230                 235                 240

Glu Thr Ile Arg Lys Asp Ile Lys Pro Arg Asp Ile Val Thr Val Lys
                245                 250                 255

Ala Ile Asp Asn Ala Phe Ala Leu Asp Met Ala Leu Gly Gly Ser Thr
            260                 265                 270

Asn Thr Val Leu His Thr Leu Ala Leu Ala Asn Glu Ala Gly Val Glu
            275                 280                 285

Tyr Ser Leu Glu Arg Ile Asn Glu Val Ala Glu Arg Val Pro His Leu
        290                 295                 300

Ala Lys Leu Ala Pro Ala Ser Asp Val Phe Ile Glu Asp Leu His Glu
305                 310                 315                 320

Ala Gly Gly Val Ser Ala Leu Asn Glu Leu Ser Lys Lys Glu Gly
                325                 330                 335

Ala Leu His Leu Asp Ala Leu Thr Val Thr Gly Lys Thr Leu Gly Glu
            340                 345                 350

Thr Ile Ala Gly His Glu Val Lys Asp Tyr Asp Val Ile His Pro Leu
        355                 360                 365

Asp Gln Pro Phe Thr Glu Lys Gly Gly Leu Ala Val Leu Phe Gly Asn
370                 375                 380

Leu Ala Pro Asp Gly Ala Ile Ile Lys Thr Gly Gly Val Gln Asn Gly
385                 390                 395                 400

Ile Thr Arg His Glu Gly Pro Ala Val Val Phe Asp Ser Gln Asp Glu
                405                 410                 415

Ala Leu Asp Gly Ile Ile Asn Arg Lys Val Lys Glu Gly Asp Val Val
            420                 425                 430

Ile Ile Arg Tyr Glu Gly Pro Lys Gly Pro Gly Met Pro Glu Met
        435                 440                 445

Leu Ala Pro Thr Ser Gln Ile Val Gly Met Gly Leu Gly Pro Lys Val
450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Gly Gly Pro Leu Ala Phe
                485                 490                 495

Val Glu Asn Gly Asp His Ile Ile Val Asp Ile Glu Lys Arg Ile Leu
            500                 505                 510

Asp Val Gln Val Pro Glu Glu Trp Glu Lys Arg Lys Ala Asn Trp
        515                 520                 525

Lys Gly Phe Glu Pro Lys Val Lys Thr Gly Tyr Leu Ala Arg Tyr Ser
530                 535                 540

Lys Leu Val Thr Ser Ala Asn Thr Gly Gly Ile Met Lys Ile
545                 550                 555

<210> SEQ ID NO 39
<211> LENGTH: 194
<212> TYPE: DNA
<213> ORGANISM: Artificial Sequence
<220> FEATURE:
<223> OTHER INFORMATION: Description of Artificial Sequence:promoter
      sequence

```
<220> FEATURE:
<221> NAME/KEY: -35_signal
<222> LOCATION: (136)..(141)
<220> FEATURE:
<221> NAME/KEY: -10_signal
<222> LOCATION: (159)..(164)

<400> SEQUENCE: 39
gctattgacg acagctatgg ttcactgtcc accaaccaaa actgtgctca gtaccgccaa    60
tatttctccc ttgaggggta caaagaggtg tccctagaag agatccacgc tgtgtaaaaa   120
ttttacaaaa aggtattgac tttccctaca gggtgtgtaa taatttaatt acaggcgggg   180
gcaaccccgc ctgt                                                    194

<210> SEQ ID NO 40
<211> LENGTH: 163
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (113)..(118)
<220> FEATURE:
<221> NAME/KEY: -10_signal
<222> LOCATION: (136)..(141)

<400> SEQUENCE: 40
gcctacctag cttccaagaa agatatccta acagcacaag agcggaaaga tgttttgttc    60
tacatccaga acaacctctg ctaaaattcc tgaaaaattt tgcaaaaagt tgttgacttt   120
atctacaagg tgtggtataa taatcttaac aacagcagga cgc                    163

<210> SEQ ID NO 41
<211> LENGTH: 127
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (34)..(39)
<220> FEATURE:
<221> NAME/KEY: -10_signal
<222> LOCATION: (58)..(63)
<220> FEATURE:
<221> NAME/KEY: -35_signal
<222> LOCATION: (75)..(80)
<220> FEATURE:
<221> NAME/KEY: -10_signal
<222> LOCATION: (98)..(103)

<400> SEQUENCE: 41
gaggaatcat agaattttgt caaaataatt ttattgacaa cgtcttatta acgttgatat    60
aatttaaatt ttatttgaca aaaatgggct cgtgttgtac aataaatgta gtgaggtgga   120
tgcaatg                                                            127

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 42
```
taaacatgag gaggagaaaa catg                                              24

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 43
attcgagaaa tggagagaat ataatatg                                          28

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 44
agaaaggagg tga                                                          13

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 17-20
<223> OTHER INFORMATION: n = a, c, g, or t

<400> SEQUENCE: 45
ttaagaaagg aggtgannnn atg                                               23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 16-20
<223> OTHER INFORMATION: n = a, c, g, or t

<400> SEQUENCE: 46
ttagaaagga ggtgannnnn atg                                               23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 14-20
<223> OTHER INFORMATION: n = a, c, g, or t

<400> SEQUENCE: 47
agaaaggagg tgannnnnnn atg                                               23

```
<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 14-19
<223> OTHER INFORMATION: n = a, c, g, or t

<400> SEQUENCE: 48
agaaaggagg tgannnnnna tg                                              22

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 49
ccctctagaa ggaggagaaa acatg                                           25

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 50
ccctctagag gaggagaaaa catg                                            24

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 51
ttagaaagga ggatttaaat atg                                             23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 52
ttagaaagga ggtttaatta atg                                             23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 53
ttagaaagga ggtgatttaa atg                                             23
```

```
<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 54
ttagaaagga ggtgtttaaa atg                                           23

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 55
attcgagaaa ggaggtgaat ataatatg                                      28

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 56
attcgagaaa ggaggtgaat aataatg                                       27

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 57
attcgtagaa aggaggtgaa ttaatatg                                      28

<210> SEQ ID NO 58
<211> LENGTH: 3291
<212> TYPE: DNA
<213> ORGANISM: Bacillus subtilis

<400> SEQUENCE: 58
atggggacta atgtacaggt ggattcagca tctgccgaat gtacacagac gatgagcgga    60
gcattaatgc tgattgaatc attaaaaaaa gagaaagtag aaatgatctt cggttatccg   120 ggcgggctg tgcttccgat ttacgataag ctatacaatt cagggttggt acatatcctt   180
ccccgtcacg aacaaggagc aattcatgca gcggagggat acgcaagggt ctccggaaaa   240
ccgggtgtcg tcattgccac gtcagggccg ggagcgacaa accttgttac aggccttgct   300
gatgccatga ttgattcatt gccgttagtc gtctttacag ggcaggtagc aacctctgta   360
atcgggagcg atgcatttca ggaagcagac attttaggga ttacgatgcc agtaacaaaa   420
cacagctacc aggttcgcca gccggaagat ctgccgcgca tcattaaaga agcgttccat   480
attgcaacaa ctggaagacc cggacctgta ttgattgata ttccgaaaga tgtagcaaca   540
attgaaggag aattcagcta cgatcatgag atgaatctcc cgggatacca gccgacaaca   600
```

```
gagccgaatt atttgcagat ccgcaagctt gtggaagccg tgagcagtgc gaaaaaaccg    660
gtgatcctgg cgggtgcggg cgtactgcac ggaaaagcgt cagaagaatt aaaaaattat    720
gctgaacagc agcaaatccc tgtggcacac acccttttgg ggctcggagg cttcccggct    780
gaccatccgc ttttcctagg gatggcggga atgcacggta cttatacagc caatatggcc    840
cttcatgaat gtgatctatt aatcagtatc ggcgcccgtt ttgatgaccg tgtcacagga    900
aacctgaaac actttgccag aaacgcaaag atagcccaca tcgatattga tccagctgaa    960
atcggaaaaa tcatgaaaac acagattcct gtagtcggag acagcaaaat tgtcctgcag   1020
gagctgatca aacaagacgg caaacaaagc gattcaagcg aatggaaaaa acagctcgca   1080
gaatggaaag aagagtatcc gctctggtat gtagataatg aagaagaagg ttttaaacct   1140
cagaaattga ttgaatatat tcatcaattt acaaaaggag aggccattgt cgcaacggat   1200
gtaggccagc atcaaatgtg gtcagcgcaa ttttatccgt tccaaaaagc agataaatgg   1260
gtcacgtcag gcggacttgg aacgatggga ttcggtcttc cggcggcgat cggcgcacag   1320
ctggccgaaa aagatgctac tgttgtcgcg gttgtcggag acggcggatt ccaaatgacg   1380
cttcaagaac tcgatgttat tcgcgaatta aatcttccgg tcaaggtagt gatttttaaat   1440 aacgcttgtc tcggaatggt cagacagtgg caggaaattt tctatgaaga acgttattca   1500
gaatctaaat tcgcttctca gcctgacttc gtcaaattgt ccgaagcata cggcattaaa   1560
ggcatcagaa tttcatcaga agcggaagca aaggaaaagc tggaagaggc attaacatca   1620
agagaacctg ttgtcattga cgtgcgggtt gccagcgaag aaaaagtatt cccgatggtg   1680
gctccgggga aagggctgca tgaaatggtg ggggtgaaac cttgaaaaga attatcacat   1740
tgactgtggt gaaccgctcc ggggtgttaa accggatcac cggtctattc acaaaaaggc   1800
attacaacat tgaaagcatt acagttggac acacagaaac agccggcgtt tccagaatca   1860
ccttcgtcgt tcatgttgaa ggtgaaaatg atgttgaaca gttaacgaaa cagctcaaca   1920
aacagattga tgtgctgaaa gtcacagaca tcacaaatca atcgattgtc cagagggagc   1980
tggccttaat caaggttgtc tccgcacctt caacaagaac agagattaat ggaatcatag   2040
aaccgtttag agcctctgtc gttgatgtca gcagagacag catcgttgtt caggtgacag   2100
gtgaatctaa caaaattgaa gcgcttattg agttattaaa accttatggc attaaagaaa   2160
tcgcgagaac aggtacaacg gcttttgcga ggggaaccag caaaaggcgt catccaataa   2220
aacaatatct attgtataaa acataacaag ggagagattg aaatggtaaa agtatatatt   2280
aacggtgata tcaaagagaa cgtattggct ggaaaaacag tagcggttat cgggtacggt   2340
tcgcaaggcc acgcacatgc cctgaacctt aaagaaagcg gagtagacgt gatcgtcggt   2400
gttagacaag gaaaatcttt cactcaagcc caagaagacg gacataaagt attttcagta   2460
aaagaagcgg cagcccaagc cgaaatcatc atggttctgc ttccggatga gcagcagcaa   2520
aaagtatacg aagctgaaat caaagatgaa ttgacagcag gaaaatcatt agtattcgct   2580
catgggttta cgtgcattt ccatcaaatt gttcctccgg cggatgtaga tgtattctta   2640
gtggccccta aaggcccggg acacttggta agaagaacat atgagcaagg agctggcgta   2700
cctgcattgt tcgcaatcta tcaagatgtg actggagaag caagagacaa agccctcgct   2760
tatgctaaag gaatcggcgg cgcaagagcg ggcgtattag aaacgacatt taagaagaa   2820 acagaaacag atttgttcgg tgagcaagca gttctttgcg gcggattaag cgcgcttgtc   2880
aaagccggat ttgaaacctt aactgaagca ggttatcagc ctgaacttgc atacttcgag   2940
tgtcttcatg agctgaaatt aatcgtagac cttatgtacg aagaaggact tgcaggaatg   3000
```

```
agatattcaa tctctgacac agcacagtgg ggagatttcg tatcaggccc tcgcgttgtg    3060
gacgccaaag taaagaatc tatgaaagaa gtattaaaag atatccaaaa cggtacattc     3120
gcaaaagagt ggatcgtcga aaccaagta aaccgtcctc gtttcaacgc tatcaatgca     3180
agcgagaacg aacatcaaat cgaagtagtg ggaagaaagc ttcgtgaaat gatgccgttt    3240
gtgaaacaag gcaagaagaa ggaagcggtg gtctccgttg cgcaaaatta a             3291
```

<210> SEQ ID NO 59
<211> LENGTH: 2363
<212> TYPE: DNA
<213> ORGANISM: Bacillus subtilis
<220> FEATURE:
<221> NAME/KEY: CDS
<222> LOCATION: (242)..(1072)
<220> FEATURE:
<221> NAME/KEY: CDS
<222> LOCATION: (1077)..(1934)
<220> FEATURE:
<221> NAME/KEY: CDS
<222> LOCATION: (1939)..(2319)

<400> SEQUENCE: 59

```
ttggtacaag cccgttgatt ttggtatact tccattgggc agtatcgcct gcgaactgca     60
cctattatta aaatagatag acattgcagc agtctgcctt gatccaaaaa aggactggga    120
cagagggatg aaactcgccg aactttagaa agtgaagaat ccttctcgtt gtaacggaag    180 gtttttggc ttgcagaaga aaacggcaga tcatctcctc taaacatgag gaggagaaaa    240 c atg aaa aca aaa ctg gat ttt cta aaa atg aag gag tct gaa gaa ccg   289
  Met Lys Thr Lys Leu Asp Phe Leu Lys Met Lys Glu Ser Glu Glu Pro
   1               5                  10                  15 att gtc atg ctg acc gct tat gat tat ccg gca gct aaa ctt gct gaa      337
Ile Val Met Leu Thr Ala Tyr Asp Tyr Pro Ala Ala Lys Leu Ala Glu
             20                  25                  30 caa gcg gga gtt gac atg att tta gtc ggt gat tca ctt gga atg gtc      385
Gln Ala Gly Val Asp Met Ile Leu Val Gly Asp Ser Leu Gly Met Val
         35                  40                  45 gtc ctc ggc ctt gat tca act gtc ggt gtg aca gtt gcg gac atg atc      433
Val Leu Gly Leu Asp Ser Thr Val Gly Val Thr Val Ala Asp Met Ile
     50                  55                  60 cat cat aca aaa gcc gtt aaa agg ggt gcg ccg aat acc ttt att gtg      481
His His Thr Lys Ala Val Lys Arg Gly Ala Pro Asn Thr Phe Ile Val
 65                  70                  75                  80 aca gat atg ccg ttt atg tct tat cac ctg tct aag gaa gat acg ctg      529
Thr Asp Met Pro Phe Met Ser Tyr His Leu Ser Lys Glu Asp Thr Leu
                 85                  90                  95 aaa aat gca gcg gct atc gtt cag gaa agc gga gct gac gca ctg aag      577
Lys Asn Ala Ala Ala Ile Val Gln Glu Ser Gly Ala Asp Ala Leu Lys
            100                 105                 110 ctt gag ggc gga gaa ggc gtg ttt gaa tcc att cgc gca ttg acg ctt      625
Leu Glu Gly Gly Glu Gly Val Phe Glu Ser Ile Arg Ala Leu Thr Leu
        115                 120                 125 gga ggc att cca gta gtc agt cac tta ggt ttg aca ccg cag tca gtc      673
Gly Gly Ile Pro Val Val Ser His Leu Gly Leu Thr Pro Gln Ser Val
    130                 135                 140 ggc gta ctg ggc ggc tat aaa gta cag ggc aaa gac gaa caa agc gcc      721
Gly Val Leu Gly Gly Tyr Lys Val Gln Gly Lys Asp Glu Gln Ser Ala
145                 150                 155                 160 aaa aaa tta ata gaa gac agt ata aaa tgc gaa gaa gca gga gct atg      769
Lys Lys Leu Ile Glu Asp Ser Ile Lys Cys Glu Glu Ala Gly Ala Met
                165                 170                 175
```

```
atg ctt gtg ctg gaa tgt gtg ccg gca gaa ctc aca gcc aaa att gcc    817
Met Leu Val Leu Glu Cys Val Pro Ala Glu Leu Thr Ala Lys Ile Ala
        180                 185                 190 gag acg cta agc ata ccg gtc att gga atc ggg gct ggt gtg aaa gcg    865
Glu Thr Leu Ser Ile Pro Val Ile Gly Ile Gly Ala Gly Val Lys Ala
    195                 200                 205 gac gga caa gtt ctc gtt tat cat gat att atc ggc cac ggt gtt gag    913
Asp Gly Gln Val Leu Val Tyr His Asp Ile Ile Gly His Gly Val Glu
210                 215                 220 aga aca cct aaa ttt gta aag caa tat acg cgc att gat gaa acc atc    961
Arg Thr Pro Lys Phe Val Lys Gln Tyr Thr Arg Ile Asp Glu Thr Ile
225                 230                 235                 240 gaa aca gca atc agc gga tat gtt cag gat gta aga cat cgt gct ttc   1009
Glu Thr Ala Ile Ser Gly Tyr Val Gln Asp Val Arg His Arg Ala Phe
                245                 250                 255 cct gaa caa aag cat tcc ttt caa atg aac cag aca gtg ctt gac ggc   1057
Pro Glu Gln Lys His Ser Phe Gln Met Asn Gln Thr Val Leu Asp Gly
            260                 265                 270 ttg tac ggg gga aaa taag atg aga cag att act gat att tca cag ctg  1106
Leu Tyr Gly Gly Lys     Met Arg Gln Ile Thr Asp Ile Ser Gln Leu
        275                 280                 285 aaa gaa gcc ata aaa caa tac cat tca gag ggc aag tca atc gga ttt   1154
Lys Glu Ala Ile Lys Gln Tyr His Ser Glu Gly Lys Ser Ile Gly Phe
        290                 295                 300 gtt ccg acg atg ggg ttt ctg cat gag ggg cat tta acc tta gca gac   1202
Val Pro Thr Met Gly Phe Leu His Glu Gly His Leu Thr Leu Ala Asp
    305                 310                 315 aaa gca aga caa gaa aac gac gcc gtt att atg agt att ttt gtg aat   1250
Lys Ala Arg Gln Glu Asn Asp Ala Val Ile Met Ser Ile Phe Val Asn
320                 325                 330                 335 cct gca caa ttc ggc cct aat gaa gat ttt gaa gca tat ccg cgc gat   1298
Pro Ala Gln Phe Gly Pro Asn Glu Asp Phe Glu Ala Tyr Pro Arg Asp
                340                 345                 350 att gag cgg gat gca gct ctt gca gaa aac gcc gga gtc gat att ctt   1346
Ile Glu Arg Asp Ala Ala Leu Ala Glu Asn Ala Gly Val Asp Ile Leu
            355                 360                 365 ttt acg cca gat gct cat gat atg tat ccc ggt gaa aag aat gtc acg   1394
Phe Thr Pro Asp Ala His Asp Met Tyr Pro Gly Glu Lys Asn Val Thr
        370                 375                 380 att cat gta gaa aga cgc aca gac gtg tta tgc ggg cgc tca aga gaa   1442
Ile His Val Glu Arg Arg Thr Asp Val Leu Cys Gly Arg Ser Arg Glu
        385                 390                 395 gga cat ttt gac ggg gtc gcg atc gta ctg acg aag ctt ttc aat cta   1490
Gly His Phe Asp Gly Val Ala Ile Val Leu Thr Lys Leu Phe Asn Leu
400                 405                 410                 415 gtc aag ccg act cgt gcc tat ttc ggt tta aaa gat gcg cag cag gta   1538
Val Lys Pro Thr Arg Ala Tyr Phe Gly Leu Lys Asp Ala Gln Gln Val
                420                 425                 430 gct gtt gtt gat ggg tta atc agc gac ttc ttc atg gat att gaa ttg   1586
Ala Val Val Asp Gly Leu Ile Ser Asp Phe Phe Met Asp Ile Glu Leu
            435                 440                 445 gtt cct gtc gat acg gtc aga gag gaa gac ggc tta gcc aaa agc tct   1634
Val Pro Val Asp Thr Val Arg Glu Glu Asp Gly Leu Ala Lys Ser Ser
        450                 455                 460 cgc aat gta tac tta aca gct gag gaa aga aaa gaa gcg cct aag ctg   1682
Arg Asn Val Tyr Leu Thr Ala Glu Glu Arg Lys Glu Ala Pro Lys Leu
465                 470                 475 tat cgg gcc ctt caa aca agt gcg gaa ctt gtc caa gcc ggt gaa aga   1730
Tyr Arg Ala Leu Gln Thr Ser Ala Glu Leu Val Gln Ala Gly Glu Arg
        480                 485                 490                 495
```

| | | |
|---|---|---|
| gat cct gaa gcg gtg ata aaa gct gca aaa gat atc att gaa acg act | | 1778 |
| Asp Pro Glu Ala Val Ile Lys Ala Ala Lys Asp Ile Ile Glu Thr Thr | | |
| 500 505 510 | | |
| | | |
| agc gga acc ata gac tat gta gag ctt tat tcc tat ccg gaa ctc gag | | 1826 |
| Ser Gly Thr Ile Asp Tyr Val Glu Leu Tyr Ser Tyr Pro Glu Leu Glu | | |
| 515 520 525 | | |
| | | |
| cct gtg aat gaa att gct gga aag atg att ctc gct gtt gca gtt gct | | 1874 |
| Pro Val Asn Glu Ile Ala Gly Lys Met Ile Leu Ala Val Ala Val Ala | | |
| 530 535 540 | | |
| | | |
| ttt tca aaa gcg cgt tta ata gat aat atc att att gat att cga gaa | | 1922 |
| Phe Ser Lys Ala Arg Leu Ile Asp Asn Ile Ile Ile Asp Ile Arg Glu | | |
| 545 550 555 | | |
| | | |
| atg gag aga ata taat atg tat cga aca atg atg agc ggc aaa ctt cac | | 1971 |
| Met Glu Arg Ile Met Tyr Arg Thr Met Met Ser Gly Lys Leu His | | |
| 560 565 570 | | |
| | | |
| agg gca act gtt acg gaa gca aac ctg aac tat gtg gga agc att aca | | 2019 |
| Arg Ala Thr Val Thr Glu Ala Asn Leu Asn Tyr Val Gly Ser Ile Thr | | |
| 575 580 585 590 | | |
| | | |
| att gat gaa gat ctc att gat gct gtg gga atg ctt cct aat gaa aaa | | 2067 |
| Ile Asp Glu Asp Leu Ile Asp Ala Val Gly Met Leu Pro Asn Glu Lys | | |
| 595 600 605 | | |
| | | |
| gta caa att gtg aat aat aat aat gga gca cgt ctt gaa acg tat att | | 2115 |
| Val Gln Ile Val Asn Asn Asn Asn Gly Ala Arg Leu Glu Thr Tyr Ile | | |
| 610 615 620 | | |
| | | |
| att cct ggt aaa cgg gga agc ggc gtc ata tgc tta aac ggt gca gcc | | 2163 |
| Ile Pro Gly Lys Arg Gly Ser Gly Val Ile Cys Leu Asn Gly Ala Ala | | |
| 625 630 635 | | |
| | | |
| gca cgc ctt gtg cag gaa gga gat aag gtc att att att tcc tac aaa | | 2211 |
| Ala Arg Leu Val Gln Glu Gly Asp Lys Val Ile Ile Ile Ser Tyr Lys | | |
| 640 645 650 | | |
| | | |
| atg atg tct gat caa gaa gcg gca agc cat gag ccg aaa gtg gct gtt | | 2259 |
| Met Met Ser Asp Gln Glu Ala Ala Ser His Glu Pro Lys Val Ala Val | | |
| 655 660 665 670 | | |
| | | |
| ctg aat gat caa aac aaa att gaa caa atg ctg ggg aac gaa cca gcc | | 2307 |
| Leu Asn Asp Gln Asn Lys Ile Glu Gln Met Leu Gly Asn Glu Pro Ala | | |
| 675 680 685 | | |
| | | |
| cgt aca att ttg tagaagaaaa gcccccttta tcggggggttt tcttttaaga tttt | | 2363 |
| Arg Thr Ile Leu | | |
| 690 | | |

<210> SEQ ID NO 60
<211> LENGTH: 293
<212> TYPE: PRT
<213> ORGANISM: Bacillus subtilis

<400> SEQUENCE: 60

Met Ser Ile Ala Val Ser Glu Glu Ala Lys Ala Val Glu Gly Leu
 1               5                  10                  15

Asn Asp Tyr Leu Ser Val Glu Glu Val Glu Thr Ile Tyr Ile Pro Leu
            20                  25                  30

Val Arg Leu Leu His Leu His Val Lys Ser Ala Ala Glu Arg Asn Lys
        35                  40                  45

His Val Asn Val Phe Leu Lys His Pro His Ser Ala Lys Ile Pro Phe
    50                  55                  60

Ile Ile Gly Ile Ala Gly Ser Val Ala Val Gly Lys Ser Thr Thr Ala
65                  70                  75                  80

Arg Ile Leu Gln Lys Leu Leu Ser Arg Leu Pro Asp Arg Pro Lys Val
                85                  90                  95

Ser Leu Ile Thr Thr Asp Gly Phe Leu Phe Pro Thr Ala Glu Leu Lys
            100                 105                 110

```
Lys Lys Asn Met Met Ser Arg Lys Gly Phe Pro Glu Ser Tyr Asp Val
            115                 120                 125

Lys Ala Leu Leu Glu Phe Leu Asn Asp Leu Lys Ser Gly Lys Asp Ser
        130                 135                 140

Val Lys Ala Pro Val Tyr Ser His Leu Thr Tyr Asp Arg Glu Glu Gly
145                 150                 155                 160

Val Phe Glu Val Val Glu Gln Ala Asp Ile Val Ile Glu Gly Ile
                165                 170                 175

Asn Val Leu Gln Ser Pro Thr Leu Glu Asp Asp Arg Glu Asn Pro Arg
            180                 185                 190

Ile Phe Val Ser Asp Phe Phe Asp Phe Ser Ile Tyr Val Asp Ala Glu
        195                 200                 205

Glu Ser Arg Ile Phe Thr Trp Tyr Leu Glu Arg Phe Arg Leu Leu Arg
        210                 215                 220

Glu Thr Ala Phe Gln Asn Pro Asp Ser Tyr Phe His Lys Phe Lys Asp
225                 230                 235                 240

Leu Ser Asp Gln Glu Ala Asp Glu Met Ala Ala Ser Ile Trp Glu Ser
                245                 250                 255

Val Asn Arg Pro Asn Leu Tyr Glu Asn Ile Leu Pro Thr Lys Phe Arg
            260                 265                 270

Ser Asp Leu Ile Leu Arg Lys Gly Asp Gly His Lys Val Glu Glu Val
        275                 280                 285

Leu Val Arg Arg Val
    290

<210> SEQ ID NO 61
<211> LENGTH: 281
<212> TYPE: PRT
<213> ORGANISM: Bacillus subtilis

<400> SEQUENCE: 61

Met Glu Gly Leu Asn Asp Tyr Leu Ser Val Glu Val Glu Thr Ile
  1               5                  10                  15

Tyr Ile Pro Leu Val Arg Leu Leu His Leu His Val Lys Ser Ala Ala
                20                  25                  30

Glu Arg Asn Lys His Val Asn Val Phe Leu Lys His Pro His Ser Ala
            35                  40                  45

Lys Ile Pro Phe Ile Ile Gly Ile Ala Gly Ser Val Ala Val Gly Lys
        50                  55                  60

Ser Thr Thr Ala Arg Ile Leu Gln Lys Leu Leu Ser Arg Leu Pro Asp
65                  70                  75                  80

Arg Pro Lys Val Ser Leu Ile Thr Thr Asp Gly Phe Leu Phe Pro Thr
                85                  90                  95

Ala Glu Leu Lys Lys Lys Asn Met Met Ser Arg Lys Gly Phe Pro Glu
            100                 105                 110

Ser Tyr Asp Val Lys Ala Leu Leu Glu Phe Leu Asn Asp Leu Lys Ser
        115                 120                 125

Gly Lys Asp Ser Val Lys Ala Pro Val Tyr Ser His Leu Thr Tyr Asp
    130                 135                 140

Arg Glu Glu Gly Val Phe Glu Val Val Glu Gln Ala Asp Ile Val Ile
145                 150                 155                 160

Ile Glu Gly Ile Asn Val Leu Gln Ser Pro Thr Leu Glu Asp Asp Arg
                165                 170                 175

Glu Asn Pro Arg Ile Phe Val Ser Asp Phe Phe Asp Phe Ser Ile Tyr
            180                 185                 190
```

```
Val Asp Ala Glu Glu Ser Arg Ile Phe Thr Trp Tyr Leu Glu Arg Phe
        195                 200                 205

Arg Leu Leu Arg Glu Thr Ala Phe Gln Asn Pro Asp Ser Tyr Phe His
        210                 215                 220

Lys Phe Lys Asp Leu Ser Asp Gln Glu Ala Asp Glu Met Ala Ala Ser
225                 230                 235                 240

Ile Trp Glu Ser Val Asn Arg Pro Asn Leu Tyr Glu Asn Ile Leu Pro
                245                 250                 255

Thr Lys Phe Arg Ser Asp Leu Ile Leu Arg Lys Gly Asp Gly His Lys
        260                 265                 270

Val Glu Glu Val Leu Val Arg Val
        275                 280

<210> SEQ ID NO 62
<211> LENGTH: 1092
<212> TYPE: DNA
<213> ORGANISM: Bacillus subtilis
<220> FEATURE:
<221> NAME/KEY: CDS
<222> LOCATION: (1)..(1089)

<400> SEQUENCE: 62
```

| | |
|---|---:|
| atg act aaa caa aca att cgc gtt gaa ttg aca tca aca aaa aaa ccg<br>Met Thr Lys Gln Thr Ile Arg Val Glu Leu Thr Ser Thr Lys Lys Pro<br>1                  5                    10                15 | 48 |
| aaa cca gac cca aat cag ctt tcg ttc gga aga gtg ttt aca gac cac<br>Lys Pro Asp Pro Asn Gln Leu Ser Phe Gly Arg Val Phe Thr Asp His<br>                 20                    25                    30 | 96 |
| atg ttt gta atg gac tat gcc gca gat aaa ggt tgg tac gat cca aga<br>Met Phe Val Met Asp Tyr Ala Ala Asp Lys Gly Trp Tyr Asp Pro Arg<br>        35                    40                    45 | 144 |
| atc att cct tat caa ccc tta tca atg gat cca act gca atg gtc tat<br>Ile Ile Pro Tyr Gln Pro Leu Ser Met Asp Pro Thr Ala Met Val Tyr<br>        50                    55                    60 | 192 |
| cac tac ggc caa acc gtg ttt gaa ggg tta aag gct tac gtg tca gag<br>His Tyr Gly Gln Thr Val Phe Glu Gly Leu Lys Ala Tyr Val Ser Glu<br>65                  70                    75                80 | 240 |
| gat gac cat gtt ctg ctt ttc aga ccg gaa aaa aat atg gaa cgc ctg<br>Asp Asp His Val Leu Leu Phe Arg Pro Glu Lys Asn Met Glu Arg Leu<br>                 85                    90                    95 | 288 |
| aat caa tca aac gac cgc ctc tgc atc ccg caa att gat gaa gaa cag<br>Asn Gln Ser Asn Asp Arg Leu Cys Ile Pro Gln Ile Asp Glu Glu Gln<br>                 100                 105                 110 | 336 |
| gtt ctt gaa ggc tta aag cag ctt gtc gca att gat aaa gac tgg att<br>Val Leu Glu Gly Leu Lys Gln Leu Val Ala Ile Asp Lys Asp Trp Ile<br>        115                    120                   125 | 384 |
| cca aat gcg gag ggc acg tcc ctt tac atc cgt ccg ttc atc atc gca<br>Pro Asn Ala Glu Gly Thr Ser Leu Tyr Ile Arg Pro Phe Ile Ile Ala<br>        130                    135                   140 | 432 |
| acc gag cct ttc ctt ggt gtt gcg gca tct cat acg tat aag ctc ttg<br>Thr Glu Pro Phe Leu Gly Val Ala Ala Ser His Thr Tyr Lys Leu Leu<br>145                  150                    155                160 | 480 |
| atc att ctt tct ccg gtc ggc tct tat tac aaa gaa ggc att aag ccg<br>Ile Ile Leu Ser Pro Val Gly Ser Tyr Tyr Lys Glu Gly Ile Lys Pro<br>                 165                 170                 175 | 528 |
| gtc aaa atc gct gtt gaa agt gaa ttt gtc cgt gcg gta aaa ggc gga<br>Val Lys Ile Ala Val Glu Ser Glu Phe Val Arg Ala Val Lys Gly Gly<br>        180                    185                   190 | 576 |
| aca gga aat gcc aaa acc gca gga aac tat gct tca agc tta aaa gcg<br>Thr Gly Asn Ala Lys Thr Ala Gly Asn Tyr Ala Ser Ser Leu Lys Ala | 624 |

```
                195                  200                       205
cag cag gta gcc gaa gag aaa gga ttt tct caa gta ctc tgg ctg gac       672
Gln Gln Val Ala Glu Glu Lys Gly Phe Ser Gln Val Leu Trp Leu Asp
        210                 215                 220 ggc att gag aag aaa tac atc gaa gaa gtc gga agc atg aac atc ttc       720
Gly Ile Glu Lys Lys Tyr Ile Glu Glu Val Gly Ser Met Asn Ile Phe
225                 230                 235                 240 ttc aaa atc aac ggt gaa atc gta aca ccg atg ctg aac ggg agc atc       768
Phe Lys Ile Asn Gly Glu Ile Val Thr Pro Met Leu Asn Gly Ser Ile
                245                 250                 255 ctg gaa ggc att acg cgc aat tca gtc atc gcc ttg ctt aag cat tgg       816
Leu Glu Gly Ile Thr Arg Asn Ser Val Ile Ala Leu Leu Lys His Trp
        260                 265                 270 ggc ctt caa gtt tca gaa cga aaa att gcg atc gat gag gtc atc caa       864
Gly Leu Gln Val Ser Glu Arg Lys Ile Ala Ile Asp Glu Val Ile Gln
    275                 280                 285 gcc cat aaa gac ggc atc ctg gaa gaa gcc ttc gga aca ggt aca gca       912
Ala His Lys Asp Gly Ile Leu Glu Glu Ala Phe Gly Thr Gly Thr Ala
290                 295                 300 gct gtt att tcc cca gtc ggc gag ctg atc tgg cag gat gaa aca ctt       960
Ala Val Ile Ser Pro Val Gly Glu Leu Ile Trp Gln Asp Glu Thr Leu
305                 310                 315                 320 tcg atc aac aac ggt gaa aca gga gaa atc gca aaa aaa cta tat gac      1008
Ser Ile Asn Asn Gly Glu Thr Gly Glu Ile Ala Lys Lys Leu Tyr Asp
                325                 330                 335 acg att aca ggc att caa aaa ggc gct gtc gca gac gaa ttc gga tgg      1056
Thr Ile Thr Gly Ile Gln Lys Gly Ala Val Ala Asp Glu Phe Gly Trp
        340                 345                 350 acg acc gaa gtc gca gcg ctg act gaa agc aag taa                      1092
Thr Thr Glu Val Ala Ala Leu Thr Glu Ser Lys
    355                 360
```

<210> SEQ ID NO 63
<211> LENGTH: 363
<212> TYPE: PRT
<213> ORGANISM: Bacillus subtilis

<400> SEQUENCE: 63

```
Met Thr Lys Gln Thr Ile Arg Val Glu Leu Thr Ser Thr Lys Lys Pro
1               5                   10                  15

Lys Pro Asp Pro Asn Gln Leu Ser Phe Gly Arg Val Phe Thr Asp His
            20                  25                  30

Met Phe Val Met Asp Tyr Ala Ala Asp Lys Gly Trp Tyr Asp Pro Arg
        35                  40                  45

Ile Ile Pro Tyr Gln Pro Leu Ser Met Asp Pro Thr Ala Met Val Tyr
    50                  55                  60

His Tyr Gly Gln Thr Val Phe Glu Gly Leu Lys Ala Tyr Val Ser Glu
65                  70                  75                  80

Asp Asp His Val Leu Leu Phe Arg Pro Glu Lys Asn Met Glu Arg Leu
                85                  90                  95

Asn Gln Ser Asn Asp Arg Leu Cys Ile Pro Gln Ile Asp Glu Glu Gln
            100                 105                 110

Val Leu Glu Gly Leu Lys Gln Leu Val Ala Ile Asp Lys Asp Trp Ile
        115                 120                 125

Pro Asn Ala Glu Gly Thr Ser Leu Tyr Ile Arg Pro Phe Ile Ile Ala
    130                 135                 140

Thr Glu Pro Phe Leu Gly Val Ala Ala Ser His Thr Tyr Lys Leu Leu
145                 150                 155                 160
```

```
Ile Ile Leu Ser Pro Val Gly Ser Tyr Tyr Lys Glu Gly Ile Lys Pro
            165                 170                 175

Val Lys Ile Ala Val Glu Ser Glu Phe Val Arg Ala Val Lys Gly Gly
        180                 185                 190

Thr Gly Asn Ala Lys Thr Ala Gly Asn Tyr Ala Ser Ser Leu Lys Ala
    195                 200                 205

Gln Gln Val Ala Glu Glu Lys Gly Phe Ser Gln Val Leu Trp Leu Asp
210                 215                 220

Gly Ile Glu Lys Lys Tyr Ile Glu Val Gly Ser Met Asn Ile Phe
225                 230                 235                 240

Phe Lys Ile Asn Gly Glu Ile Val Thr Pro Met Leu Asn Gly Ser Ile
                245                 250                 255

Leu Glu Gly Ile Thr Arg Asn Ser Val Ile Ala Leu Leu Lys His Trp
            260                 265                 270

Gly Leu Gln Val Ser Glu Arg Lys Ile Ala Ile Asp Glu Val Ile Gln
        275                 280                 285

Ala His Lys Asp Gly Ile Leu Glu Glu Ala Phe Gly Thr Gly Thr Ala
    290                 295                 300

Ala Val Ile Ser Pro Val Gly Glu Leu Ile Trp Gln Asp Glu Thr Leu
305                 310                 315                 320

Ser Ile Asn Asn Gly Glu Thr Gly Glu Ile Ala Lys Lys Leu Tyr Asp
                325                 330                 335

Thr Ile Thr Gly Ile Gln Lys Gly Ala Val Ala Asp Glu Phe Gly Trp
            340                 345                 350

Thr Thr Glu Val Ala Ala Leu Thr Glu Ser Lys
        355                 360

<210> SEQ ID NO 64
<211> LENGTH: 1071
<212> TYPE: DNA
<213> ORGANISM: Bacillus subtilis
<220> FEATURE:
<221> NAME/KEY: CDS
<222> LOCATION: (1)..(1068)

<400> SEQUENCE: 64 ttg aat aag ctt att gaa cga gaa aaa act gta tat tat aag gaa aag      48
Met Asn Lys Leu Ile Glu Arg Glu Lys Thr Val Tyr Tyr Lys Glu Lys
 1               5                  10                  15 ccc gac ccg tct tcc ttg ggg ttt gga caa tat ttt aca gat tat atg     96
Pro Asp Pro Ser Ser Leu Gly Phe Gly Gln Tyr Phe Thr Asp Tyr Met
            20                  25                  30 ttt gtg atg gac tac gaa gag ggg att gga tgg cat cat ccg aga att    144
Phe Val Met Asp Tyr Glu Glu Gly Ile Gly Trp His His Pro Arg Ile
        35                  40                  45 gcg ccg tac gca ccg ctt acg ctt gat ccg tct tca tct gtt ttt cat    192
Ala Pro Tyr Ala Pro Leu Thr Leu Asp Pro Ser Ser Ser Val Phe His
    50                  55                  60 tac ggc cag gct gtt ttt gaa gga tta aaa gca tac aga aca gac gac    240
Tyr Gly Gln Ala Val Phe Glu Gly Leu Lys Ala Tyr Arg Thr Asp Asp
65                  70                  75                  80 ggc agg gtg ctg ctg ttc cgt ccg gat caa aat atc aaa cgg ctg aac    288
Gly Arg Val Leu Leu Phe Arg Pro Asp Gln Asn Ile Lys Arg Leu Asn
                85                  90                  95 aga tcg tgt gag cgc atg agc atg ccc cct tta gac gaa gag ctg gtg    336
Arg Ser Cys Glu Arg Met Ser Met Pro Pro Leu Asp Glu Glu Leu Val
            100                 105                 110 ctt gag gca ttg acg caa tta gtt gag ctg gag aaa gat tgg gtt cca    384
Leu Glu Ala Leu Thr Gln Leu Val Glu Leu Glu Lys Asp Trp Val Pro
```

```
              115                 120                 125
aag gaa aaa gga acg tca ctg tat att cgt cct ttt gtc att gcc aca        432
Lys Glu Lys Gly Thr Ser Leu Tyr Ile Arg Pro Phe Val Ile Ala Thr
130                 135                 140 gaa ccg agt ctc ggt gtg aag gca tcc agg agc tat aca ttt atg atc        480
Glu Pro Ser Leu Gly Val Lys Ala Ser Arg Ser Tyr Thr Phe Met Ile
145                 150                 155                 160 gtg ctt tcg cct gtc ggc tcc tat tat ggc gac gat cag ctg aag ccg        528
Val Leu Ser Pro Val Gly Ser Tyr Tyr Gly Asp Asp Gln Leu Lys Pro
                165                 170                 175 gtt aga atc tat gtc gaa gat gag tat gtg agg gcg gtc aac gga gga        576
Val Arg Ile Tyr Val Glu Asp Glu Tyr Val Arg Ala Val Asn Gly Gly
            180                 185                 190 gtc ggg ttt gca aaa acg gct gga aac tat gcc gcc agt ctt cag gca        624
Val Gly Phe Ala Lys Thr Ala Gly Asn Tyr Ala Ala Ser Leu Gln Ala
        195                 200                 205 cag cgg aaa gcg aat gaa ctg ggc tat gac cag gta ctg tgg ctg gac        672
Gln Arg Lys Ala Asn Glu Leu Gly Tyr Asp Gln Val Leu Trp Leu Asp
    210                 215                 220 gcc atc gaa aag aaa tat gtg gaa gaa gta ggg agc atg aac atc ttt        720
Ala Ile Glu Lys Lys Tyr Val Glu Glu Val Gly Ser Met Asn Ile Phe
225                 230                 235                 240 ttc gtc ata aac ggg gaa gct gtc aca cct gct tta agc gga agc att        768
Phe Val Ile Asn Gly Glu Ala Val Thr Pro Ala Leu Ser Gly Ser Ile
                245                 250                 255 tta agc ggg gtt aca cgt gcg tct gcg att gaa ttg att cga agc tgg        816
Leu Ser Gly Val Thr Arg Ala Ser Ala Ile Glu Leu Ile Arg Ser Trp
            260                 265                 270 ggc att ccg gtt cgt gaa gag aga ata tcg att gat gag gtg tat gcg        864
Gly Ile Pro Val Arg Glu Glu Arg Ile Ser Ile Asp Glu Val Tyr Ala
        275                 280                 285 gcc tct gca cgc gga gaa ttg aca gag gtc ttt ggc aca ggc acg gca        912
Ala Ser Ala Arg Gly Glu Leu Thr Glu Val Phe Gly Thr Gly Thr Ala
    290                 295                 300 gca gtc gtt acg cct gtc ggt gaa ctc aac atc cat gga aaa acg gtg        960
Ala Val Val Thr Pro Val Gly Glu Leu Asn Ile His Gly Lys Thr Val
305                 310                 315                 320 att gta ggc gac ggg caa atc ggg gac ctc tcg aaa aag ctg tat gaa       1008
Ile Val Gly Asp Gly Gln Ile Gly Asp Leu Ser Lys Lys Leu Tyr Glu
                325                 330                 335 acg ata aca gat att cag ctt ggc aag gta aaa ggc ccg ttt aac tgg       1056
Thr Ile Thr Asp Ile Gln Leu Gly Lys Val Lys Gly Pro Phe Asn Trp
            340                 345                 350 aca gtg gaa gtg tga                                                    1071
Thr Val Glu Val
        355

<210> SEQ ID NO 65
<211> LENGTH: 356
<212> TYPE: PRT
<213> ORGANISM: Bacillus subtilis

<400> SEQUENCE: 65

Met Asn Lys Leu Ile Glu Arg Glu Lys Thr Val Tyr Tyr Lys Glu Lys
 1               5                  10                  15

Pro Asp Pro Ser Ser Leu Gly Phe Gly Gln Tyr Phe Thr Asp Tyr Met
            20                  25                  30

Phe Val Met Asp Tyr Glu Glu Gly Ile Gly Trp His His Pro Arg Ile
        35                  40                  45

Ala Pro Tyr Ala Pro Leu Thr Leu Asp Pro Ser Ser Ser Val Phe His
```

```
                50                  55                  60
Tyr Gly Gln Ala Val Phe Glu Gly Leu Lys Ala Tyr Arg Thr Asp Asp
 65                  70                  75                  80

Gly Arg Val Leu Leu Phe Arg Pro Asp Gln Asn Ile Lys Arg Leu Asn
                 85                  90                  95

Arg Ser Cys Glu Arg Met Ser Met Pro Pro Leu Asp Glu Glu Leu Val
            100                 105                 110

Leu Glu Ala Leu Thr Gln Leu Val Glu Leu Glu Lys Asp Trp Val Pro
        115                 120                 125

Lys Glu Lys Gly Thr Ser Leu Tyr Ile Arg Pro Phe Val Ile Ala Thr
130                 135                 140

Glu Pro Ser Leu Gly Val Lys Ala Ser Arg Ser Tyr Thr Phe Met Ile
145                 150                 155                 160

Val Leu Ser Pro Val Gly Ser Tyr Gly Asp Asp Gln Leu Lys Pro
                165                 170                 175

Val Arg Ile Tyr Val Glu Asp Glu Tyr Val Arg Ala Val Asn Gly Gly
            180                 185                 190

Val Gly Phe Ala Lys Thr Ala Gly Asn Tyr Ala Ala Ser Leu Gln Ala
        195                 200                 205

Gln Arg Lys Ala Asn Glu Leu Gly Tyr Asp Gln Val Leu Trp Leu Asp
210                 215                 220

Ala Ile Glu Lys Lys Tyr Val Glu Val Gly Ser Met Asn Ile Phe
225                 230                 235                 240

Phe Val Ile Asn Gly Glu Ala Val Thr Pro Ala Leu Ser Gly Ser Ile
                245                 250                 255

Leu Ser Gly Val Thr Arg Ala Ser Ala Ile Glu Leu Ile Arg Ser Trp
            260                 265                 270

Gly Ile Pro Val Arg Glu Glu Arg Ile Ser Ile Asp Glu Val Tyr Ala
        275                 280                 285

Ala Ser Ala Arg Gly Glu Leu Thr Glu Val Phe Gly Thr Gly Thr Ala
        290                 295                 300

Ala Val Val Thr Pro Val Gly Glu Leu Asn Ile His Gly Lys Thr Val
305                 310                 315                 320

Ile Val Gly Asp Gly Gln Ile Gly Asp Leu Ser Lys Lys Leu Tyr Glu
                325                 330                 335

Thr Ile Thr Asp Ile Gln Leu Gly Lys Val Lys Gly Pro Phe Asn Trp
            340                 345                 350

Thr Val Glu Val
        355

<210> SEQ ID NO 66
<211> LENGTH: 1428
<212> TYPE: DNA
<213> ORGANISM: Bacillus subtilis
<220> FEATURE:
<221> NAME/KEY: CDS
<222> LOCATION: (1)..(1425)

<400> SEQUENCE: 66 atg tta aac ggc caa aaa gaa tat cgc gtg gaa aaa gac ttc ctt ggg      48
Met Leu Asn Gly Gln Lys Glu Tyr Arg Val Glu Lys Asp Phe Leu Gly
 1               5                  10                  15 gaa aaa caa att gaa gca gat gtt tat tac gga att cag acg ctc cgt      96
Glu Lys Gln Ile Glu Ala Asp Val Tyr Tyr Gly Ile Gln Thr Leu Arg
            20                  25                  30 gct tct gaa aat ttt ccg atc aca gga tac aaa atc cat gag gaa atg     144
Ala Ser Glu Asn Phe Pro Ile Thr Gly Tyr Lys Ile His Glu Glu Met
```

```
              35                  40                  45
att aac gca ctg gcg att gtg aaa aaa gct gcg gct ctt gcc aac atg      192
Ile Asn Ala Leu Ala Ile Val Lys Lys Ala Ala Ala Leu Ala Asn Met
 50                  55                  60 gac gtg aaa cgg ctg tat gaa gga att ggc caa gct atc gta caa gcc      240
Asp Val Lys Arg Leu Tyr Glu Gly Ile Gly Gln Ala Ile Val Gln Ala
 65                  70                  75                  80 gct gac gag att ctg gaa ggc aag tgg cac gat cag ttt atc gtc gat      288
Ala Asp Glu Ile Leu Glu Gly Lys Trp His Asp Gln Phe Ile Val Asp
                 85                  90                  95 ccg att cag ggc ggt gcc gga act tct atg aac atg aac gcg aat gag      336
Pro Ile Gln Gly Gly Ala Gly Thr Ser Met Asn Met Asn Ala Asn Glu
            100                 105                 110 gtt atc gga aac cgg gcg ctt gaa atc atg gga cat aaa aag gga gat      384
Val Ile Gly Asn Arg Ala Leu Glu Ile Met Gly His Lys Lys Gly Asp
        115                 120                 125 tat atc cat tta agt cca aac aca cat gtg aac atg tca cag tct cag      432
Tyr Ile His Leu Ser Pro Asn Thr His Val Asn Met Ser Gln Ser Gln
130                 135                 140 aac gat gtg ttc ccg act gct atc cat att tcc aca ttg aag ctc tta      480
Asn Asp Val Phe Pro Thr Ala Ile His Ile Ser Thr Leu Lys Leu Leu
145                 150                 155                 160 gaa aaa ctg ctg aaa aca atg gaa gat atg cat agt gtg ttt aaa caa      528
Glu Lys Leu Leu Lys Thr Met Glu Asp Met His Ser Val Phe Lys Gln
                165                 170                 175 aaa gca cag gag ttt cac tct gtt att aaa atg ggc cgg aca cac ctt      576
Lys Ala Gln Glu Phe His Ser Val Ile Lys Met Gly Arg Thr His Leu
            180                 185                 190 caa gat gcg gtt ccg atc cgt ctt ggc cag gaa ttc gaa gct tac agc      624
Gln Asp Ala Val Pro Ile Arg Leu Gly Gln Glu Phe Glu Ala Tyr Ser
        195                 200                 205 cgt gtt ctc gag cgt gat atc aaa cga atc aag caa tcg cgc cag cac      672
Arg Val Leu Glu Arg Asp Ile Lys Arg Ile Lys Gln Ser Arg Gln His
210                 215                 220 ctg tat gaa gtc aac atg ggc gca act gct gtt ggt aca ggg ctg aac      720
Leu Tyr Glu Val Asn Met Gly Ala Thr Ala Val Gly Thr Gly Leu Asn
225                 230                 235                 240 gct gat cct gaa tat atc aaa cag gta gta aag cac ctt gct gat att      768
Ala Asp Pro Glu Tyr Ile Lys Gln Val Val Lys His Leu Ala Asp Ile
                245                 250                 255 agc ggg ctt cct ctt gtc ggc gct gat cat ctt gtt gat gcg aca caa      816
Ser Gly Leu Pro Leu Val Gly Ala Asp His Leu Val Asp Ala Thr Gln
            260                 265                 270 aat aca gat gcc tat aca gag gta tca gct tca tta aaa gtc tgc atg      864
Asn Thr Asp Ala Tyr Thr Glu Val Ser Ala Ser Leu Lys Val Cys Met
        275                 280                 285 atg aac atg tcg aag atc gca aac gac ctg cgc tta atg gcg tcg gga      912
Met Asn Met Ser Lys Ile Ala Asn Asp Leu Arg Leu Met Ala Ser Gly
290                 295                 300 ccg cgc gcc gga ctt gcg gaa att tct ctg cct gca cgt cag ccg ggt      960
Pro Arg Ala Gly Leu Ala Glu Ile Ser Leu Pro Ala Arg Gln Pro Gly
305                 310                 315                 320 tca tct att atg ccg ggg aaa gtc aat ccg gtt atg gcg gag ctg atc     1008
Ser Ser Ile Met Pro Gly Lys Val Asn Pro Val Met Ala Glu Leu Ile
                325                 330                 335 aac caa att gcg ttc cag gtt atc gga aat gac aat aca atc tgc ctt     1056
Asn Gln Ile Ala Phe Gln Val Ile Gly Asn Asp Asn Thr Ile Cys Leu
            340                 345                 350 gct tca gaa gcc ggc cag ctt gag ttg aac gtc atg gag ccc gtg ctt     1104
Ala Ser Glu Ala Gly Gln Leu Glu Leu Asn Val Met Glu Pro Val Leu
```

```
                  355                 360                 365
gtc ttt aat ttg ctt caa tcc atc agc atc atg aac aac ggc ttc cgt      1152
Val Phe Asn Leu Leu Gln Ser Ile Ser Ile Met Asn Asn Gly Phe Arg
370                 375                 380 tcg ttc act gac aac tgc tta aaa ggc att gaa gcc aac gaa aag cgt      1200
Ser Phe Thr Asp Asn Cys Leu Lys Gly Ile Glu Ala Asn Glu Lys Arg
385                 390                 395                 400 atg aag caa tac gta gaa aaa agc gca ggc gtg atc aca gct gtc aat      1248
Met Lys Gln Tyr Val Glu Lys Ser Ala Gly Val Ile Thr Ala Val Asn
                405                 410                 415 ccg cat ctt ggg tat gaa gcg gca gct aga att gcc agg gaa gca att      1296
Pro His Leu Gly Tyr Glu Ala Ala Ala Arg Ile Ala Arg Glu Ala Ile
            420                 425                 430 atg aca ggg caa tct gtc cgg gat ctt tgt ctg cag cat gat gtg ctg      1344
Met Thr Gly Gln Ser Val Arg Asp Leu Cys Leu Gln His Asp Val Leu
        435                 440                 445 act gaa gaa gaa ttg gat att att tta aac cca tat gag atg acc aaa      1392
Thr Glu Glu Glu Leu Asp Ile Ile Leu Asn Pro Tyr Glu Met Thr Lys
    450                 455                 460 cca ggt atc gca ggg aaa gaa cta tta gaa aaa taa                      1428
Pro Gly Ile Ala Gly Lys Glu Leu Leu Glu Lys
465                 470                 475

<210> SEQ ID NO 67
<211> LENGTH: 475
<212> TYPE: PRT
<213> ORGANISM: Bacillus subtilis

<400> SEQUENCE: 67

Met Leu Asn Gly Gln Lys Glu Tyr Arg Val Glu Lys Asp Phe Leu Gly
 1               5                  10                  15

Glu Lys Gln Ile Glu Ala Asp Val Tyr Tyr Gly Ile Gln Thr Leu Arg
            20                  25                  30

Ala Ser Glu Asn Phe Pro Ile Thr Gly Tyr Lys Ile His Glu Glu Met
        35                  40                  45

Ile Asn Ala Leu Ala Ile Val Lys Lys Ala Ala Leu Ala Asn Met
    50                  55                  60

Asp Val Lys Arg Leu Tyr Glu Gly Ile Gly Gln Ala Ile Val Gln Ala
65                  70                  75                  80

Ala Asp Glu Ile Leu Glu Gly Lys Trp His Asp Gln Phe Ile Val Asp
                85                  90                  95

Pro Ile Gln Gly Gly Ala Gly Thr Ser Met Asn Met Asn Ala Asn Glu
            100                 105                 110

Val Ile Gly Asn Arg Ala Leu Glu Ile Met Gly His Lys Lys Gly Asp
        115                 120                 125

Tyr Ile His Leu Ser Pro Asn Thr His Val Asn Met Ser Gln Ser Gln
    130                 135                 140

Asn Asp Val Phe Pro Thr Ala Ile His Ile Ser Thr Leu Lys Leu Leu
145                 150                 155                 160

Glu Lys Leu Leu Lys Thr Met Glu Asp Met His Ser Val Phe Lys Gln
                165                 170                 175

Lys Ala Gln Glu Phe His Ser Val Ile Lys Met Gly Arg Thr His Leu
            180                 185                 190

Gln Asp Ala Val Pro Ile Arg Leu Gly Gln Glu Phe Glu Ala Tyr Ser
        195                 200                 205

Arg Val Leu Glu Arg Asp Ile Lys Arg Ile Lys Gln Ser Arg Gln His
    210                 215                 220
```

| | | | | | | | | | | | | | | | |
|---|---|---|---|---|---|---|---|---|---|---|---|---|---|---|---|
| Leu | Tyr | Glu | Val | Asn | Met | Gly | Ala | Thr | Ala | Val | Gly | Thr | Gly | Leu | Asn |
| 225 | | | | | 230 | | | | | 235 | | | | | 240 |
| Ala | Asp | Pro | Glu | Tyr | Ile | Lys | Gln | Val | Val | Lys | His | Leu | Ala | Asp | Ile |
| | | | 245 | | | | | 250 | | | | | 255 | | |
| Ser | Gly | Leu | Pro | Leu | Val | Gly | Ala | Asp | His | Leu | Val | Asp | Ala | Thr | Gln |
| | | | 260 | | | | | 265 | | | | | 270 | | |
| Asn | Thr | Asp | Ala | Tyr | Thr | Glu | Val | Ser | Ala | Ser | Leu | Lys | Val | Cys | Met |
| | | 275 | | | | | 280 | | | | | 285 | | | |
| Met | Asn | Met | Ser | Lys | Ile | Ala | Asn | Asp | Leu | Arg | Leu | Met | Ala | Ser | Gly |
| | 290 | | | | | 295 | | | | | 300 | | | | |
| Pro | Arg | Ala | Gly | Leu | Ala | Glu | Ile | Ser | Leu | Pro | Ala | Arg | Gln | Pro | Gly |
| 305 | | | | | 310 | | | | | 315 | | | | | 320 |
| Ser | Ser | Ile | Met | Pro | Gly | Lys | Val | Asn | Pro | Val | Met | Ala | Glu | Leu | Ile |
| | | | | 325 | | | | | 330 | | | | | 335 | |
| Asn | Gln | Ile | Ala | Phe | Gln | Val | Ile | Gly | Asn | Asp | Asn | Thr | Ile | Cys | Leu |
| | | | 340 | | | | | 345 | | | | | 350 | | |
| Ala | Ser | Glu | Ala | Gly | Gln | Leu | Glu | Leu | Asn | Val | Met | Glu | Pro | Val | Leu |
| | | 355 | | | | | 360 | | | | | 365 | | | |
| Val | Phe | Asn | Leu | Leu | Gln | Ser | Ile | Ser | Ile | Met | Asn | Asn | Gly | Phe | Arg |
| | 370 | | | | | 375 | | | | | 380 | | | | |
| Ser | Phe | Thr | Asp | Asn | Cys | Leu | Lys | Gly | Ile | Glu | Ala | Asn | Glu | Lys | Arg |
| 385 | | | | | 390 | | | | | 395 | | | | | 400 |
| Met | Lys | Gln | Tyr | Val | Glu | Lys | Ser | Ala | Gly | Val | Ile | Thr | Ala | Val | Asn |
| | | | | 405 | | | | | 410 | | | | | 415 | |
| Pro | His | Leu | Gly | Tyr | Glu | Ala | Ala | Arg | Ile | Ala | Arg | Glu | Ala | Ile | |
| | | | 420 | | | | | 425 | | | | | 430 | | |
| Met | Thr | Gly | Gln | Ser | Val | Arg | Asp | Leu | Cys | Leu | Gln | His | Asp | Val | Leu |
| | | 435 | | | | | 440 | | | | | 445 | | | |
| Thr | Glu | Glu | Glu | Leu | Asp | Ile | Ile | Leu | Asn | Pro | Tyr | Glu | Met | Thr | Lys |
| | 450 | | | | | 455 | | | | | 460 | | | | |
| Pro | Gly | Ile | Ala | Gly | Lys | Glu | Leu | Leu | Glu | Lys | | | | | |
| 465 | | | | 470 | | | | | 475 | | | | | | |

<210> SEQ ID NO 68
<211> LENGTH: 768
<212> TYPE: DNA
<213> ORGANISM: Bacillus subtilis
<220> FEATURE:
<221> NAME/KEY: CDS
<222> LOCATION: (1)..(765)

<400> SEQUENCE: 68

| atg | aaa | cga | gaa | agc | aac | att | caa | gtg | ctc | agc | cgt | ggt | caa | aaa | gat | 48 |
|---|---|---|---|---|---|---|---|---|---|---|---|---|---|---|---|---|
| Met | Lys | Arg | Glu | Ser | Asn | Ile | Gln | Val | Leu | Ser | Arg | Gly | Gln | Lys | Asp | |
| 1 | | | | 5 | | | | | 10 | | | | | 15 | | |

| cag | cct | gtg | agc | cag | att | tat | caa | gta | tca | aca | atg | act | tct | cta | tta | 96 |
|---|---|---|---|---|---|---|---|---|---|---|---|---|---|---|---|---|
| Gln | Pro | Val | Ser | Gln | Ile | Tyr | Gln | Val | Ser | Thr | Met | Thr | Ser | Leu | Leu | |
| | | | 20 | | | | | 25 | | | | | 30 | | | |

| gac | gga | gta | tat | gac | gga | gat | ttt | gaa | ctg | tca | gag | att | ccg | aaa | tat | 144 |
|---|---|---|---|---|---|---|---|---|---|---|---|---|---|---|---|---|
| Asp | Gly | Val | Tyr | Asp | Gly | Asp | Phe | Glu | Leu | Ser | Glu | Ile | Pro | Lys | Tyr | |
| | | 35 | | | | | 40 | | | | | 45 | | | | |

| gga | gac | ttc | ggt | atc | gga | acc | ttt | aac | aag | ctt | gac | gga | gag | ctg | att | 192 |
|---|---|---|---|---|---|---|---|---|---|---|---|---|---|---|---|---|
| Gly | Asp | Phe | Gly | Ile | Gly | Thr | Phe | Asn | Lys | Leu | Asp | Gly | Glu | Leu | Ile | |
| | 50 | | | | | 55 | | | | | 60 | | | | | |

| ggg | ttt | gac | ggc | gaa | ttt | tac | cgt | ctt | cgc | tca | gac | gga | acc | gcg | aca | 240 |
|---|---|---|---|---|---|---|---|---|---|---|---|---|---|---|---|---|
| Gly | Phe | Asp | Gly | Glu | Phe | Tyr | Arg | Leu | Arg | Ser | Asp | Gly | Thr | Ala | Thr | |
| 65 | | | | | 70 | | | | | 75 | | | | | 80 | |

| ccg | gtc | caa | aat | gga | gac | cgt | tca | ccg | ttc | tgt | tca | ttt | acg | ttc | ttt | 288 |
|---|---|---|---|---|---|---|---|---|---|---|---|---|---|---|---|---|

```
Pro Val Gln Asn Gly Asp Arg Ser Pro Phe Cys Ser Phe Thr Phe Phe
            85                  90                  95 aca ccg gac atg acg cac aaa att gat gcg aaa atg aca cgc gaa gac       336
Thr Pro Asp Met Thr His Lys Ile Asp Ala Lys Met Thr Arg Glu Asp
            100                 105                 110 ttt gaa aaa gag atc aac agc atg ctg cca agc aga aac tta ttt tat       384
Phe Glu Lys Glu Ile Asn Ser Met Leu Pro Ser Arg Asn Leu Phe Tyr
            115                 120                 125 gca att cgc att gac gga ttg ttt aaa aag gtg cag aca aga aca gta       432
Ala Ile Arg Ile Asp Gly Leu Phe Lys Lys Val Gln Thr Arg Thr Val
        130                 135                 140 gaa ctt caa gaa aaa cct tac gtg cca atg gtt gaa gcg gtc aaa aca       480
Glu Leu Gln Glu Lys Pro Tyr Val Pro Met Val Glu Ala Val Lys Thr
145                 150                 155                 160 cag ccg att ttc aac ttc gac aac gtg aga gga acg att gta ggt ttc       528
Gln Pro Ile Phe Asn Phe Asp Asn Val Arg Gly Thr Ile Val Gly Phe
                165                 170                 175 ttg aca cca gct tat gca aac gga atc gcc gtt tct ggc tat cac ctg       576
Leu Thr Pro Ala Tyr Ala Asn Gly Ile Ala Val Ser Gly Tyr His Leu
            180                 185                 190 cac ttc att gac gaa gga cgc aat tca ggc gga cac gtt ttt gac tat       624
His Phe Ile Asp Glu Gly Arg Asn Ser Gly Gly His Val Phe Asp Tyr
            195                 200                 205 gtg ctt gag gat tgc acg gtt acg att tct caa aaa atg aac atg aat       672
Val Leu Glu Asp Cys Thr Val Thr Ile Ser Gln Lys Met Asn Met Asn
210                 215                 220 ctc aga ctt ccg aac aca gcg gat ttc ttt aat gcg aat ctg gat aac       720
Leu Arg Leu Pro Asn Thr Ala Asp Phe Phe Asn Ala Asn Leu Asp Asn
225                 230                 235                 240 cct gat ttt gcg aaa gat atc gaa aca act gaa gga agc cct gaa taa       768
Pro Asp Phe Ala Lys Asp Ile Glu Thr Thr Glu Gly Ser Pro Glu
                245                 250                 255

<210> SEQ ID NO 69
<211> LENGTH: 255
<212> TYPE: PRT
<213> ORGANISM: Bacillus subtilis

<400> SEQUENCE: 69

Met Lys Arg Glu Ser Asn Ile Gln Val Leu Ser Arg Gly Gln Lys Asp
1               5                   10                  15

Gln Pro Val Ser Gln Ile Tyr Gln Val Ser Thr Met Thr Ser Leu Leu
            20                  25                  30

Asp Gly Val Tyr Asp Gly Asp Phe Glu Leu Ser Glu Ile Pro Lys Tyr
        35                  40                  45

Gly Asp Phe Gly Ile Gly Thr Phe Asn Lys Leu Asp Gly Glu Leu Ile
    50                  55                  60

Gly Phe Asp Gly Glu Phe Tyr Arg Leu Arg Ser Asp Gly Thr Ala Thr
65                  70                  75                  80

Pro Val Gln Asn Gly Asp Arg Ser Pro Phe Cys Ser Phe Thr Phe Phe
                85                  90                  95

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160
```

```
Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
    210                 215                 220

Leu Arg Leu Pro Asn Thr Ala Asp Phe Phe Asn Ala Asn Leu Asp Asn
225                 230                 235                 240

Pro Asp Phe Ala Lys Asp Ile Glu Thr Thr Glu Gly Ser Pro Glu
                245                 250                 255

<210> SEQ ID NO 70
<211> LENGTH: 1254
<212> TYPE: DNA
<213> ORGANISM: Escherichia coli
<220> FEATURE:
<221> NAME/KEY: CDS
<222> LOCATION: (1)..(1251)

<400> SEQUENCE: 70
```

| | | | | | | | | | | | | | | | | |
|---|---|---|---|---|---|---|---|---|---|---|---|---|---|---|---|---|
| atg | aca | ttc | tcc | ctt | ttt | ggt | gac | aaa | ttt | acc | cgc | cac | tcc | ggc | att | 48 |
| Met | Thr | Phe | Ser | Leu | Phe | Gly | Asp | Lys | Phe | Thr | Arg | His | Ser | Gly | Ile | |
| 1 | | | | 5 | | | | | 10 | | | | | 15 | | |
| acg | ctg | ttg | atg | gaa | gat | ctg | aac | gac | ggt | tta | cgc | acg | cct | ggc | gcg | 96 |
| Thr | Leu | Leu | Met | Glu | Asp | Leu | Asn | Asp | Gly | Leu | Arg | Thr | Pro | Gly | Ala | |
| | | | 20 | | | | | 25 | | | | | 30 | | | |
| att | atg | ctc | ggc | ggc | ggt | aat | ccg | gcg | cag | atc | ccg | gaa | atg | cag | gac | 144 |
| Ile | Met | Leu | Gly | Gly | Gly | Asn | Pro | Ala | Gln | Ile | Pro | Glu | Met | Gln | Asp | |
| | | | 35 | | | | | 40 | | | | | 45 | | | |
| tac | ttc | cag | acg | cta | ctg | acc | gac | atg | ctg | gaa | agt | ggc | aaa | gcg | act | 192 |
| Tyr | Phe | Gln | Thr | Leu | Leu | Thr | Asp | Met | Leu | Glu | Ser | Gly | Lys | Ala | Thr | |
| | 50 | | | | | 55 | | | | | 60 | | | | | |
| gat | gca | ctg | tgt | aac | tac | gac | ggt | cca | cag | ggg | aaa | acg | gag | cta | ctc | 240 |
| Asp | Ala | Leu | Cys | Asn | Tyr | Asp | Gly | Pro | Gln | Gly | Lys | Thr | Glu | Leu | Leu | |
| 65 | | | | | 70 | | | | | 75 | | | | | 80 | |
| aca | ctg | ctt | gcc | gga | atg | ctg | cgc | gag | aag | ttg | ggt | tgg | gat | atc | gaa | 288 |
| Thr | Leu | Leu | Ala | Gly | Met | Leu | Arg | Glu | Lys | Leu | Gly | Trp | Asp | Ile | Glu | |
| | | | | 85 | | | | | 90 | | | | | 95 | | |
| cca | cag | aat | att | gca | cta | aca | aac | ggc | agc | cag | agc | gcg | ttt | ttc | tac | 336 |
| Pro | Gln | Asn | Ile | Ala | Leu | Thr | Asn | Gly | Ser | Gln | Ser | Ala | Phe | Phe | Tyr | |
| | | | | 100 | | | | | 105 | | | | | 110 | | |
| tta | ttt | aac | ctg | ttt | gcc | gga | cgc | cgt | gcc | gat | ggt | cgg | gtc | aaa | aaa | 384 |
| Leu | Phe | Asn | Leu | Phe | Ala | Gly | Arg | Arg | Ala | Asp | Gly | Arg | Val | Lys | Lys | |
| | | | 115 | | | | | 120 | | | | | 125 | | | |
| gtg | ctg | ttc | ccg | ctt | gca | ccg | gaa | tac | att | ggc | tat | gct | gac | gcc | gga | 432 |
| Val | Leu | Phe | Pro | Leu | Ala | Pro | Glu | Tyr | Ile | Gly | Tyr | Ala | Asp | Ala | Gly | |
| | | 130 | | | | | 135 | | | | | 140 | | | | |
| ctg | gaa | gaa | gat | ctg | ttt | gtc | tct | gcg | cgt | ccg | aat | att | gaa | ctg | ctg | 480 |
| Leu | Glu | Glu | Asp | Leu | Phe | Val | Ser | Ala | Arg | Pro | Asn | Ile | Glu | Leu | Leu | |
| 145 | | | | | 150 | | | | | 155 | | | | | 160 | |
| ccg | gaa | ggc | cag | ttt | aaa | tac | cac | gtc | gat | ttt | gag | cat | ctg | cat | att | 528 |
| Pro | Glu | Gly | Gln | Phe | Lys | Tyr | His | Val | Asp | Phe | Glu | His | Leu | His | Ile | |
| | | | | 165 | | | | | 170 | | | | | 175 | | |
| ggc | gaa | gaa | acc | ggg | atg | att | tgc | gtc | tcc | cgg | ccg | acg | aat | cca | aca | 576 |
| Gly | Glu | Glu | Thr | Gly | Met | Ile | Cys | Val | Ser | Arg | Pro | Thr | Asn | Pro | Thr | |
| | | | 180 | | | | | 185 | | | | | 190 | | | |
| ggc | aat | gtg | att | act | gac | gaa | gag | ttg | ctg | aag | ctt | gac | gcg | ctg | ggc | 624 |
| Gly | Asn | Val | Ile | Thr | Asp | Glu | Glu | Leu | Leu | Lys | Leu | Asp | Ala | Leu | Gly | |

```
                195                 200                 205
aat caa cac ggc att ccg ctg gtg att gat aac gct tat ggc gtc ccg      672
Asn Gln His Gly Ile Pro Leu Val Ile Asp Asn Ala Tyr Gly Val Pro
    210                 215                 220 ttc ccg ggt atc atc ttc agt gaa gcg cgc ccg cta tgg aat ccg aat      720
Phe Pro Gly Ile Ile Phe Ser Glu Ala Arg Pro Leu Trp Asn Pro Asn
225                 230                 235                 240 atc gtg ctg tgc atg agt ctt tcc aag ctg ggt cta cct ggc tcc cgc      768
Ile Val Leu Cys Met Ser Leu Ser Lys Leu Gly Leu Pro Gly Ser Arg
                245                 250                 255 tgc ggc att atc atc gcc aat gaa aaa atc atc acc gcc atc acc aat      816
Cys Gly Ile Ile Ile Ala Asn Glu Lys Ile Ile Thr Ala Ile Thr Asn
            260                 265                 270 atg aac ggc att atc agc ctg gca cct ggc ggt att ggt ccg gcg atg      864
Met Asn Gly Ile Ile Ser Leu Ala Pro Gly Gly Ile Gly Pro Ala Met
        275                 280                 285 atg tgt gaa atg att aag cgt aac gat ctg ctg cgc ctg tct gaa aca      912
Met Cys Glu Met Ile Lys Arg Asn Asp Leu Leu Arg Leu Ser Glu Thr
    290                 295                 300 gtc atc aaa ccg ttt tac tac cag cgt gtt cag gaa act atc gcc atc      960
Val Ile Lys Pro Phe Tyr Tyr Gln Arg Val Gln Glu Thr Ile Ala Ile
305                 310                 315                 320 att cgc cgc tat tta ccg gaa aat cgc tgc ctg att cat aaa ccg gaa     1008
Ile Arg Arg Tyr Leu Pro Glu Asn Arg Cys Leu Ile His Lys Pro Glu
                325                 330                 335 gga gcc att ttc ctc tgg cta tgg ttt aag gat ttg ccc att acg acc     1056
Gly Ala Ile Phe Leu Trp Leu Trp Phe Lys Asp Leu Pro Ile Thr Thr
            340                 345                 350 aag cag ctc tat cag cgc ctg aaa gca cgc ggc gtg ctg atg gtg ccg     1104
Lys Gln Leu Tyr Gln Arg Leu Lys Ala Arg Gly Val Leu Met Val Pro
        355                 360                 365 ggg cac aac ttc ttc cca ggg ctg gat aaa ccg tgg ccg cat acg cat     1152
Gly His Asn Phe Phe Pro Gly Leu Asp Lys Pro Trp Pro His Thr His
    370                 375                 380 caa tgt atg cgc atg aac tac gta cca gag ccg gag aaa att gag gcg     1200
Gln Cys Met Arg Met Asn Tyr Val Pro Glu Pro Glu Lys Ile Glu Ala
385                 390                 395                 400 ggg gtg aag att ctg gcg gaa gag ata gaa aga gcc tgg gct gaa agt     1248
Gly Val Lys Ile Leu Ala Glu Glu Ile Glu Arg Ala Trp Ala Glu Ser
                405                 410                 415 cac taa                                                             1254
His

<210> SEQ ID NO 71
<211> LENGTH: 417
<212> TYPE: PRT
<213> ORGANISM: Escherichia coli

<400> SEQUENCE: 71

Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60

Asp Ala Leu Cys Asn Tyr Asp Gly Pro Gln Gly Lys Thr Glu Leu Leu
65                  70                  75                  80
```

```
Thr Leu Leu Ala Gly Met Leu Arg Glu Lys Leu Gly Trp Asp Ile Glu
             85                  90                  95
Pro Gln Asn Ile Ala Leu Thr Asn Gly Ser Gln Ser Ala Phe Phe Tyr
        100                 105                 110
Leu Phe Asn Leu Phe Ala Gly Arg Arg Ala Asp Gly Arg Val Lys Lys
    115                 120                 125
Val Leu Phe Pro Leu Ala Pro Glu Tyr Ile Gly Tyr Ala Asp Ala Gly
130                 135                 140
Leu Glu Glu Asp Leu Phe Val Ser Ala Arg Pro Asn Ile Glu Leu Leu
145                 150                 155                 160
Pro Glu Gly Gln Phe Lys Tyr His Val Asp Phe Glu His Leu His Ile
                165                 170                 175
Gly Glu Glu Thr Gly Met Ile Cys Val Ser Arg Pro Thr Asn Pro Thr
            180                 185                 190
Gly Asn Val Ile Thr Asp Glu Glu Leu Leu Lys Leu Asp Ala Leu Gly
        195                 200                 205
Asn Gln His Gly Ile Pro Leu Val Ile Asp Asn Ala Tyr Gly Val Pro
    210                 215                 220
Phe Pro Gly Ile Ile Phe Ser Glu Ala Arg Pro Leu Trp Asn Pro Asn
225                 230                 235                 240
Ile Val Leu Cys Met Ser Leu Ser Lys Leu Gly Leu Pro Gly Ser Arg
                245                 250                 255
Cys Gly Ile Ile Ile Ala Asn Glu Lys Ile Ile Thr Ala Ile Thr Asn
            260                 265                 270
Met Asn Gly Ile Ile Ser Leu Ala Pro Gly Ile Gly Pro Ala Met
        275                 280                 285
Met Cys Glu Met Ile Lys Arg Asn Asp Leu Leu Arg Leu Ser Glu Thr
    290                 295                 300
Val Ile Lys Pro Phe Tyr Tyr Gln Arg Val Gln Glu Thr Ile Ala Ile
305                 310                 315                 320
Ile Arg Arg Tyr Leu Pro Glu Asn Arg Cys Leu Ile His Lys Pro Glu
                325                 330                 335
Gly Ala Ile Phe Leu Trp Leu Trp Phe Lys Asp Leu Pro Ile Thr Thr
            340                 345                 350
Lys Gln Leu Tyr Gln Arg Leu Lys Ala Arg Gly Val Leu Met Val Pro
        355                 360                 365
Gly His Asn Phe Phe Pro Gly Leu Asp Lys Pro Trp Pro His Thr His
    370                 375                 380
Gln Cys Met Arg Met Asn Tyr Val Pro Glu Pro Glu Lys Ile Glu Ala
385                 390                 395                 400
Gly Val Lys Ile Leu Ala Glu Glu Ile Glu Arg Ala Trp Ala Glu Ser
                405                 410                 415
His

<210> SEQ ID NO 72
<211> LENGTH: 8803
<212> TYPE: DNA
<213> ORGANISM: Artificial Sequence
<220> FEATURE:
<223> OTHER INFORMATION: Description of Artificial Sequence:
      Recombinant pAN294 plasmid

<400> SEQUENCE: 72
tgcgccgcta cagggcgcgt ccattcgcca ttcaggctgc gcaactgttg ggaagggcga    60
tcggtgcggg cctcttcgct attacgccag ctggcgaaag ggggatgtgc tgcaaggcga   120
```

```
ttaagttggg taacgccagg gttttcccag tcacgacgtt gtaaaacgac ggccagtgaa    180
ttgtaatacg actcactata gggcgaattg ggcccgacgt cgcatgctgg atgaaaagcc    240
gatgaccgct tttcaggtct gtcagcagct ttttcctgct gtatatgaaa aggaattgtt    300
tttaacgatg tcagaaacgg caggtcacct tgatgtgttg gaggctgaag aagccatcac    360
gtcatattgg gaaggaaata ccgtatactt taaaacaatg aagaggtgaa atgggtgaaa    420
catatagcgg gaaaaaggat ttggataacc ggcgcttcag gagggcttgg agaaagaatc    480
gcatacttat gcgcggctga aggagcccat gtcctgctgt cggctagacg cgaggatcgt    540
ttgatagaaa tcaaaaggaa ataaccgag gaatggagcg gacagtgtga gattttcct    600 ctggatgtcg gccgcctaga ggatatcgcc cgggtccgcg atcagatcgg ctcgattgat    660
gtactgatta caatgcagg cttcggtata tttgaaacgg ttttagactc tacattggat    720
gacatgaaag cgatgtttga tgtgaatgtc ttcggcctga tcgcctgtac aaaagcggtg    780
cttccgcaaa tgcttgagca aaaaaaggga catatcatca atatcgcctc tcaagcgggg    840
aaaatcgcca caccgaagtc tagcctgtat tccgcgacca acatgccgt gttaggttac    900 tcaaacgctt tgcggatgga gctttcggga accggcattt atgtgacaac agtcaacccg    960
ggcccgattc agacggactt ttttttccatt gctgataaag gcggggacta cgccaaaaat   1020
gtcggccgct ggatgcttga tcctgatgac gtggcagctc aaattacagc tgcaattttt   1080
acgaaaaagc gggagatcaa tcttccgcgt ttaatgaatg ccggcactaa gctgtatcag   1140
ctgtttccag ctcttgtaga aaagctggca ggacgcgcgc tcatgaaaaa ataatgatag   1200
aactgcctgt ggtggagtgg cttgtttctc acggggcagt ttttgatagt ggaagggaga   1260
gattgttgaa tgtcagttca ttcagaagtc cttcatgctc tgcttaaaga tccgtttatt   1320
cagaaactga ttgatgcaga gcctgtattc tgggcaaatt caggcaagaa agaggggcca   1380 ttacccgtg cagatgagtg ggcaaccgag atagcggaag cggaaaaaag aatgcagcgg   1440
tttgcacctt acattgccga ggtgtttcct gagacgaaag gcgctaaagg aatcatcgag   1500
tctccgcttt ttgaggtgca gcatatgaag ggaaagctgg aagcggcata tcagcagcca   1560
tttcccggaa gatggctttt aaagtgcgac catgagcttc cgatttcagg atcgattaaa   1620
gcgaggggcg ggatttatga agtgttaaag tatgctgaaa atctcgcgct tcaagaagga   1680
atgcttcagg aaaccgatga ttaccgcatc ttacaggaag agcggtttac cgggtttttc   1740
tcccgctatt cgattgctgt cggttcgaca ggaaatctag gtttaagcat cggcatcatc   1800
ggcgcggcac tcgggtttcg cgtgacagtg catatgtccg ccgatgctaa gcagtggaaa   1860
aaggatctcc tccgccaaaa gggagtcact gttatggagt acgaaacaga ttacagtgaa   1920
gcggtgaacg aagggagacg gcaggcggaa caagatccat tctgttattt tattgatgat   1980
gaacattctc gtcagctgtt cttaggatat gctgttgctg caagccgatt aaaaacacag   2040
cttgactgta tgaatataaa gccaagtctt gagacgccct tgtttgtgta tctgccgtgc   2100
ggagtcggcg gaggaccggg cggtgtagca tttgggctga agcttttata cggagatgat   2160
gttcatgtgt ttttcgcaga accaactcat tcaccttgta tgctgttagg ctttattca   2220 ggacttcacg agaagatctc cgtccaggat atcggcctgg ataatcagac ggctgctgac   2280 ggacttgcccg tagggaggcc gtcaggattt gtcggcaagc tgattgaacc gcttctgagc   2340
ggctgttata cggtagagga caatacgctt tatactttgc ttcatatgct ggctgtatct   2400
gaagataaat atttagagcc ctctgctctt gctggcatgt tcgggccggt tcagcttttt   2460
tcgacagaag agggaaggcg ctatgctcag aaatataaga tggaacatgc cgtacatgtc   2520
```

```
gtctggggaa cgggaggaag catggttcca aaagatgaaa tggctgcgta taaccgaatc   2580
ggtgctgatt tgctaaaaaa acgaaatgga aaataagcag acagtgaaaa ggttttccgt   2640
tacaatcttt gtaagggttt taacctacag agagtcaggt gtaaacagtg aaaaataaag   2700
aacttaacct acatacttta tatacacagc acaatcggga gtcttggtct ggttttgggg   2760
ggcatttgtc gattgctgta tctgaagaag aggcaaaagc tgtggaagga ttgaatgatt   2820
atctatctgt tgaagaagtg gagacgatct atattccgct tgttcgcttg cttcatttac   2880
atgtcaagtc tgcggctgaa cgcaataagc atgtcaatgt tttttttgaag cacccacatt   2940 cagccaaaat tccgtttatt atcggcattg ccggcagtgt cgcagtcgga aaaagcacga   3000
cggcgcggat cttgcagaag ctgctttcgc gtttgcctga ccgtccaaaa gtgagcctta   3060
tcacgacaga tggttttta tttcctactg ccgagctgaa aaagaaaaat atgatgtcaa   3120
gaaaaggatt tcctgaaagc tatgatgtaa aggcgctgct cgaattttg aatgacttaa   3180 aatcaggaaa ggacagcgta aaggccccgg tgtattccca tctaacctat daccgcgagg   3240
aaggtgtgtt cgaggttgta gaacaggcgg atattgtgat tattgaaggc attaatgttc   3300
ttcagtcgcc caccttggag gatgaccggg aaaacccgcg tattttttgtt tccgatttct   3360 ttgatttttc gatttatgtg gatgcggagg aaagccggat tttcacttgg tatttagagc   3420
gttttcgcct gcttcgggaa acagcttttc aaaatcctga ttcatatttt cataaattta   3480
aagacttgtc cgatcaggag gctgacgaga tggcagcctc gatttgggag agtgtcaacc   3540
ggccgaattt atatgaaaat attttgccaa ctaaattcag gtcagatctc attttgcgta   3600
agggagacgg gcataaggtc gaggaagtgt tggtaaggag ggtatgaaat gtgctgcagc   3660
tcgagcaata gttacccta ttatcaagat aagaaagaaa aggatttttc gctacgctca   3720
aatcctttaa aaaacacaa aagaccacat tttttaatgt ggtctttatt cttcaactaa   3780
agcacccatt agttcaacaa acgaaaattg gataaagtgg gatattttta aaatatatat   3840
ttatgttaca gtaatattga cttttaaaaa aggattgatt ctaatgaaga aagcagacaa   3900
gtaagcctcc taaattcact ttagataaaa atttaggagg catatcaaat gaactttaat   3960
aaaattgatt tagacaattg gaagagaaaa gagatatttta atcattattt gaaccaacaa   4020 acgacttta gtataaccac agaaattgat attagtgttt tataccgaaa cataaaacaa   4080
gaaggatata aattttaccc tgcatttat ttcttagtga caagggtgat aaactcaaat   4140
acagctttta gaactggtta caatagcgac ggagagttag gttattggga taagttagag   4200
ccactttata caattttga tggtgtatct aaaacattct ctggtatttg gactcctgta   4260
aagaatgact tcaaagagtt ttatgattta taccttctg atgtagagaa atataatggt   4320
tcggggaaat tgtttcccaa aacacctata cctgaaaatg ctttttctct ttctattatt   4380
ccatggactt catttactgg gtttaactta aatatcaata ataatagtaa ttaccttcta   4440
cccattatta cagcaggaaa attcattaat aaaggtaatt caatatattt accgctatct   4500
ttacaggtac atcattctgt tgtgatggt tatcatgcag gattgttat gaactctatt   4560 caggaattgt cagataggcc taatgactgg ctttttataat atgagataat gccgactgta   4620
ctttttacag tcggttttct aatgtcacta acctgccccg ttagttgaag aaggtttta   4680 tattacagct gtcgactcgt gatcttcgga caggctgttc agctttttct caatgcgatc   4740
cagctgcgct tttcggtttt tcgcatactt gaagcctgta acagccgcaa agacgacagc   4800
ggcaaatata ataaatacaa acagctgaaa catcacatca cctatattca tgttcttcac   4860
ctcatgtttg cgggagagat tcattctctt ccgttttta tttaaagcgg cttttccaga   4920
```

```
cgggaacggt gttttgtggt ctccatttc atttgccgat aggcgaacgc taaaaatggc    4980
aggccgagca gggtaatgcc gctcaggaca gaaaaaatat aaatcggccg ccagcgcca     5040 aacaggtcta tacatatccc cccgacccaa gggccgatga cgtttccgag ctgtggaaaa    5100
ccgattgccc cgaaataagt gccttttaat cctggttttg caatctggtc tacatacaaa    5160
tccatcatag agaataaaag cacttcgccg attgtaaatg tgatgacaat catcacaatt    5220
gatggaacac cgtgtgatac ggtgaaaatg gccatgctga tgctaaccat cacattaccg    5280
agcatcagag aacaaagcgg cgaaaaccgt tttgcaaaat ggacaatggg aaattgcgtc    5340
gccaacacaa cgattgcgtt taatgtcagc atcagcccat acagcttcgt tccattgccg    5400 atcaagggt tctgcgccat atactgaggg aatgtggaac tgaattgtga gtagccgaag    5460
gtgcatagcg taatgccgac caaagcaatg gtaaaaagat aatccttttg cgtgaccata    5520
aacgcttccc gcacgctcat atttcgggac tgggctggtg ctgataagga tggatgtttt    5580
ttaaattgga gggcaagcac aattccgtat agtccgtaaa tgactgcagg caccaaaaag    5640
ggcgtagtcg attgcgatga gccgaaatat aggccaagca caggtccgaa gacaacgccg    5700
atattaatag ccgcatagcg taaattaaaa actagcagtc tcgttttttc ttctgtcata    5760
tcagacaaca aggcctttga agcgggctca aacagtgatt tgcaaagacc gtttaatgcg    5820
tttactacaa aaacaccca gagattagat gctgccgcaa agcctgcaaa taccagcatc    5880
catccgaaaa tcgatacaag catcatgttt tttctgccga atttatctga gatatatccg    5940
ccgtaaaagc ttgcgaggat gccgactgat gagctcgcgg cgatgaccag ccctgcatag    6000
gaagctgatg cgccttggac ggctgtcaaa taaatcgcta aaaaggaat gctcatcgat    6060 gttgccattc tgccgaaaat ggttccgatt ataattgtac gcgttggatg catagcttga    6120
gtattctata gtgtcaccta aatagcttgg cgtaatcatg gtcatagctg tttcctgtgt    6180
gaaattgtta ccgctcaca attccacaca acatacgagc cggaagcata agtgtaaag     6240 cctggggtgc ctaatgagtg agctaactca cattaattgc gttgcgctca ctgcccgctt    6300
tccagtcggg aaacctgtcg tgccagctgc attaatgaat cggccaacgc gcgggggagag   6360 gcggtttgcg tattgggcgc tcttccgctt cctcgctcac tgactcgctg cgctcggtcg    6420
ttcggctgcg gcgagcggta tcagctcact caaaggcggt aatacggtta tccacagaat    6480
caggggataa cgcaggaaag aacatgtgag caaaaggcca gcaaaggcc aggaaccgta     6540 aaaaggccgc gttgctggcg ttttttcgata ggctccgccc ccctgacgag catcacaaaa    6600
atcgacgctc aagtcagagg tggcgaaacc cgacaggact ataaagatac caggcgtttc    6660
cccctggaag ctccctcgtg cgctctcctg ttccgaccct gccgcttacc ggatacctgt    6720
ccgcctttct cccttcggga agcgtggcgc tttctcatag ctcacgctgt aggtatctca    6780
gttcggtgta ggtcgttcgc tccaagctgg gctgtgtgca cgaaccccc gttcagcccg     6840 accgctgcgc cttatccggt aactatcgtc ttgagtccaa cccggtaaga cacgacttat    6900
cgccactggc agcagccact ggtaacagga ttagcagagc gaggtatgta ggcggtgcta    6960
cagagttctt gaagtggtgg cctaactacg gctacactag aaggacagta tttggtatct    7020
gcgctctgct gaagccagtt accttcggaa aaagagttgg tagctcttga tccggcaaac    7080
aaaccaccgc tggtagcggt ggtttttttg tttgcaagca gcagattacg cgcagaaaaa    7140
aaggatctca agaagatcct ttgatctttt ctacgggtc tgacgctcag tggaacgaaa     7200
actcacgtta agggattttg gtcatgagat tatcaaaaag gatcttcacc tagatccttt    7260
taaattaaaa atgaagtttt aaatcaatct aaagtatata tgagtaaact tggtctgaca    7320
```

```
gttaccaatg cttaatcagt gaggcaccta tctcagcgat ctgtctattt cgttcatcca    7380
tagttgcctg actcccgtc gtgtagataa ctacgatacg ggagggctta ccatctggcc    7440
ccagtgctgc aatgataccg cgagacccac gctcaccggc tccagattta tcagcaataa    7500
accagccagc cggaagggcc gagcgcagaa gtggtcctgc aactttatcc gcctccatcc    7560
agtctattaa ttgttgccgg gaagctagag taagtagttc gccagttaat agtttgcgca    7620
acgttgttgg cattgctaca ggcatcgtgg tgtcacgctc gtcgtttggt atggcttcat    7680
tcagctccgg ttcccaacga tcaaggcgag ttacatgatc ccccatgttg tgcaaaaaag    7740
cggttagctc cttcggtcct ccgatcgttg tcagaagtaa gttggccgca gtgttatcac    7800
tcatggttat ggcagcactg cataattctc ttactgtcat gccatccgta agatgctttt    7860
ctgtgactgg tgagtactca accaagtcat tctgagaata ccgcgccgg cgaccgagtt    7920 gctcttgccc ggcgtcaata cgggataata gtgtatgaca tagcagaact ttaaaagtgc    7980
tcatcattgg aaaacgttct cggggcgaaa actctcaag gatcttaccg ctgttgagat    8040
ccagttcgat gtaacccact cgtgcaccca actgatcttc agcatctttt actttcacca    8100
gcgtttctgg gtgagcaaaa acaggaaggc aaaatgccgc aaaaaaggga ataagggcga    8160
cacggaaatg ttgaatactc atactcttcc ttttcaata ttattgaagc atttatcagg    8220
gttattgtct catgagcgga tacatatttg aatgtattta gaaaaataaa caaatagggg    8280
ttccgcgcac atttccccga aaagtgccac ctgtatgcgg tgtgaaatac cgcacagatg    8340
cgtaaggaga aaataccgca tcaggcgaaa ttgtaaacgt taatatttg ttaaaattcg    8400 cgttaaatat ttgttaaatc agctcatttt ttaaccaata ggccgaaatc ggcaaaatcc    8460
cttataaatc aaaagaatag accgagatag ggttgagtgt tgttccagtt tggaacaaga    8520
gtccactatt aaagaacgtg gactccaacg tcaaagggcg aaaaaccgtc tatcagggcg    8580
atggcccact acgtgaacca tcacccaaat caagtttttt gcggtcgagg tgccgtaaag    8640
ctctaaatcg aaccctaaa gggagccccc gatttagagc ttgacgggga aagccggcga    8700
acgtggcgag aaaggaaggg aagaaagcga aggagcggg cgctagggcg ctggcaagtg    8760
tagcggtcac gctgcgcgta accaccacac ccgccgcgct taa                      8803
```

<210> SEQ ID NO 73
<211> LENGTH: 8320
<212> TYPE: DNA
<213> ORGANISM: Artificial Sequence
<220> FEATURE:
<223> OTHER INFORMATION: Description of Artificial Sequence:
      Recombinant pAN296 plasmid

<400> SEQUENCE: 73

```
tgcgccgcta cagggcgcgt ccattcgcca ttcaggctgc gcaactgttg ggaagggcga      60
tcggtgcggg cctcttcgct attacgccag ctggcgaaag ggggatgtgc tgcaaggcga     120
ttaagttggg taacgccagg gttttcccag tcacgacgtt gtaaaacgac ggccagtgaa     180
ttgtaatacg actcactata gggcgaattg ggcccgacgt cgcatgctgg atgaaaagcc     240
gatgaccgct tttcaggtct gtcagcagct ttttcctgct gtatatgaaa aggaattgtt     300
tttaacgatg tcagaaacgg caggtcacct tgatgtgttg gaggctgaag aagccatcac     360
gtcatattgg gaaggaaata ccgtatactt aaaacaatg aagaggtgaa atgggtgaaa     420
catatagcgg gaaaaaggat ttggataacc ggcgcttcag gagggcttgg agaaagaatc     480
gcatacttat gcgcggctga aggagcccat gtcctgctgt cggctagacg cgaggatcgt     540
ttgatagaaa tcaaaaggaa aataaccgag gaatggagcg gacagtgtga gattttccct     600
```

```
ctggatgtcg gccgcctaga ggatatcgcc cgggtccgcg atcagatcgg ctcgattgat      660
gtactgatta acaatgcagg cttcggtata tttgaaacgg ttttagactc tacattggat      720
gacatgaaag cgatgtttga tgtgaatgtc ttcggcctga tcgcctgtac aaaagcggtg      780
cttccgcaaa tgcttgagca aaaaaaggga catatcatca atatcgcctc tcaagcgggg      840
aaaatcgcca caccgaagtc tagcctgtat tccgcgacca acatgccgt gttaggttac       900
tcaaacgctt tgcggatgga gctttcggga accggcattt atgtgacaac agtcaacccg      960
ggcccgattc agacggactt ttttttccatt gctgataaag cggggacta cgccaaaaat     1020
gtcggccgct ggatgcttga tcctgatgac gtggcagctc aaattacagc tgcaattttt     1080
acgaaaaagc gggagatcaa tcttccgcgt ttaatgaatg ccggcactaa gctgtatcag     1140
ctgtttccag ctcttgtaga aaagctggca ggacgcgcgc tcatgaaaaa ataatgatag     1200
aactgcctgt ggtggagtgg cttgtttctc acggggcagt ttttgatagt ggaagggaga     1260
gattgttgaa tgtcagttca ttcagaagtc cttcatgctc tgcttaaaga tccgtttatt     1320
cagaaactga ttgatgcaga gcctgtattc tgggcaaatt caggcaagaa agaggggcca     1380
ttaccccgtg cagatgagtg ggcaaccgag atagcggaag cggaaaaaag aatgcagcgg     1440
tttgcacctt acattgccga ggtgtttcct gagacgaaag gcgctaaagg aatcatcgag     1500
tctccgcttt ttgaggtgca gcatatgaag ggaaagctgg aagcggcata tcagcagcca     1560
tttcccggaa gatggctttt aaagtgcgac catgagcttc cgatttcagg atcgattaaa     1620
gcgaggggcg ggatttatga agtgttaaag tatgctgaaa atctcgcgct tcaagaagga     1680
atgcttcagg aaaccgatga ttaccgcatc ttacaggaag agcggtttac cgggttttc      1740
tcccgctatt cgattgctgt cggttcgaca ggaaatctag gtttaagcat cggcatcatc     1800
ggcgcggcac tcgggtttcg cgtgacagtg catatgtccg ccgatgctaa gcagtggaaa     1860
aaggatctcc tccgccaaaa gggagtcact gttatggagt acgaaacaga ttacagtgaa     1920
gcggtgaacg aagggagacg gcaggcggaa caagatccat tctgttattt tattgatgat     1980
gaacattctc gtcagctgtt cttaggatat gctgttgctg caagccgatt aaaaacacag     2040
cttgactgta tgaatataaa gccaagtctt gagacgccct tgtttgtgta tctgccgtgc     2100
ggagtcggcg gaggaccggg cggtgtagca tttgggctga agcttttata cggagatgat     2160
gttcatgtgt ttttcgcaga accaactcat tcaccttgta tgctgttagg gctttattca     2220
ggacttcacg agaagatctc cgtccaggat atcggcctgg ataatcagac ggctgctgac     2280
ggacttgccg tagggaggcc gtcaggattt gtcggcaagc tgattgaacc gcttctgagc     2340
ggctgttata cggtagagga caatacgctt tatactttgc ttcatatgct ggctgtatct     2400
gaagataaat atttagagcc ctctgctctt gctggcatgt tcgggccggt tcagcttttt     2460
tcgacagaag agggaaggcg ctatgctcag aaatataaga tggaacatgc cgtacatgtc     2520
gtctggggaa cgggaggaag catggttcca aaagatgaaa tggctgcgta taccgaatc      2580
ggtgctgatt tgctaaaaaa acgaaatgga aaataagcag acagtgaaaa ggttttccgt     2640
tacaatcttt gtaagggttt taacctacag agagtcaggt gtaaacagtg aaaaataaag     2700
aacttaacct acatacttta tatacacagc acaatcggga gtcttctgca gctcgagcaa     2760
tagttaccct tattatcaag ataagaaaga aaaggatttt tcgctacgct caaatccttt     2820
aaaaaaacac aaaagaccac attttttaat gtggtcttta ttcttcaact aaagcaccca     2880
ttagttcaac aaacgaaaat tggataaagt gggatatttt taaatatat atttatgtta     2940
cagtaatatt gacttttaaa aaaggattga ttctaatgaa gaaagcagac aagtaagcct     3000
```

```
cctaaattca ctttagataa aaatttagga ggcatatcaa atgaacttta ataaaattga    3060
tttagacaat tggaagagaa aagagatatt taatcattat ttgaaccaac aaacgacttt    3120
tagtataacc acagaaattg atattagtgt tttataccga aacataaaac aagaaggata    3180
taaattttac cctgcattta ttttcttagt gacaagggtg ataaactcaa atacagcttt    3240
tagaactggt tacaatagcg acggagagtt aggttattgg ataagttag agccacttta     3300
tacaatttttt gatggtgtat ctaaaacatt ctctggtatt tggactcctg taaagaatga   3360
cttcaaagag ttttatgatt tataccttc tgatgtagag aaatataatg gttcggggaa     3420
attgtttccc aaaacaccta tacctgaaaa tgcttttct ctttctatta ttccatggac     3480
ttcatttact gggtttaact taaatatcaa taataatagt aattaccttc tacccattat    3540
tacagcagga aaattcatta ataaaggtaa ttcaatatat ttaccgctat ctttacaggt    3600
acatcattct gtttgtgatg ttatcatgc aggattgttt atgaactcta ttcaggaatt     3660
gtcagatagg cctaatgact ggcttttata atatgagata atgccgactg tacttttttac  3720
agtcggtttt ctaatgtcac taacctgccc cgttagttga agaaggtttt tatattacag   3780
ctgtcgacta aggtcgagga agtgttggta aggagggtat gaaatgtgca tcatattgaa   3840
ctgtatgtct ctgatttgga ggcgtctagg cggttttggg gctggttctt aaaagaactt   3900
ggttataaag agtatcaaaa atggagctca ggcatcagct ggaagaaaga tcgttttttac  3960
ctagtgattg tgcaggcgaa agagccattt ctagagccgg aataccatag atgccgagtc   4020
ggtctgaacc atctcgcatt tcatgctgaa tccaagcttc aagtcgatca gatgactgaa   4080
aaattgacgg caaaaggcta tcgtgtgttg taccgagaca ggcatccttt tgccggagga   4140
gacgggcatt atgcagtctt ttgtgaggat ccagaccgga ttaaggtaga gctcgttgcc   4200
ccaagctgtt aatcgtgatc ttcggacagg ctgttcagct ttttctcaat gcgatccagc   4260
tgcgcttttc ggttttttcgc atacttgaag cctgtaacag ccgcaaagac gacagcggca  4320
aatataataa atacaaacag ctgaaacatc acatcaccta tattcatgtt cttcacctca   4380
tgtttgcggg agagattcat tctcttccgt ttttttattta aagcggcttt tccagacggg  4440
aacggtgttt tgtggtctcc atttttcattt gccgataggc gaacgctaaa aatggcaggc   4500
cgagcagggt aatgccgctc aggacagaaa aaatataaat cggccggcca gcgcaaaca    4560
ggtctataca tatcccccg acccaagggc cgatgacgtt tccgagctgt ggaaaaccga    4620
ttgcccgaa ataagtgcct tttaatcctg gttttgcaat ctggtctaca tacaaatcca    4680
tcatagagaa taaaagcact tcgccgattg taaatgtgat gacaatcatc acaattgatg   4740
gaacaccgtg tgatacggtg aaaatggcca tgctgatgct aaccatcaca ttaccgagca   4800
tcagagaaca aagcggcgaa aaccgttttg caaaatggac aatgggaaat tgcgtcgcca   4860
acacaacgat tgcgtttaat gtcagcatca gcccatacag cttcgttcca ttgccgatca   4920
aggggttctg cgccatatac tgagggaatg tggaactgaa ttgtgagtag ccgaaggtgc   4980
atagcgtaat gccgaccaaa gcaatggtaa aaagataatc cttttgcgtg accataaacg   5040
cttcccgcac gctcatattt cgggactggg ctggtgctga taaggatgga tgttttttaa   5100
attggagggc aagcacaatt ccgtatagtc cgtaaatgac tgcaggcacc aaaaagggcg   5160
tagtcgattg cgatgagccg aaatataggc caagcacagg tccgaagaca acgccgatat   5220
taatagccgc atagcgtaaa ttaaaaacta gcagtctcgt ttttcttct gtcatatcag    5280
acaacaaggc ctttgaagcg ggctcaaaca gtgatttgca aagaccgttt aatgcgttta    5340
ctacaaaaaa cacccagaga ttagatgctg ccgcaaagcc tgcaaatacc agcatccatc   5400
```

```
cgaaaatcga tacaagcatc atgttttttc tgccgaattt atctgagata tatccgccgt   5460
aaaagcttgc gaggatgccg actgatgagc tcgcggcgat gaccagccct gcataggaag   5520
ctgatgcgcc ttggacggct gtcaaataaa tcgctaaaaa aggaatgctc atcgatgttg   5580
ccattctgcc gaaaatggtt ccgattataa ttgtaacgcg ttggatgcat agcttgagta   5640
ttctatagtg tcacctaaat agcttggcgt aatcatggtc atagctgttt cctgtgtgaa   5700
attgttatcc gctcacaatt ccacacaaca tacgagccgg aagcataaag tgtaaagcct   5760
ggggtgccta atgagtgagc taactcacat taattgcgtt gcgctcactg cccgctttcc   5820
agtcgggaaa cctgtcgtgc cagctgcatt aatgaatcgg ccaacgcgcg gggagaggcg   5880
gtttgcgtat tgggcgctct tccgcttcct cgctcactga ctcgctgcgc tcggtcgttc   5940
ggctgcggcg agcggtatca gctcactcaa aggcggtaat acggttatcc acagaatcag   6000
gggataacgc aggaaagaac atgtgagcaa aaggccagca aaaggccagg aaccgtaaaa   6060
aggccgcgtt gctggcgttt ttcgataggc tccgcccccc tgacgagcat cacaaaaatc   6120
gacgctcaag tcagaggtgg cgaaacccga caggactata agataccag gcgtttcccc   6180 ctggaagctc cctcgtgcgc tctcctgttc cgaccctgcc gcttaccgga tacctgtccg   6240
cctttctccc ttcgggaagc gtggcgcttt ctcatagctc acgctgtagg tatctcagtt   6300
cggtgtaggt cgttcgctcc aagctgggct gtgtgcacga accccccgtt cagcccgacc   6360
gctgcgcctt atccggtaac tatcgtcttg agtccaaccc ggtaagacac gacttatcgc   6420
cactggcagc agccactggt aacaggatta gcagagcgag gtatgtaggc ggtgctacag   6480
agttcttgaa gtggtggcct aactacggct acactagaag gacagtattt ggtatctgcg   6540
ctctgctgaa gccagttacc ttcggaaaaa gagttggtag ctcttgatcc ggcaaacaaa   6600
ccaccgctgg tagcggtggt ttttttgttt gcaagcagca gattacgcgc agaaaaaaag   6660
gatctcaaga agatcctttg atcttttcta cggggtctga cgctcagtgg aacgaaaact   6720
cacgttaagg gattttggtc atgagattat caaaaaggat cttcacctag atccttttaa   6780
attaaaaatg aagttttaaa tcaatctaaa gtatatatga gtaaacttgg tctgacagtt   6840
accaatgctt aatcagtgag gcacctatct cagcgatctg tctatttcgt tcatccatag   6900
ttgcctgact ccccgtcgtg tagataacta cgatacggga gggcttacca tctggcccca   6960
gtgctgcaat gataccgcga acccacgctc accggctcc agatttatca gcaataaacc   7020
agccagccgg aagggccgag cgcagaagtg gtcctgcaac tttatccgcc tccatccagt   7080
ctattaattg ttgccgggaa gctagagtaa gtagttcgcc agttaatagt ttgcgcaacg   7140
ttgttggcat tgctacaggc atcgtggtgt cacgctcgtc gtttggtatg gcttcattca   7200
gctccggttc ccaacgatca aggcgagtta catgatcccc catgttgtgc aaaaaagcgg   7260
ttagctcctt cggtcctccg atcgttgtca gaagtaagtt ggccgcagtg ttatcactca   7320
tggttatggc agcactgcat aattctctta ctgtcatgcc atccgtaaga tgcttttctg   7380
tgactggtga gtactcaacc aagtcattct gagaataccg cgcccggcga ccgagttgct   7440
cttgcccggc gtcaatacgg gataatagtg tatgacatag cagaacttta aaagtgctca   7500
tcattggaaa acgttcttcg gggcgaaaac tctcaaggat cttaccgctg ttgagatcca   7560
gttcgatgta acccactcgt gcacccaact gatcttcagc atcttttact ttcaccagcg   7620
tttctgggtg agcaaaaaca ggaaggcaaa atgccgcaaa aagggaata agggcgacac   7680 ggaaatgttg aatactcata ctcttccttt ttcaatatta ttgaagcatt tatcagggtt   7740
attgtctcat gagcggatac atatttgaat gtatttagaa aaataaacaa ataggggttc   7800
```

```
cgcgcacatt tccccgaaaa gtgccacctg tatgcggtgt gaaataccgc acagatgcgt    7860
aaggagaaaa taccgcatca ggcgaaattg taaacgttaa tattttgtta aaattcgcgt    7920
taaatatttg ttaaatcagc tcattttta accaataggc cgaaatcggc aaaatccctt    7980
ataaatcaaa agaatagacc gagatagggt tgagtgttgt tccagtttgg aacaagagtc    8040
cactattaaa gaacgtggac tccaacgtca aagggcgaaa aaccgtctat cagggcgatg    8100
gcccactacg tgaaccatca cccaaatcaa gttttttgcg gtcgaggtgc cgtaaagctc    8160
taaatcggaa ccctaaaggg agccccgat ttagagcttg acggggaaag ccggcgaacg     8220
tggcgagaaa ggaagggaag aaagcgaaag gagcgggcgc tagggcgctg gcaagtgtag    8280
cggtcacgct gcgcgtaacc accacacccg ccgcgcttaa                          8320
```

```
<210> SEQ ID NO 74
<211> LENGTH: 250
<212> TYPE: PRT
<213> ORGANISM: Clostridium acetobutylicum

<400> SEQUENCE: 74

Asn Lys Arg Ala Ala Phe Met Leu Leu Leu Phe Leu Arg Ser Val Leu
  1               5                  10                  15

Lys Val Ile Leu Val Leu Asp Val Gly Asn Thr Asn Ile Val Leu Gly
             20                  25                  30

Ile Tyr Asn Asp Thr Lys Leu Thr Ala Glu Trp Arg Leu Ser Thr Asp
         35                  40                  45

Val Leu Arg Ser Ala Asp Glu Tyr Gly Ile Gln Val Met Asn Leu Phe
     50                  55                  60

Gln Gln Asp Lys Leu Asp Pro Thr Leu Val Glu Gly Val Ile Ile Ser
 65                  70                  75                  80

Ser Val Val Pro Asn Ile Met Tyr Ser Leu Glu His Met Ile Arg Lys
                 85                  90                  95

Tyr Phe Lys Ile Asn Pro Leu Val Val Gly Pro Gly Ile Lys Thr Gly
            100                 105                 110

Ile Asn Ile Lys Tyr Asp Asn Pro Lys Glu Val Gly Ala Asp Arg Ile
        115                 120                 125

Val Asn Ala Val Ala Ala His Glu Ile Tyr Lys Arg Ser Leu Ile Ile
    130                 135                 140

Ile Asp Phe Gly Thr Ala Thr Thr Phe Cys Ala Val Arg Glu Asn Gly
145                 150                 155                 160

Asp Tyr Leu Gly Gly Ala Ile Cys Pro Gly Ile Lys Val Ser Ser Glu
                165                 170                 175

Ala Leu Phe Glu Lys Ala Ala Lys Leu Pro Arg Val Glu Leu Ile Lys
            180                 185                 190

Pro Ala Tyr Ala Ile Cys Lys Asn Thr Ile Ser Ser Ile Gln Ser Gly
        195                 200                 205

Ile Val Tyr Arg Tyr Leu Arg Gln Val Lys Tyr Leu Phe Glu Lys Leu
    210                 215                 220

Lys Glu Asn Leu Pro Asp Gly Arg Arg Thr Arg Thr Ser Leu Val Leu
225                 230                 235                 240

Ala Thr Gly Gly Leu Ala Lys Leu Ile Asn
                245                 250

<210> SEQ ID NO 75
<211> LENGTH: 258
<212> TYPE: PRT
<213> ORGANISM: Rhodobacter capsulatus
```

<400> SEQUENCE: 75

| Met | Leu | Leu | Cys | Ile | Asp | Cys | Gly | Asn | Thr | Asn | Thr | Val | Phe | Ser | Val |
|---|---|---|---|---|---|---|---|---|---|---|---|---|---|---|---|
| 1 | | | | 5 | | | | | 10 | | | | | 15 | |

| Trp | Asp | Gly | Thr | Asp | Phe | Ala | Ala | Thr | Trp | Arg | Ile | Ala | Thr | Asp | His |
| | | | 20 | | | | | 25 | | | | | 30 | | |

| Arg | Arg | Thr | Ala | Asp | Glu | Tyr | Phe | Val | Trp | Leu | Asn | Thr | Leu | Met | Gln |
| | | 35 | | | | | 40 | | | | | 45 | | | |

Leu Lys Gly Leu Gln Gly Arg Ile Ser Glu Ala Ile Ser Ser Thr
              50                  55                  60

Ala Pro Arg Val Val Phe Asn Leu Arg Val Leu Cys Asn Arg Tyr Phe
 65                  70                  75                  80

Asp Cys Arg Pro Tyr Val Val Gly Lys Pro Gly Cys Glu Leu Pro Val
                 85                  90                  95

Ala Pro Arg Val Asp Pro Gly Thr Thr Val Gly Pro Asp Arg Leu Val
                100                 105                 110

Asn Thr Val Ala Gly Tyr Asp Arg His Gly Gly Asp Leu Ile Val Val
                115                 120                 125

Asp Phe Gly Thr Ala Thr Thr Phe Asp Val Val Ala Pro Asp Gly Ala
130                 135                 140

Tyr Ile Gly Gly Val Ile Ala Pro Gly Val Asn Leu Ser Leu Glu Ala
145                 150                 155                 160

Leu His Met Ala Ala Ala Leu Pro His Val Asp Val Thr Lys Pro
                165                 170                 175

Gln Gly Val Ile Gly Thr Asn Thr Val Ala Cys Ile Gln Ser Gly Val
                180                 185                 190

Tyr Trp Gly Tyr Ile Gly Leu Val Glu Gly Ile Val Arg Gln Ile Arg
                195                 200                 205

Met Glu Arg Asp Arg Pro Met Lys Val Ile Ala Thr Gly Gly Leu Ala
                210                 215                 220

Ser Leu Phe Asp Leu Gly Phe Asp Leu Phe Asp Lys Val Glu Asp Asp
225                 230                 235                 240

Leu Thr Met His Gly Leu Arg Leu Ile Phe Asp Tyr Asn Lys Gly Leu
                245                 250                 255

Gly Ala

<210> SEQ ID NO 76
<211> LENGTH: 10801
<212> TYPE: DNA
<213> ORGANISM: Artificial Sequence
<220> FEATURE:
<223> OTHER INFORMATION: Description of Artificial Sequence:
      Recombinant pAN240 plasmid

<400> SEQUENCE: 76

```
gaattttgcg gccgcttcga aagctgtaat ataaaaacct tcttcaacta acggggcagg      60
ttagtgacat tagaaaaccg actgtaaaaa gtacagtcgg cattatctca tattataaaa     120
gccagtcatt aggcctatct gacaattcct gaatagagtt cataaacaat cctgcatgat     180
aaccatcaca aacagaatga tgtacctgta aagatagcgg taaatatatt gaattacctt     240
tattaatgaa ttttcctgct gtaataatgg gtagaaggta attactatta ttattgatat     300
ttaagttaaa cccagtaaat gaagtccatg gaataataga aagagaaaaa gcattttcag     360
gtataggtgt tttgggaaac aatttccccg aaccattata tttctctaca tcagaaaggt     420
ataaatcata aaactctttg aagtcattct ttacaggagt ccaaatacca gagaatgttt     480
```

```
tagatacacc atcaaaaatt gtataaagtg gctctaactt atcccaataa cctaactctc    540
cgtcgctatt gtaaccagtt ctaaaagctg tatttgagtt tatcaccctt gtcactaaga    600
aaataaatgc agggtaaaat ttatatcctt cttgttttat gtttcggtat aaaacactaa    660
tatcaatttc tgtggttata ctaaaagtcg tttgttggtt caaataatga ttaaatatct    720
cttttctctt ccaattgtct aaatcaattt tattaaagtt catttgatat gcctcctaaa    780
tttttatcta aagtgaattt aggaggctta cttgtctgct ttcttcatta gaatcaatcc    840 tttttttaaaa gtcaatatta ctgtaacata aatatatatt ttaaaaatat cccactttat    900
ccaattttcg tttgttgaac taatgggtgc tttagttgaa gaataaagac cacattaaaa    960
aatgtggtct tttgtgtttt tttaaaggat ttgagcgtag cgaaaaatcc ttttctttct   1020
tatcttgata ataagggtaa ctattgaatt cggtaccaag agtttgtaga aacgcaaaaa   1080
ggccatccgt caggatggcc ttctgcttaa tttgatgcct ggcagtttat ggcgggcgtc   1140
ctgcccgcca ccctccgggc cgttgcttcg caacgttcaa atccgctccc ggcggatttg   1200
tcctactcag gagagcgttc accgacaaac aacagataaa acgaaaggcc cagtctttcg   1260
actgagcctt tcgttttatt tgatgcctgg cagttcccta ctctcgcatg gggagacccc   1320
acactaccat cggcgctacg gcgtttcact tctgagttcg gcatggggtc aggtgggacc   1380
accgcgctac tgccgccagg caaattctgt tttatcagac cgcttctgcg ttctgattta   1440
atctgtatca ggctgaaaat cttctctcat ccgccaaaac aggatcctac ggaaatggag   1500
cggcaaaacc gttttactct caaaatctta aagaaaaacc cccgataaag ggggcttttc   1560
ttctacaaaa ttgtacgggc tggttcgttc cccagcattt gttcaatttt gttttgatca   1620
ttcagaacag ccactttcgg ctcatggctt gccgcttctt gatcagacat cattttgtag   1680
gaaataataa tgaccttatc tccttcctgc acaaggcgtg cggctgcacc gtttaagcat   1740
atgacgccgc ttccccgttt accaggaata atatacgttt caagacgtgc tccattatta   1800
ttattcacaa tttgtacttt ttcattagga agcattccca cagcatcaat gagatcttca   1860
tcaattgtaa tgcttcccac atagttcagg tttgcttccg taacagttgc cctgtgaagt   1920
ttgccgctca tcattgttcg atacatatta tattctctcc atttctcgaa tatcaataat   1980
gatattatct attaaacgcg cttttgaaaa agcaactgca acagcgagaa tcatcttttcc   2040 agcaatttca ttcacaggct cgagttccgg ataggaataa agctctacat agtctatggt   2100
tccgctagtc gtttcaatga tatcttttgc agcttttatc accgcttcag gatctctttc   2160
accggcttgg acaagttccg cacttgtttg aagggcccga tacagcttag gcgcttcttt   2220
tctttcctca gctgttaagt atacattgcg agagcttttg gctaagccgt cttcctctct   2280
gaccgtatcg acaggaacca attcaatatc catgaagaag tcgctgatta acccatcaac   2340
aacagctacc tgctgcgcat cttttaaacc gaaataggca cgagtcggct tgactagatt   2400
gaaaagcttc gtcagtacga tcgcgacccc gtcaaaatgt ccttctcttg agcgcccgca   2460
taacacgtct gtgcgtcttt ctacatgaat cgtgacattc ttttcaccgg gatacatatc   2520
atgagcatct ggcgtaaaaa gaatatcgac tccggcgttt tctgcaagag ctgcatcccg   2580
ctcaatatcg cgcggatatg cttcaaaatc ttcattaggg ccgaattgtg caggattcac   2640
aaaaatactc ataataacgg cgtcgttttc ttgtcttgct ttgtctgcta aggttaaatg   2700
cccctcatgc agaaacccca tcgtcggaac aaatccgatt gacttgccct ctgaatggta   2760
ttgttttatg gcttctttca gctgtgaaat atcagtaatc tgtctcatct tattttcccc   2820
cgtacaagcc gtcaagcact gtctggttca tttgaaagga atgcttttgt tcagggaaag   2880
```

```
cacgatgtct tacatcctga acatatccgc tgattgctgt ttcgatggtt tcatcaatgc  2940
gcgtatattg ctttacaaat ttaggtgttc tctcaacacc gtggccgata atatcatgat  3000
aaacgagaac ttgtccgtcc gctttcacac cagccccgat tccaatgacc ggtatgctta  3060
gcgtctcggc aattttggct gtgagttctg ccggcacaca ttccagcaca agcatcatag  3120
ctcctgcttc ttcgcatttt atactgtctt ctattaattt tttggcgctt tgttcgtctt  3180
tgccctgtac tttatagccg cccagtacgc cgactgactg cggtgtcaaa cctaagtgac  3240
tgactactgg aatgcctcca agcgtcaatg cgcgaatgga ttcaaacacg ccttctccgc  3300
cctcaagctt cagtgcgtca gctccgcttt cctgaacgat agccgctgca ttttttcagcg  3360
tatcttcctt agacaggtga taagacataa acggcatatc tgtcacaata aaggtattcg  3420
gcgcacccct tttaacggct tttgtatgat ggatcatgtc cgcaactgtc acaccgacag  3480
ttgaatcaag gccgaggacg accattccaa gtgaatcacc gactaaaatc atgtcaactc  3540
ccgcttgttc agcaagttta gctgccggat aatcataagc ggtcagcatg acaatcggtt  3600
cttcagactc cttcattttt agaaaatcca gttttgtttt catgttttct cctccttcta  3660
gagcgtcctg ctgttgttaa gattattata ccacaccttg tagataaagt caacaacttt  3720
ttgcaaaatt tttcaggaat tttagcagag gttgttctgg atgtagaaca aaacatcttt  3780
ccgctcttgt gctgttagga tatcttttctt ggaagctagg taggcctcga gttatggcag  3840
ttggttaaaa ggaaacaaaa agaccgtttt cacacaaaac ggtctttttc gatttcttt  3900
tacagtcaca gccactttg caaaaaccgg acagcttcat gccttataac tgctgtttcg  3960
gtcgacgatg atctgccgtt ttcttctgca agccaaaaaa ccttccgtta caacgagaag  4020
gattcttcac tttctaaagt tcggcgagtt tcatccctct gtcccagtcc tttttttggat  4080
caaggcagac tgctgcaatg tctatctatt ttaataatag gtgcagttcg caggcgatac  4140
tgcccaatgg aagtatacca aaatcaacgg gcttgtacca acacattagc ccaattcgat  4200
atcggcagaa tagattttt taatgccttc gttcgtttct aaaagcagaa cgccttcatc  4260
atctataacct aacgccttac cgtaaaaggt tccgtttaac gttctggctc tcatattagt  4320
gccaataccg agcgcatagc tttcccataa aagcttaatc ggcgtaaatc cgtgcgtcat  4380
ataatcccgg taccgtttct caaagcatag taaaatatgc tggatgacgc cggcccgatc  4440
aatttttttcc ccagcagctt ggctgaggct tgtcgcgatg tccttcaatt catctggaaa  4500
atcattaggc tgctggttaa cgttaatgcc gatcccaatg atcactgaac gtacgcggtc  4560
ttcttcagcc tgcatttccg ttaggatacc gactgttttt tttccgttaa tcaaaatatc  4620
atttggccat ttaatatccg tttggatgcc tgctgcctct tctattccct gcacaacagc  4680
tactgcagca agcagagtca gctgcggtgt ttttttggagc ggaatgtcag gccgcaaaat  4740
caggctcatc caaacaccgt ttccttcttg agaatgccat accctagaca ttcggcccct  4800
tccggctgtt tgtttgtcag ccaccacaag ggtgccttcc ggtgcgttat tattcgcgag  4860
ctcatgagcc gttttttgcg tgcttgaaag aacgtcatgg taaataagat gctggcccat  4920
cacttccgtt tttaatccaa aacgaatttc gctttcactg agttttccgg gttttttgat  4980
gagccgatat ccttttcttc taacggcttc tacttcataa ccctctttcc gaagctcttc  5040
aatatgcttc cacacagcag ttcttgaaca gccgagagca tcactgattt tttggccgga  5100
aataaattca ttgccggcct gagaaaataa ttcaataagg tcttttctta atgttgaccg  5160
catgtcttca gccactcctc tatgtgtttc ttttgattgg agagcttccc tgtcacaaca  5220
gcctgctcga tccactgtaa ttcttctgac acccatttttc cggccggccg gtttcgaagc  5280
```

-continued

```
gcaagcaagt ccttacccgt gatatcaaga tccttaaggc ttttgatcgg caggttttga    5340
taagcgtact gaatgtcctt cagtttcttt tcatccagtt tttcgttttg ccgaagctgc    5400
gatattttgg ccgctgagag cagtgctttt ttcccagctc tgtacattgt cattgcgtca    5460
aggctctggc caaacgtatc ggcaatgtga atggcttcct tgatcacttt tcccgggagc    5520
ttccaggctt tcaggaaaag gggcgcgtct ttcaaaacta tgccaaggtt aattaaaaga    5580
gcagcccaaa gctcctcacg ggatgttaaa gagaagaatg gaaactcact cgttgaaatc    5640
aggttttctc gtttatgata aaaaccagga agctcttcat acaatctcgt ttgaatgagt    5700
gtttgaagcg cctggcgaga agctcttccc tgcagcaatt tctcaaactc tatagttttt    5760
cgttcgactg aaacatggga gaggagtgat ttttcttttcg caatggcttc ttctgtttcc    5820
ggtgaaagcg taaagccaag ctggctcata agcgtacgg ctctcagcat acgaagcgca    5880
tcctcttgaa atctatcctc aggctttcca acggttcgaa tcactttctg atcaatatct    5940
ttcttgccgc caaataatc aagcaccttc ccgtccgctg tcatggccat cgcattgatc    6000
gttaaatctc tgcgttttag atcctcttct aatgatgaga taaattgcac ttctgacggt    6060
cttctgaaat caacataatc agattcagtc cggaatgtcg tgacttcata ggtttcatcc    6120
tcccagagca caataatggt cccgtgctct ttgcctacat caacagtccg ctgaaacagc    6180
cgttctactt gatcaggtgc cgcatctgtc gcgatatcga catctccgat cgttcgtttc    6240
atatagctgt cacgaactgc gcccccgaca aaataagcct gatggcccgc ttcgattaag    6300
atgcggagca cggaagtgc tttgataaaa actttttcca tgtgatcact ccggttctgc    6360
taaatcggca taaatctgtt catactggct gacaattttt ttagaagaaa attcattttc    6420
aagcatctct attgccgcct ttgtaaaacg attgcttagc tgttcatctt ctaaaatgct    6480
catcgcgcgg gctgttgcgg ccgtaacatc accgacatcc accaaaaatc cgctcacatt    6540
gttttttata acctcaggga taccgccaat gtttgttcca atacaaggca ctccgcaagc    6600
catcgcttca agcaggacaa ggccaaagct ttctttttca gatagcagca gcttcaaatc    6660
gctaatagaa taaagatctt caacacggtc ttgatttcca agcattaaga cttggtcttc    6720
caagccatat tttctgataa gctcgcaggc tgtcgatttc tccggaccgt ctccgactaa    6780
aagcagcttc gctttcgttt tgccagcgat attgcggaac acacggatga catcctgcac    6840
gcgtgcagcc actggtaaca ggattagcag agcgaggtat gtaggcggtg ctacagagtt    6900
cttgaagtgg tggcctaact acggctacac tagaaggaca gtatttggta tctgcgctct    6960
gctgaagcca gttaccttcg gaaaagagt tggtagctct tgatccggca aacaaaccac    7020
cgctggtagc ggtggttttt tgtttgcaa gcagcagatt acgcgcagaa aaaaggatc    7080
tcaagaagat cctttgatct tttctacggg gtctgacgct cagtggaacg aaaactcacg    7140
ttaagggatt ttggtcatga gattatcaaa aaggatcttc acctagatcc ttttaaatta    7200
aaaatgaagt tttaaatcaa tctaaagtat atatgagtaa acttggtctg acagttacca    7260
atgcttaatc agtgaggcac ctatctcagc gatctgtcta tttcgttcat ccatagttgc    7320
ctgactcccc gtcgtgtaga taactacgat acgggagggc ttaccatctg gccccagtgc    7380
tgcaatgata ccgcgagacc cacgctcacc ggctccagat ttatcagcaa taaaccagcc    7440
agccggaagg gccgagcgca gaagtggtcc tgcaacttta tccgcctcca tccagtctat    7500
taattgttgc cgggaagcta gagtaagtag ttcgccagtt aatagtttgc gcaacgttgt    7560
tgccattgct acaggcatcg tggtgtcacg ctcgtcgttt ggtatggctt cattcagctc    7620
cggttcccaa cgatcaaggc gagttacatg atcccccatg ttgtgcaaaa aagcggttag    7680
```

```
ctccttcggt cctccgatcg ttgtcagaag taagttggcc gcagtgttat cactcatggt    7740
tatggcagca ctgcataatt ctcttactgt catgccatcc gtaagatgct tttctgtgac    7800
tggtgagtac tcaaccaagt cattctgaga atagtgtatg cggcgaccga gttgctcttg    7860
cccggcgtca atacgggata ataccgcgcc acatagcaga actttaaaag tgctcatcat    7920
tggaaaacgt tcttcggggc gaaaactctc aaggatctta ccgctgttga gatccagttc    7980
gatgtaaccc actcgtgcac ccaactgatc ttcagcatct tttactttca ccagcgtttc    8040
tgggtgagca aaaacaggaa ggcaaaatgc cgcaaaaaag gaataagggc gacacggaa     8100
atgttgaata ctcatactct tcctttttca atattattga agcatttatc agggttattg    8160
tctcatgagc ggatacatat ttgaatgtat ttagaaaaat aaacaaatag gggttccgcg    8220
cacatttccc cgaaaagtgc cacctgacgt ctaagaaacc attattatca tgacattaac    8280
ctataaaaat aggcgtatca cgaggccctt tcgtctcgca tgcggatcag tgagggtttg    8340
caactgcggg tcaaggatct ggatttcgat cacggcacga tcatcgtgcg ggagggcaag    8400
ggctccaagg atcgggcctt gatgttaccc gagagcttgg cacccagcct gcgcgagcag    8460
gggaattgat ccggtggatg accttttgaa tgacctttaa tagattatat tactaattaa    8520
ttggggaccc tagaggtccc cttttttatt ttaaaatttt tttcacaaaa cggtttacaa    8580
gcataacggg ttttgctgcc cgcaaacggg ctgttctggt gttgctagtt tgttatcaga    8640
atcgcagatc cggcttcagg tttgccggct gaaagcgcta tttcttccag aattgccatg    8700
atttttttcc cacgggaggc gtcactggct cccgtgttgt cggcagcttt gattcgataa    8760
gcagcatcgc ctgtttcagg ctgtctatgt gtgactgttg agctgtaaca agttgtctca    8820
ggtgttcaat ttcatgttct agttgctttg ttttactggt ttcacctgtt ctattaggtg    8880
ttacatgctg ttcatctgtt acattgtcga tctgttcatg gtgaacagct ttaaatgcac    8940
caaaaactcg taaaagctct gatgtatcta tcttttttac accgttttca tctgtgcata    9000
tggacagttt tccctttgat atctaacggt gaacagttgt tctactttgt tttgttagtc    9060
ttgatgcttc actgatagat acaagagcca taagaacctc agatccttcc gtatttagcc    9120
agtatgttct ctagtgtggt tcgttgtttt tgcgtgagcc atgagaacga accattgaga    9180
tcatgcttac tttgcatgtc actcaaaaat tttgcctcaa aactggtgag ctgaattttt    9240
gcagttaaag catcgtgtag tgttttttctt agtccgttac gtaggtagga atctgatgta    9300
atggttgttg gtattttgtc accattcatt tttatctggt tgttctcaag ttcggttacg    9360
agatccattt gtctatctag ttcaacttgg aaaatcaacg tatcagtcgg gcggcctcgc    9420
ttatcaacca ccaatttcat attgctgtaa gtgtttaaat ctttacttat tggtttcaaa    9480
acccattggt taagcctttt aaactcatgg tagttatttt caagcattaa catgaactta    9540
aattcatcaa ggctaatctc tatatttgcc ttgtgagttt tcttttgtgt tagttctttt    9600
aataaccact cataaatcct catagagtat tgttttcaa aagacttaac atgttccaga    9660
ttatatttta tgaatttttt taactggaaa agataaggca atatctcttc actaaaaact    9720
aattctaatt tttcgcttga aacttggca tagtttgtcc actggaaaat ctcaaagcct    9780
ttaaccaaag gattcctgat ttccacagtt ctcgtcatca gctctctggt tgctttagct    9840
aatacaccat aagcattttc cctactgatg ttcatcatct gagcgtattg gttataagtg    9900
aacgataccg tccgttcttt ccttgtaggg ttttcaatcg tggggttgag tagtgccaca    9960
cagcataaaa ttagcttggt ttcatgctcc gttaagtcat agcgactaat cgctagttca   10020
tttgctttga aaacaactaa ttcagacata catctcaatt ggtctaggtg attttaatca   10080
```

```
ctataccaat tgagatgggc tagtcaatga taattactag tccttttcct ttgagttgtg    10140
ggtatctgta aattctgcta gacctttgct ggaaaacttg taaattctgc tagaccctct    10200
gtaaattccg ctagaccttt gtgtgttttt tttgtttata ttcaagtggt tataatttat    10260
agaataaaga aagaataaaa aaagataaaa agaatagatc ccagccctgt gtataactca    10320
ctactttagt cagttccgca gtattacaaa aggatgtcgc aaacgctgtt tgctcctcta    10380
caaaacagac cttaaaaccc taaggctta  agtagcaccc tcgcaagctc gggcaaatcg    10440
ctgaatattc cttttgtctc cgaccatcag gcacctgagt cgctgtcttt ttcgtgacat    10500
tcagttcgct gcgctcacgg ctctggcagt gaatgggggt aaatggcact acaggcgcct    10560
tttatggatt catgcaagga aactacccat aatacaagaa aagcccgtca cgggcttctc    10620
agggcgtttt atggcgggtc tgctatgtgg tgctatctga cttttgctg  ttcagcagtt    10680 cctgccctct gattttccag tctgaccact tcggattatc ccgtgacagg tcattcagac    10740
tggctaatgc acccagtaag gcagcggtat catcaacagg cttacccgtc ttactgtcaa    10800
c                                                                    10801

<210> SEQ ID NO 77
<211> LENGTH: 8654
<212> TYPE: DNA
<213> ORGANISM: Artificial Sequence
<220> FEATURE:
<223> OTHER INFORMATION: Description of Artificial Sequence:
      Recombinant pAN236 plasmid

<400> SEQUENCE: 77
ctcgaggcct acctagcttc caagaaagat atcctaacag cacaagagcg gaaagatgtt      60
ttgttctaca tccagaacaa cctctgctaa aattcctgaa aaattttgca aaagttgtt     120 gactttatct acaaggtgtg gtataataat cttaacaaca gcaggacgct ctagaggagg     180
agacatcatg aaaattggaa ttatcggcgg aggctccgtt ggtctttat gcgcctatta     240 tttgtcactt tatcacgacg tgactgttgt gacgaggcgg caagaacagg ctgcggccat     300
tcagtctgaa ggaatccggc tttataaagg cggggaggaa ttcagggctg attgcagtgc     360
ggacacgagt atcaattcgg actttgacct gcttgtcgtg acagtgaagc agcatcagct     420
tcaatctgtt ttttcgtcgc ttgaacgaat cgggaagacg aatatattat ttttgcaaaa     480
cggcatgggg catatccacg acctaaaaga ctggcacgtt ggccattcca tttatgttgg     540
aatcgttgag cacggagctg taagaaaatc ggatacagct gttgatcata caggcctagg     600
tgcgataaaa tggagcgcgt tcgacgatgc tgaaccagac cggctgaaca tcttgtttca     660
gcataaccat tcggattttc cgatttatta tgagacggat tggtaccgtc tgctgacggg     720
caagctgatt gtaaatgcgt gtattaatcc tttaactgcg ttattgcaag tgaaaaatgg     780
agaactgctg acaacgccag cttatctggc ttttatgaag ctggtatttc aggaggcatg     840
ccgcatttta aaacttgaaa atgaagaaaa ggcttgggag cgggttcagg ccgtttgtgg     900
gcaaacgaaa gagaatcgtt catcaatgct ggttgacgtc attggaggcc ggcagacgga     960
agctgacgcc attatcggat acttattgaa ggaagcaagt cttcaaggtc ttgatgccgt    1020
ccacctagag tttttatatg cagcatcaa  agcattggag cgaaatacaa acaaagtctt    1080
ttgagctttt tcggtaacat gctatactca tttcggatca ctaactattt attggaggat    1140
cctgttttgg cggatgagag aagatttttca gcctgataca gattaaatca gaacgcagaa    1200
gcggtctgat aaaacagaat ttgcctggcg gcagtagcgc ggtggtccca cctgacccca    1260
tgccgaactc agaagtgaaa cgccgtagcg ccgatggtag tgtgggtct  ccccatgcga    1320
```

```
gagtagggaa ctgccaggca tcaaataaaa cgaaaggctc agtcgaaaga ctgggccttt    1380
cgttttatct gttgtttgtc ggtgaacgct ctcctgagta ggacaaatcc gccgggagcg    1440
gatttgaacg ttgcgaagca acggcccgga gggtggcggg caggacgccc gccataaact    1500
gccaggcatc aaattaagca aaggccatc ctgacggatg gcctttttgc gtttctacaa    1560
actcttggta cccagaaaaa gcggcaaaag cggctgttaa aaaagcgaaa tcgaagaagc    1620
tgtctgccgc taagacggaa tatcaaagc gttctgctgt tgtgtcatct ttaaaagtca    1680
cagccgatga atcccagcaa gatgtcctaa aatacttgaa cacccagaaa gataaaggaa    1740
atgcagacca aattcattct tattatgtgg tgaacgggat tgctgttcat gcctcaaaag    1800
aggttatgga aaaagtggtg cagtttcccg aagtggaaaa ggtgcttcct aatgagaaac    1860
ggcagctttt taagtcatcc tccccattta atatgaaaaa agcacagaaa gctattaaag    1920
caactgacgg tgtggaatgg aatgtagacc aaatcgatgc cccaaaagct tgggcacttg    1980
gatatgatgg aactggcacg gttgttgcgt ccattgatac cggggtggaa tggaatcatc    2040
cggcattaaa agagaaatat cgcggatata atccggaaaa tcctaatgag cctgaaaatg    2100
aaatgaactg gtatgatgcc gtagcaggcg aggcaagccc ttatgatgat ttggctcatg    2160
gaacccacgt gacaggcacg atggtgggct ctgaacctga tggaacaaat caatcggtg     2220 tagcacctgg cgcaaaatgg attgctgtta aagcgttctc tgaagatggc ggcactgatg    2280
ctgacatttt ggaagctggt gaatgggttt tagcaccaaa ggacgcggaa ggaaatcccc    2340
acccggaaat ggctcctgat gttgtcaata actcatgggg aggggctct ggacttgatg     2400 aatggtacag agacatggtc aatgcctggc gttcggccga tattttccct gagttttcag    2460
cggggaatac ggatctcttt attcccggcg ggcctggttc tatcgcaaat ccggcaaact    2520
atccagaatc gtttgcaact ggagcgactg agaattccaa ttccccatgg agagaaaaga    2580
aaatcgctaa tgttgattac tttgaacttc tgcatattct tgaatttaaa aaggctgaaa    2640
gagtaaaaga ttgtgctgaa atattagagt ataaacaaaa tcgtgaaaca ggcgaaagaa    2700
agttgtatcg agtgtggttt tgtaaatcca ggctttgtcc aatgtgcaac tggaggagag    2760
caatgaaaca tggcattcag tcacaaaagg ttgttgctga agttattaaa caaaagccaa    2820
cagttcgttg gttgtttctc acattaacag ttaaaaatgt ttatgatggc gaagaattaa    2880
ataagagttt gtcagatatg gctcaaggat ttcgccgaat gatgcaatat aaaaaaatta    2940
ataaaaatct tgttggtttt atgcgtgcaa cggaagtgac aataaataat aaagataatt    3000
cttataatca gcacatgcat gtattggtat gtgtggaacc aacttatttt aagaatacag    3060
aaaactacgt gaatcaaaaa caatggattc aatttggaa aaaggcaatg aaattagact    3120
atgatccaaa tgtaaaagtt caaatgattc gaccgaaaaa taaatataaa tcggatatac    3180
aatcggcaat tgacgaaact gcaaaatatc ctgtaaagga tacggatttt atgaccgatg    3240
atgaagaaaa gaatttgaaa cgtttgtctg atttggagga aggtttacac cgtaaaaggt    3300
taatctccta tggtggtttg ttaaaagaaa tacataaaaa attaaaccctt gatgacacag    3360 aagaaggcga tttgattcat acagatgatg acgaaaaagc cgatgaagat ggattttcta    3420
ttattgcaat gtggaattgg gaacggaaaa attatttat taagagtag ttcaacaaac      3480 gggccatatt gttgtataag tgatgaaata ctgaatttaa aacttagttt atatgtggta    3540 aaatgttta atcaagttta ggaggaatta attatgaagt gtaatgaatg taacagggtt     3600
caattaaaag agggaagcgt atcattaacc ctataaacta cgtctgccct cattattgga    3660
gggtgaaatg tgaatacatc ctattcacaa tcgaatttac gacacaacca aatttttaatt   3720
```

```
tggctttgca ttttatctttt ttttagcgta ttaaatgaaa tggttttgaa cgtctcatta    3780
cctgatattg caaatgattt taataaacca cctgcgagta caaactgggt gaacacagcc    3840
tttatgttaa cctttttccat tggaacagct gtatatggaa agctatctga tcaattaggc   3900
atcaaaaggt tactcctatt tggaattata ataaattgtt tcgggtcggt aattgggttt   3960
gttggccatt ctttcttttc cttacttatt atggctcgtt ttattcaagg gctggtgca    4020 gctgcatttc cagcactcgt aatggttgta gttgcgcgct atattccaaa ggaaaatagg   4080
ggtaaagcat ttggtcttat tggatcgata gtagccatgg gagaaggagt cggtccagcg   4140
attggtggaa tgatagccca ttatattcat tggtcctatc ttctactcat tcctatgata   4200
acaattatca ctgttccgtt tcttatgaaa ttattaaaga agaagtaag gataaaaggt    4260 cattttgata tcaaaggaat tatactaatg tctgtaggca ttgtattttt tatgttgttt   4320
acaacatcat atagcatttc ttttcttatc gttagcgtgc tgtcattcct gatatttgta   4380
aaacatatca ggaaagtaac agatcctttt gttgatcccg gattagggaa aaatatacct   4440
tttatgattg gagttctttg tgggggaatt atatttggaa cagtagcagg gtttgtctct   4500
atggttcctt tatgatgaa agatgttcac cagctaagta ctgccgaaat cggaagtgta   4560
attattttcc ctggaacaat gagtgtcatt attttcggct acattggtgg gatacttgtt   4620
gatagaagag gtcctttata cgtgttaaac atcggagtta catttctttc tgttagcttt   4680
ttaactgctt cctttctttt agaaacaaca tcatggttca tgacaattat aatcgtattt   4740
gttttaggtg ggctttcgtt caccaaaaca gttatatcaa caattgtttc aagtagcttg   4800
aaacagcagg aagctggtgc tggaatgagt ttgcttaact ttaccagctt tttatcagag   4860
ggaacaggta ttgcaattgt aggtggttta ttatccatac ccttacttga tcaaaggttg   4920
ttacctatgg aagttgatca gtcaacttat ctgtatagta atttgttatt acttttttca   4980
ggaatcattg tcattagttg gctggttacc ttgaatgtat ataaacattc tcaaagggat   5040
ttctaaatcg ttaagggatc aactttggga gagagttcaa aattgatcct ttttttataa   5100
cagttcgaag cggccgcaat tcttgaagac gaaagggcct cgtgatacgc ctatttttat   5160
aggttaatgt catgataata atggtttctt agacgtcagg tggcactttt cggggaaatg   5220
tgcgcggaac ccctatttgt ttattttttct aaatacattc aaatatgtat ccgctcatga   5280
gacaataacc ctgataaatg cttcaataat attgaaaaag gaagagtatg agtattcaac   5340
atttccgtgt cgcccttatt cccttttttg cggcattttg ccttcctgtt tttgctcacc   5400
cagaaacgct ggtgaaagta aaagatgctg aagatcagtt gggtgcacga gtgggttaca   5460
tcgaactgga tctcaacagc ggtaagatcc ttgagagttt tcgccccgaa gaacgttttc   5520
caatgatgag cacttttaaa gttctgctat gtggcgcggt attatcccgt attgacgccg   5580
ggcaagagca actcggtcgc cgcatacact attctcagaa tgacttggtt gagtactcac   5640
cagtcacaga aaagcatctt acggatggca tgacagtaag agaattatgc agtgctgcca   5700
taaccatgag tgataacact gcggccaact tacttctgac aacgatcgga ggaccgaagg   5760
agctaaccgc ttttttgcac aacatggggg atcatgtaac tcgccttgat cgttgggaac   5820
cggagctgaa tgaagccata ccaaacgacg agcgtgacac cacgatgcct gcagcaatgg   5880
caacaacgtt gcgcaaacta ttaactggcg aactacttac tctagcttcc cggcaacaat   5940
taatagactg gatggaggcg gataaagttg caggaccact tctgcgctcg gcccttccgg   6000
ctggctggtt tattgctgat aaatctggag ccggtgagcg tgggtctcgc ggtatcattg   6060
cagcactggg gccagatggt aagccctccc gtatcgtagt tatctacacg acggggagtc   6120
```

```
aggcaactat ggatgaacga aatagacaga tcgctgagat aggtgcctca ctgattaagc    6180
attggtaact gtcagaccaa gtttactcat atatacttta gattgattta aaacttcatt    6240
tttaatttaa aaggatctag gtgaagatcc tttttgataa tctcatgacc aaaatccctt    6300
aacgtgagtt ttcgttccac tgagcgtcag accccgtaga aagatcaaa ggatcttctt     6360 gagatccttt ttttctgcgc gtaatctgct gcttgcaaac aaaaaaacca ccgctaccag    6420
cggtggtttg tttgccggat caagagctac caactctttt tccgaaggta actggcttca    6480
gcagagcgca gataccaaat actgtccttc tagtgtagcc gtagttaggc caccacttca    6540
agaactctgt agcaccgcct acatacctcg ctctgctaat cctgttacca gtggctgctg    6600
ccagtggcga taagtcgtgt cttaccgggt tggactcaag acgatagtta ccggataagg    6660
cgcagcggtc gggctgaacg gggggttcgt gcacacagcc cagcttggag cgaacgacct    6720
acaccgaact gagataccta cagcgtgagc tatgagaaag cgccacgctt cccgaaggga    6780
gaaaggcgga caggtatccg gtaagcggca gggtcggaac aggagagcgc acgagggagc    6840
ttccaggggg aaacgcctgg tatctttata gtcctgtcgg gtttcgccac ctctgacttg    6900
agcgtcgatt tttgtgatgc tcgtcagggg ggcggagcct atggaaaaac gccagcaacg    6960
cggccttttt acggttcctg gccttttgct ggccttttgc tcacatgttc tttcctgcgt    7020
tatccsctga ttctgtggat aaccgtatta ccgcctttga gtgagctgat accgctcgcc    7080
gcagccgaac gaccgagcgc agcgagtcag tgagcgagga agcggaagag cgcctgatgc    7140
ggtattttct ccttacgcat ctgtgcgta tttcacaccg catatggtgc actctcagta    7200
caatctgctc tgatgccgca tagttaagcc agtatacact ccgctatcgc tacgtgactg    7260
ggtcatggct gcgccccgac acccgccaac cccgctgac gcgccctgac gggcttgtct    7320
gctcccggca tccgcttaca gacaagctgt gaccgtctcc gggagctgca tgtgtcagag    7380
gttttcaccg tcatcaccga aacgcgcgag gcagctgcgg taaagctcat cagcgtggtc    7440
gtgaagcgat tcacagatgt ctgcctgttc atccgcgtcc agctcgttga gtttctccag    7500
aagcgttaat gtctggcttc tgataaagcg ggccatgtta agggcggttt ttcctgtttt    7560
ggtcacttga tgcctccgtg taagggggaa tttctgttca tgggggtaat gataccgatg    7620
aaacgagaga ggatgctcac gatacgggtt actgatgatg aacatgcccg gttactggaa    7680
cgttgtgagg gtaaacaact ggcggtatgg atgcggcggg accagagaaa aatcactcag    7740
ggtcaatgcc agcgcttcgt taatacagat gtaggtgttc cacagggtag ccagcagcat    7800
cctgcgatgc agatccggaa cataatggtg cagggcgctg acttccgcgt tccagactt    7860 tacgaaacac ggaaaccgaa gaccattcat gttgttgctc aggtcgcaga cgttttgcag    7920
cagcagtcgc ttcacgttcg ctcgcgtatc ggtgattcat tctgctaacc agtaaggcaa    7980
ccccgccagc ctagccgggt cctcaacgac aggagcacga tcatgcgcac ccgtggccag    8040
gacccaacgc tgcccgagat gcgccgcgtg cggctgctgg agatggcgga cgcgatggat    8100
atgttctgcc aagggttggt ttgcgcattc acagttctcc gcaagaattg attggctcca    8160
attcttggag tggtgaatcc gttagcgagg tgccgccggc ttccattcag tcgaggtgg    8220 cccggctcca tgcaccgcga cgcaacgcgg ggaggcagac aaggtatagg gcggcgccta    8280
caatccatgc caacccgttc catgtgctcg ccgaggcgg ataaatcgcc gtgacgatca    8340
gcggtccagt gatcgaagtt aggctggtaa gagccgcgag cgatccttga agctgtccct    8400
gatggtcgtc atctacctgc ctggacagca tggcctgcaa cgcgggcatc ccgatgccgc    8460
cggaagcgag aagaatcata atgggggaagg ccatccagcc tcgcgtcggc ggccgcttcg    8520
```

| | |
|---|---|
| tcgaccgaaa cagcagttat aaggcatgaa gctgtccggt ttttgcaaaa gtggctgtga | 8580 |
| ctgtaaaaag aaatcgaaaa agaccgtttt gtgtgaaaac ggtcttttg tttccttta | 8640 |
| accaactgcc ataa | 8654 |

<210> SEQ ID NO 78
<211> LENGTH: 8093
<212> TYPE: DNA
<213> ORGANISM: Artificial Sequence
<220> FEATURE:
<223> OTHER INFORMATION: Description of Artificial Sequence:
      Recombinant pAN423 plasmid

<400> SEQUENCE: 78

| | |
|---|---|
| ggcggccgct tcgtcgaccg aaacagcagt tataaggcat gaagctgtcc ggttttgca | 60 |
| aaagtggctg tgactgtaaa agaaatcga aaagaccgt tttgtgtgaa acggtctt | 120 |
| ttgtttcctt ttaaccaact gccataactc gaggcctacc tagcttccaa gaaagatatc | 180 |
| ctaacagcac aagagcggaa agatgttttg ttctacatcc agaacaacct ctgctaaaat | 240 |
| tcctgaaaaa ttttgcaaaa agttgttgac tttatctaca aggtgtggta taataatctt | 300 |
| aacaacagca ggacgctcta gaaaaggagg aatttaaatg tatcgtacga tgatgagcgg | 360 |
| caaacttcac agggcaactg ttacggaagc aaacctgaac tatgtgggaa gcattacaat | 420 |
| tgatgaagat ctcattgatg ctgtgggaat gcttcctaat gaaaaagtac aaattgtgaa | 480 |
| taataataat ggagcacgtc ttgaaacgta tattattcct ggtaaacggg aagcggcgt | 540 |
| catatgctta acggtgcag ccgcacgcct tgtgcaggaa ggagataagg tcattattat | 600 |
| ttcctacaaa atgatgtctg atcaagaagc ggcaagccat gagccgaaag tggctgttct | 660 |
| gaatgatcaa aacaaaattg aacaaatgct ggggaacgaa ccagcccgta caattttgta | 720 |
| aaggatcctg ttttggcgga tgagagaaga ttttcagcct gatacagatt aaatcagaac | 780 |
| gcagaagcgg tctgataaaa cagaatttgc ctggcggcag tagcgcggtg gtcccacctg | 840 |
| accccatgcc gaactcagaa gtgaaacgcc gtagcgccga tggtagtgtg gggtctcccc | 900 |
| atgcgagagt agggaactgc caggcatcaa ataaaacgaa aggctcagtc gaaagactgg | 960 |
| gcctttcgtt ttatctgttg tttgtcggtg aacgctctcc tgagtaggac aaatccgccg | 1020 |
| ggagcggatt tgaacgttgc gaagcaacgg cccggagggt ggcgggcagg acgcccgcca | 1080 |
| taaactgcca ggcatcaaat taagcagaag gccatcctga cggatggcct ttttgcgttt | 1140 |
| ctacaaactc ttggtaccca gaaaagcgg caaaagcggc tgttaaaaaa gcgaaatcga | 1200 |
| agaagctgtc tgccgctaag acggaatatc aaaagcgttc tgctgttgtg tcatctttaa | 1260 |
| aagtcacagc cgatgaatcc cagcaagatg tcctaaaata cttgaacacc agaaagata | 1320 |
| aaggaaatgc agaccaaatt cattcttatt atgtggtgaa cgggattgct gttcatgcct | 1380 |
| caaaagaggt tatggaaaaa gtggtgcagt ttcccgaagt ggaaaaggtg cttcctaatg | 1440 |
| agaaacggca gcttttaag tcatcctccc catttaatat gaaaaaagca cagaaagcta | 1500 |
| ttaaagcaac tgacggtgtg gaatggaatg tagaccaaat cgatgccccca aaagcttggg | 1560 |
| cacttggata tgatggaact ggcacggttg ttgcgtccat tgataccggg gtggaatgga | 1620 |
| atcatccggc attaaaagag aaatatcgcg gatataatcc ggaaaatcct aatgagcctg | 1680 |
| aaaatgaaat gaactggtat gatgccgtag caggcgaggc aagcccttat gatgatttgg | 1740 |
| ctcatgaac ccacgtgaca ggcacgatgg tgggctctga acctgatgga acaaatcaaa | 1800 |
| tcggtgtagc acctggcgca aaatggattg ctgttaaagc gttctctgaa gatggcggca | 1860 |

```
ctgatgctga cattttggaa gctggtgaat gggttttagc accaaaggac gcggaaggaa   1920
atccccaccc ggaaatggct cctgatgttg tcaataactc atggggaggg ggctctggac   1980
ttgatgaatg gtacagagac atggtcaatg cctggcgttc ggccgatatt ttccctgagt   2040
tttcagcggg gaatacggat ctctttattc ccggcgggcc tggttctatc gcaaatccgg   2100
caaactatcc agaatcgttt gcaactggag cgactgagaa ttccaattcc ccatggagag   2160 aaagaaaat cgctaatgtt gattactttg aacttctgca tattcttgaa tttaaaaagg    2220
ctgaaagagt aaaagattgt gctgaaatat tagagtataa acaaaatcgt gaaacaggcg   2280
aaagaaagtt gtatcgagtg tggttttgta aatccaggct ttgtccaatg tgcaactgga   2340
ggagagcaat gaaacatggc attcagtcac aaaaggttgt tgctgaagtt attaaacaaa   2400
agccaacagt tcgttggttg tttctcacat taacagttaa aaatgtttat gatggcgaag   2460
aattaaataa gagtttgtca gatatggctc aaggatttcg ccgaatgatg caatataaaa   2520
aaattaataa aaatcttgtt ggttttatgc gtgcaacgga agtgacaata aataataaag   2580
ataattctta taatcagcac atgcatgtat tggtatgtgt ggaaccaact tattttaaga   2640
atacagaaaa ctacgtgaat caaaaacaat ggattcaatt ttggaaaaag gcaatgaaat   2700
tagactatga tccaaatgta aaagttcaaa tgattcgacc gaaaaataaa tataaatcgg   2760
atatacaatc ggcaattgac gaaactgcaa aatatcctgt aaaggatacg gattttatga   2820
ccgatgatga agaaaagaat ttgaaacgtt tgtctgattt ggaggaaggt ttacaccgta   2880
aaaggttaat ctcctatggt ggtttgttaa aagaaataca taaaaaatta aaccttgatg   2940
acacagaaga aggcgatttg attcatacag atgatgacga aaaagccgat gaagatggat   3000
tttctattat tgcaatgtgg aattgggaac ggaaaaatta ttttattaaa gagtagttca   3060
acaaacgggc catattgttg tataagtgat gaaatactga atttaaaact tagtttatat   3120
gtggtaaaat gttttaatca agtttaggag gaattaatta tgaagtgtaa tgaatgtaac   3180
agggttcaat taaagagggg aagcgtatca ttaaccctat aaactacgtc tgccctcatt   3240
attggagggt gaaatgtgaa tacatcctat tcacaatcga atttacgaca caaccaaatt   3300
ttaatttggc tttgcatttt atctttttt agcgtattaa atgaaatggt tttgaacgtc     3360
tcattacctg atattgcaaa tgattttaat aaaccacctg cgagtacaaa ctgggtgaac   3420
acagccttta tgttaaccett ttccattgga acagctgtat atggaaagct atctgatcaa   3480
ttaggcatca aaaggttact cctatttgga attataataa attgtttcgg gtcggtaatt   3540
gggtttgttg gccattcttt cttttcctta cttattatgg ctcgttttat tcaaggggct   3600
ggtgcagctg catttccagc actcgtaatg gttgtagttg cgcgctatat tccaaggaa    3660 aatagggta aagcatttgg tcttattgga tcgatagtag ccatgggaga aggagtcggt   3720
ccagcgattg gtggaatgat agcccattat attcattggt cctatcttct actcattcct   3780
atgataacaa ttatcactgt tccgtttctt atgaaattat aaagaaaga agtaaggata    3840 aaaggtcatt ttgatatcaa aggaattata ctaatgtctg taggcattgt attttttatg   3900
ttgtttacaa catcatatag catttctttt cttatcgtta gcgtgctgtc attcctgata   3960
tttgtaaaac atatcaggaa agtaacagat ccttttgttg atcccggatt agggaaaaat   4020 ataccttta tgattggagt tctttgtggg ggaattatat ttggaacagt agcagggttt    4080
gtctctatgg ttccttatat gatgaaagat gttcaccagc taagtactgc cgaaatcgga   4140
agtgtaatta ttttccctgg aacaatgagt gtcattattt tcggctacat tggtgggata   4200
cttgttgata gaagaggtcc tttatacgtg ttaaacatcg gagttacatt tctttctgtt   4260
```

```
agcttttaa  ctgcttcctt  tcttttagaa  acaacatcat  ggttcatgac  aattataatc   4320
gtatttgttt  taggtgggct  ttcgttcacc  aaaacagtta  tatcaacaat  tgtttcaagt   4380
agcttgaaac  agcaggaagc  tggtgctgga  atgagtttgc  ttaactttac  cagctttta   4440
tcagagggaa  caggtattgc  aattgtaggt  ggtttattat  ccatacccct  acttgatcaa   4500
aggttgttac  ctatggaagt  tgatcagtca  acttatctgt  atagtaattt  gttattactt   4560
ttttcaggaa  tcattgtcat  tagttggctg  gttaccttga  atgtatataa  acattctcaa   4620
agggatttct  aaatcgttaa  gggatcaact  ttgggagaga  gttcaaaatt  gatccttttt   4680
ttataacagt  tcgaagcggc  cgcaattctt  gaagacgaaa  gggcctcgtg  atacgcctat   4740
ttttataggt  taatgtcatg  ataataatgg  tttcttagac  gtcaggtggc  acttttcggg   4800
gaaatgtgcg  cggaacccct  atttgtttat  ttttctaaat  acattcaaat  atgtatccgc   4860
tcatgagaca  ataaccctga  taaatgcttc  aataatattg  aaaaaggaag  agtatgagta   4920
ttcaacattt  ccgtgtcgcc  cttattccct  tttttgcggc  attttgcctt  cctgtttttg   4980
ctcacccaga  aacgctggtg  aaagtaaaag  atgctgaaga  tcagttgggt  gcacgagtgg   5040
gttacatcga  actggatctc  aacagcggta  agatccttga  gagttttcgc  ccgaagaac   5100
gttttccaat  gatgagcact  tttaaagttc  tgctatgtgg  cgcggtatta  tcccgtattg   5160
acgccgggca  agagcaactc  ggtcgccgca  tacactattc  tcagaatgac  ttggttgagt   5220
actcaccagt  cacagaaaag  catcttacgg  atggcatgac  agtaagagaa  ttatgcagtg   5280
ctgccataac  catgagtgat  aacactgcgg  ccaacttact  tctgacaacg  atcggaggac   5340
cgaaggagct  aaccgctttt  ttgcacaaca  tgggggatca  tgtaactcgc  cttgatcgtt   5400
gggaaccgga  gctgaatgaa  gccataccaa  acgacgagcg  tgacaccacg  atgcctgcag   5460
caatggcaac  aacgttgcgc  aaactattaa  ctggcgaact  acttactcta  gcttcccggc   5520
aacaattaat  agactggatg  gaggcggata  aagttgcagg  accacttctg  cgctcggccc   5580
ttccggctgg  ctggtttatt  gctgataaat  ctggagccgg  tgagcgtggg  tctcgcggta   5640
tcattgcagc  actggggcca  gatggtaagc  cctcccgtat  cgtagttatc  tacacgacgg   5700
ggagtcaggc  aactatggat  gaacgaaata  gacagatcgc  tgagataggt  gcctcactga   5760
ttaagcattg  gtaactgtca  gaccaagttt  actcatatat  actttagatt  gatttaaaac   5820
ttcatttta  atttaaaagg  atctaggtga  agatcctttt  tgataatctc  atgaccaaaa   5880
tcccttaacg  tgagttttcg  ttccactgag  cgtcagaccc  cgtagaaaag  atcaaaggat   5940
cttcttgaga  tcctttttt  ctgcgcgtaa  tctgctgctt  gcaaacaaaa  aaaccaccgc   6000
taccagcggt  ggtttgtttg  ccggatcaag  agctaccaac  tcttttccg  aaggtaactg   6060
gcttcagcag  agcgcagata  ccaaatactg  tccttctagt  gtagccgtag  ttaggccacc   6120
acttcaagaa  ctctgtagca  ccgcctacat  acctcgctct  gctaatcctg  ttaccagtgg   6180
ctgctgccag  tggcgataag  tcgtgtctta  ccgggttgga  ctcaagacga  tagttaccgg   6240
ataaggcgca  gcggtcgggc  tgaacggggg  gttcgtgcac  acagcccagc  ttggagcgaa   6300
cgacctacac  cgaactgaga  tacctacagc  gtgagctatg  agaaagcgcc  acgcttcccg   6360
aagggagaaa  ggcggacagg  tatccggtaa  gcggcagggt  cggaacagga  gagcgcacga   6420
gggagcttcc  agggggaaac  gcctggtatc  tttatagtcc  tgtcgggttt  cgccacctct   6480
gacttgagcg  tcgatttttg  tgatgctcgt  caggggggcg  gagcctatgg  aaaaacgcca   6540
gcaacgcggc  cttttacgg  ttcctggcct  tttgctggcc  ttttgctcac  atgttctttc   6600
ctgcgttatc  ccctgattct  gtggataacc  gtattaccgc  ctttgagtga  gctgataccg   6660
```

```
ctcgccgcag ccgaacgacc gagcgcagcg agtcagtgag cgaggaagcg gaagagcgcc   6720
tgatgcggta ttttctcctt acgcatctgt gcggtatttc acaccgcata tggtgcactc   6780
tcagtacaat ctgctctgat gccgcatagt taagccagta tacactccgc tatcgctacg   6840
tgactgggtc atggctgcgc cccgacaccc gccaacaccc gctgacgcgc cctgacgggc   6900
ttgtctgctc ccggcatccg cttacagaca agctgtgacc gtctccggga gctgcatgtg   6960
tcagaggttt tcaccgtcat caccgaaacg cgcgaggcag ctgcggtaaa gctcatcagc   7020
gtggtcgtga agcgattcac agatgtctgc ctgttcatcc gcgtccagct cgttgagttt   7080
ctccagaagc gttaatgtct ggcttctgat aaagcgggcc atgttaaggg cggttttttc   7140
ctgtttggtc acttgatgcc tccgtgtaag ggggaatttc tgttcatggg ggtaatgata   7200
ccgatgaaac gagagaggat gctcacgata cgggttactg atgatgaaca tgcccggtta   7260
ctggaacgtt gtgagggtaa acaactggcg gtatggatgc ggcgggacca gagaaaaatc   7320
actcagggtc aatgccagcg cttcgttaat acagatgtag gtgttccaca gggtagccag   7380
cagcatcctg cgatgcagat ccggaacata atggtgcagg cgctgactt ccgcgtttcc    7440
agactttacg aaacacggaa accgaagacc attcatgttg ttgctcaggt cgcagacgtt   7500
ttgcagcagc agtcgcttca cgttcgctcg cgtatcggtg attcattctg ctaaccagta   7560
aggcaacccc gccagcctag ccgggtcctc aacgacagga gcacgatcat cgcacccgt    7620
ggccaggacc caacgctgcc cgagatgcgc cgcgtgcggc tgctggagat ggcggacgcg   7680
atggatatgt tctgccaagg gttggtttgc gcattcacag ttctccgcaa gaattgattg   7740
gctccaattc ttggagtggt gaatccgtta gcgaggtgcc gccggcttcc attcaggtcg   7800
aggtggcccg gctccatgca ccgcgacgca acgcggggag gcagacaagg tatagggcgg   7860
cgcctacaat ccatgccaac ccgttccatg tgctcgccga ggcggcataa atcgccgtga   7920
cgatcagcgg tccagtgatc gaagttaggc tggtaagagc cgcgagcgat ccttgaagct   7980
gtccctgatg gtcgtcatct acctgcctgg acagcatggc ctgcaacgcg gcatcccga    8040
tgccgccgga agcgagaaga atcataatgg ggaaggccat ccagcctcgc gtc          8093
```

<210> SEQ ID NO 79
<211> LENGTH: 8098
<212> TYPE: DNA
<213> ORGANISM: Artificial Sequence
<220> FEATURE:
<223> OTHER INFORMATION: Description of Artificial Sequence: Recombinant pAN429 plasmid

<400> SEQUENCE: 79

```
ggcggccgct tcgtcgaccg aaacagcagt tataaggcat gaagctgtcc ggttttttgca    60
aaagtggctg tgactgtaaa aagaaatcga aaaagaccgt tttgtgtgaa acggtctttt   120
ttgtttcctt ttaaccaact gccataactc gaggcctacc tagcttccaa gaaagatatc   180
ctaacagcac aagagcggaa agatgttttg ttctacatcc agaacaacct ctgctaaaat   240
tcctgaaaaa ttttgcaaaa agttgttgac tttatctaca aggtgtggta taataatctt   300
aacaacagca ggacgctcta gattagaaag gaggtttaat taatgtatcg tacgatgatg   360
agcggcaaac ttcacagggc aactgttacg gaagcaaacc tgaactatgt gggaagcatt   420
acaattgatg aagatctcat tgatgctgtg gaatgcttc ctaatgaaaa agtacaaatt    480
gtgaataata ataatggagc acgtcttgaa acgtatatta ttcctggtaa acggggaagc   540
ggcgtcatat gcttaaacgg tgcagccgca cgccttgtgc aggaaggaga taaggtcatt   600
attatttcct acaaaatgat gtctgatcaa gaagcggcaa gccatgagcc gaaagtggct   660
```

```
gttctgaatg atcaaaacaa aattgaacaa atgctgggga acgaaccagc ccgtacaatt      720
ttgtaaagga tcctgttttg gcggatgaga gaagattttc agcctgatac agattaaatc      780
agaacgcaga agcggtctga taaaacagaa tttgcctggc ggcagtagcg cggtggtccc      840
acctgacccc atgccgaact cagaagtgaa acgccgtagc gccgatggta gtgtggggtc      900
tccccatgcg agagtaggga actgccaggc atcaaataaa acgaaaggct cagtcgaaag      960
actgggcctt tcgttttatc tgttgtttgt cggtgaacgc tctcctgagt aggacaaatc     1020
cgccgggagc ggatttgaac gttgcgaagc aacggcccgg agggtggcgg gcaggacgcc     1080
cgccataaac tgccaggcat caaattaagc agaaggccat cctgacggat ggcctttttg     1140
cgtttctaca aactcttggt acccagaaaa agcggcaaaa gcggctgtta aaaaagcgaa     1200
atcgaagaag ctgtctgccg ctaagacgga atatcaaaag cgttctgctg ttgtgtcatc     1260
tttaaaagtc acagccgatg aatcccagca agatgtccta aaatacttga cacccagaa      1320 agataaagga aatgcagacc aaattcattc ttattatgtg gtgaacggga ttgctgttca     1380
tgcctcaaaa gaggttatgg aaaaagtggt gcagtttccc gaagtggaaa aggtgcttcc     1440
taatgagaaa cggcagcttt ttaagtcatc ctccccattt aatatgaaaa agcacagaa      1500 agctattaaa gcaactgacg gtgtggaatg gaatgtagac caaatcgatg ccccaaaagc     1560
ttgggcactt ggatatgatg gaactggcac ggttgttgcg tccattgata ccggggtgga     1620
atggaatcat ccggcattaa aagagaaata tcgcggatat aatccggaaa atcctaatga     1680
gcctgaaaat gaaatgaact ggtatgatgc cgtagcaggc gaggcaagcc cttatgatga     1740
tttggctcat ggaacccacg tgacaggcac gatggtgggc tctgaacctg atggaacaaa     1800
tcaaatcggt gtagcacctg cgcaaaatg gattgctgtt aaagcgttct ctgaagatgg     1860
cggcactgat gctgacattt ggaagctggt gaatgggtt ttagcaccaa aggacgcgga      1920
aggaaatccc cacccggaaa tggctcctga tgttgtcaat aactcatggg aggggggctc     1980
tggacttgat gaatggtaca gagacatggt caatgcctgg cgttcggccg atattttccc     2040
tgagttttca gcggggaata cggatctctt tattcccggc gggcctggtt ctatcgcaaa     2100
tccggcaaac tatccagaat cgtttgcaac tggagcgact gagaattcca attccccatg     2160
gagagaaaag aaaatcgcta atgttgatta ctttgaactt ctgcatattc ttgaatttaa     2220
aaaggctgaa agagtaaaag attgtgctga aatattagag tataaacaaa atcgtgaaac     2280
aggcgaaaga aagttgtatc gagtgtggtt ttgtaaatcc aggctttgtc caatgtgcaa     2340
ctggaggaga gcaatgaaac atggcattca gtcacaaaag gttgttgctg aagttattaa     2400
acaaaagcca acagttcgtt ggttgttttct cacattaaca gttaaaaatg tttatgatgg     2460
cgaagaatta aataagagtt tgtcagatat ggctcaagga tttcgccgaa tgatgcaata     2520
taaaaaaatt aataaaaatc ttgttggttt tatgcgtgca acggaagtga caataaataa     2580
taaagataat tcttataatc agcacatgca tgtattggta tgtgtggaac caacttattt     2640
taagaataca gaaaactacg tgaatcaaaa acaatggatt caattttgga aaaaggcaat     2700
gaaattagac tatgatccaa atgtaaaagt tcaaatgatt cgaccgaaaa ataaatataa     2760
atcggatata caatcggcaa ttgacgaaac tgcaaaatat cctgtaaagg atacggattt     2820
tatgaccgat gatgaagaaa agaatttgaa acgtttgtct gatttggagg aaggtttaca     2880
ccgtaaaagg ttaatctcct atggtggttt gttaaaagaa atacataaaa aattaaacct     2940
tgatgacaca gaagaaggcg atttgattca tacagatgat gacgaaaaag ccgatgaaga     3000 tggatttttct attattgcaa tgtggaattg ggaacggaaa aattattttta ttaaagagta     3060
```

```
gttcaacaaa cgggccatat tgttgtataa gtgatgaaat actgaattta aaacttagtt    3120
tatatgtggt aaaatgtttt aatcaagttt aggaggaatt aattatgaag tgtaatgaat    3180
gtaacagggt tcaattaaaa gagggaagcg tatcattaac cctataaact acgtctgccc    3240
tcattattgg agggtgaaat gtgaatacat cctattcaca atcgaattta cgacacaacc    3300
aaattttaat ttggctttgc attttatctt ttttagcgt attaaatgaa atggttttga     3360
acgtctcatt acctgatatt gcaaatgatt ttaataaacc acctgcgagt acaaactggg    3420
tgaacacagc ctttatgtta acctttccca ttggaacagc tgtatatgga aagctatctg    3480
atcaattagg catcaaaagg ttactcctat ttggaattat aataaattgt ttcgggtcgg    3540
taattgggtt tgttggccat tctttctttt ccttacttat tatggctcgt tttattcaag    3600
gggctggtgc agctgcattt ccagcactcg taatggttgt agttgcgcgc tatattccaa    3660
aggaaaatag gggtaaagca tttggtctta ttggatcgat agtagccatg ggagaaggag    3720
tcggtccagc gattggtgga atgatagccc attatattca ttggtcctat cttctactca    3780
ttcctatgat aacaattatc actgttccgt ttcttatgaa attattaaag aaagaagtaa    3840
ggataaaagg tcattttgat atcaaaggaa ttatactaat gtctgtaggc attgtatttt    3900
ttatgttgtt tacaacatca tatagcattt cttttcttat cgttagcgtg ctgtcattcc    3960
tgatatttgt aaaacatatc aggaaagtaa cagatccttt tgttgatccc ggattaggga    4020
aaaatatacc ttttatgatt ggagttcttt gtggggaat tatatttgga acagtagcag     4080
ggtttgtctc tatggttcct tatatgatga aagatgttca ccagctaagt actgccgaaa    4140
tcggaagtgt aattattttc cctggaacaa tgagtgtcat tattttcggc tacattggtg    4200
ggatacttgt tgatagaaga ggtcctttat acgtgttaaa catcggagtt acatttctt      4260 ctgttagctt tttaactgct tcctttcttt tagaaacaac atcatggttc atgacaatta    4320
taatcgtatt tgttttaggt gggctttcgt tcaccaaaac agttatatca acaattgttt    4380
caagtagctt gaaacagcag gaagctggtg ctggaatgag tttgcttaac tttaccagct    4440
ttttatcaga gggaacaggt attgcaattg taggtggttt attatccata cccttacttg    4500
atcaaaggtt gttacctatg gaagttgatc agtcaactta tctgtatagt aatttgttat    4560
tacttttttc aggaatcatt gtcattagtt ggctggttac cttgaatgta tataaacatt    4620
ctcaaaggga tttctaaatc gttaagggat caactttggg agagagttca aaattgatcc    4680
tttttttata acagttcgaa gcggccgcaa ttcttgaaga cgaaagggcc tcgtgatacg    4740
cctattttta taggttaatg tcatgataat aatggtttct tagacgtcag gtggcacttt    4800
tcggggaaat gtgcgcggaa cccctatttg tttatttttc taaatacatt caaatatgta    4860
tccgctcatg agacaataac cctgataaat gcttcaataa tattgaaaaa ggaagagtat    4920
gagtattcaa catttccgtg tcgcccttat tccctttttt gcggcatttt gccttcctgt    4980
ttttgctcac ccagaaacgc tggtgaaagt aaaagatgct gaagatcagt tgggtgcacg    5040
agtgggttac atcgaactgg atctcaacag cggtaagatc cttgagagtt ttcgccccga    5100
agaacgtttt ccaatgatga gcactttaa agttctgcta tgtggcgcgg tattatcccg     5160
tattgacgcc gggcaagagc aactcggtcg ccgcatacac tattctcaga atgacttggt    5220
tgagtactca ccagtcacag aaaagcatct tacggatggc atgacagtaa gagaattatg    5280
cagtgctgcc ataaccatga gtgataacac tgcggccaac ttacttctga acgatcgg      5340 aggaccgaag gagctaaccg cttttttgca acatgggg gatcatgtaa ctcgccttga      5400
tcgttgggaa ccggagctga atgaagccat accaaacgac gagcgtgaca ccacgatgcc    5460
```

```
tgcagcaatg gcaacaacgt tgcgcaaact attaactggc gaactactta ctctagcttc   5520
ccggcaacaa ttaatagact ggatggaggc ggataaagtt gcaggaccac ttctgcgctc   5580
ggcccttccg gctggctggt ttattgctga taaatctgga gccggtgagc gtgggtctcg   5640
cggtatcatt gcagcactgg ggccagatgg taagccctcc cgtatcgtag ttatctacac   5700
gacggggagt caggcaacta tggatgaacg aaatagacag atcgctgaga taggtgcctc   5760
actgattaag cattggtaac tgtcagacca agtttactca tatatacttt agattgattt   5820
aaaacttcat ttttaattta aaaggatcta ggtgaagatc ctttttgata atctcatgac   5880
caaaatccct taacgtgagt tttcgttcca ctgagcgtca gaccccgtag aaaagatcaa   5940
aggatcttct tgagatcctt ttttctgcg cgtaatctgc tgcttgcaaa caaaaaaacc   6000
accgctacca gcggtggttt gtttgccgga tcaagagcta ccaactcttt ttccgaaggt   6060
aactggcttc agcagagcgc agataccaaa tactgtcctt ctagtgtagc cgtagttagg   6120
ccaccacttc aagaactctg tagcaccgcc tacatacctc gctctgctaa tcctgttacc   6180
agtggctgct gccagtggcg ataagtcgtg tcttaccggg ttggactcaa gacgatagtt   6240
accggataag gcgcagcggt cgggctgaac ggggggttcg tgcacacagc ccagcttgga   6300
gcgaacgacc tacaccgaac tgagatacct acagcgtgag ctatgagaaa gcgccacgct   6360
tcccgaaggg agaaaggcgg acaggtatcc ggtaagcggc agggtcggaa caggagagcg   6420
cacgagggag cttccagggg gaaacgcctg gtatctttat agtcctgtcg ggtttcgcca   6480
cctctgactt gagcgtcgat ttttgtgatg ctcgtcaggg gggcggagcc tatggaaaaa   6540
cgccagcaac gcggccttt tacggttcct ggccttttgc tggccttttg ctcacatgtt   6600
ctttcctgcg ttatccctg attctgtgga taaccgtatt accgcctttg agtgagctga   6660
taccgctcgc cgcagccgaa cgaccgagcg cagcgagtca gtgagcgagg aagcggaaga   6720
gcgcctgatg cggtattttc tccttacgca tctgtgcggt atttcacacc gcatatggtg   6780
cactctcagt acaatctgct ctgatgccgc atagttaagc cagtatacac tccgctatcg   6840
ctacgtgact gggtcatggc tgcgccccga cacccgccaa cacccgctga cgcgccctga   6900
cgggcttgtc tgctcccggc atccgcttac agacaagctg tgaccgtctc cgggagctgc   6960
atgtgtcaga ggttttcacc gtcatcaccg aaacgcgcga ggcagctgcg gtaaagctca   7020
tcagcgtggt cgtgaagcga ttcacagatg tctgcctgtt catccgcgtc cagctcgttg   7080
agtttctcca gaagcgttaa tgtctggctt ctgataaagc gggccatgtt aagggcggtt   7140
ttttcctgtt tggtcacttg atgcctccgt gtaaggggga atttctgttc atgggggtaa   7200
tgataccgat gaaacgagag aggatgctca cgatacgggt tactgatgat gaacatgccc   7260
ggttactgga acgttgtgag ggtaaacaac tggcggtatg gatgcggcgg gaccagagaa   7320
aaatcactca gggtcaatgc cagcgcttcg ttaatacaga tgtaggtgtt ccacagggta   7380
gccagcagca tcctgcgatg cagatccgga acataatggt gcagggcgct gacttccgcg   7440
tttccagact ttacgaaaca cggaaaccga agaccattca tgttgttgct caggtcgcag   7500
acgttttgca gcagcagtcg cttcacgttc gctcgcgtat cggtgattca ttctgctaac   7560
cagtaaggca accccgccag cctagccggg tcctcaacga caggagcacg atcatgcgca   7620
cccgtggcca ggacccaacg ctgcccgaga tgcgccgcgt gcggctgctg gagatggcgg   7680
acgcgatgga tatgttctgc caagggttgg tttgcgcatt cacagttctc cgcaagaatt   7740
gattggctcc aattcttgga gtggtgaatc cgttagcgag gtgccgccgg cttccattca   7800
ggtcgaggtg gcccggctcc atgcaccgcg acgcaacgcg gggaggcaga caaggtatag   7860
```

```
ggcggcgcct acaatccatg ccaacccgtt ccatgtgctc gccgaggcgg cataaatcgc   7920
cgtgacgatc agcggtccag tgatcgaagt taggctggta agagccgcga gcgatccttg   7980
aagctgtccc tgatggtcgt catctacctg cctggacagc atggcctgca acgcgggcat   8040
cccgatgccg ccggaagcga aagaatcat aatggggaag gccatccagc ctcgcgtc    8098

<210> SEQ ID NO 80
<211> LENGTH: 4450
<212> TYPE: DNA
<213> ORGANISM: Artificial Sequence
<220> FEATURE:
<223> OTHER INFORMATION: Description of Artificial Sequence:
      Recombinant pAN443 plasmid

<400> SEQUENCE: 80
ccatcgaatg gccagatgat taattcctaa ttttgttga cactctatca ttgatagagt     60
tattttacca ctccctatca gtgatagaga aagtgaaat gaatagttcg acaaaaatct    120
agattagaaa ggaggattta aatatgagac agattactga tatttcacag ctgaaagaag    180
ccataaaaca ataccattca gagggcaagt caatcggatt tgttccgacg atggggtttc    240
tgcatgaggg gcatttaacc ttagcagaca aagcaagaca agaaaacgac gccgttatta    300
tgagtatttt tgtgaatcct gcacaattcg cccctaatga agattttgaa gcatatccgc    360
gcgatattga gcgggatgca gctcttgcag aaaacgccgg agtcgatatt cttttacgc    420 cagatgctca tgtatatgtat cccggtgaaa agaatgtcac gattcatgta gaaagacgca    480
cagacgtgtt atgcgggcgc tcaagagaag gacattttga cggggtcgcg atcgtactga    540
cgaagctttt caatctagtc aagccgactc gtgcctattt cggtttaaaa gatgcgcagc    600
aggtagctgt tgttgatggg ttaatcagcg acttcttcat ggatattgaa ttggttcctg    660
tcgatacggt cagagaggaa gacggcttag ccaaaagctc tcgcaatgta tacttaacag    720
ctgaggaaag aaagaagcg cctaagctgt atcgggccct tcaaacaagt gcggaacttg    780
tccaagccgg tgaaagagat cctgaagcgg tgataaaagc tgcaaaagat atcattgaaa    840
cgactagcgg aaccatagac tatgtagagc tttattccta tccggaactc gagcctgtga    900
atgaaattgc tggaaagatg attctcgctg ttgcagttgc ttttcaaaa gcgcgtttaa    960 tagataatat cattattgat attcgtagaa aggaggtgaa ttaatatgta tcgtacgatg   1020
atgagcggca aacttcacag ggcaactgtt acggaagcaa acctgaacta tgtgggaagc   1080
attacaattg atgaagatct cattgatgct gtgggaatgc ttcctaatga aaagtacaa   1140 attgtgaata ataataatgg agcacgtctt gaaacgtata ttattcctgg taacggggga   1200
agcggcgtca tatgcttaaa cggtgcagcc gcacgccttg tgcaggaagg agataaggtc   1260
attattattt cctacaaaat gatgtctgat caagaagcgg caagccatga gccgaaagtg   1320
gctgttctga tgatcaaaa caaaattgaa caaatgctgg gaacgaacc agcccgtaca   1380 atttttgtaaa ggatccccg gggatccctc gaggtcgacc tgcaggggga ccatggtctc   1440
agcgcttgga gccacccgca gttcgaaaaa taataagctt gacctgtgaa gtgaaaatg   1500 gcgcacattg tgcgacattt ttttgtctg ccgtttaccg ctactgcgtc acggatctcc   1560
acgcgccctg tagcggcgca ttaagcgcgg cgggtgtggt ggttacgcgc agcgtgaccg   1620
ctacacttgc cagcgcccta gcgcccgctc ctttcgcttt cttcccttcc tttctcgcca   1680
cgttcgccgg ctttccccgt caagctctaa atcgggggct ccctttaggg ttccgattta   1740
gtgctttacg gcacctcgac cccaaaaaac ttgattaggg tgatggttca cgtagtgggc   1800
```

```
catcgccctg atagacggtt tttcgcccctt tgacgttgga gtccacgttc tttaatagtg    1860
gactcttgtt ccaaactgga acaacactca accctatctc ggtctattct tttgatttat    1920
aagggatttt gccgatttcg gcctattggt taaaaaatga gctgatttaa caaaaattta    1980
acgcgaattt taacaaaata ttaacgctta caatttcagg tggcactttt cggggaaatg    2040
tgcgcggaac ccctatttgt ttatttttct aaatacattc aaatatgtat ccgctcatga    2100
gacaataacc ctgataaatg cttcaataat attgaaaaag gaagagtatg agtattcaac    2160
atttccgtgt cgcccttatt ccctttttg cggcattttg ccttcctgtt tttgctcacc    2220
cagaaacgct ggtgaaagta aaagatgctg aagatcagtt gggtgcacga gtgggttaca    2280
tcgaactgga tctcaacagc ggtaagatcc ttgagagttt tcgccccgaa aacgttttc    2340
caatgatgag cacttttaaa gttctgctat gtggcgcggt attatcccgt attgacgccg    2400
ggcaagagca actcggtcgc cgcatacact attctcagaa tgacttggtt gagtactcac    2460
cagtcacaga aaagcatctt acggatggca tgacagtaag agaattatgc agtgctgcca    2520
taaccatgag tgataacact gcggccaact tacttctgac aacgatcgga ggaccgaagg    2580
agctaaccgc ttttttgcac aacatggggg atcatgtaac tcgccttgat cgttgggaac    2640
cggagctgaa tgaagccata ccaaacgacg agcgtgacac cacgatgcct gtagcaatgg    2700
caacaacgtt gcgcaaacta ttaactggcg aactacttac tctagcttcc cggcaacaat    2760
tgatagactg gatggaggcg gataaagttg caggaccact tctgcgctcg gcccttccgg    2820
ctggctggtt tattgctgat aaatctggag ccggtgagcg tggctctcgc ggtatcattg    2880
cagcactggg gccagatggt aagccctccc gtatcgtagt tatctacacg acggggagtc    2940
aggcaactat ggatgaacga atagacaga tcgctgagat aggtgcctca ctgattaagc    3000
attggtagga attaatgatg tctcgtttag ataaaagtaa agtgattaac agcgcattag    3060
agctgcttaa tgaggtcgga atcgaaggtt taacaacccg taaactcgcc cagaagctag    3120
gtgtagagca gcctacattg tattggcatg taaaaaataa gcgggctttg ctcgacgcct    3180
tagccattga gatgttagat aggcaccata ctcacttttg ccccttagaa ggggaaagct    3240
ggcaagattt tttacgtaat aacgctaaaa gttttagatg tgctttacta agtcatcgcg    3300
atggagcaaa agtacattta ggtacacggc ctacagaaaa acagtatgaa actctcgaaa    3360
atcaattagc cttttatgc caacaaggtt tttcactaga gaatgcatta tatgcactca    3420
gcgcagtggg gcattttact ttaggttgcg tattggaaga tcaagagcat caagtcgcta    3480
aagaagaaag ggaaacacct actactgata gtatgccgcc attattacga caagctatcg    3540
aattatttga tcaccaaggt gcagagccag ccttcttatt cggccttgaa ttgatcatat    3600
gcggattaga aaacaactt aaatgtgaaa gtgggtctta aaagcagcat aaccttttc    3660
cgtgatggta acttcactag tttaaaagga tctaggtgaa gatcctttt gataatctca    3720
tgaccaaaat cccttaacgt gagttttcgt tccactgagc gtcagacccc gtagaaaaga    3780
tcaaaggatc ttcttgagat cctttttttc tgcgcgtaat ctgctgcttg caaacaaaaa    3840
aaccaccgct accagcggtg gtttgtttgc cggatcaaga gctaccaact cttttttccga    3900
aggtaactgg cttcagcaga gcgcagatac caaatactgt ccttctagtg tagccgtagt    3960
taggccacca cttcaagaac tctgtagcac cgcctacata cctcgctctg ctaatcctgt    4020
taccagtggc tgctgccagt ggcgataagt cgtgtcttac cgggttggac tcaagacgat    4080
agttaccgga taaggcgcag cggtcgggct gaacggggg ttcgtgcaca cagcccagct    4140
tggagcgaac gacctacacc gaactgagat acctacagcg tgagctatga gaaagcgcca    4200
```

-continued

| | |
|---|---|
| cgcttcccga agggagaaag gcggacaggt atccggtaag cggcagggtc ggaacaggag | 4260 |
| agcgcacgag ggagcttcca gggggaaacg cctggtatct ttatagtcct gtcgggtttc | 4320 |
| gccacctctg acttgagcgt cgattttgt gatgctcgtc aggggggcgg agcctatgga | 4380 |
| aaaacgccag caacgcggcc ttttacggt tcctggcctt tgctggcct tttgctcaca | 4440 |
| tgacccgaca | 4450 |

<210> SEQ ID NO 81
<211> LENGTH: 10212
<212> TYPE: DNA
<213> ORGANISM: Artificial Sequence
<220> FEATURE:
<223> OTHER INFORMATION: Description of Artificial Sequence:
      Recombinant pAN251 plasmid

<400> SEQUENCE: 81

| | |
|---|---|
| gcggccgcta aaagagctt gaggatttgc ggagtgaaaa tcagacattg cggaatcagc | 60 |
| tagagatgac agaagaggat tacaaggcac tgatcgatat catggatcgg gccagaaaaa | 120 |
| tggttgtttc gaaggaagac ggaagaatga aaaagcggc tcaagaaacg taaagaaacg | 180 |
| cctgaaatga accggcccta tagtaagaat aggccggttg ttttgatttc tatgcagact | 240 |
| ctcccggtgt catttcgcga tccatatcag gatgccagat gagcgggtct tccccttgt | 300 |
| cccgcgccat atcatactta acagttttaa agttcatttt gttccaaaat tccgctgatt | 360 |
| tcattctcgg atttgtccgg atcggcattt tgaatgattt tgcaaattca accaaggctc | 420 |
| tcccgtatcc cctgttctgg tagcccggaa gaacctcaag cttccacagc tccaaataat | 480 |
| cctggcggtt gtcaaaatag ggattcgatt tgccgttaac ttgatacaga ctcattcgtg | 540 |
| ctacaagttt atcgccaaaa taaatcccgt aaaaggcga ggtgctgtca ttttcaataa | 600 |
| tattatcctg aagttcttca agcattgaaa gctcctgaat gccgtattct ttgaatttct | 660 |
| tgaattcttc cagcgtttta tagttgataa gcagacgttc tacctttgtc aaacaaatct | 720 |
| ccccctttgt tgtttctaca tatattgtaa acgctttatt taaaaaatcc aaatatttaa | 780 |
| actttaattt taagcacatg ggatctttga gaagtaattt cttcttactt ctgctatgat | 840 |
| aatacgtaaa tgcgtcgacc gaaacagcag ttataaggca tgaagctgtc cggttttgc | 900 |
| aaaagtggct gtgactgtaa aagaaatcg aaaagaccg ttttgtgtga aacggtctt | 960 |
| tttgtttcct tttaaccaac tgccataact cgaggcctac ctagcttcca agaaagatat | 1020 |
| cctaacagca caagagcgga aagatgtttt gttctacatc cagaacaacc tctgctaaaa | 1080 |
| ttcctgaaaa attttgcaaa aagttgttga ctttatctac aaggtgtggt ataataatct | 1140 |
| taacaacagc aggacgctct agaggaggag acatcatgaa aattggaatt atcggcggag | 1200 |
| gctccgttgg tcttttatgc gcctattatt tgtcacttta tcacgacgtg actgttgtga | 1260 |
| cgaggcggca agaacaggct gcggccattc agtctgaagg aatccggctt tataaaggcg | 1320 |
| gggaggaatt cagggctgat tgcagtgcgg acacgagtat caattcggac tttgacctgc | 1380 |
| ttgtcgtgac agtgaagcag catcagcttc aatctgtttt ttcgtcgctt gaacgaatcg | 1440 |
| ggaagacgaa tatattattt ttgcaaaacg gcatggggca tatccacgac ctaaaagact | 1500 |
| ggcacgttgg ccattccatt tatgttggaa tcgttgagca cggagctgta agaaaatcgg | 1560 |
| atacagctgt tgatcataca ggcctaggtg cgataaaatg gagcgcgttc gacgatgctg | 1620 |
| aaccagaccg gctgaacatc ttgtttcagc ataaccattc ggattttccg atttattatg | 1680 |
| agacggattg gtaccgtctg ctgacgggca agctgattgt aaatgcgtgt attaatcctt | 1740 |
| taactgcgtt attgcaagtg aaaaatggag aactgctgac aacgccagct tatctggctt | 1800 |

```
ttatgaagct ggtatttcag gaggcatgcc gcattttaaa acttgaaaat gaagaaaagg   1860
cttgggagcg ggttcaggcc gtttgtgggc aaacgaaaga gaatcgttca tcaatgctgg   1920
ttgacgtcat tggaggccgg cagacggaag ctgacgccat tatcggatac ttattgaagg   1980
aagcaagtct tcaaggtctt gatgccgtcc acctagagtt tttatatggc agcatcaaag   2040
cattggagcg aaatacaaac aaagtctttt gagcttttc ggtaacatgc tatactcatt    2100
tcggatcact aactatttat tggagaaagg aagttctaga agatgcagct aactgaactt   2160
tccatcaaaa atcagaatgt gtttgtacag cactatatag atggcaaaga agaaatgtct   2220
tcttttttg attacagtat tcatcataag gacatgtggc gcgaaagact ggaagactta    2280
tcttcccggt ttttcgcaag agaggaattg gcggcgtact taacctctta ccataataaa   2340
ttcggttcaa gtgcgatgca gtctgctatt gagaagctga aggacccgtc aagtgccgct   2400
gtagtcggcg gacagcaggc aggactttta acaggaccgc tttacaccat acataaaatc   2460
atttcaatca ttgttttagc aaagcaacaa gaaaaggaac tgcaagtgcc tgtcatacca   2520
atcttctggg tggctggaga agaccacgat ttggatgaga ttaattttgt tcacacatct   2580
gaagagaatg ggcctgtgaa aaaaagctg cctcagtctt attggaagaa atcatcagca    2640
gcgagtacat cgcttgatca ggaaaagtgt gccgcgtgga tagatgatgt ttttgccgct   2700
tttgaagaaa cagaccatac gaatacactt ctcgacaatg tgaaacgatg tttaagggaa   2760
tctgttacgt ttactgactt cttgaactg ctgatcgcgg atttgttcca agaagagggc    2820
ttagtttat aaattctgg ggatcctgtt ttggcggatg agagaagatt ttcagcctga     2880
tacagattaa atcagaacgc agaagcggtc tgataaaaca gaatttgcct ggcggcagta   2940
gcgcggtggt cccacctgac cccatgccga actcagaagt gaaacgccgt agcgccgatg   3000
gtagtgtggg gtctccccat gcgagagtag ggaactgcca ggcatcaaat aaaacgaaag   3060
gctcagtcga aagactgggc ctttcgtttt atctgttgtt tgtcggtgaa cgctctcctg   3120
agtaggacaa atccgccggg agcggatttg aacgttgcga agcaacggcc cggagggtgg   3180
cgggcaggac gcccgccata aactgccagg catcaaatta agcagaaggc catcctgacg   3240
gatggccttt ttgcgtttct acaaactctt ggtacccaga aaaagcggca aaagcggctg   3300
ttaaaaagc gaaatcgaag aagctgtctg ccgctaagac ggaatatcaa aagcgttctg    3360
ctgttgtgtc atctttaaaa gtcacagccg atgaatccca gcaagatgtc ctaaaatact   3420
tgaacaccca gaaagataaa ggaaatgcag accaaattca ttcttattat gtggtgaacg   3480
ggattgctgt tcatgcctca aaagaggtta tggaaaaagt ggtgcagttt cccgaagtgg   3540
aaaaggtgct tcctaatgag aaacggcagc ttttttaagtc atcctcccca tttaatatga   3600
aaaaagcaca gaaagctatt aaagcaactg acggtgtgga atggaatgta gaccaaatcg   3660
atgccccaaa agcttgggca cttggatatg atggaactgg cacgttgtt gcgtccattg    3720
ataccggggt ggaatggaat catccggcat taaaagagaa atatcgcgga tataatccgg   3780
aaaatcctaa tgagcctgaa aatgaaatga actggtatga tgccgtagca ggcgaggcaa   3840
gcccttatga tgatttggct catggaaccc acgtgacagg cacgatggtg ggctctgaac   3900
ctgatggaac aaatcaaatc ggtgtagcac ctggcgcaaa atggattgct gttaaagcgt   3960
tctctgaaga tggcggcact gatgctgaca ttttggaagc tggtgaatgg ttttagcac    4020
caaaggacgc ggaaggaaat ccccacccgg aaatggctcc tgatgttgtc aataactcat   4080
ggggagggg ctctgacctt gatgaatggt acagagacat ggtcaatgcc tggcgttcgg    4140
ccgatatttt ccctgagttt tcagcgggga atacggatct ctttattccc ggcgggcctg   4200
```

```
gttctatcgc aaatccggca aactatccag aatcgtttgc aactggagcg actgagaatt    4260
ccaattcccc atggagagaa aagaaaatcg ctaatgttga ttactttgaa cttctgcata    4320
ttcttgaatt taaaaaggct gaaagagtaa aagattgtgc tgaaatatta gagtataaac    4380
aaaatcgtga aacaggcgaa agaaagttgt atcgagtgtg gttttgtaaa tccaggcttt    4440
gtccaatgtg caactggagg agagcaatga acatggcat tcagtcacaa aaggttgttg    4500
ctgaagttat taaacaaaag ccaacagttc gttggttgtt tctcacatta acagttaaaa    4560
atgtttatga tggcgaagaa ttaaataaga gtttgtcaga tatggctcaa ggatttcgcc    4620
gaatgatgca atataaaaaa attaataaaa atcttgttgg ttttatgcgt gcaacggaag    4680
tgacaataaa taataaagat aattcttata atcagcacat gcatgtattg gtatgtgtgg    4740
aaccaactta ttttaagaat acagaaaact acgtgaatca aaaacaatgg attcaatttt    4800
ggaaaaaggc aatgaaatta gactatgatc caaatgtaaa agttcaaatg attcgaccga    4860
aaaataaata taaatcggat atacaatcgg caattgacga aactgcaaaa tatcctgtaa    4920
aggatacgga ttttatgacc gatgatgaag aaaagaattt gaaacgtttg tctgatttgg    4980
aggaaggttt acaccgtaaa aggttaatct cctatggtgg tttgttaaaa gaaatacata    5040
aaaaattaaa ccttgatgac acagaagaag gcgatttgat tcatacagat gatgacgaaa    5100
aagccgatga agatggattt tctattattg caatgtggaa ttgggaacgg aaaaattatt    5160
ttattaaaga gtagttcaac aaacgggcca tattgttgta taagtgatga aatactgaat    5220
ttaaaactta gtttatatgt ggtaaaatgt tttaatcaag tttaggagga attaattatg    5280
aagtgtaatg aatgtaacag ggttcaatta aaagagggaa gcgtatcatt aaccctataa    5340
actacgtctg ccctcattat tggagggtga aatgtgaata catcctattc acaatcgaat    5400
ttacgacaca accaaatttt aatttggctt tgcattttat ctttttttag cgtattaaat    5460
gaaatggttt tgaacgtctc attacctgat attgcaaatg attttaataa accacctgcg    5520
agtacaaact gggtgaacac agcctttatg ttaacctttt ccattggaac agctgtatat    5580
ggaaagctat ctgatcaatt aggcatcaaa aggttactcc tatttggaat tataataaat    5640
tgtttcgggt cggtaattgg gtttgttggc cattctttct tttccttact tattatggct    5700
cgttttattc aaggggctgg tgcagctgca tttccagcac tcgtaatggt tgtagttgcg    5760
cgctatattc caaaggaaaa tagggtaaa gcatttggtc ttattggatc gatagtagcc    5820
atgggagaag gagtcggtcc agcgattggt ggaatgatag cccattatat tcattggtcc    5880
tatcttctac tcattcctat gataacaatt atcactgttc cgtttcttat gaaattatta    5940 aagaagaag taaggataaa aggtcatttt gatatcaaag gaattatact aatgtctgta    6000
ggcattgtat ttttatgtt gtttacaaca tcatatagca tttctttct tatcgttagc    6060 gtgctgtcat tcctgatatt tgtaaaacat atcaggaaag taacagatcc ttttgttgat    6120
cccggattag ggaaaaatat acctttatg attggagttc tttgtggggg aattatattt    6180
ggaacagtag cagggtttgt ctctatggtt ccttatatga tgaaagatgt tcaccagcta    6240
agtactgccg aaatcggaag tgtaattatt ttccctggaa caatgagtgt cattatttc    6300 ggctacattg gtgggatact tgttgataga agaggtcctt tatacgtgtt aaacatcgga    6360
gttacatttc tttctgttag ctttttaact gcttcctttc ttttagaaac aacatcatgg    6420
ttcatgacaa ttataatcgt atttgtttta ggtgggcttt cgttcaccaa acagttata    6480 tcaacaattg tttcaagtag cttgaaacag caggaagctg gtgctggaat gagtttgctt    6540
aactttacca gcttttatc agagggaaca ggtattgcaa ttgtaggtgg tttattatcc    6600
```

```
atacccttac ttgatcaaag gttgttacct atggaagttg atcagtcaac ttatctgtat    6660
agtaatttgt tattactttt ttcaggaatc attgtcatta gttggctggt taccttgaat    6720
gtatataaac attctcaaag ggatttctaa atcgttaagg gatcaacttt gggagagagt    6780
tcaaaattga tcctttttt ataacagttc gaagcggccg caattcttga agacgaaagg    6840
gcctcgtgat acgcctattt ttataggtta atgtcatgat aataatggtt tcttagacgt    6900
caggtggcac ttttcgggga aatgtgcgcg gaacccctat tgtttattt ttctaaatac    6960 attcaaatat gtatccgctc atgagacaat aaccctgata aatgcttcaa taatattgaa    7020
aaaggaagag tatgagtatt caacatttcc gtgtcgccct tattccctt tttgcggcat    7080 tttgccttcc tgttttgct cacccagaaa cgctggtgaa agtaaaagat gctgaagatc    7140
agttgggtgc acgagtgggt tacatcgaac tggatctcaa cagcggtaag atccttgaga    7200
gttttcgccc cgaagaacgt tttccaatga tgagcacttt taaagttctg ctatgtggcg    7260
cggtattatc ccgtattgac gccgggcaag agcaactcgg tcgccgcata cactattctc    7320
agaatgactt ggttgagtac tcaccagtca cagaaaagca tcttacggat ggcatgacag    7380
taagagaatt atgcagtgct gccataacca tgagtgataa cactgcggcc aacttacttc    7440
tgacaacgat cggaggaccg aaggagctaa ccgcttttt gcacaacatg ggggatcatg    7500
taactcgcct tgatcgttgg gaaccggagc tgaatgaagc cataccaaac gacgagcgtg    7560
acaccacgat gcctgcagca atggcaacaa cgttgcgcaa actattaact ggcgaactac    7620
ttactctagc ttcccggcaa caattaatag actggatgga ggcggataaa gttgcaggac    7680
cacttctgcg ctcggccctt ccggctggct ggtttattgc tgataaatct ggagccggtg    7740
agcgtgggtc tcgcggtatc attgcagcac tggggccaga tggtaagccc tcccgtatcg    7800
tagttatcta cacgacgggg agtcaggcaa ctatggatga acgaaataga cagatcgctg    7860
agataggtgc ctcactgatt aagcattggt aactgtcaga ccaagtttac tcatatatac    7920
tttagattga tttaaaactt catttttaat ttaaaaggat ctaggtgaag atccttttg    7980 ataatctcat gaccaaaatc ccttaacgtg agttttcgtt ccactgagcg tcagaccccg    8040
tagaaaagat caaaggatct cttgagatc cttttttct gcgcgtaatc tgctgcttgc    8100
aaacaaaaaa accaccgcta ccagcggtgg tttgtttgcc ggatcaagag ctaccaactc    8160
tttttccgaa ggtaactggc ttcagcagag cgcagatacc aaatactgtc cttctagtgt    8220
agccgtagtt aggccaccac ttcaagaact ctgtagcacc gcctacatac ctcgctctgc    8280
taatcctgtt accagtggct gctgccagtg gcgataagtc gtgtcttacc gggttggact    8340
caagacgata gttaccggat aaggcgcagc ggtcgggctg aacggggggt tcgtgcacac    8400
agcccagctt ggagcgaacg acctacaccg aactgagata cctacagcgt gagctatgag    8460
aaagcgccac gcttcccgaa gggagaaagg cggacaggta tccggtaagc ggcagggtcg    8520
gaacaggaga gcgcacgagg gagcttccag ggggaaacgc ctggtatctt tatagtcctg    8580
tcgggtttcg ccacctctga cttgagcgtc gatttttgtg atgctcgtca ggggggcgga    8640 gcctatgaa aaacgccagc aacgcggcct ttttacggtt cctggccttt tgctggcctt    8700
ttgctcacat gttctttcct gcgttatccc ctgattctgt ggataaccgt attaccgcct    8760
ttgagtgagc tgataccgct cgccgcagcc gaacgaccga gcgcagcgag tcagtgagcg    8820
aggaagcgga gagcgcctg atgcggtatt ttctccttac gcatctgtgc ggtatttcac    8880
accgcatatg gtgcactctc agtacaatct gctctgatgc cgcatagtta agccagtata    8940
cactccgcta tcgctacgtg actgggtcat ggctgcgccc cgacacccgc caacacccgc    9000
```

```
tgacgcgccc tgacgggctt gtctgctccc ggcatccgct tacagacaag ctgtgaccgt      9060
ctccgggagc tgcatgtgtc agaggttttc accgtcatca ccgaaacgcg cgaggcagct      9120
gcggtaaagc tcatcagcgt ggtcgtgaag cgattcacag atgtctgcct gttcatccgc      9180
gtccagctcg ttgagtttct ccagaagcgt taatgtctgg cttctgataa agcgggccat      9240
gttaagggcg gttttttcct gtttggtcac ttgatgcctc cgtgtaaggg ggaatttctg      9300
ttcatggggg taatgatacc gatgaaacga gagaggatgc tcacgatacg ggttactgat      9360
gatgaacatg cccggttact ggaacgttgt gagggtaaac aactggcggt atggatgcgg      9420
cgggaccaga gaaaaatcac tcagggtcaa tgccagcgct tcgttaatac agatgtaggt      9480
gttccacagg gtagccagca gcatcctgcg atgcagatcc ggaacataat ggtgcagggc      9540
gctgacttcc gcgtttccag actttacgaa acacggaaac cgaagaccat tcatgttgtt      9600
gctcaggtcg cagacgtttt gcagcagcag tcgcttcacg ttcgctcgcg tatcggtgat      9660
tcattctgct aaccagtaag gcaaccccgc cagcctagcc gggtcctcaa cgacaggagc      9720
acgatcatgc gcacccgtgg ccaggaccca acgctgcccg agatgcgccg cgtgcggctg      9780
ctggagatgg cggacgcgat ggatatgttc tgccaagggt tggtttgcgc attcacagtt      9840
ctccgcaaga attgattggc tccaattctt ggagtggtga atccgttagc gaggtgccgc      9900
cggcttccat tcaggtcgag gtggcccggc tccatgcacc cgacgcaac gcggggaggc      9960 agacaaggta tagggcggcg cctacaatcc atgccaaccc gttccatgtg ctcgccgagg     10020
cggcataaat cgccgtgacg atcagcggtc cagtgatcga agttaggctg gtaagagccg     10080
cgagcgatcc ttgaagctgt ccctgatggt cgtcatctac ctgcctggac agcatggcct     10140
gcaacgcggg catcccgatg ccgccggaag cgagaagaat cataatgggg aaggccatcc     10200
agcctcgcgt cg                                                          10212
```

<210> SEQ ID NO 82
<211> LENGTH: 10426
<212> TYPE: DNA
<213> ORGANISM: Artificial Sequence
<220> FEATURE:
<223> OTHER INFORMATION: Description of Artificial Sequence:
      Recombinant pAN267 plasmid

<400> SEQUENCE: 82

```
aacaaaattc tccagtcttc acatcggttt gaaaggagga agcggaagaa tgaagtaaga       60 gggattttg actccgaagt aagtcttcaa aaaatcaaat aaggagtgtc aagaatgttt      120
gcaaaacgat tcaaaaccctc tttactgccg ttattcgctg gattttttatt gctgtttcat      180 ttggttctgg caggaccggc ggctgcgagt gctgaaacgg cgaacaaatc gaatgagctt      240
acagcaccgt cgatcaaaag cggaaccatt cttcatgcat ggaattggtc gttcaatacg      300
ttaaaacaca atatgaagga tattcatgat gcaggatata cagccattca gacatctccg      360
attaaccaag taaggaagg gaatcaagga gataaaagca tgtcgaactg gtactggctg      420
tatcagccga catcgtatca aattggcaac cgttacttag gtactgaaca agaatttaaa      480
gaaatgtgtg cagccgctga agaatatggc ataaggtca ttgttgacgc ggtcatcaat      540
cataccacca gtgattatgc cgcgatttcc aatgaggtta agagtattcc aaactggaca      600
catggaaaca cacaaattaa aaactggtct gatcgaaata gtacataatg gatttcctta      660
cgcgaaatac gggcagacat ggcctgcccg gttattatta ttttttgacac cagaccaact      720 ggtaatggta gcgaccggcg ctcaggatcg tctcggtacc aagagtttgt agaaacgcaa      780
```

```
aaaggccatc cgtcaggatg gccttctgct taatttgatg cctggcagtt tatggcgggc    840
gtcctgcccg ccaccctccg ggccgttgct tcgcaacgtt caaatccgct cccggcggat    900
ttgtcctact caggagagcg ttcaccgaca acaacagat aaaacgaaag gcccagtctt     960
tcgactgagc ctttcgtttt atttgatgcc tggcagttcc ctactctcgc atggggagac   1020
cccacactac catcggcgct acggcgtttc acttctgagt tcggcatggg gtcaggtggg   1080
accaccgcgc tactgccgcc aggcaaattc tgttttatca gaccgcttct gcgttctgat   1140
ttaatctgta tcaggctgaa atcttctct catccgccaa acaggatcc atcacgaagc     1200
gtcgtatcga aaaaattaat tttgcgcaac ggagaccacc gcttccttct tcttgccttg   1260
tttcacaaac ggcatcattt cacgaagctt tcttcccact acttcgattt gatgttcgtt   1320
ctcgcttgca ttgatagcgt tgaaacgagg acggtttact tggttttcga cgatccactc   1380
ttttgcgaat gtaccgtttt ggatatcttt taatacttct ttcatagatt cttttacttt   1440
agcgtccaca acgcgagggc ctgatacgaa atctccccac tgtgctgtgt cagagattga   1500
atatctcatt cctgcaagtc cttcttcgta cataaggtct acgattaatt tcagctcatg   1560
aagacactcg aagtatgcaa gttcaggctg ataacctgct tcagttaagg tttcaaatcc   1620
ggctttgaca agcgcgctta atccgccgca aagaactgct tgctcaccga acaaatctgt   1680
ttctgttcct tctttaaatg tcgtttctaa tacgcccgct cttgcgccgc cgattccttt   1740
agcataagcg agggctttgt ctcttgcttc tccagtcaca tcttgataga ttgcgaacaa   1800
tgcaggtacg ccagctcctt gctcatatgt tcttcttacc aagtgtcccg ggcctttagg   1860
ggccactaag aatacatcta catccgccgg aggaacaatt tgatggaaat gcacgttaaa   1920
tccatgagcg aatactaatg attttcctgc tgtcaattca tctttgattt cagcttcgta   1980
tactttttgc tgctgctcat ccggaagcag aaccatgatg atttcggctt gggctgccgc   2040
ttcttttact gaaaatactt tatgtccgtc ttcctttgggct tgagtgaaag attttccttg   2100
tctaacaccg acgatcacgt ctactccgct ttctttaagg ttcagggcat gtgcgtggcc   2160
ttgcgaaccg tacccgataa ccgctactgt ttttccagcc aatacgttct ctttgatatc   2220
accgttataa tatactttta ccatttcaat ctctcccttg ttatgtttta tacaatagat   2280
attgttttat tggatgacgc cttttgctgg ttcccctcgc aaaagccgtt gtacctgttc   2340
tcgcgatttc tttaatgcca taaggttta ataactcaat aagcgcttca attttgttag    2400
attcacctgt cacctgaaca acgatgctgt ctctgctgac atcaacgaca gaggctctaa   2460
acggttctat gattccatta atctctgttc ttgttgaagg tgcggagaca accttgatta   2520
aggccagctc cctctggaca atcgattgat ttgtgatgtc tgtgactttc agcacatcaa   2580
tctgtttgtt gagctgtttc gttaactgtt caacatcatt ttcaccttca acatgaacga   2640
cgaaggtgat tctggaaacg ccggctgttt ctgtgtgtcc aactgtaatg ctttcaatgt   2700
tgtaatgcct ttttgtgaat agaccggtga tccggtttaa caccccggag cggttccacca   2760
cagtcaatgt gataattctt ttcaaggttt cacccccacc atttcatgca gccctttccc   2820
cggagccacc atcgggaata cttttttcttc gctggcaacc cgcacgtcaa tgacaacagg   2880
ttctcttgat gttaatgcct cttccagctt ttcctttgct tccgcttctg atgaaattct   2940
gatgccttta atgccgtatg cttcggacaa tttgacgaag tcaggctgag aagcgaattt   3000
agattctgaa taacgttctt catagaaaat ttcctgccac tgtctgacca ttccgagaca   3060
agcgttattt aaaatcacta ccttgaccgg aagatttaat tcgcgaataa catcgagttc   3120
ttgaagcgtc atttggaatc cgccgtctcc gacaaccgcg acaacagtag catcttttc    3180
```

```
ggccagctgt gcgccgatcg ccgccggaag accgaatccc atcgttccaa gtccgcctga    3240
cgtgacccat ttatctgctt tttgaacgg ataaaattgc gctgaccaca tttgatgctg     3300
gcctacatcc gttgcgacaa tggcctctcc ttttgtaaat tgatgaatat attcaatcaa    3360
tttctgaggt ttaaaacctt cttcttcatt atctacatac cagagcggat actcttcttt    3420
ccattctgcg agctgttttt tccattcgct tgaatcgctt tgtttgccgt cttgtttgat    3480
cagctcctgc aggacaattt tgctgtctcc gactacagga atctgtgttt tcatgatttt    3540
tccgatttca gctggatcaa tatcgatgtg ggctatcttt gcgtttctgg caaagtgttt    3600
caggtttcct gtgacacggt catcaaaacg ggcgccgata ctgattaata gatcacattc    3660
atgaagggcc atattggctg tataagtacc gtgcattccc gccatcccta ggaaaagcgg    3720
atggtcagcc gggaagcctc cgagcccaa  aagggtgtgt gccacaggga tttgctgctg    3780
ttcagcataa ttttttaatt cttctgacgc ttttccgtgc agtacgcccg cacccgccag    3840
gatcaccggt ttttcgcac  tgctcacggc ttccacaagc ttgcggatct gcaaataatt    3900
cggctctgtt gtcggctggt atcccgggag attcatctca tgatcgtagc tgaattctcc    3960
ttcaattgtt gctacatctt tcggaatatc aatcaataca ggtccgggtc ttccagttgt    4020
tgcaatatgg aacgcttctt taatgatgcg cggcagatct tccggctggc gaacctggta    4080
gctgtgtttt gttactggca tcgtaatccc taaaatgtct gcttcctgaa atgcatcgct    4140
cccgattaca gaggttgcta cctgccctgt aaagacgact aacggcaatg aatcaatcat    4200
ggcatcagca aggcctgtaa caaggtttgt cgctcccggc ctgacgtggc aatgacgaca    4260
ccggtttccg gagacccttg cgtatccctc cgctgcatga attgctcctt gttcgtgacg    4320
ggaaggatat gtaccaacct gaatgtatag cttatcgtaa atcggaagca cagccccgcc    4380
cggataaccg aagatcattt ctactttctc ttttttaat  gattcaatca gcattaatcg    4440
tccgctcatc gtctgtgtac attcggcaga tgctgaatcc acctgtacat tagtccccat    4500
tttatctcct cctctagagc gtcctgctgt tgttaagatt attataccac accttgtaga    4560
taaagtcaac aacttttgc  aaaattttc  aggaatttta gcagaggttg ttctggatgt    4620
agaacaaaac atctttccgc tcttgtgctg ttaggatatc tttcttggaa gctaggtagg    4680
cctcgagtta tggcagttgg ttaaaaggaa acaaaaagac cgttttcaca caaaacggtc    4740
tttttcgatt tcttttaca  gtcacagcca cttttgcaaa aaccggacag cttcatgcct    4800
tataactgct gtttcggtcg acgaagcggc cgccgtttaa acgaattcct gcagctggcg    4860
aatggcgatt ttcgttcgtg aatacatgtt ataataacta taactaataa cgtaacgtga    4920
ctggcaagag atatttttaa aacaatgaat aggtttacac ttactttagt tttatggaaa    4980
tgaaagatca tatcatatat aatctagaat aaaattaact aaaataatta ttatctagat    5040
aaaaaattta gaagccaatg aaatctataa ataaactaaa ttaagtttat ttaattaaca    5100
actatggata taaataggt  actaatcaaa atagtgagga ggatatattt gaatacatac    5160
gaacaaatta ataaagtgaa aaaatactt  cggaaacatt taaaaaataa ccttattggt    5220
acttacatgt ttggatcagg agttgagagt ggactaaaac caaatagtga tcttgacttt    5280
ttagtcgtcg tatctgaacc attgacagat caaagtaaag aaatacttat acaaaaaatt    5340
agacctattt caaaaaaaat aggagataaa agcaacttac gatatattga attaacaatt    5400
attattcagc aagaaatggt accgtggaat catcctccca aacaagaatt tatttatgga    5460
gaatggttac aagagcttta tgaacaagga tacattcctc agaaggaatt aaattcagat    5520
ttaaccataa tgctttacca agcaaaacga aaaaataaaa gaatatacgg aaattatgac    5580
```

```
ttagaggaat tactacctga tattccattt tctgatgtga aagagccat tatggattcg    5640 tcagaggaat taatagataa ttatcaggat gatgaaacca actctatatt aactttatgc    5700
cgtatgattt taactatgga cacgggtaaa atcataccaa aagatattgc gggaaatgca    5760
gtggctgaat cttctccatt agaacatagg gagagaattt tgttagcagt tcgtagttat    5820
cttggagaga atattgaatg gactaatgaa aatgtaaatt taactataaa ctatttaaat    5880
aacagattaa aaaaattata aaaaaattga aaaaatggtg gaaacactt tttcaatttt    5940 tttgttttat tatttaatat ttgggaaata ttcattctaa ttggtaatca gattttagaa    6000
aacaataaac ccttgcatag ggggatcgat atccgtttag ctgggcggt gatagcttct    6060 cgttcaggca gtacgcctct tttcttttcc agacctgagg gaggcggaaa tggtgtgagg    6120
ttcccgggga aaagccaaat aggcgatcgc gggagtgctt tatttgaaga tcaggctatc    6180
actgcggtca atagatttca caatgtgatg gctggacagc ctgaggaact ctcgaacccg    6240
aatggaaaca accagatatt tatgaatcag cgcggctcac atggcgttgt gctggcaaat    6300
gcaggttcat cctctgtctc tatcaatacg gcaacaaaat tgcctgatgg caggtatgac    6360
aataaagctg gagcgggttc atttcaagtg aacgatggta aactgacagg cacgatcaat    6420
gccaggtctg tagctgtgct ttatcctgat gatattgcaa aagcgcctca tgttttcctt    6480
gagaattaca aaacaggtgt aacacattct ttcaatgatc aactgacgat taccttgcgt    6540
gcagatgcga atacaacaaa agccgtttat caaatcaata atggaccaga cgacaggcgt    6600
ttaaggatgg agatcaattc acaatcggaa aaggagatcc aatttggcaa acatacacc    6660 atcatgttaa aaggaacgaa cagtgatggt gtaacgagga ccgagaaata cagttttgtt    6720
aaaagagatc cagcgtcggc caaaaccatc ggctatcaaa atccgaatca ttggagccag    6780
gtaaatgctt atatctataa acatgatggg agccgagtaa ttgaattgac cggatcttgg    6840
cctggaaaac caatgactaa aaatgcgac ggaatttaca cgctgacgct gcctgcggac    6900
acggatacaa ccaacgcaaa agtgattttt aataatggca gcgcccaagt gcccggtcag    6960
aatcagcctg gctttgatta cgtgctaaat ggtttatata atgactcggg cttaagcggt    7020
tctcttcccc attgagggca aggctagacg ggacttaccg aaagaaacca tcaatgatgg    7080 tttcttttt gttcataaat cagacaaaac ttttctcttg caaaagtttg tgaagtgttg    7140
cacaatataa atgtgaaata cttcacaaac aaaaagacat caaagagaaa catacccctgc    7200 aaggatgctg atattgtctg catttgcgcc ggagcaaacc aaaaacctgg tgagacacgc    7260
cttgaattag tagaaaagaa cttgaagatt ttcaaaggca tcgttagtga agtcatggcg    7320
agcggatttg acggcatttt cttagtcggg cggcacctcg ctaacggatt caccactcca    7380
agaattggag ccaatcaatt cttgcggaga actgtgaatg cgcaaaccaa cccttggcag    7440
aacatatcca tcgcgtccgc catctccagc agccgcacgc ggcgcatctc gggcagcgtt    7500
gggtcctggc cacgggtgcg catgatcgtg ctcctgtcgt tgaggacccg gctaggctgg    7560
cggggttgcc ttactggtta gcagaatgaa tcaccgatac gcgagcgaac gtgaagcgac    7620
tgctgctgca aaacgtctgc gacctgagca acaacatgaa tggtcttcgg tttccgtgtt    7680
tcgtaaagtc tggaaacgcg gaagtcagcg ccctgcacca ttatgttccg gatctgcatc    7740
gcaggatgct gctggctacc ctgtggaaca cctacatctg tattaacgaa gcgctggcat    7800
tgaccctgag tgatttttct ctggtcccgc cgcatccata ccgccagttg tttaccctca    7860
caacgttcca gtaaccgggc atgttcatca tcagtaaccc gtatcgtgag catcctctct    7920
cgtttcatcg gtatcattac ccccatgaac agaaatcccc cttacacgga ggcatcagtg    7980
```

```
accaaacagg aaaaaaccgc ccttaacatg gcccgcttta tcagaagcca gacattaacg      8040
cttctggaga aactcaacga gctggacgcg gatgaacagg cagacatctg tgaatcgctt      8100
cacgaccacg ctgatgagct ttaccgcagc tgcctcgcgc gtttcggtga tgacggtgaa      8160
aacctctgac acatgcagct cccggagacg gtcacagctt gtctgtaagc ggatgccggg      8220
agcagacaag cccgtcaggg cgcgtcagcg ggtgttggcg ggtgtcgggg cgcagccatg      8280
acccagtcac gtagcgatag cggagtgtat actggcttaa ctatgcggca tcagagcaga      8340
ttgtactgag agtgcaccat atgcggtgtg aaataccgca cagatgcgta aggagaaaat      8400
accgcatcag gcgctcttcc gcttcctcgc tcactgactc gctgcgctcg tcgttcggc       8460 tgcggcgagc ggtatcagct cactcaaagg cggtaatacg gttatccaca gaatcagggg      8520
ataacgcagg aaagaacatg tgagcaaaag gccagcaaaa ggccaggaac cgtaaaaagg      8580
ccgcgttgct ggcgtttttc cataggctcc gcccccctga cgagcatcac aaaaatcgac      8640
gctcaagtca gaggtggcga aacccgacag gactataaag ataccaggcg tttccccctg      8700
gaagctccct cgtgcgctct cctgttccga ccctgccgct taccggatac ctgtccgcct      8760
ttctcccttc gggaagcgtg gcgctttctc atagctcacg ctgtaggtat ctcagttcgg      8820
tgtaggtcgt tcgctccaag ctgggctgtg tgcacgaacc ccccgttcag cccgaccgct      8880
gcgccttatc cggtaactat cgtcttgagt ccaacccggt aagacacgac ttatcgccac      8940
tggcagcagc cactggtaac aggattagca gagcgaggta tgtaggcggt gctacagagt      9000
tcttgaagtg gtggcctaac tacggctaca ctagaaggac agtatttggt atctgcgctc      9060
tgctgaagcc agttaccttc ggaaaaagag ttggtagctc ttgatccggc aaacaaacca      9120
ccgctggtag cggtggtttt tttgtttgca agcagcagat tacgcgcaga aaaaaaggat      9180
ctcaagaaga tcctttgatc ttttctacgg ggtctgacgc tcagtggaac gaaaactcac      9240
gttaagggat tttggtcatg agattatcaa aaaggatctt cacctagatc cttttaaatt      9300
aaaaatgaag ttttaaatca atctaaagta tatatgagta aacttggtct gacagttacc      9360
aatgcttaat cagtgaggca cctatctcag cgatctgtct atttcgttca tccatagttg      9420
cctgactccc cgtcgtgtag ataactacga tacgggaggg cttaccatct ggccccagtg      9480
ctgcaatgat accgcgagac ccacgctcac cggctccaga tttatcagca ataaaccagc      9540
cagccggaag ggccgagcgc agaagtggtc ctgcaacttt atccgcctcc atccagtcta      9600
ttaattgttg ccgggaagct agagtaagta gttcgccagt taatagtttg cgcaacgttg      9660
ttgccattgc tgcaggcatc gtggtgtcac gctcgtcgtt tggtatggct tcattcagct      9720
ccggttccca acgatcaagg cgagttacat gatcccccat gttgtgcaaa aaagcggtta      9780
gctccttcgg tcctccgatc gttgtcagaa gtaagttggc cgcagtgtta tcactcatgg      9840
ttatggcagc actgcataat tctcttactg tcatgccatc cgtaagatgc ttttctgtga      9900
ctggtgagta ctcaaccaag tcattctgag aatagtgtat gcggcgaccg agttgctctt      9960
gcccggcgtc aacacgggat aataccgcgc cacatagcag aactttaaaa gtgctcatca     10020
ttggaaaacg ttcttcgggg cgaaaactct caaggatctt accgctgttg agatccagtt     10080
cgatgtaacc cactcgtgca cccaactgat cttcagcatc ttttactttc accagcgttt     10140
ctgggtgagc aaaaacagga aggcaaaatg ccgcaaaaaa gggaataagg gcgacacgga     10200
aatgttgaat actcatactc ttcctttttc aatattattg aagcatttat cagggttatt     10260
gtctcatgag cggatacata tttgaatgta tttagaaaaa taaacaaata ggggttccgc     10320
gcacatttcc ccgaaaagtg ccacctgacg tctaagaaac cattattatc atgacattaa     10380
```

```
cctataaaaa taggcgtatc acgaggccct ttcgtcttca agaatt                 10426
```

<210> SEQ ID NO 83
<211> LENGTH: 4191
<212> TYPE: DNA
<213> ORGANISM: Artificial Sequence
<220> FEATURE:
<223> OTHER INFORMATION: Description of Artificial Sequence:
      Recombinant pAN263 plasmid

<400> SEQUENCE: 83

```
ccaatacgca aaccgcctct ccccgcgcgt tggccgattc attaatgcag cccggatccg     60
aaagaagagg atatcccggt tttacagaag gcattggatg atccaaaggt gtccatcaga    120
agacaggctg ttgtgtactt aggaatgatt gaaacacctg atgttcttcc tctattgtat    180
aaagcacttg aggacaaagc tgtatcagtc agaagaacgg ccggagactg cctgtctgat    240
atcggcgatc ctcaagccat tcctgctatg atcaagtcat taagcgactc cagcaagctt    300
gttcgctggc gtgccgccat gttcctgtac gaagtcggcg atgaaagtgc aattgaagct    360
ttgcgcgctg ccgaagatga ccccgaattt gaggtcagcc ttcaagtcaa aatggcgctt    420
gaacgtattg agcatggaga agaagcaaaa ggttctgttt ggaaacaaat gacggaaagc    480
agaaaaaaag gcgaataaag ataaaaaagg tgcagatcat gcacctttt tatgtgaatt     540
ggtcgaccga aacagcagtt ataaggcatg aagctgtccg gttttttgcaa aagtggctgt    600
gactgtaaaa agaaatcgaa aaagaccgtt ttgtgtgaaa acggtctttt tgtttccttt     660
taaccaactg ccataactcg aggcctacct agcttccaag aaagatatcc taacagcaca    720
agagcggaaa gatgttttgt tctacatcca gaacaacctc tgctaaaatt cctgaaaaat    780
tttgcaaaaa gttgttgact ttatctacaa ggtgtggtat aataatctta acaacagcag    840
gacgctctag aggaggagac accatggcag aattacgcag taatatgatc acacaaggaa    900
tcgatagagc tccgcaccgc agtttgcttc gtgcagcagg ggtaaaagaa gaggatttcg    960
gcaagccgtt tattgcggtg tgtaattcat acattgatat cgttcccggt catgttcact   1020
tgcaggagtt tgggaaaatc gtaaaagaag caatcagaga agcaggggg gttccgtttg   1080
aatttaatac cattggggta gatgatggca tcgcaatggg gcatatcggt atgagatatt   1140
cgctgccaag ccgtgaaatt atcgcagact ctgtggaaac ggttgtatcc gcacactggt   1200
ttgacggaat ggtctgtatt ccgaactgcg acaaaatcac accgggaatg cttatggcgg   1260
caatgcgcat caacattccg acgatttttg tcagcggcgg accgatggcg gcaggaagaa   1320
caagttacgg gcgaaaaatc tcccttttcct cagtattcga aggggtaggc gcctaccaag   1380
cagggaaaat caacgaaaac gagcttcaag aactagagca gttcggatgc caacgtgcg    1440
ggtcttgctc aggcatgttt acggcgaact caatgaactg tctgtcagaa gcacttggtc   1500
ttgctttgcc gggtaatgga accattctgg caacatctcc ggaacgcaaa gagtttgtga   1560
gaaatcggc tgcgcaatta atggaaacga ttcgcaaaga tatcaaaccg cgtgatattg    1620
ttacagtaaa agcgattgat aacgcgtttg cactcgatat ggcgctcgga ggttctacaa   1680
ataccgttct tcatacccct gcccttgcaa acgaagccgg cgttgaatac tctttagaac   1740
gcattaacga agtcgctgag cgcgtgccgc acttggctaa gctggcgcct gcatcggatg   1800
tgtttattga agatcttcac gaagcgggcg gcgtttcagc ggctctgaat gagctttcga   1860
agaaagaagg agcgcttcat ttagatgcgc tgactgttac aggaaaaact cttggagaaa   1920
ccattgccgg acatgaagta aaggattatg acgtcattca cccgctggat caaccattca   1980
ctgaaaaggg aggccttgct gtttttattcg gtaatctagc tccggacggc gctatcatta   2040
```

```
aaacaggcgg cgtacagaat gggattacaa gacacgaagg gccggctgtc gtattcgatt      2100
ctcaggacga ggcgcttgac ggcattatca accgaaaagt aaaagaaggc gacgttgtca      2160
tcatcagata cgaagggcca aaaggcggac ctggcatgcc ggaaatgctg gcgccaacat      2220
cccaaatcgt tggaatggga ctcgggccaa aagtggcatt gattacggac ggacgttttt      2280
ccggagcctc ccgtggcctc tcaatcggcc acgtatcacc tgaggccgct gagggcgggc      2340
cgcttgcctt tgttgaaaac ggagaccata ttatcgttga tattgaaaaa cgcatcttgg      2400
atgtacaagt gccagaagaa gagtgggaaa acgaaaagc gaactggaaa ggttttgaac       2460
cgaaagtgaa aaccggctac ctggcacgtt attctaaact tgtgacaagt gccaacaccg      2520
gcggtattat gaaaatctag acccctggcg taatagcgaa gaggcccgca ccgatcgccc      2580
ttcccaacag ttgcgcagcc tgaatggcga atgagcttgc gccgtcccgt caagtcagcg      2640
taatgctctg ccagtgttac aaccaattaa ccaattctga ttagaaaaac tcatcgagca      2700
tcaaatgaaa ctgcaattta ttcatatcag gattatcaat accatatttt tgaaaaagcc      2760
gtttctgtaa tgaaggagaa aactcaccga ggcagttcca taggatggca agatcctggt      2820
atcggtctgc gattccgact cgtccaacat caatacaacc tattaatttc ccctcgtcaa      2880
aaataaggtt atcaagtgag aaatcaccat gagtgacgac tgaatccggt gagaatggca      2940
aaaggttatg catttctttc cagacttgtt caacaggcca gccattacgc tcgtcatcaa      3000
aatcactcgc atcaaccaaa ccgttattca ttcgtgattg cgcctgagcg agacgaaata      3060
cgcgatcgct gttaaaagga caattacaaa caggaatcga atgcaaccgg cgcaggaaca      3120
ctgccagcgc atcaacaata ttttcacctg aatcaggata ttcttctaat acctggaatg      3180
ctgttttccc agggatcgca gtggtgagta accatgcatc atcaggagta cggataaaat      3240
gcttgatggt cggaagaggc ataaattccg tcagccagtt tagtctgacc atctcatctg      3300
taacatcatt ggcaacgcta cctttgccat gtttcagaaa caactctggc gcatcgggct      3360
tcccatacaa tcaatagatt gtcgcacctg attgcccgac attatcgcga gcccatttat      3420
acccatataa atcagcatcc atgttggaat ttaatcgcgg cctcgacgag caagacgttt      3480
cccgttgaat atggctcata cacccttg tattactgtt tatgtaagca gacagtttta       3540
ttgttcatga tgatatattt ttatcttgtg caatgtaaca tcagagattt tgagacactc      3600
gacaagatga tcttcttgag atcgttttgg tctgcgcgta atctcttgct ctgaaaacga      3660
aaaaaccgcc ttgcagggcg ttttttcgaa ggttctctga ctaccaact ctttgaaccg       3720 aggtaactgg cttggaggag cgcagtcacc aaaacttgtc ctttcagttt agccttaacc      3780
ggcgcatgac ttcaagacta actcctctaa atcaattacc agtggctgct gccagtggtg      3840
cttttgcatg tctttccggg ttggactcaa gacgatagtt accggataag gcgcagcggt      3900
cggactgaac gggggttcg tgcatacagt ccagcttgga gcgaactgcc tacccggaac       3960
tgagtgtcag gcgtggaatg agacaaacgc ggccataaca gcggaatgac accggtaaac      4020
cgaaaggcag gaacaggaga gcgcacgagg gagccgccag gggaaacgcc tggtatcttt      4080
atagtcctgt cgggtttcgc caccactgat ttgagcgtca gatttcgtga tgcttgtcag      4140
gggggcggag cctatggaaa aacggctttg ccgcggccct ctcacttccc t               4191
```

<210> SEQ ID NO 84
<211> LENGTH: 702
<212> TYPE: DNA
<213> ORGANISM: Bacillus subtilis
<220> FEATURE:
<221> NAME/KEY: CDS

<222> LOCATION: (1)..(699)

<400> SEQUENCE: 84

| | | | | | | | | | | | | | | | | |
|---|---|---|---|---|---|---|---|---|---|---|---|---|---|---|---|---|
| ttg | tta | ctg | gtt | atc | gat | gtg | ggg | aac | acc | aat | act | gta | ctt | ggt | gta | 48 |
| Met | Leu | Leu | Val | Ile | Asp | Val | Gly | Asn | Thr | Asn | Thr | Val | Leu | Gly | Val | |
| 1 | | | | 5 | | | | | 10 | | | | | 15 | | |
| tat | cat | gat | gga | aaa | tta | gaa | tat | cac | tgg | cgt | ata | gaa | aca | agc | agg | 96 |
| Tyr | His | Asp | Gly | Lys | Leu | Glu | Tyr | His | Trp | Arg | Ile | Glu | Thr | Ser | Arg | |
| | | | 20 | | | | | 25 | | | | | 30 | | | |
| cat | aaa | aca | gaa | gat | gag | ttt | ggg | atg | att | ttg | cgc | tcc | tta | ttt | gat | 144 |
| His | Lys | Thr | Glu | Asp | Glu | Phe | Gly | Met | Ile | Leu | Arg | Ser | Leu | Phe | Asp | |
| | | 35 | | | | | 40 | | | | | 45 | | | | |
| cac | tcc | ggg | ctt | atg | ttt | gaa | cag | ata | gat | ggc | att | att | att | tcg | tca | 192 |
| His | Ser | Gly | Leu | Met | Phe | Glu | Gln | Ile | Asp | Gly | Ile | Ile | Ile | Ser | Ser | |
| | 50 | | | | | 55 | | | | | 60 | | | | | |
| gta | gtg | ccg | cca | atc | atg | ttt | gcg | tta | gaa | aga | atg | tgc | aca | aaa | tac | 240 |
| Val | Val | Pro | Pro | Ile | Met | Phe | Ala | Leu | Glu | Arg | Met | Cys | Thr | Lys | Tyr | |
| 65 | | | | | 70 | | | | | 75 | | | | | 80 | |
| ttt | cat | atc | gag | cct | caa | att | gtt | ggt | cca | ggt | atg | aaa | acc | ggt | tta | 288 |
| Phe | His | Ile | Glu | Pro | Gln | Ile | Val | Gly | Pro | Gly | Met | Lys | Thr | Gly | Leu | |
| | | | | 85 | | | | | 90 | | | | | 95 | | |
| aat | ata | aaa | tat | gac | aat | ccg | aaa | gaa | gta | ggg | gca | gac | aga | atc | gta | 336 |
| Asn | Ile | Lys | Tyr | Asp | Asn | Pro | Lys | Glu | Val | Gly | Ala | Asp | Arg | Ile | Val | |
| | | | 100 | | | | | 105 | | | | | 110 | | | |
| aat | gct | gtc | gct | gcg | ata | cac | ttg | tac | ggc | aat | cca | tta | att | gtt | gtc | 384 |
| Asn | Ala | Val | Ala | Ala | Ile | His | Leu | Tyr | Gly | Asn | Pro | Leu | Ile | Val | Val | |
| | | 115 | | | | | 120 | | | | | 125 | | | | |
| gat | ttc | gga | acc | gcc | aca | acg | tac | tgc | tat | att | gat | gaa | aac | aaa | caa | 432 |
| Asp | Phe | Gly | Thr | Ala | Thr | Thr | Tyr | Cys | Tyr | Ile | Asp | Glu | Asn | Lys | Gln | |
| | 130 | | | | | 135 | | | | | 140 | | | | | |
| tac | atg | ggc | ggg | gcg | att | gcc | cct | ggg | att | aca | att | tcg | aca | gag | gcg | 480 |
| Tyr | Met | Gly | Gly | Ala | Ile | Ala | Pro | Gly | Ile | Thr | Ile | Ser | Thr | Glu | Ala | |
| 145 | | | | | 150 | | | | | 155 | | | | | 160 | |
| ctt | tac | tcg | cgt | gca | gca | aag | ctt | cct | cgt | atc | gaa | atc | acc | cgg | ccc | 528 |
| Leu | Tyr | Ser | Arg | Ala | Ala | Lys | Leu | Pro | Arg | Ile | Glu | Ile | Thr | Arg | Pro | |
| | | | | 165 | | | | | 170 | | | | | 175 | | |
| gac | aat | att | atc | gga | aaa | aac | act | gtt | agc | gcg | atg | caa | tct | gga | att | 576 |
| Asp | Asn | Ile | Ile | Gly | Lys | Asn | Thr | Val | Ser | Ala | Met | Gln | Ser | Gly | Ile | |
| | | | 180 | | | | | 185 | | | | | 190 | | | |
| tta | ttt | ggc | tat | gtc | ggc | caa | gtg | gaa | gga | atc | gtt | aag | cga | atg | aaa | 624 |
| Leu | Phe | Gly | Tyr | Val | Gly | Gln | Val | Glu | Gly | Ile | Val | Lys | Arg | Met | Lys | |
| | | 195 | | | | | 200 | | | | | 205 | | | | |
| tgg | cag | gca | aaa | cag | gac | cca | agg | tca | ttg | cga | cag | gag | gcc | tgg | cgc | 672 |
| Trp | Gln | Ala | Lys | Gln | Asp | Pro | Arg | Ser | Leu | Arg | Gln | Glu | Ala | Trp | Arg | |
| | 210 | | | | | 215 | | | | | 220 | | | | | |
| cgc | tca | ttg | cga | acg | aat | cag | att | gta | tag | | | | | | | 702 |
| Arg | Ser | Leu | Arg | Thr | Asn | Gln | Ile | Val | | | | | | | | |
| 225 | | | | 230 | | | | | | | | | | | | |

<210> SEQ ID NO 85
<211> LENGTH: 233
<212> TYPE: PRT
<213> ORGANISM: Bacillus subtilis

<400> SEQUENCE: 85

Met Leu Leu Val Ile Asp Val Gly Asn Thr Asn Thr Val Leu Gly Val
1               5                   10                  15

Tyr His Asp Gly Lys Leu Glu Tyr His Trp Arg Ile Glu Thr Ser Arg
            20                  25                  30

His Lys Thr Glu Asp Glu Phe Gly Met Ile Leu Arg Ser Leu Phe Asp
        35                  40                  45

His Ser Gly Leu Met Phe Glu Gln Ile Asp Gly Ile Ile Ile Ser Ser
    50                  55                  60

Val Val Pro Pro Ile Met Phe Ala Leu Glu Arg Met Cys Thr Lys Tyr
 65                  70                  75                  80

Phe His Ile Glu Pro Gln Ile Val Gly Pro Gly Met Lys Thr Gly Leu
                 85                  90                  95

Asn Ile Lys Tyr Asp Asn Pro Lys Glu Val Gly Ala Asp Arg Ile Val
            100                 105                 110

Asn Ala Val Ala Ala Ile His Leu Tyr Gly Asn Pro Leu Ile Val Val
        115                 120                 125

Asp Phe Gly Thr Ala Thr Thr Tyr Cys Tyr Ile Asp Glu Asn Lys Gln
130                 135                 140

Tyr Met Gly Gly Ala Ile Ala Pro Gly Ile Thr Ile Ser Thr Glu Ala
145                 150                 155                 160

Leu Tyr Ser Arg Ala Ala Lys Leu Pro Arg Ile Glu Ile Thr Arg Pro
                165                 170                 175

Asp Asn Ile Ile Gly Lys Asn Thr Val Ser Ala Met Gln Ser Gly Ile
            180                 185                 190

Leu Phe Gly Tyr Val Gly Gln Val Glu Gly Ile Val Lys Arg Met Lys
        195                 200                 205

Trp Gln Ala Lys Gln Asp Pro Arg Ser Leu Arg Gln Glu Ala Trp Arg
210                 215                 220

Arg Ser Leu Arg Thr Asn Gln Ile Val
225                 230

<210> SEQ ID NO 86
<211> LENGTH: 1623
<212> TYPE: DNA
<213> ORGANISM: Bacillus subtilis
<220> FEATURE:
<221> NAME/KEY: CDS
<222> LOCATION: (1)..(1620)

<400> SEQUENCE: 86 atg tat ttg gca ttc cag gtg caa aaa ttg atg cgg tat ttg acg ctt      48
Met Tyr Leu Ala Phe Gln Val Gln Lys Leu Met Arg Tyr Leu Thr Leu
 1               5                  10                  15 tac aag ata aag gac ctg aaa tta tcg ttg ccc ggc acg aac aaa acg      96
Tyr Lys Ile Lys Asp Leu Lys Leu Ser Leu Pro Gly Thr Asn Lys Thr
            20                  25                  30 cag caa ttc atg gcc caa gca gtc ggc cgt tta act gga aaa ccg gga     144
Gln Gln Phe Met Ala Gln Ala Val Gly Arg Leu Thr Gly Lys Pro Gly
        35                  40                  45 gtc gtg tta gtc aca tca gga ccg ggt gcc tct aac ttg gca aca ggc     192
Val Val Leu Val Thr Ser Gly Pro Gly Ala Ser Asn Leu Ala Thr Gly
    50                  55                  60 ctg ctg aca gcg aac act gaa gga gac cct gtc gtt gcg ctt gct gga     240
Leu Leu Thr Ala Asn Thr Glu Gly Asp Pro Val Val Ala Leu Ala Gly
 65                  70                  75                  80 aac gtg atc cgt gca tat cgt tta aaa cgg aca cat caa tct ttg gat     288
Asn Val Ile Arg Ala Tyr Arg Leu Lys Arg Thr His Gln Ser Leu Asp
                85                  90                  95 aat gcg gcg cta ttc cag ccg att aca aaa tac agt gta gaa gtt caa     336
Asn Ala Ala Leu Phe Gln Pro Ile Thr Lys Tyr Ser Val Glu Val Gln
            100                 105                 110 gat gta aaa aat ata ccg gaa gct gtt aca aat gca ttt agg ata gcg     384
Asp Val Lys Asn Ile Pro Glu Ala Val Thr Asn Ala Phe Arg Ile Ala
        115                 120                 125

| | |
|---|---|
| tca gca ggg cag gct ggg gcc gct ttt gtg agc ttt ccg caa gat gtt<br>Ser Ala Gly Gln Ala Gly Ala Ala Phe Val Ser Phe Pro Gln Asp Val<br>130                        135                      140 | 432 |
| gtg aat gaa gtc aca aat acg aaa aac gtg cgt gct gtt gca gcg cca<br>Val Asn Glu Val Thr Asn Thr Lys Asn Val Arg Ala Val Ala Ala Pro<br>145                    150                    155                    160 | 480 |
| aaa ctc ggt cct gca gca gat gat gca atc agt gcg gcc ata gca aaa<br>Lys Leu Gly Pro Ala Ala Asp Asp Ala Ile Ser Ala Ala Ile Ala Lys<br>                  165                    170                    175 | 528 |
| atc caa aca gca aaa ctt cct gtc gtt ttg gtc ggc atg aaa ggc gga<br>Ile Gln Thr Ala Lys Leu Pro Val Val Leu Val Gly Met Lys Gly Gly<br>              180                    185                    190 | 576 |
| aga ccg gaa gca att aaa gcg gtt cgc aag ctt ttg aaa aag gtt cag<br>Arg Pro Glu Ala Ile Lys Ala Val Arg Lys Leu Leu Lys Lys Val Gln<br>         195                    200                    205 | 624 |
| ctt cca ttt gtt gaa aca tat caa gct gcc ggt acc ctt tct aga gat<br>Leu Pro Phe Val Glu Thr Tyr Gln Ala Ala Gly Thr Leu Ser Arg Asp<br>210                        215                      220 | 672 |
| tta gag gat caa tat ttt ggc cgt atc ggt ttg ttc cgc aac cag cct<br>Leu Glu Asp Gln Tyr Phe Gly Arg Ile Gly Leu Phe Arg Asn Gln Pro<br>225                        230                    235                    240 | 720 |
| ggc gat tta ctg cta gag cag gca gat gtt gtt ctg acg atc ggc tat<br>Gly Asp Leu Leu Leu Glu Gln Ala Asp Val Val Leu Thr Ile Gly Tyr<br>                  245                    250                    255 | 768 |
| gac ccg att gaa tat gat ccg aaa ttc tgg aat atc aat gga gac cgg<br>Asp Pro Ile Glu Tyr Asp Pro Lys Phe Trp Asn Ile Asn Gly Asp Arg<br>            260                    265                    270 | 816 |
| aca att atc cat tta gac gag att atc gct gac att gat cat gct tac<br>Thr Ile Ile His Leu Asp Glu Ile Ile Ala Asp Ile Asp His Ala Tyr<br>              275                    280                    285 | 864 |
| cag cct gat ctt gaa ttg atc ggt gac att ccg tcc acg atc aat cat<br>Gln Pro Asp Leu Glu Leu Ile Gly Asp Ile Pro Ser Thr Ile Asn His<br>290                        295                    300 | 912 |
| atc gaa cac gat gct gtg aaa gtg gaa ttt gca gag cgt gag cag aaa<br>Ile Glu His Asp Ala Val Lys Val Glu Phe Ala Glu Arg Glu Gln Lys<br>305                        310                    315                    320 | 960 |
| atc ctt tct gat tta aaa caa tat atg cat gaa ggt gag cag gtg cct<br>Ile Leu Ser Asp Leu Lys Gln Tyr Met His Glu Gly Glu Gln Val Pro<br>                  325                    330                    335 | 1008 |
| gca gat tgg aaa tca gac aga gcg cac cct ctt gaa atc gtt aaa gag<br>Ala Asp Trp Lys Ser Asp Arg Ala His Pro Leu Glu Ile Val Lys Glu<br>            340                    345                    350 | 1056 |
| ttg cgt aat gca gtc gat gat cat gtt aca gta act tgc gat atc ggt<br>Leu Arg Asn Ala Val Asp Asp His Val Thr Val Thr Cys Asp Ile Gly<br>         355                    360                    365 | 1104 |
| tcg cac tcc att tgg atg tca cgt tat ttc cgc agc tac gag ccg tta<br>Ser His Ser Ile Trp Met Ser Arg Tyr Phe Arg Ser Tyr Glu Pro Leu<br>370                        375                    380 | 1152 |
| aca tta atg atc agt aac ggt atg caa aca ctc ggc gtt gcg ctt cct<br>Thr Leu Met Ile Ser Asn Gly Met Gln Thr Leu Gly Val Ala Leu Pro<br>385                        390                    395                    400 | 1200 |
| tgg gca atc ggc gct tca ttg gtg aaa ccg gga gaa aaa gtg gtt tct<br>Trp Ala Ile Gly Ala Ser Leu Val Lys Pro Gly Glu Lys Val Val Ser<br>                  405                    410                    415 | 1248 |
| gtc tct ggt gac ggc ggt ttc tta ttc tca gca atg gaa tta gag aca<br>Val Ser Gly Asp Gly Gly Phe Leu Phe Ser Ala Met Glu Leu Glu Thr<br>            420                    425                    430 | 1296 |
| gca gtt cga cta aaa gca cca att gta cac att gta tgg aac gac agc<br>Ala Val Arg Leu Lys Ala Pro Ile Val His Ile Val Trp Asn Asp Ser<br>         435                    440                    445 | 1344 |

```
aca tat gac atg gtg cat ttc cag caa ttg aaa aaa tat aac cgt aca    1392
Thr Tyr Asp Met Val His Phe Gln Gln Leu Lys Lys Tyr Asn Arg Thr
    450                 455                 460 tct gcg gtc gat ttc gga aat atc gat atc gtg aaa tat gcg gaa agc    1440
Ser Ala Val Asp Phe Gly Asn Ile Asp Ile Val Lys Tyr Ala Glu Ser
465                 470                 475                 480 ttc gga gca act gcg ttg cgc gta gaa tca cca gac cag ctg gca gat    1488
Phe Gly Ala Thr Ala Leu Arg Val Glu Ser Pro Asp Gln Leu Ala Asp
                485                 490                 495 gtt ctg cgt caa ggc atg aac gct gaa ggt cct gtc atc atc gat gtc    1536
Val Leu Arg Gln Gly Met Asn Ala Glu Gly Pro Val Ile Ile Asp Val
            500                 505                 510 ccg gtt gac tac agt gat aac att aat tta gca agt gac aag ctt ccg    1584
Pro Val Asp Tyr Ser Asp Asn Ile Asn Leu Ala Ser Asp Lys Leu Pro
        515                 520                 525 aaa gaa ttc ggg gaa ctc atg aaa acg aaa gct ctc tag                1623
Lys Glu Phe Gly Glu Leu Met Lys Thr Lys Ala Leu
    530                 535                 540
```

<210> SEQ ID NO 87
<211> LENGTH: 540
<212> TYPE: PRT
<213> ORGANISM: Bacillus subtilis

<400> SEQUENCE: 87

```
Met Tyr Leu Ala Phe Gln Val Gln Lys Leu Met Arg Tyr Leu Thr Leu
1               5                   10                  15

Tyr Lys Ile Lys Asp Leu Lys Leu Ser Leu Pro Gly Thr Asn Lys Thr
            20                  25                  30

Gln Gln Phe Met Ala Gln Ala Val Gly Arg Leu Thr Gly Lys Pro Gly
        35                  40                  45

Val Val Leu Val Thr Ser Gly Pro Gly Ala Ser Asn Leu Ala Thr Gly
    50                  55                  60

Leu Leu Thr Ala Asn Thr Glu Gly Asp Pro Val Val Ala Leu Ala Gly
65                  70                  75                  80

Asn Val Ile Arg Ala Tyr Arg Leu Lys Arg Thr His Gln Ser Leu Asp
                85                  90                  95

Asn Ala Ala Leu Phe Gln Pro Ile Thr Lys Tyr Ser Val Glu Val Gln
            100                 105                 110

Asp Val Lys Asn Ile Pro Glu Ala Val Thr Asn Ala Phe Arg Ile Ala
        115                 120                 125

Ser Ala Gly Gln Ala Gly Ala Ala Phe Val Ser Phe Pro Gln Asp Val
    130                 135                 140

Val Asn Glu Val Thr Asn Thr Lys Asn Val Arg Ala Val Ala Ala Pro
145                 150                 155                 160

Lys Leu Gly Pro Ala Ala Asp Asp Ala Ile Ser Ala Ala Ile Ala Lys
                165                 170                 175

Ile Gln Thr Ala Lys Leu Pro Val Val Leu Val Gly Met Lys Gly Gly
            180                 185                 190

Arg Pro Glu Ala Ile Lys Ala Val Arg Lys Leu Leu Lys Lys Val Gln
        195                 200                 205

Leu Pro Phe Val Glu Thr Tyr Gln Ala Ala Gly Thr Leu Ser Arg Asp
    210                 215                 220

Leu Glu Asp Gln Tyr Phe Gly Arg Ile Gly Leu Phe Arg Asn Gln Pro
225                 230                 235                 240

Gly Asp Leu Leu Leu Glu Gln Ala Asp Val Val Leu Thr Ile Gly Tyr
                245                 250                 255
```

-continued

```
Asp Pro Ile Glu Tyr Asp Pro Lys Phe Trp Asn Ile Asn Gly Asp Arg
            260                 265                 270

Thr Ile Ile His Leu Asp Glu Ile Ala Asp Ile Asp His Ala Tyr
    275                 280                 285

Gln Pro Asp Leu Glu Leu Ile Gly Asp Ile Pro Ser Thr Ile Asn His
    290                 295                 300

Ile Glu His Asp Ala Val Lys Val Glu Phe Ala Glu Arg Glu Gln Lys
305                 310                 315                 320

Ile Leu Ser Asp Leu Lys Gln Tyr Met His Glu Gly Glu Gln Val Pro
                325                 330                 335

Ala Asp Trp Lys Ser Asp Arg Ala His Pro Leu Glu Ile Val Lys Glu
            340                 345                 350

Leu Arg Asn Ala Val Asp Asp His Val Thr Val Thr Cys Asp Ile Gly
        355                 360                 365

Ser His Ser Ile Trp Met Ser Arg Tyr Phe Arg Ser Tyr Glu Pro Leu
    370                 375                 380

Thr Leu Met Ile Ser Asn Gly Met Gln Thr Leu Gly Val Ala Leu Pro
385                 390                 395                 400

Trp Ala Ile Gly Ala Ser Leu Val Lys Pro Gly Glu Lys Val Val Ser
                405                 410                 415

Val Ser Gly Asp Gly Gly Phe Leu Phe Ser Ala Met Glu Leu Glu Thr
            420                 425                 430

Ala Val Arg Leu Lys Ala Pro Ile Val His Ile Val Trp Asn Asp Ser
        435                 440                 445

Thr Tyr Asp Met Val His Phe Gln Gln Leu Lys Lys Tyr Asn Arg Thr
    450                 455                 460

Ser Ala Val Asp Phe Gly Asn Ile Asp Ile Val Lys Tyr Ala Glu Ser
465                 470                 475                 480

Phe Gly Ala Thr Ala Leu Arg Val Glu Ser Pro Asp Gln Leu Ala Asp
                485                 490                 495

Val Leu Arg Gln Gly Met Asn Ala Glu Gly Pro Val Ile Ile Asp Val
            500                 505                 510

Pro Val Asp Tyr Ser Asp Asn Ile Asn Leu Ala Ser Asp Lys Leu Pro
        515                 520                 525

Lys Glu Phe Gly Glu Leu Met Lys Thr Lys Ala Leu
    530                 535                 540

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: ribosome
      binding site
<220> FEATURE:
<221> NAME/KEY: misc_feature
<222> LOCATION: 14-20
<223> OTHER INFORMATION: n = a, c, g, or t

<400> SEQUENCE: 88
agaaaggagg tgannnnnnn atg                                           23

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: PanC
      C terminus
```

```
<400> SEQUENCE: 89

Ile Arg Glu Met Glu Arg Ile
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: PanC
      C terminus

<400> SEQUENCE: 90

Ile Arg Glu Arg Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: PanC
      C terminus

<400> SEQUENCE: 91

Ile Arg Arg Lys Glu Val Asn
1               5

<210> SEQ ID NO 92
<211> LENGTH: 6688
<212> TYPE: DNA
<213> ORGANISM: Artificial Sequence
<220> FEATURE:
<223> OTHER INFORMATION: Description of Artificial Sequence:
      Recombinant pAN336 plasmid

<400> SEQUENCE: 92
```

| | | | |
|---|---|---|---|
| tgcgccgcta caggggcgcgt ccattcgcca ttcaggctgc gcaactgttg ggaagggcga | 60 |
| tcggtgcggg cctcttcgct attacgccag ctggcgaaag ggggatgtgc tgcaaggcga | 120 |
| ttaagttggg taacgccagg gttttcccag tcacgacgtt gtaaaacgac ggccagtgaa | 180 |
| ttgtaatacg actcactata gggcgaattg ggcccgacgt cgcatgcacc aggcttctca | 240 |
| ggcgctgact tagaaaacct cttgaatgaa gctgcgcttg tagcggctcg tcaaaacaag | 300 |
| aaaaaaatcg atgcgcgtga tattgacgaa gcgacggacc gtgtaattgc cggacccgct | 360 |
| aagaagagcc gcgttatctc caagaaagaa cgcaatatcg tggcttatca cgaaggcgga | 420 |
| cacaccgtta tcggtctcgt tttagatgag gcagatatgg ttcataaagt aacgattgtt | 480 |
| cctcggggcc aggctggcgg ttatgctgtt atgctgccaa gagaagaccg ttatttccaa | 540 |
| acaaagccgg agctgcttga taaaattgtc ggcctcttgg gcggacgtgt tgctgaagag | 600 |
| attatcttcg gtgaagtcag cacaggggcg cacaatgact ccagcgtgc gacgaatatt | 660 |
| gcaagacgaa tggttacaga attcggtatg tcagaaaaac tgggaccgtt gcaatttgga | 720 |
| cagtctcagg gcggtcaggt attcttaggc cgtgatttca caacgaaca gaactacagt | 780 |
| gatcaaatcg cttacgaaat tgatcaggaa attcagcgca tcatcaaaga atgttatgag | 840 |
| cgtgcgaaac aaatcctgac tgaaaatcgt gacaagcttg aattgattgc ccaaacgctt | 900 |
| ctgaaagttg aaacgcttga cgctgaacaa atcaaacacc ttatcgatca tggaacatta | 960 |
| cctgagcgta atttctcaga tgatgaaaag aacgatgatg tgaaagtaaa cattctgaca | 1020 |
| aaaacagaag aaagaaga cgatacgaaa gagtaattcg ctttctttct aaaaaaactg | 1080 |

```
ccggctgacg ctggcagttt ttttatgtaa atgattggct cagctgcggc ttttacaatc    1140
atccaattct ggtatcgatt tgtttacaaa tgagccgctg atcgtgtatg gtattgtaga    1200
atgtttgtaa aaagtaaagt agagaaacta ttcaaaagtg gtgatagagg ttgttactgg    1260
ttatcgatgt ggggaacacc ctgcagctcg agtgaaatac cgcacagatg cgtaaggaga    1320
aaataccgca tcaggcgata aacccagcga accatttgag gtgataggta agattatacc    1380
gaggtatgaa acgagaatt ggacctttac agaattactc tatgaagcgc catatttaaa    1440
aagctaccaa gacgaagagg atgaagagga tgaggaggca gattgccttg aatatattga    1500
caatactgat aagataatat atcttttata tagaagatat cgccgtatgt aaggatttca    1560
gggggcaagg cataggcagc gcgcttatca atatatctat agaatgggca agcataaaa    1620 acttgcatgg actaatgctt gaaacccagg acaataacct tatagcttgt aaattctatc    1680
ataattgtgg tttcaaaatc ggctccgtcg atactatgtt atacgccaac tttcaaaaca    1740
actttgaaaa agctgttttc tggtatttaa ggttttagaa tgcaaggaac agtgaattgg    1800
agttcgtctt gttataatta gcttcttggg gtatctttaa atactgtaga aagaggaag    1860 gaaataataa atggctaaaa tgagaatatc accggaattg aaaaaactga tcgaaaaata    1920
ccgctgcgta aaagatacgg aaggaatgtc tcctgctaag gtatataagc tggtgggaga    1980
aaatgaaaac ctatatttaa aaatgacgga cagccggtat aaagggacca cctatgatgt    2040
ggaacgggaa aaggacatga tgctatggct ggaaggaaag ctgcctgttc caaaggtcct    2100
gcactttgaa cggcatgatg gctggagcaa tctgctcatg agtgaggccg atggcgtcct    2160
ttgctcggaa gagtatgaag atgaacaaag ccctgaaaag attatcgagc tgtatgcgga    2220
gtgcatcagg ctcttttcact ccatcgacat atcggattgt ccctatacga atagcttaga    2280
cagccgctta gccgaattgg attacttact gaataacgat ctggccgatg tggattgcga    2340
aaactgggaa gaagcactc catttaaaga tccgcgcgag ctgtatgatt ttttaaagac    2400
ggaaaagccc gaagaggaac ttgtcttttc ccacggcgac ctgggagaca gcaacatctt    2460
tgtgaaagat ggcaaagtaa gtggctttat tgatcttggg agaagcggca gggcggacaa    2520
gtggtatgac attgccttct gcgtccggtc gatcagggag gatatcgggg aagaacagta    2580
tgtcgagcta tttttttgact tactggggat caagcctgat tgggagaaaa taaaatatta    2640 tatttttactg gatgaattgt tttagtacct agatttagat gtctaaaaag ctttaactac    2700 aagctttta gacatctaat cttttctgaa gtacatccgc aactgtccat actctgatgt    2760
tttatatctt ttctaaaagt tcgctagata ggggtcccga gcgcctacga ggaatttgta    2820
tcgccattcg ccattcaggc tgcgcaactg ttgggaaggg cgatcggtgc ggtcgactgg    2880
caggcaaaac aggacccaag gtcattgcga caggaggcct ggcgccgctc attgcgaacg    2940
aatcagattg tatagacatc gttgatccat tcttaaccct aaaagggctg gaattgattt    3000
atgaaagaaa ccgcgtagga agtgtatagg aggtttagta atggattatt tagtaaaagc    3060
acttgcgtat gacggaaaag ttcgggctta tgcagcgaga acgactgata tggtaaatga    3120
ggggcagaga cgccatggta cgtggccgac agcatccgct gcactaggcc gtacaatgac    3180
agcttcactt atgctcggcg ctatgctgaa gggcgatgat aagctgaccg tgaaaatcga    3240
gggcggaggt ccgatcggag ctattgtagc tgatgccaat gccaaaggag aagtcagagc    3300
ctatgtctct aacccgcaag ttcattttga tttaaatgaa caaggtaagc ttgatgtcag    3360
acgtgcggtt ggaacaaacg gaacgttaag tgtcgtaaaa gatttaggtt tgcgcgagtt    3420
cttcacagga caagtagaaa tcgtttcagg agaattagga gatgattta cttactatct    3480
```

```
tgtgtcatct gagcaggttc cttcatcagt gggcgtaggt gtgctcgtaa atcctgacaa    3540
taccattctt gcggcagggg gctttattat tcagctgatg ccgggaacag atgatgaaac    3600
aatcacaaaa attgaacagc gtctatctca agtagagccg atttctaagc tcatccaaaa    3660
agggctgaca ccagaagaaa ttttagaaga agtcctaggc gagaaacctg agattttgga    3720
aacgatgcct gtcagattcc attgcccttg ttcaaaagaa cggttcgaaa cagccatttt    3780
aggactaggc aaaaaagaaa ttcaagatat gatagaagaa gatggacaag ccgaagcagt    3840
atgccatttt tgtaatgaaa agtacttatt tacaaaagaa gagctggaag ggcttcgtga    3900
ccaaactacc cgctaagctc tttagcgggt ttttaatttg agaaaagggg ctgaaagcag    3960
gtttgaaatc aagaacaatc tggacgcgtt ggatgcatag cttgagtatt ctatagtgtc    4020
acctaaatag cttggcgtaa tcatggtcat agctgtttcc tgtgtgaaat tgttatccgc    4080
tcacaattcc acacaacata cgagccggaa gcataaagtg taaagcctgg ggtgcctaat    4140
gagtgagcta actcacatta attgcgttgc gctcactgcc cgctttccag tcgggaaacc    4200
tgtcgtgcca gctgcattaa tgaatcggcc aacgcgcggg gagaggcggt ttgcgtattg    4260
ggcgctcttc cgcttcctcg ctcactgact cgctgcgctc ggtcgttcgg ctgcggcgag    4320
cggtatcagc tcactcaaag gcggtaatac ggttatccac agaatcaggg gataacgcag    4380
gaaagaacat gtgagcaaaa ggccagcaaa aggccaggaa ccgtaaaaag gccgcgttgc    4440
tggcgttttt cgataggctc cgcccccctg acgagcatca caaaaatcga cgctcaagtc    4500
agaggtggcg aaacccgaca ggactataaa gataccaggc gtttccccct ggaagctccc    4560
tcgtgcgctc tcctgttccg accctgccgc ttaccggata cctgtccgcc tttctccctt    4620
cgggaagcgt ggcgctttct catagctcac gctgtaggta tctcagttcg gtgtaggtcg    4680
ttcgctccaa gctgggctgt gtgcacgaac cccccgttca gcccgaccgc tgcgccttat    4740
ccggtaacta tcgtcttgag tccaacccgg taagacacga cttatcgcca ctggcagcag    4800
ccactggtaa caggattagc agagcgaggt atgtaggcgg tgctacagag ttcttgaagt    4860
ggtggcctaa ctacggctac actagaagga cagtatttgg tatctgcgct ctgctgaagc    4920
cagttacctt cggaaaaaga gttggtagct cttgatccgg caaacaaacc accgctggta    4980
gcggtggttt ttttgtttgc aagcagcaga ttacgcgcag aaaaaaagga tctcaagaag    5040
atcctttgat cttttctacg gggtctgacg ctcagtggaa cgaaaactca cgttaaggga    5100
ttttggtcat gagattatca aaaaggatct tcacctagat ccttttaaat taaaaatgaa    5160
gttttaaatc aatctaaagt atatatgagt aaacttggtc tgacagttac caatgcttaa    5220
tcagtgaggc acctatctca gcgatctgtc tatttcgttc atccatagtt gcctgactcc    5280
ccgtcgtgta gataactacg atacgggagg gcttaccatc tggccccagt gctgcaatga    5340
taccgcgaga cccacgctca ccggctccag atttatcagc aataaaccag ccagccggaa    5400
gggccgagcg cagaagtggt cctgcaactt tatccgcctc catccagtct attaattgtt    5460
gccgggaagc tagagtaagt agttcgccag ttaatagttt cgcaacgttg ttggcattg    5520 ctacaggcat cgtggtgtca cgctcgtcgt ttggtatggc ttcattcagc tccggttccc    5580
aacgatcaag gcgagttaca tgatccccca tgttgtgcaa aaaagcggtt agctccttcg    5640
gtcctccgat cgttgtcaga agtaagttgg ccgcagtgtt atcactcatg gttatggcag    5700
cactgcataa ttctcttact gtcatgccat ccgtaagatg cttttctgtg actggtgagt    5760
actcaaccaa gtcattctga gaataccgcg cccggcgacc gagttgctct tgcccggcgt    5820
caatacggga taatagtgta tgacatagca gaactttaaa agtgctcatc attggaaaac    5880
```

```
gttcttcggg gcgaaaactc tcaaggatct taccgctgtt gagatccagt tcgatgtaac    5940
ccactcgtgc acccaactga tcttcagcat cttttacttt caccagcgtt tctgggtgag    6000
caaaaacagg aaggcaaaat gccgcaaaaa agggaataag ggcgacacgg aaatgttgaa    6060
tactcatact cttcctttt caatattatt gaagcattta tcagggttat tgtctcatga     6120
gcggatacat atttgaatgt atttagaaaa ataaacaaat aggggttccg cgcacatttc    6180
cccgaaaagt gccacctgta tgcggtgtga ataccgcac agatgcgtaa ggagaaaata     6240
ccgcatcagg cgaaattgta acgttaata ttttgttaaa attcgcgtta aatatttgtt     6300
aaatcagctc attttttaac cataggccg aaatcggcaa atcccttat aaatcaaaag      6360 aatagaccga gatagggttg agtgttgttc cagtttggaa caagagtcca ctattaaaga    6420
acgtggactc caacgtcaaa gggcgaaaaa ccgtctatca gggcgatggc ccactacgtg    6480
aaccatcacc caaatcaagt tttttgcggt cgaggtgccg taaagctcta atcggaacc     6540 ctaaagggag cccccgattt agagcttgac ggggaaagcc ggcgaacgtg gcgagaaagg    6600
aagggaagaa agcgaaagga cgggcgcta gggcgctggc aagtgtagcg gtcacgctgc     6660
gcgtaaccac cacacccgcc gcgcttaa                                       6688

<210> SEQ ID NO 93
<211> LENGTH: 8503
<212> TYPE: DNA
<213> ORGANISM: Artificial Sequence
<220> FEATURE:
<223> OTHER INFORMATION: Description of Artificial Sequence:
      Recombinant pAN004 plasmid

<400> SEQUENCE: 93
gaattttgcg gccgcttcga aagctgtaat ataaaaacct tcttcaacta acggggcagg      60
ttagtgacat tagaaaaccg actgtaaaaa gtacagtcgg cattatctca tattataaaa     120
gccagtcatt aggcctatct gacaattcct gaatagagtt cataaacaat cctgcatgat     180
aaccatcaca aacagaatga tgtacctgta aagatagcgg taaatatatt gaattacctt     240
tattaatgaa ttttcctgct gtaataatgg gtagaaggta attactatta ttattgatat     300
ttaagttaaa cccagtaaat gaagtccatg gaataataga aagagaaaaa gcattttcag     360
gtataggtgt tttgggaaac aatttccccg aaccattata tttctctaca tcagaaaggt     420
ataaatcata aaactctttg aagtcattct ttacaggagt ccaaatacca gagaatgttt     480
tagatacacc atcaaaaatt gtataagtg gctctaactt atcccaataa cctaactctc      540
cgtcgctatt gtaaccagtt ctaaaagctg tatttgagtt tatcacccct tgtcactaaga    600 aaataaatgc agggtaaaat ttatatcctt cttgttttat gtttcggtat aaaacactaa     660
tatcaatttc tgtggttata ctaaaagtcg tttgttggtt caaataatga ttaaatatct     720
cttttctctt ccaattgtct aaatcaattt tattaaagtt catttgatat gcctcctaaa     780 ttttatcta aagtgaattt aggaggctta cttgtctgct ttcttcatta gaatcaatcc      840
ttttttaaaa gtcaatatta ctgtaacata aatatatatt ttaaaatat cccactttat     900 ccaattttcg tttgttgaac taatgggtgc tttagttgaa gaataaagac cacattaaaa    960
aatgtggtct tttgtgttt tttaaaggat ttgagcgtag cgaaaaatcc ttttcttttct   1020 tatcttgata ataagggtaa ctattgaatt cggtaccaag agtttgtaga aacgcaaaaa    1080
ggccatccgt caggatggcc ttctgcttaa tttgatgcct ggcagtttat ggcgggcgtc    1140
ctgcccgcca cctccgggc cgttgcttcg caacgttcaa atccgctccc ggcggatttg     1200
tcctactcag gagagcgttc accgacaaac aacagataaa acgaaaggcc cagtctttcg   1260
```

```
actgagcctt tcgttttatt tgatgcctgg cagttccta ctctcgcatg gggagacccc    1320
acactaccat cggcgctacg gcgtttcact tctgagttcg gcatggggtc aggtgggacc    1380
accgcgctac tgccgccagg caaattctgt tttatcagac cgcttctgcg ttctgattta    1440
atctgtatca ggctgaaaat cttctctcat ccgccaaaac aggatcctac ggaaatggag    1500
cggcaaaacc gttttactct caaaatctta aagaaaaacc cccgataaag ggggcttttc    1560
ttctacaaaa ttgtacgggc tggttcgttc cccagcattt gttcaatttt gttttgatca    1620
ttcagaacag ccactttcgg ctcatggctt ccgcttctt gatcagacat cattttgtag    1680
gaaataataa tgaccttatc tccttcctgc acaaggcgtg cggctgcacc gtttaagcat    1740
atgacgccgc ttccccgttt accaggaata atatacgttt caagacgtgc tccattatta    1800
ttattcacaa tttgtacttt ttcattagga agcattccca cagcatcaat gagatcttca    1860
tcaattgtaa tgcttcccac atagttcagg tttgcttccg taacagttgc cctgtgaagt    1920
ttgccgctca tcattgttcg atacatatta tattctctcc atttctcgaa tatcaataat    1980
gatattatct attaaacgcg cttttgaaaa agcaactgca acagcgagaa tcatctttcc    2040
agcaatttca ttcacaggct cgagttccgg ataggaataa agctctacat agtctatggt    2100
tccgctagtc gtttcaatga tatcttttgc agcttttatc accgcttcag gatctctttc    2160
accggcttgg acaagttccg cacttgtttg aagggcccga tacagcttag gcgcttcttt    2220
tctttcctca gctgttaagt atacattgcg agagcttttg gctaagccgt cttcctctct    2280
gaccgtatcg acaggaacca attcaatatc catgaagaag tcgctgatta acccatcaac    2340
aacagctacc tgctgcgcat cttttaaacc gaaataggca cgagtcggct tgactagatt    2400
gaaaagcttc gtcagtacga tcgcgacccc gtcaaaatgt ccttctcttg agcgcccgca    2460
taacacgtct gtgcgtcttt ctacatgaat cgtgacattc ttttcaccgg gatacatatc    2520
atgagcatct ggcgtaaaaa gaatatcgac tccggcgttt tctgcaagag ctgcatcccg    2580
ctcaatatcg cgcggatatg cttcaaaatc ttcattaggg ccgaattgtg caggattcac    2640
aaaaatactc ataataacgg cgtcgttttc ttgtcttgct ttgtctgcta aggttaaatg    2700
cccctcatgc agaaacccca tcgtcggaac aaatccgatt gacttgccct ctgaatggta    2760
ttgttttatg gcttctttca gctgtgaaat atcagtaatc tgtctcatct tattttcccc    2820
cgtacaagcc gtcaagcact gtctggttca tttgaaagga atgctttgt tcagggaaag    2880
cacgatgtct tacatcctga acatatccgc tgattgctgt ttcgatggtt tcatcaatgc    2940
gcgtatattg ctttacaaat ttaggtgttc tctcaacacc gtggccgata atatcatgat    3000
aaacgagaac ttgtccgtcc gctttcacac cagccccgat tccaatgacc ggtatgctta    3060
gcgtctcggc aattttggct gtgagttctg ccggcacaca ttccagcaca agcatcatag    3120
ctcctgcttc ttcgcatttt atactgtctt ctattaattt tttggcgctt tgttcgtctt    3180
tgccctgtac tttatagccg cccagtacgc cgactgactg cggtgtcaaa cctaagtgac    3240
tgactactgg aatgcctcca agcgtcaatg cgcgaatgga ttcaaacacg ccttctccgc    3300
cctcaagctt cagtgcgtca gctccgcttt cctgaacgat agccgctgca ttttcagcg    3360
tatcttcctt agacaggtga taagacataa acggcatatc tgtcacaata aaggtattcg    3420
gcgcacccct tttaacggct tttgtatgat ggatcatgtc cgcaactgtc acaccgacag    3480
ttgaatcaag gccgaggacg accattccaa gtgaatcacc gactaaaatc atgtcaactc    3540
ccgcttgttc agcaagttta gctgccggat aatcataagc ggtcagcatg acaatcggtt    3600
cttcagactc cttcattttt agaaaatcca gttttgtttt catgttttct cctccttcta    3660
```

```
gagcgtcctg ctgttgttaa gattattata ccacaccttg tagataaagt caacaacttt    3720
ttgcaaaatt tttcaggaat tttagcagag gttgttctgg atgtagaaca aaacatcttt    3780
ccgctcttgt gctgttagga tatctttctt ggaagctagg taggcctcga gttatggcag    3840
ttggttaaaa ggaaacaaaa agaccgtttt cacacaaaac ggtctttttc gatttctttt    3900
tacagtcaca gccacttttg caaaaaccgg acagcttcat gccttataac tgctgtttcg    3960
gtcgacaagc ttcgcgaagc ggccgcaaaa ttcactggcc gtcgttttac aacgtcgtga    4020
ctgggaaaac cctggcgtta cccaacttaa tcgccttgca gcacatcccc ctttcgccag    4080
ctggcgtaat agcgaagagg cccgcaccga tcgcccttcc caacagttgc gcagcctgaa    4140
tggcgaatgg cgcctgatgc ggtatttttc tccttacgcat ctgtgcggta tttcacaccg    4200
catatggtgc actctcagta caatctgctc tgatgccgca tagttaagcc agccccgaca    4260
cccgccaaca cccgctgact atgcttgtaa accgttttgt gaaaaatttt taaaataaa    4320 aaaggggacc tctagggtcc ccaattaatt agtaatataa tctattaaag gtcattcaaa    4380
aggtcatcca ccggatcagc ttagtaaagc cctcgctaga ttttaatgcg gatgttgcga    4440
ttacttcgcc aactattgcg ataacaagaa aaagccagcc tttcatgata tatctcccaa    4500
tttgtgtagg gcttattatg cacgcttaaa aataataaaa gcagacttga cctgatagtt    4560
tggctgtgag caattatgtg cttagtgcat ctaacgcttg agttaagccg cgccgcgaag    4620
cggcgtcggc ttgaacgaat tgttagacat tatttgccga ctaccttggt gatctcgcct    4680
ttcacgtagt ggacaaattc ttccaactga tctgcgcgcg aggccaagcg atcttcttct    4740
tgtccaagat aagcctgtct agcttcaagt atgacgggct gatactgggc cggcaggcgc    4800
tccattgccc agtcggcagc gacatccttc ggcgcgattt tgccggttac tgcgctgtac    4860
caaatgcggg acaacgtaag cactacattt cgctcatcgc cagcccagtc gggcggcgag    4920
ttccatagcg ttaaggtttc atttagcgcc tcaaatagat cctgttcagg aaccggatca    4980
aagagttcct ccgccgctgg acctaccaag gcaacgctat gttctcttgc ttttgtcagc    5040
aagatagcca gatcaatgtc gatcgtggct ggctcgaaga tacctgcaag aatgtcattg    5100
cgctgccatt ctccaaattg cagttcgcgc ttagctggat aacgccacgg aatgatgtcg    5160
tcgtgcacaa caatggtgac ttctacagcg cggagaatct cgctctctcc agggaagcc    5220 gaagtttcca aaggtcgtt gatcaaagct cgccgcgttg tttcatcaag ccttacggtc    5280
accgtaacca gcaaatcaat atcactgtgt ggcttcaggc cgccatccac tgcggagccg    5340
tacaaatgta cggccagcaa cgtcggttcg agatggcgct cgatgacgcc aactacctct    5400
gatagttgag tcgatacttc ggcgatcacc gcttccctca tgatgtttaa ctttgtttta    5460
gggcgactgc cctgctgcgt aacatcgttg ctgctccata acatcaaaca tcgacccacg    5520
gcgtaacgcg cttgctgctt ggatgcccga ggcatagact gtaccccaaa aaacagtca    5580 taacaagcca tgaaaaccgc cactgcgccg ttaccaccgc tgcgttcggt caaggttctg    5640
gaccagttgc gtgagcgcat acgctacttg cattacagct tacgaaccga acaggcttat    5700
gtccactggg ttcgtgcctt catccgtttc cacggtgtgc gtcacccggc aaccttgggc    5760
agcagcgaag tcgaggcatt tctgtcctgg ctggcgaacg agcgcaaggt tcggtctcc    5820 acgcatcgtc aggcattggc ggccttgctg ttcttctacg gcaaggtgct gtgcacggat    5880 ctgcccggc ttcaggagat cggaagacct cggccgtcgc ggcgcttgcc ggtggtgctg    5940
accccggatg aagtggttcg catcctcggt tttctgaag gcgagcatcg tttgttcgcc    6000
cagcttctgt atggaacggg catgcggatc agtgagggtt tgcaactgcg ggtcaaggat    6060
```

```
ctggatttcg atcacggcac gatcatcgtg cgggagggca agggctccaa ggatcgggcc   6120
ttgatgttac ccgagagctt ggcacccagc ctgcgcgagc aggggaattg atccggtgga   6180
tgaccttttg aatgaccttt aatagattat attactaatt aattggggac cctagaggtc   6240
ccctttttta ttttaaaaat ttttcacaa aacggtttac aagcataacg ggttttgctg    6300
cccgcaaacg ggctgttctg gtgttgctag tttgttatca gaatcgcaga tccggcttca   6360
ggtttgccgg ctgaaagcgc tatttcttcc agaattgcca tgattttttc cccacgggag   6420
gcgtcactgg ctcccgtgtt gtcggcagct ttgattcgat aagcagcatc gcctgtttca   6480
ggctgtctat gtgtgactgt tgagctgtaa caagttgtct caggtgttca atttcatgtt   6540
ctagttgctt tgttttactg gtttcacctg ttctattagg tgttacatgc tgttcatctg   6600
ttacattgtc gatctgttca tggtgaacag ctttaaatgc accaaaaact cgtaaaagct   6660
ctgatgtatc tatctttttt acaccgtttt catctgtgca tatggacagt tttccctttg   6720
atatctaacg gtgaacagtt gttctacttt tgtttgttag tcttgatgct tcactgatag   6780
atacaagagc cataagaacc tcagatcctt ccgtatttag ccagtatgtt ctctagtgtg   6840
gttcgttgtt tttgcgtgag ccatgagaac gaaccattga gatcatgctt actttgcatg   6900
tcactcaaaa attttgcctc aaaactggtg agctgaattt ttgcagttaa agcatcgtgt   6960 agtgttttc ttagtccgtt acgtaggtag gaatctgatg taatggttgt tggtattttg    7020
tcaccattca tttttatctg gttgttctca agttcggtta cgagatccat ttgtctatct   7080
agttcaactt ggaaaatcaa cgtatcagtc gggcggcctc gcttatcaac caccaatttc   7140
atattgctgt aagtgtttaa atctttactt attggtttca aaacccattg gttaagcctt   7200
ttaaactcat ggtagttatt ttcaagcatt aacatgaact taaattcatc aaggctaatc   7260
tctatatttg ccttgtgagt tttcttttgt gttagttctt ttaataacca ctcataaatc   7320
ctcatagagt atttgttttc aaaagactta acatgttcca gattatattt tatgaatttt   7380
tttaactgga aaagataagg caatatctct tcactaaaaa ctaattctaa tttttcgctt   7440
gagaacttgg catagtttgt ccactggaaa atctcaaagc ctttaaccaa aggattcctg   7500
atttccacag ttctcgtcat cagctctctg gttgctttag ctaatacacc ataagcattt   7560
tccctactga tgttcatcat ctgagcgtat tggttataag tgaacgatac cgtccgttct   7620
ttccttgtag ggttttcaat cgtggggttg agtagtgcca cacagcataa aattagcttg   7680
gtttcatgct ccgttaagtc atagcgacta atcgctagtt catttgcttt gaaaacaact   7740
aattcagaca tacatctcaa ttggtctagg tgattttaat cactatacca attgagatgg   7800
gctagtcaat gataattact agtccttttc ctttgagttg tgggtatctg taaattctgc   7860
tagacctttg ctggaaaact tgtaaattct gctagaccct ctgtaaattc cgctagacct   7920
ttgtgtgttt ttttttgttta tattcaagtg gttataattt atagaataaa gaaagaataa   7980 aaaagataa aaagaataga tcccagccct gtgtataact cactacttta gtcagttccg    8040
cagtattaca aaaggatgtc gcaaacgctg tttgctcctc tacaaaacag accttaaaac   8100
cctaaaggct taagtagcac cctcgcaagc tcgggcaaat cgctgaatat tccttttgtc   8160
tccgaccatc aggcacctga gtcgctgtct ttttcgtgac attcagttcg ctgcgctcac   8220
ggctctggcg tgaatgggg gtaaatggca ctacaggcgc ttttatgga ttcatgcaag     8280 gaaactaccc ataatacaag aaaagcccgt cacgggcttc tcagggcgtt ttatggcggg   8340
tctgctatgt ggtgctatct gacttttgc tgttcagcag ttcctgccct ctgatttttcc   8400 agtctgacca cttcggatta tcccgtgaca ggtcattcag actggctaat gcacccagta   8460
```

-continued aggcagcggt atcatcaaca ggcttacccg tcttactgtc aac         8503

<210> SEQ ID NO 94
<211> LENGTH: 7381
<212> TYPE: DNA
<213> ORGANISM: Artificial Sequence
<220> FEATURE:
<223> OTHER INFORMATION: Description of Artificial Sequence:recombinant
      pAN006 plasmid

<400> SEQUENCE: 94

| | | | | |
|---|---|---|---|---|
| ttgcggccgc | ttcgaaagct | gtaatataaa | aaccttcttc | aactaacggg gcaggttagt | 60 |
| gacattagaa | aaccgactgt | aaaaagtaca | gtcggcatta | tctcatatta taaaagccag | 120 |
| tcattaggcc | tatctgacaa | ttcctgaata | gagttcataa | acaatcctgc atgataacca | 180 |
| tcacaaacag | aatgatgtac | ctgtaaagat | agcggtaaat | atattgaatt cctttatta | 240 |
| atgaattttc | ctgctgtaat | aatgggtaga | aggtaattac | tattattatt gatatttaag | 300 |
| ttaaacccag | taaatgaagt | ccatggaata | atagaaagag | aaaaagcatt tcaggtata | 360 |
| ggtgttttgg | gaaacaattt | ccccgaacca | ttatatttct | ctacatcaga aaggtataaa | 420 |
| tcataaaact | ctttgaagtc | attctttaca | ggagtccaaa | taccagagaa tgttttagat | 480 |
| acaccatcaa | aaattgtata | aagtggctct | aacttatccc | aataacctaa ctctccgtcg | 540 |
| ctattgtaac | cagttctaaa | agctgtattt | gagtttatca | cccttgtcac taagaaaata | 600 |
| aatgcagggt | aaaatttata | tccttcttgt | tttatgtttc | ggtataaaac actaatatca | 660 |
| atttctgtgg | ttatactaaa | agtcgtttgt | tggttcaaat | aatgattaaa tatctctttt | 720 |
| ctcttccaat | tgtctaaatc | aattttatta | aagttcattt | gatatgcctc ctaaattttt | 780 |
| atctaaagtg | aatttaggag | gcttacttgt | ctgctttctt | cattagaatc aatccttttt | 840 |
| taaaagtcaa | tattactgta | acataaatat | atattttaaa | aatatcccac tttatccaat | 900 |
| tttcgtttgt | tgaactaatg | ggtgctttag | ttgaagaata | aagaccacat taaaaaatgt | 960 |
| ggtcttttgt | gttttttttaa | aggatttgag | cgtagcgaaa | aatcctttc tttcttatct | 1020 |
| tgataataag | ggtaactatt | gaattcggta | ccaagagttt | gtagaaacgc aaaaaggcca | 1080 |
| tccgtcagga | tggccttctg | cttaatttga | tgcctggcag | tttatggcgg gcgtcctgcc | 1140 |
| cgccaccctc | cgggccgttg | cttcgcaacg | ttcaaatccg | ctcccggcgg atttgtccta | 1200 |
| ctcaggagag | cgttcaccga | caaacaacag | ataaaacgaa | aggcccagtc tttcgactga | 1260 |
| gcctttcgtt | ttatttgatg | cctggcagtt | ccctactctc | gcatgggag accccacact | 1320 |
| accatcggcg | ctacggcgtt | tcacttctga | gttcggcatg | gggtcaggtg gaccaccgc | 1380 |
| gctactgccg | ccaggcaaat | tctgttttat | cagaccgctt | ctgcgttctg atttaatctg | 1440 |
| tatcaggctg | aaaatcttct | ctcatccgcc | aaaacaggat | cctacggaaa tggagcggca | 1500 |
| aaaccgtttt | actctcaaaa | tcttaaaaga | aaaccccga | taaggggggc ttttcttcta | 1560 |
| caaaattgta | cgggctggtt | cgttccccag | catttgttca | attttgtttt gatcattcag | 1620 |
| aacagccact | ttcggctcat | ggcttgccgc | ttcttgatca | gacatcattt tgtaggaaat | 1680 |
| aataatgacc | ttatctcctt | cctgcacaag | gcgtgcggct | gcaccgttta agcatatgac | 1740 |
| gccgcttccc | cgtttaccag | gaataatata | cgtttcaaga | cgtgctccat tattattatt | 1800 |
| cacaatttgt | acttttttcat | taggaagcat | tcccacagca | tcaatgagat cttcatcaat | 1860 |
| tgtaatgctt | cccacatagt | tcaggttttgc | ttccgtaaca | gttgccctgt gaagtttgcc | 1920 |
| gctcatcatt | gttcgataca | tattatattc | tctccatttc | tcgaatatca ataatgatat | 1980 |

```
tatctattaa acgcgctttt gaaaaagcaa ctgcaacagc gagaatcatc tttccagcaa    2040
tttcattcac aggctcgagt tccgatagg aataaagctc tacatagtct atggttccgc     2100
tagtcgtttc aatgatatct tttgcagctt ttatcaccgc ttcaggatct cttttcaccgg   2160 cttggacaag ttccgcactt gtttgaaggg cccgatacag cttaggcgct tcttttcttt    2220
cctcagctgt taagtataca ttgcgagagc ttttggctaa gccgtcttcc tctctgaccg    2280
tatcgacagg aaccaattca atatccatga agaagtcgct gattaaccca tcaacaacag    2340
ctacctgctg cgcatctttt aaaccgaaat aggcacgagt cggcttgact agattgaaaa    2400
gcttcgtcag tacgatcgcg accccgtcaa aatgtccttc tcttgagcgc cgcataaca     2460 cgtctgtgcg tctttctaca tgaatcgtga cattcttttc accgggatac atatcatgag    2520
catctggcgt aaaaagaata tcgactccgg cgttttctgc aagagctgca tcccgctcaa    2580
tatcgcgcgg atatgcttca aaatcttcat tagggccgaa ttgtgcagga ttcacaaaaa    2640
tactcataat aacggcgtcg ttttcttgtc ttgctttgtc tgctaaggtt aaatgcccct    2700
catgcagaaa ccccatcgtc ggaacaaatc cgattgactt gccctctgaa tggtattgtt    2760
ttatggcttc tttcagctgt gaaatatcag taatctgtct catcttattt tcccccgtac    2820
aagccgtcaa gcactgtctg gttcatttga aaggaatgct tttgttcagg gaaagcacga    2880
tgtcttacat cctgaacata tccgctgatt gctgtttcga tggtttcatc aatgcgcgta    2940 tattgctttta caaatttagg tgttctctca acaccgtggc cgataatatc atgataaacg    3000
agaacttgtc cgtccgcttt cacaccagcc ccgattccaa tgaccggtat gcttagcgtc    3060
tcggcaattt tggctgtgag ttctgccggc acacattcca gcacaagcat catagctcct    3120
gcttcttcgc attttatact gtcttctatt aattttttgg cgctttgttc gtctttgccc    3180
tgtactttat agccgcccag tacgccgact gactgcggtg tcaaacctaa gtgactgact    3240
actggaatgc ctccaagcgt caatgcgcga atggattcaa acacgccttc tccgccctca    3300
agcttcagtg cgtcagctcc gctttcctga acgatagccg ctgcattttt cagcgtatct    3360
tccttagaca ggtgataaga cataaacggc atatctgtca caataaaggt attcggcgca    3420 cccctttttaa cggcttttgt atgatggatc atgtccgcaa ctgtcacacc gacagttgaa    3480
tcaaggccga ggacgaccat tccaagtgaa tcaccgacta aaatcatgtc aactcccgct    3540
tgttcagcaa gtttagctgc cggataatca taagcggtca gcatgacaat cggttcttca    3600
gactccttca ttttttagaaa atccagtttt gttttcatgt tttctcctcc tctagagcgt    3660
cctgctgttg ttaagattat tataccacac cttgtagata aagtcaacaa cttttttgcaa    3720 aatttttcag gaattttagc agaggttgtt ctggatgtag aacaaaacat ctttccgctc    3780
ttgtgctgtt aggatatctt tcttggaagc taggtaggcc tcgagttatg gcagttggtt    3840
aaaaggaaac aaaaagaccg ttttcacaca aaacggtctt tttcgatttc tttttacagt    3900
cacagccact tttgcaaaaa ccggacagct tcatgcctta taactgctgt ttcggtcgac    3960
ctgcaggcat gcaagcttcg cgaagcggcc gccgacgcga ggctggatgg ccttccccat    4020
tatgattctt ctcgcttccg gcggcatcgg gatgcccgcg ttgcaggcca tgctgtccag    4080
gcaggtagat gacgaccatc agggacagct tcaaggatcg ctcgcggctc ttaccagcct    4140
aacttcgatc actggaccgc tgatcgtcac ggcgatttat gccgcctcgg cgagcacatg    4200 gaacggggttg gcatggattg taggcgccgc cctataccttg tctgcctcc ccgcgttgcg    4260 tcgcggtgca tggagccggg ccacctcgac ctgaatggaa gccggcggca cctcgctaac    4320
ggattcacca ctccaagaat tggagccaat caattcttgc ggagaactgt gaatgcgcaa    4380
```

```
accaacccctt ggcagaacat atccatcgcg tccgccatct ccagcagccg cacgcggcgc    4440
atctcgggca gcgttgggtc ctggccacgg gtgcgcatga tcgtgctcct gtcgttgagg    4500
acccggctag gctggcgggg ttgccttact ggttagcaga atgaatcacc gatacgcgag    4560
cgaacgtgaa gcgactgctg ctgcaaaacg tctgcgacct gagcaacaac atgaatggtc    4620
ttcggtttcc gtgtttcgta aagtctggaa acgcggaagt cagcgccctg caccattatg    4680
ttccggatct gcatcgcagg atgctgctgg ctaccctgtg gaacacctac atctgtatta    4740
acgaagcgct ggcattgacc ctgagtgatt tttctctggt cccgccgcat ccataccgcc    4800
agttgtttac cctcacaacg ttccagtaac cgggcatgtt catcatcagt aacccgtatc    4860
gtgagcatcc tctctcgttt catcggtatc attaccccca tgaacagaaa ttccccctta    4920
cacggaggca tcaagtgacc aaacaggaaa aaaccgccct taacatggcc cgctttatca    4980
gaagccagac attaacgctt ctggagaaac tcaacgagct ggacgcggat gaacaggcag    5040
acatctgtga atcgcttcac gaccacgctg atgagcttta ccgcagctgc ctcgcgcgtt    5100
tcggtgatga cggtgaaaac ctctgacaca tgcagctccc ggagacggtc acagcttgtc    5160
tgtaagcgga tgccgggagc agacaagccc gtcaggcgc gtcagcgggt gttggcgggt    5220
gtcggggcgc agccatgacc cagtcacgta gcgatagcgg agtgtatact ggcttaacta    5280
tgcggcatca gagcagattg tactgagagt gcaccatatg cggtgtgaaa taccgcacag    5340
atgcgtaagg agaaaatacc gcatcaggcg ctcttccgct tcctcgctca ctgactcgct    5400
gcgctcggtc gttcggctgc ggcgagcggt atcagctcac tcaaaggcgg taatacggtt    5460
atccacagaa tcaggggata acgcaggaaa gaacatgtga gcaaaaggcc agcaaaaggc    5520
caggaaccgt aaaaaggccg cgttgctggc gtttttccat aggctccgcc ccctgacga    5580 gcatcacaaa aatcgacgct caagtcagag gtggcgaaac ccgacaggac tataaagata    5640
ccaggcgttt ccccctggaa gctccctcgt gcgctctcct gttccgaccc tgccgcttac    5700
cggatacctg tccgcctttc tcccttcggg aagcgtggcg ctttctcata gctcacgctg    5760
taggtatctc agttcggtgt aggtcgttcg ctccaagctg ggctgtgtgc acgaaccccc    5820
cgttcagccc gaccgctgcg ccttatccgg taactatcgt cttgagtcca acccggtaag    5880
acacgactta tcgccactgg cagcagccac tggtaacagg attagcagag cgaggtatgt    5940
aggcggtgct acagagttct tgaagtggtg gcctaactac ggctacacta aggacagt    6000 atttggtatc tgcgctctgc tgaagccagt taccttcgga aaaagagttg gtagctcttg    6060
atccggcaaa caaaccaccg ctggtagcgg tggtttttt gtttgcaagc agcagattac    6120
gcgcagaaaa aaaggatctc aagaagatcc tttgatcttt tctacggggt ctgacgctca    6180
gtggaacgaa aactcacgtt aagggatttt ggtcatgaga ttatcaaaaa ggatcttcac    6240
ctagatcctt ttaaattaaa aatgaagttt taaatcaatc taagtatat atgagtaaac    6300 ttggtctgac agttaccaat gcttaatcag tgaggcacct atctcagcga tctgtctatt    6360
tcgttcatcc atagttgcct gactccccgt cgtgtagata actacgatac gggagggctt    6420
accatctggc cccagtgctg caatgatacc gcgagaccca cgctcaccgg ctccagattt    6480
atcagcaata aaccagccag ccggaagggc cgagcgcaga agtggtcctg caactttatc    6540
cgcctccatc cagtctatta attgttgccg ggaagctaga gtaagtagtt cgccagttaa    6600
tagtttgcgc aacgttgttg ccattgctgc aggcatcgtg gtgtcacgct cgtcgtttgg    6660
tatggcttca ttcagctccg gttcccaacg atcaaggcga gttacatgat cccccatgtt    6720
gtgcaaaaaa gcggttagct ccttcggtcc tccgatcgtt gtcagaagta agttggccgc    6780
```

-continued

```
agtgttatca ctcatggtta tggcagcact gcataattct cttactgtca tgccatccgt    6840
aagatgcttt tctgtgactg gtgagtactc aaccaagtca ttctgagaat agtgtatgcg    6900
gcgaccgagt tgctcttgcc cggcgtcaat acgggataat accgcgccac atagcagaac    6960
tttaaaagtg ctcatcattg gaaaacgttc ttcggggcga aaactctcaa ggatcttacc    7020
gctgttgaga tccagttcga tgtaacccac tcgtgcaccc aactgatctt cagcatcttt    7080
tactttcacc agcgtttctg ggtgagcaaa acaggaagg caaaatgccg caaaaaggg     7140 aataagggcg acacggaaat gttgaatact catactcttc cttttcaat attattgaag    7200 catttatcag ggttattgtc tcatgagcgg atacatattt gaatgtattt agaaaaataa    7260
acaaataggg gttccgcgca catttccccg aaaagtgcca cctgacgtct aagaaaccat    7320
tattatcatg acattaacct ataaaaatag gcgtatcacg aggcccttc gtcttcaaga    7380 a                                                                  7381
```

<210> SEQ ID NO 95
<211> LENGTH: 36
<212> TYPE: DNA
<213> ORGANISM: Artificial Sequence
<220> FEATURE:
<223> OTHER INFORMATION: Description of artificial sequence:
      synthetic oligonucleotide

<400> SEQUENCE: 95

```
ctagattaga aaggaggatt taaatatgta tcgtac                                 36
```

<210> SEQ ID NO 96
<211> LENGTH: 32
<212> TYPE: DNA
<213> ORGANISM: Artificial Sequence
<220> FEATURE:
<223> OTHER INFORMATION: Description of artificial sequence: synthetic
      oligonucleotide

<400> SEQUENCE: 96

```
taatctttcc tcctaaattt atacatagca tg                                      32
```

<210> SEQ ID NO 97
<211> LENGTH: 36
<212> TYPE: DNA
<213> ORGANISM: Artificial Sequence
<220> FEATURE:
<223> OTHER INFORMATION: Description of artificial sequence: synthetic
      oligonucleotide

<400> SEQUENCE: 97

```
ctagattaga aaggaggttt aattaatgta tcgtac                                  36
```

<210> SEQ ID NO 98
<211> LENGTH: 32
<212> TYPE: DNA
<213> ORGANISM: Artificial Sequence
<220> FEATURE:
<223> OTHER INFORMATION: Description of artificial sequence: synthetic
      oligonucleotide

<400> SEQUENCE: 98

```
taatctttcc tccaaattaa ttacatagca tg                                      32
```

METHODS AND MICROORGANISMS FOR PRODUCTION OF PANTO-COMPOUNDS

RELATED APPLICATIONS

The instant application is a continuation application of U.S. patent application Ser. No. 09/667,569, filed Sep. 21, 2000 (abandoned), which is a continuation-in-part of U.S. patent application Ser. No. 09/400,494, filed Sep. 21, 1999 (abandoned). The instant application also claims the benefit of prior filed provisional U.S. Patent Application Ser. No. 60/210,072, filed Jun. 7, 2000, prior filed provisional U.S. Patent Application Ser. No. 60/221,836, filed Jul. 28, 2000 and prior filed provisional U.S. Patent Application Ser. No. 60/227,860, filed Aug. 24, 2000. The entire contents of the above-referenced patent applications are incorporated herein by this reference.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_Listing_13311_00034. The size of the text file is 340 KB, and the text file was created on Nov. 21, 2008.

BACKGROUND OF THE INVENTION

Pantothenate, also known as pantothenic acid or vitamin B5, is a member of the B complex of vitamins and is a nutritional requirement for mammals, including livestock and humans (e.g., from food sources, as a water soluble vitamin supplement or as a feed additive). In cells, pantothenate is used primarily for the biosynthesis of coenzyme A (CoA) and acyl carrier protein (ACP). These coenzymes function in the metabolism of acyl moieties which form thioesters with the sulfhydryl group of the 4'-phosphopantetheine portion of these molecules. These coenzymes are essential in all cells, participating in over 100 different intermediary reactions in cellular metabolism.

The conventional means of synthesizing pantothenate (in particular, the bioactive D isomer) is via chemical synthesis from bulk chemicals, a process which is hampered by excessive substrate cost as well as the requirement for optical resolution of racemic intermediates (e.g., resolution of DL-pantolactone to obtain D-pantolactone for chemical condensation with P-alanine). Accordingly, researchers have recently looked to bacterial or microbial systems that produce enzymes useful in pantothenate biosynthesis processes (as bacteria are themselves capable of synthesizing pantothenate). In particular, bioconversion processes have been evaluated as a means of favoring production of the D isomer of pantothenic acid, e.g., using microorganisms which selectively hydrolyze a DL-pantothenic acid ester to D-pantothenic acid; microorganisms which selectively decompose L-pantolactone resulting in D-pantolactone alone; and microorganisms which selectively hydrolyze DL-pantolactone to D-pantoic acid.

There is still, however, significant need for improved pantothenate production processes, in particular, for processes requiring reduced quantities of substrates and/or less expensive substrates. To this end, methods of direct microbial synthesis have recently been examined as a means of improving D-pantothenate production. In microbes, pantothenate biosynthetis is a multistep pathway resulting in condensation of pantoate (derived from α-ketoisovalerate) and β-alanine to form D-pantothenate. The isoleucine-valine (ilv) pathway biosynthetic enzymes, acetohydroxyacid synthetase (the ilvBN or alsS gene product), acetohydroxyacid isomeroreductase (the ilvC gene product) and dihydroxyacid dehydratase (the ilvD gene product) catalyze the conversion of pyruvate to α-ketoisovalerate. The reactions are further catalyzed by the pantothenate (pan) pathway biosynthetic enzymes ketopantoate hydroxymethyltransferase (the panB gene product), ketopantoate reductase (the panE gene product), aspartate-α-decarboxylase (the panD gene product) and pantothenate synthetase (the panC gene product).

The genes encoding the enzymes involved in the biosynthesis of pantothenic acid in *Salmonella typhimurium* and *Escherichia coli* have recently been identified and characterized (Frodyma and Downs (1998) *J. Biol. Chem.* 273:5572-5576 and Jackowski (1996) pp. 687-694, In Neidhardt et al (ed.) *Escherichia coli* and *Salmonella*: Cellular and Molecular Biology, $2^{nd}$ ed. *Am. Soc. Microbiol.* Wash, D.C.). In *E. coli*, for example, the biosynthesis of pantothenic acid consists of four key steps. The first reaction is catalyzed by the panB gene product, ketopantoate hydroxymethyltransferase, and uses the L-valine intermediate α-ketoisovalerate to generate ketopantoate, which is subsequently reduced to pantoate by the panE gene product, ketopantoate reductase. The panD gene product, aspartate-α-decarboxylase, generates β-alanine from aspartate. The panC gene product, pantothenate synthetase, subsequently ligates β-alanine with pantoate to yield D-pantothenate.

The authors Dusch et al. described the identification of the *Corynebacterium glutamicum* panD gene and reported that expression of the *C. glutamicum* panD gene in *E. coli* yielded a strain producing pantothenate with a specific productivity of 140 ng of pantothenate per mg (dry weight) per hour. (Dusch et al. (1999) *Appl. Environ. Microbiol.* 65:1530-1539).

The authors Sahm and Eggeling have further identified the *Corynebacterium glutamicum* panB and panC genes and have described a genetically engineered strain of *C. glutamicum* which overexpresses the panBC genes (Sahm and Eggeling (1999) *Appl. Environ. Microbiol.* 65:1973-1979). The engineered strain produces pantothenate, however, it was necessary to overexpress the genes responsible for α-ketoisovalerate production in the host organism in order that pantothenic acid production could be detected. Moreover, without the addition of β-alanine, no substantial amounts of pantothenate accumulated with the strain constructed.

Likewise, a method of producing D-pantothenic acid has been described that takes advantage of a sodium salicylate resistant mutant strain of *E. coli* which produces D-pantothenic acid when cultured in the presence of β-alanine (U.S. Pat. No. 5,518,906). Generation of *E. coli* strains resistant to α-ketoisovaleric acid and/or α-ketobutyric acid, and/or α-aminobutyric acid, and/or β-hydroxyaspartic acid and/or O-methyl-threonine, in addition to salicylic acid, further increased pantothenic acid production. Moreover, transformation of a plasmid DNA carrying the panb, panC and panD genes into the salicylic acid resistant mutant strain resulted in increased pantothenate production, however, up to 20 g/L β-alanine or more was fed in the examples given. The panB-panC-panD genes are clustered on the *E. coli* chromosome.

Finally, a method of producing D-pantothenic acid has been described which utilizes a salicylic acid-resistant, α-ketoisovalerate-resistant, α-ketobutyrate-resistant, β-hydroxyaspartate-resistant, o-methylthreonine-resistent *E. coli* strain transformed with pantothenate biosynthesis gene-containing DNA fragments and/or branched amino acid biosynthesis gene-containing DNA fragments and cultured in the presence of β-alanine (U.S. Pat. No. 5,932,457).

Pantothenate production in bacteria results from the condensation of pantoate and β-alanine and involves the pantothenate biosynthetic enzymes ketopantoate hydroxymethyltransferase (the panB gene product), ketopantoate reductase (the panE gene product), aspartate-α-decarboxylase (the panD gene product) and pantothenate synthetase (the panC gene product). Although pantothenate is biologically active as a vitamin, it is further metabolized in all cells to Coenzyme A (CoA) which participates as an acyl group carrier in the tricarboxylic acid (TCA) cycle, fatty acid metabolism and numerous other reactions of intermediary metabolism. The initial (and possibly rate-controlling) step in the conversion of pantothenate to Coenzyme A (CoA) is phosphorylation of pantothenate by pantothenate kinase. A pantothenate kinase activity was first identified in *Salmonella typhimurium* by screening for temperature-sensitive mutants which synthesized CoA at permissive temperatures but excreted pantothenate at non-permissive temperatures. The mutations were mapped in the *Salmonella* chromosome and the genetic locus was designated coaA. The gene encodes the enzyme that catalyzes the first step in the biosynthesis of coenzyme A from pantothenate (Dunn and Snell (1979) *J. Bacteriol.* 140:805-808). *Escherichia coli* temperature sensitive mutants have also been isolated and characterized (Vallari and Rock (1987) *J. Bacteriol.* 169:5795-5800). These mutants (named coaA15 (Ts)) are defective in the conversion of pantothenate to CoA and further exhibit a temperature-sensitive growth phenotype, indicating that pantothenate kinase activity is essential for growth. Moreover, it was noted that CoA inhibited pantothenate kinase activity to the same degree in the mutant as compared to the wild-type enzyme.

Feedback resistant *E. coli* mutants (named coaA16(Fr)) have also been isolated that posses a pantothenate kinase activity that is refractory to feedback inhibition by CoA (Vallari and Jackowski (1988) *J. Bacteriol.* 170:3961-3966). The mutation responsible for the reversion is, suprisingly, not genetically linked to the coaA gene by transduction. Additional data described therein support the view that the total cellular CoA content is controlled by both modulation of biosynthesis at the pantothenate kinase step and possibly by degradation of CoA to 4'-phosphopantetheine.

The wild-type *E. coli* coaA gene was cloned by functional complementation of *E. coli* temperature-sensitive mutants. The sequence of the wild-type gene was determined (Song and Jackowski (1992) *J. Bacteriol.* 174:6411-6417 and Flamm et al. (1988) *Gene* (Amst.) 74:555-558). Strains containing multiple copies of the coaA gene possessed 76-fold higher specific activity of pantothenate kinase, however, there was only a 2.7-fold increase in the steady state level of CoA (Song and Jackowski, supra). It has further been reported that the prokaryotic enzyme (encoded by coaA in *E. coli* and a variety of other microorganisms) is feedback inhibited by CoA both in vivo and in vitro with CoA being about five times more potent than acetyl-CoA in inhibiting the enzyme (Song and Jackowski, supra and Vallari et al., supra). Moreover, it has been reported that the panB gene product in *E. coli* is inhibited by CoA (Powers and Snell (1976) *J. Biol. Chem.* 251:3786-3793). These data further support the view that feedback inhibition of pantothenate kinase activity is a critical factor controlling intracellular CoA concentration.

Using standard search and alignment tools, coaA homologues have been identified in *Hemophilus influenzae, Mycobacterium tuberculosis, Vibrio cholerae, Streptococcus pyogenes* and *Bacillus subtilis*. By contrast, proteins with significant similarity could not be identified in eukaryotic cells including *Saccharomyces cerevisiae* or in mammalian expressed sequence tag (EST) databases. Using a genetic selection strategy, a cDNA encoding pantothenate kinase activity has recently been identified from *Aspergillus nidulans* (Calder et al. (1999) *J. Biol. Chem.* 274:2014-2020). The eukaryotic pantothenate kinase gene (panK) has distinct primary structure and unique regulatory properties that clearly distinguish it from its prokaryotic counterpart. A mammalian pantothenate kinase gene (mpanK1α) has also been isolated which encodes a protein having homology to the *A. nidulans* PanK protein and to the predicted gene product of GenBank™ Accession Number 927798 identified in the *S. cerevisiae* genome (Rock et al. (2000) *J. Biol. Chem.* 275:1377-1383).

SUMMARY OF THE INVENTION

The present invention is based, at least in part, on the discovery of key enzyme-encoding genes of the pantothenate biosynthetic pathway in *Bacillus subtilis*. In particular, the present inventors have identified the panE gene of *B. subtilis*. Overexpression or deregulation of the panE gene in *B. subtilis* results in enhanced production of the panE gene product, ketopantoate reductase, further resulting in increased production of pantothenate. Likewise, mutations in this gene reduce pantothenate production in *B. subtilis* >90%. The present inventors have further identified the presumptive panBCD operon in *B. subtilis*, overexpression or deregulation of which results in increased pantothenate production. The present inventors have further demonstrated that overexpression or deregulation of the panD gene in *B. subtilis* (resulting in enhanced production of the panD gene product, aspartate-α-decarboxylase) further results in increased production of pantothenate, in particular, in combination with deregulation of genes encoding key enzymes of the isoleucine-valine (ilv) biosynthetic pathway.

Accordingly, the present invention features methods of producing pantothenate, as well as other compounds of the pantothenate biosynthetic pathway (e.g., ketopantoate, pantoate and β-alanine), termed "panto-compounds" herein, using microorganisms in which the pantothenate biosynthetic pathway and/or isoleucine-valine biosynthetic pathway has been manipulated such that pantothenate or other desired panto-compounds are produced. In one embodiment, the invention features a method of producing a panto-compound (e.g., pantothenate or pantoate) that involves culturing a microorganism which overexpresses the panE gene product, ketopantoate reductase, also referred to herein as a ketopantoate reductase-overexpressing or "KPAR-O" microorganism, under conditions such that the panto-compound (e.g., pantothenate or pantoate) is produced. In another embodiment, the present invention features a method of producing panto-compounds (e.g., pantothenate or pantoate) which includes culturing a microorganism which overexpresses at least one pantothenate biosynthetic enzyme (e.g., at least one of the panB, panC or panD gene products), preferably in a KPAR-O microorganism, under conditions such that the panto-compound (e.g., pantothenate or pantoate) is produced.

Yet another aspect of the invention features methods of producing panto-compounds which are independent of the need to feed precursors (e.g., β-alanine or aspartate and/or α-ketoisovalerate or valine). In one embodiment, the invention features a method of producing pantothenate in a manner independent of precursor feed that includes culturing an aspartate-α-decarboxylase-overexpressing (AαD-O) microorganism having a deregulated isoleucine-valine (ilv) pathway under conditions such that pantothenate is produced. In another embodiment, the invention features a method of producing pantothenate in a manner independent of precursor feed that includes culturing an AαD-O microorganism having a deregulated pantothenate (pan) pathway and a deregulated isoleucine-valine (ilv) pathway, under conditions such that pantothenate is produced. In another embodiment, the invention features a method of producing pantothenate in a manner independent of aspartate or β-alanine feed that includes culturing an AαD-O microorganism under conditions such that pantothenate is produced. In another embodiment, the invention features a method of producing pantothenate in a manner independent of valine or α-ketoisovalerate feed that includes culturing a microorganism having a deregulated isoleucine-valine (ilv) biosynthetic pathway under conditions such that pantothenate is produced. In yet another embodiment, the invention features a high yield production method for producing pantothenate that includes culturing a manipulated microorganism under conditions such that pantothenate is produced at a significantly high yield (e.g., at a level greater than 10 g/L, 20 g/L, 30 g/L or 40 g/L).

The methods of the present invention further feature microorganisms that overexpresses acetohydroxyacid synthetase or acetohydroxyacid isomeroreductase (e.g., microorganisms transformed with a vector that includes an ilvBNC nucleic acid sequence), microorganisms that overexpresses dihydroxyacid dehydratase (e.g., microorganisms transformed with a vector that includes an ilvD nucleic acid sequence), microorganisms that overexpresses aspartate-α-decarboxylase (e.g. microorganisms transformed with a vector that includes a panD nucleic acid sequence), microorganisms having a deregulated isoleucine-valine (ilv) biosynthetic pathway and microorganisms having a deregulated pantothenate biosynthetic pathway (e.g., microorganisms that overexpress any of ketopantoate hydroxymethyltransferase, ketopantoate reductase, pantothenate synthetase and aspartate-α-decarboxylase, for example, microorganisms transformed with a vector comprising a panBCD nucleic acid sequence or a vector comprising a panE1 nucleic acid sequence). In one embodiment, the recombinant microorganism is Gram positive (e.g., microorganisms belonging to the genus *Bacillus, Cornyebacterium, Lactobacillus, Lactococci* or *Streptomyces*). In another embodiment, the recombinant microorganism is Gram negative. Particularly preferred is a *Bacillus* recombinant microorganism (e.g., *Bacillus licheniformis, Bacillus amyloliquefaciens, Bacillus subtilis, Bacillus pumilus, Bacillus halodurans*, and the like). Recombinant vectors that contain the genes encoding *Bacillus* pantothenate and/or isoleucine-valine biosynthetic enzymes (e.g., *B. subtilis* pantothenate and/or isoleucine-valine biosynthetic enzymes) are also described.

Also featured are methods of producing β-alanine that include culturing an aspartate-α-decarboxylase-overexpressing (AαD-O) microorganism under conditions such that β-alanine is produced and methods of producing β-alanine that involve contacting a composition comprising aspartate with an isolated *Bacillus* aspartate-α-decarboxylase enzyme under conditions such that β-alanine is produced.

The production methods of the present invention further can include recovering the panto-compound (e.g., pantothenate or pantoate).

The present invention further features recombinant microorganisms (e.g., AαD-O microorganisms, microorganisms having a deregulated isoleucine-valine (ilv) pathway, microorganisms overexpressing at least one of ketopantoate hydroxymethyltransferase (the panB gene product), pantothenate synthetase (the panC gene product), aspartate-α-decarboxylase (the panD gene product), ketopantoate reductase (the panE1 gene product) and microorganisms having a deregulated panBCD operon. Also featured are panB, pan C, panD, panE, ilvB, ilvN, alsS, ilvC, and/or ilvD nucleic acid molecules, as well as vectors including such nucleic acid molecules and gene products encoded by such nucleic acid molecules.

The methodology of the present invention further includes, for example in addition to overexpressing at least one pantothenate biosynthetic enzyme, deleting or mutating a second pantothenate biosynthetic enzyme, said second pantothenate biosynthetic enzyme preferably being downstream of the desired product in the pantothenate biosynthetic pathway. For example, mutating panC, in addition to overexpressing the panE gene product, results in even further enhanced or increased production of pantoate. Accordingly, in one embodiment, the invention features a method of producing pantoate which includes culturing a microorganism which overexpresses the panE gene product and which has a deletion in the panC gene. In another embodiment, the invention features a method of producing pantoate which includes culturing a microorganism which overexpresses the panE gene product and/or panB gene product and which has a deletion in the panC gene. Other exemplary embodiments include a method of producing ketopantoate which includes culturing a microorganism which overexpresses the panB gene product and which has a deletion in the panE gene and a method of producing β-alanine which includes culturing a microorganism which overexpresses the panD gene product and which has a deletion in the panC gene. Also included are methods of producing panto-compounds which include overexpressing at least one valine biosynthetic enzyme in a microorganism which has at least one pantothenate biosynthetic enzyme deleted.

The present invention is also based at least in part, on the identification and characterization of a previously unidentified microbial pantothenate kinase gene, coaX. CoaX was first identified in *Bacillus subtilis* and corresponds to an open reading frame in a portion of the chromosomal DNA that includes the 5' end of the ftsH gene, and all of the yacB, yacC, yacD, cysK and pabB genes. The present inventors have demonstrated that the yacB open reading frame encodes a novel pantothenate kinase activity, the gene being unrelated by homology to any previously known pantothenate kinase gene. The gene has been renamed coaX, as it encodes the enzyme which catalyzes the first step in the pathway from pantothenate to CoaA.

Accordingly, the present invention features new and improved methods of producing pantothenate and other key compounds of the pantothenate biosynthetic pathway (e.g., panto-compounds) utilizing microorganisms having modified pantothenate kinase activity. In particular, the present invention features recombinant microorganisms that contain the coaX gene or that contain a mutant coaX gene, having reduced pantothenate kinase activity. In one embodiment, the invention features such recombinant microorganisms further having a deregulated pantothenate biosynthetic pathway. In another embodiment, the invention features such recombinant microorganisms further having a deregulated isoleucine-valine (ilv) pathway. In a preferred embodiment, the microorganisms belong to the genus *Bacillus* (e.g., *B. subtilis*).

The present invention also features recombinant microorganisms (e.g., microorganisms belonging to the genus *Bacillus*, for example, *B. subtilis*) that contain the coaA gene or that contain a mutant coaA gene, optionally including a coaX gene or mutant thereof, having reduced pantothenate kinase activity. In one embodiment, the invention features such recombinant microorganisms further having a deregulated pantothenate biosynthetic pathway or having a deregulated isoleucine-valine (ilv) pathway.

Also featured are vectors that contain isolated coaX or coaA genes as well as mutant coaX and/or coaA genes. Isolated nucleic acid molecules that contain isolated coaX genes or mutant coaX genes are featured in addition to isolated CoaX proteins and mutant CoaX proteins.

The nucleic acids, vectors and recombinant microorganisms described above are particularly useful in the methodologies of the present invention. In particular, the invention features methods of enhancing panto-compound production (e.g., ketopantoate, pantoate and or pantothenate production) that include culturing a recombinant microorganism having a mutant coaX gene under conditions such that panto-compound production is enhanced. In one embodiment, the recombinant microorganism further includes a mutant coaA gene. In another embodiment, the recombinant microorganism further includes a mutant avtA and/or mutant ilvE gene and/or mutant ansB gene and/or mutant alsD gene. Also featured are methods for identifying pantothenate modulators utilizing the recombinant microorganisms and purified CoaX proteins of the present invention.

Other features and advantages of the invention will be apparent from the following detailed description and claims.

BRIEF DESCRIPTION OF THE DRAWINGS

FIG. 20A-B depicts a multiple sequence alignment (MSA) of the amino acid sequences encoded by six known or predicted microbial coaA genes. SEQ ID NOs:4-6 and 1-3 correspond to the amino acid sequences of *Mycobacterium leprae* (SwissProt™ Accession No. Q9X795), *Mycobacterium tuberculosis* (SwissProt™ Accession No. O53440), *Streptomyces coelicolor* (SwissProt™ Accession No. O86799), *Haemophilus influenzae* (SwissProt™ Accession No. P44793), *Escherichia coli* SwissProt™ Accession No. P15044) and *Bacillus subtilis* (SwissProt™ Accession No. P54556), respectively. The alignment was generated using ClustalW MSA software at the GenomeNet CLUSTALW Server at the Institute for Chemical Research, Kyoto University. The following parameters were used: Pairwise Alignment, K-tuple (word) size=1, Window size=5, Gap Penalty=3, Number of Top Diagonals=5, Scoring Method=Percent; Multiple Alignment, Gap Open Penalty=10, Gap Extension Penalty=0.0, Weight Transition=No, Hydrophilic residues=Gly, Pro, Ser, Asn, Asp, Gln, Glu, Arg and Lys, Hydrophobic Gaps=Yes; and Scoring Matrix=BLOSUM.

FIG. 23A-D depicts a multiple sequence alignment (MSA) of the amino acid sequences encoded by fourteen known or predicted microbial coaX genes. SEQ ID NOs:9, 74, 7-8, 75, 11, 10 and 12-18 correspond to the amino acid sequences of *Bacillus subtilis* (SwissProt™ Accession No. P37564), *Clostridium acetobulyticum* (WIT™ Accession No. RCA03301, Argonne National Laboratories), *Streptomyces coelicolor* (PIR™ Accession No. T36391), *Mycobacterium tuberculosis* (SwissProt™ Accession No. O06282), *Rhodobacter capsulatus* (WIT™ Accession No. RRC02473), *Desulfovibrio vulgaris* (DBJ™ Accession No. BAA21476.1), *Deinococcus radiodurans* (SwissProt™ Accession No. Q9RX54), *Thermotoga maritima* (GenBank™ Accession No. AAD35964.1), *Treponema pallidum* (SwissProt™ Accession No. O83446), *Borrelia burgdorferi* (SwissProt™ Accession No. O51477), *Aquifex aeolicus* (SwissProt™ Accession No. O67753), *Synechocystis* sp. (SwissProt™ Accession No. P74045), *Helicobacter pylori* (SwissProt™ Accession No. O25533), and *Bordetella pertussis* (SwissProt™ Accession No. Q45338), respectively. The alignment was generated using ClustalW MSA software at the GenomeNet CLUSTALW Server at the Institute for Chemical Research, Kyoto University. The following parameters were used: Pairwise Alignment, K-tuple (word) size=1, Window size=5, Gap Penalty=3, Number of Top Diagonals=5, Scoring Method=Percent; Multiple Alignment, Gap Open Penalty=10, Gap Extension Penalty=0.0, Weight Transition=No, Hydrophilic residues=Gly, Pro, Ser, Asn, Asp, Gln, Glu, Arg and Lys, Hydrophobic Gaps=Yes; and Scoring Matrix=BLOSUM.

FIG. 24 depicts a multiple sequence alignment of a portion of the protein sequences of the coaA gene products from the following microorganisms: *Bacillus subtilis*, *Escherichia coli*, *Haemophilus influenzae*, *Mycobacterium leprae*, *Mycobacterium tuberculosis*, and *Streptomyces coelicolor*. The residues that are mutated in *E. coli* coaA15(Ts) and *B. subtilis* coaA282A are indicated below and above the alignment, respectively. The portions correspond to amino acid residues 168-187 of SEQ ID NO:3, 167-186 of SEQ ID NO:2, 165-184 of SEQ ID NO:1, 169-188 of SEQ ID NO:4, 169-188 of SEQ ID NO:5 and 179-198 of SEQ ID NO:6, respectively.

DETAILED DESCRIPTION OF THE INVENTION

The present invention features new and improved methods of producing pantothenate and other key compounds of the pantothenate biosynthetic pathway (referred to herein as "panto-compounds", for example, pantothenate, ketopantoate, pantoate and β-alanine) using microorganisms in which the pantothenate biosynthetic pathway has been manipulated such that pantothenate or other desired panto-compounds are produced.

The new and improved methodologies of the present invention include methods of producing panto-compounds (e.g., pantothenate) in microorganisms having at least one enzyme of the pantothenate biosynthetic pathway manipulated such that pantothenate or other desired panto-compounds are produced (e.g., produced at an increased level). For example, the invention features methods of producing panto-compounds (e.g., pantothenate) in microorganisms having at least one of ketopantoate hydroxymethyltransferase, ketopantoate reductase, pantothenate synthetase or aspartate-α-decarboxylase manipulated such that pantothenate or other desired panto-compounds are produced. The methodologies of the present invention also include methods of producing panto-compounds (e.g., pantothenate) in microorganisms having at least one valine-isoleucine biosynthetic enzyme, described herein, manipulated such that pantothenate or other desired panto-compounds are produced. For example, the invention features methods of producing panto-compounds (e.g., pantothenate) in microorganisms having at least one of acetohydroxyacid synthetase, acetohydroxyacid isomeroreductase or dihydroxyacid dehydratase manipulated such that pantothenate or other desired panto-compounds are produced.

The invention also features methods of producing panto-compounds that involve culturing a ketopantoate reductase-overexpressing (KPAR-O) microorganism under conditions such that the panto-compound is produced. The invention also features methods of producing pantothenate in a manner independent of precursor feed that involve culturing an aspartate-α-decarboxylase-overexpressing (AαD-O) microorganism under conditions such that pantothenate is produced. Also featured are β-alanine independent high yield pantothenate production methods as well as methods of producing β-alanine. The present invention also features methods for enhancing production of panto-compounds that involve culturing pantothenate kinase mutants. In particular, the present invention features new and improved methods of producing pantothenate and other key compounds of the pantothenate biosynthetic pathway (e.g., panto-compounds) utilizing microorganisms having modified pantothenate kinase activity, for example, microorganisms that include the coaX gene or that include a mutant coaX gene, having reduced pantothenate kinase activity.

In order that the present invention may be more readily understood, certain terms are first defined herein.

Figure 1:
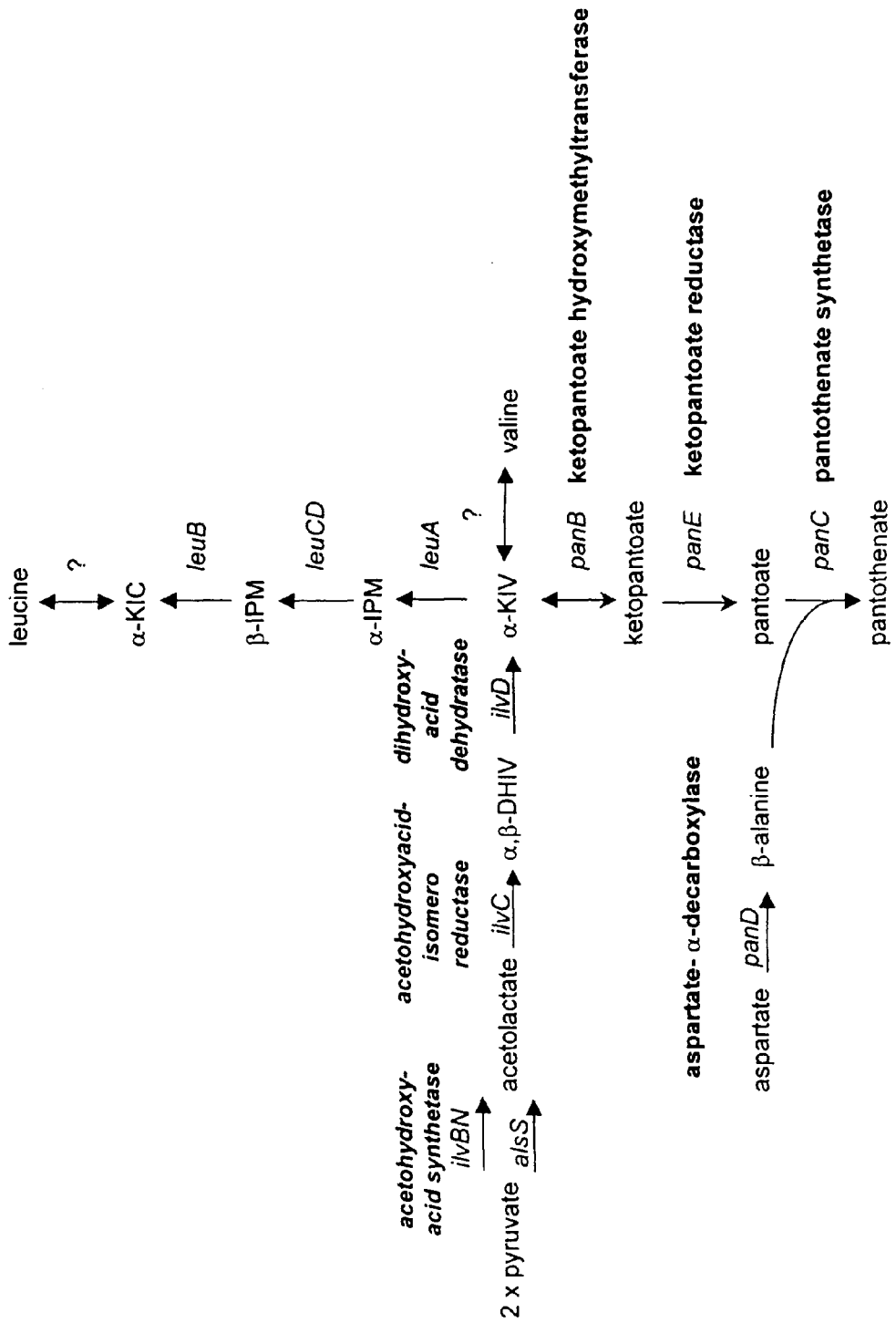
FIG. 1 is a schematic representation of the pantothenate biosynthetic pathway.
Figure 2:
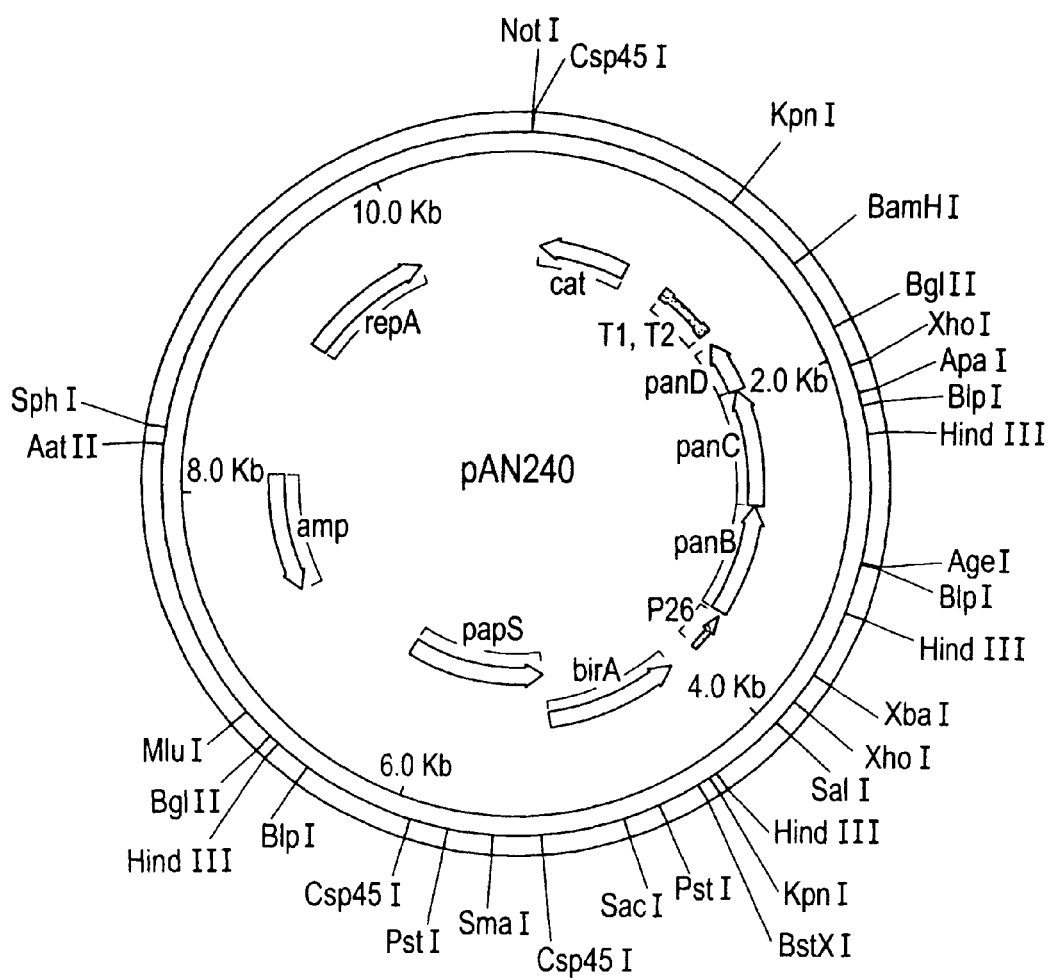
FIG. 2 is a schematic representation of the plasmid pAN240, containing sequences ligated upstream of the $P_{26}$panBCD cassette, equivalent to the integrated version in strain PA221.

The term "pantothenate biosynthetic pathway" includes the biosynthetic pathway involving pantothenate biosynthetic enzymes (e.g., polypeptides encoded by biosynthetic enzyme-encoding genes), compounds (e.g., precursors, substrates, intermediates or products), cofactors and the like utilized in the formation or synthesis of pantothenate. The term "pantothenate biosynthetic pathway" includes the biosynthetic pathway leading to the synthesis of pantothenate in a microorganisms (e.g., in vivo) as well as the biosynthetic pathway leading to the synthesis of pantothenate in vitro. FIG. 1 includes a schematic representation of the pantothenate biosynthetic pathway. Pantothenate biosynthetic enzymes are depicted in bold and their corresponding genes indicated in italics.

The term "pantothenate biosynthetic enzyme" includes any enzyme utilized in the formation of a compound (e.g., intermediate or product) of the pantothenate biosynthetic pathway. According to FIG. 1, synthesis of pantoate from α-ketoisovalerate (α-KIV) proceeds via the intermediate, ketopantoate. Formation of ketopantoate is catalyzed by the pantothenate biosynthetic enzyme ketopantoate hydroxymethyltransferase (the panB gene product). Formation of pantoate is catalyzed by the pantothenate biosynthetic enzyme ketopantoate reductase (the panE gene product). Synthesis of β-alanine from aspartate is catalyzed by the pantothenate biosynthetic enzyme aspartate-α-decarboxylase (the panD gene product). Formation of pantothenate from pantoate and β-alanine (e.g., condensation) is catalyzed by the pantothenate biosynthetic enzyme pantothenate synthetase (the panC gene product).

The term "isoleucine-valine biosynthetic pathway" includes the biosynthetic pathway involving isoleucine-valine biosynthetic enzymes (e.g., polypeptides encoded by biosynthetic enzyme-encoding genes), compounds (e.g., precursors, substrates, intermediates or products), cofactors and the like utilized in the formation or synthesis of conversion of pyruvate to valine or isoleucine. The term "isoleucine-valine biosynthetic pathway" includes the biosynthetic pathway leading to the synthesis of valine or isoleucine in a microorganisms (e.g., in vivo) as well as the biosynthetic pathway leading to the synthesis of valine or isoleucine in vitro. FIG. 1 includes a schematic representation of the isoleucine-valine biosynthetic pathway. Isoleucine-valine biosynthetic enzymes are depicted in bold italics and their corresponding genes indicated in italics The term "isoleucine-valine biosynthetic enzyme" includes any enzyme utilized in the formation of a compound (e.g., intermediate or product) of the isoleucine-valine biosynthetic pathway. According to FIG. 1, synthesis of valine from pyruvate proceeds via the intermediates, acetolactate, α,β-dihydroxyisovalerate (α,β-DHIV) and α-ketoisovalerate (α-KIV). Formation of acetolactate from pyruvate is catalyzed by the isoleucine-valine biosynthetic enzyme acetohydroxyacid synthetase (the ilvBN gene product, or alternatively, the alsS gene product). Formation of α,β-DHIV from acetolactate is catalyzed by the isoleucine-valine biosynthetic enzyme acetohydroxyacidisomero reductase (the ilvC gene product). Synthesis of α-KIV from α,β-DHIV is catalyzed by the isoleucine-valine biosynthetic enzyme dihydroxyacid dehydratase (the ilvD gene product). Moreover, valine and isoleucine can be interconverted by branched chain amino acid transaminases.

As used herein, each of ketopantoate, pantoate, β-alanine and pantothenate are "panto-compounds". The term "panto-compound" includes a compound (e.g., a substrate, intermediate or product) in the pantothenate biosynthetic pathway which is downstream from a particular pantothenate biosynthetic enzyme. In one example, a panto-compound is downstream of the pantothenate biosynthetic enzyme ketopantoate hydroxymethyltransferase (the panB gene product) and can include ketopantoate, pantoate and/or pantothenate. In another example, a panto-compound is downstream of the pantothenate biosynthetic enzyme ketopantoate reductase (the panE gene product) and can include pantoate and/or pantothenate. In yet another example, a panto-compound is downstream of the pantothenate biosynthetic enzyme pantothenate synthetase (the panC gene product) and can include pantothenate. In yet another example, a panto-compound is downstream of the pantothenate biosynthetic enzyme aspartate-α-decarboxylase (the panD gene product) and can include β-alanine and/or pantothenate.

Preferred panto-compounds include pantothenate and pantoate. The term "pantothenate" includes the free acid form of pantothenate, also referred to as "pantothenic acid" as well as any salt thereof (e.g., derived by replacing the acidic hydrogen of pantothenate or pantothenic acid with a cation, for example, calcium, sodium, potassium, ammonium), also referred to as a "pantothenate salt". The term "panto-compound" also includes alcohol derivatives of pantothenate. Preferred pantothenate salts are calcium pantothenate or sodium pantothenate. A preferred alcohol derivative is pantothenol. Pantothenate salts and/or alcohols of the present invention include salts and/or alcohols prepared via conventional methods from the free acids described herein. In another embodiment, calcium pantothenate is synthesized directly by a microorganism of the present invention. A pantothenate salt of the present invention can likewise be converted to a free acid form of pantothenate or pantothenic acid by conventional methodology.

The term "pantoate" includes the free acid form of pantoate, also referred to as "pantoic acid" as well as any salt thereof (e.g., derived by replacing the acidic hydrogen of pantoate or pantoic acid with a cation, for example, calcium, sodium, potassium, ammonium), also referred to as a "pantoate salt". Preferred pantoate salts are calcium pantoate or sodium pantoate. Pantoate salts of the present invention include salts prepared via conventional methods from the free acids described herein. A pantoate salt of the present invention can likewise be converted to a free acid form of pantoate or pantoic acid by conventional methodology. Moreover, a free acid form of pantoate or pantoic acid can be converted to pantolactone by conventional methodology.

Figure 16:
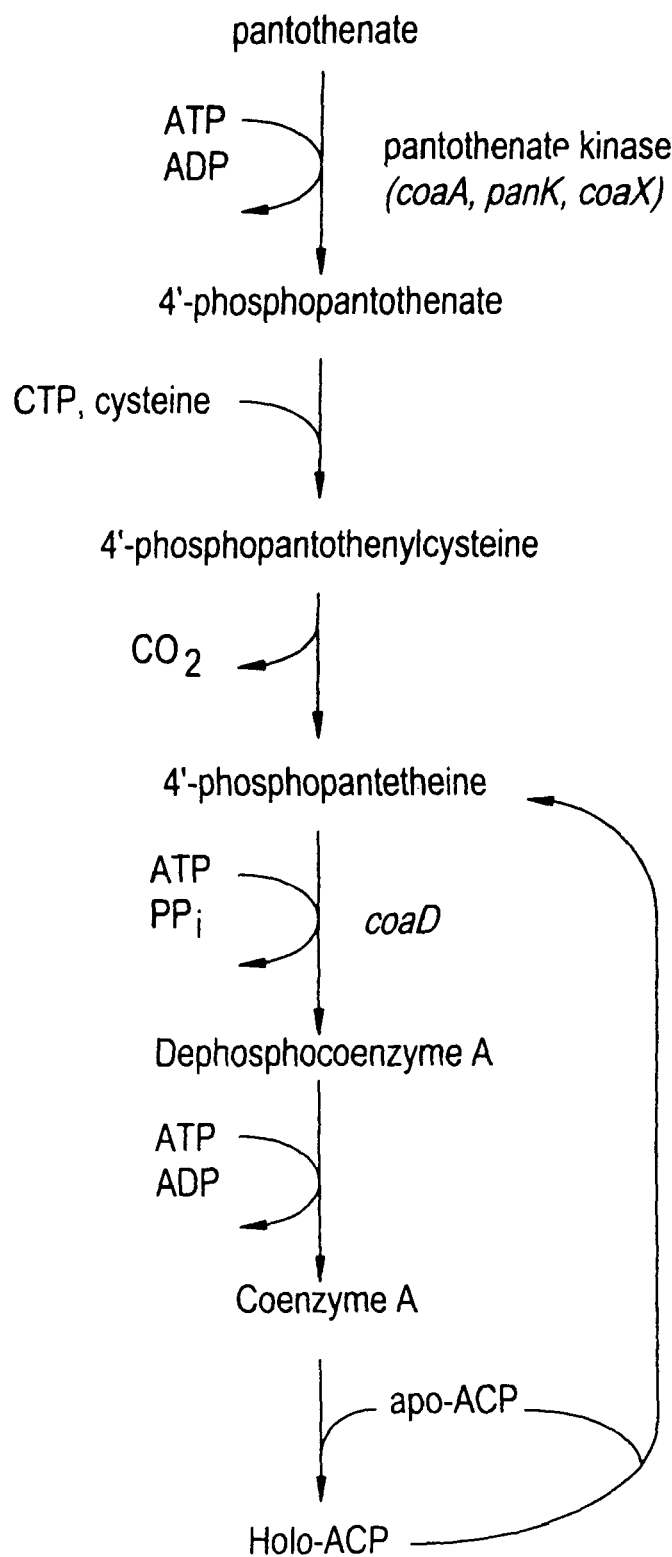
FIG. 16 is a schematic representation of the Coenzyme A biosynthetic pathway in *E. coli*.
Figure 17:
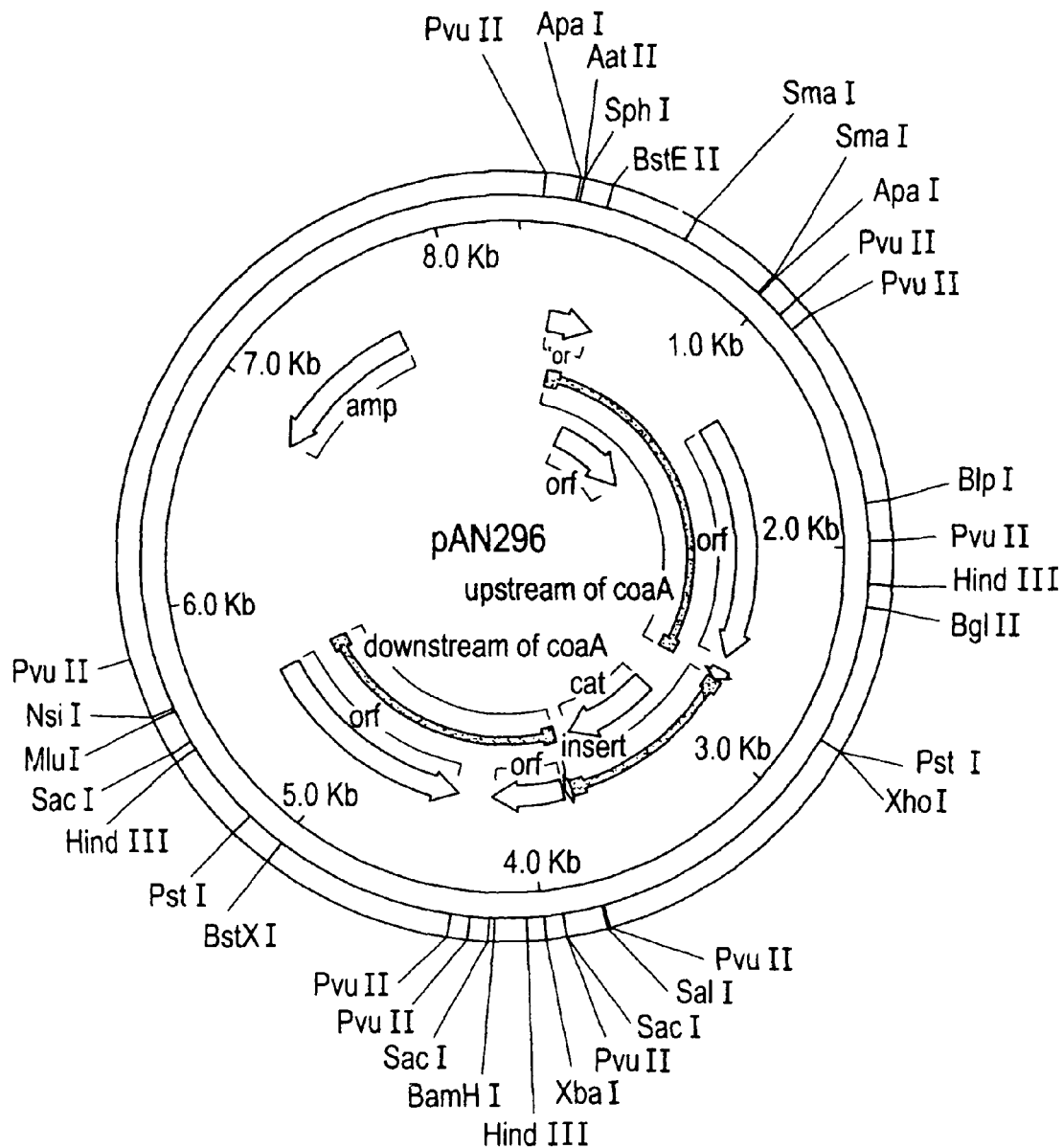
FIG. 17 is a schematic representation of the structure of pAN296, a plasmid designed to delete most of the *B. subtilis* coaA gene and substitute a chloramphenicol resistance gene.

The term "CoA biosynthetic pathway" includes the biosynthetic pathway involving CoA biosynthetic enzymes (e.g., polypeptides encoded by biosynthetic enzyme-encoding genes), compounds (e.g., precursors, substrates, intermediates or products), cofactors and the like utilized in the formation or synthesis of CoA from pantothenate. A schematic representation of the CoA biosynthetic pathway in *E. coli* is set forth as FIG. 16. (The pathway depicted is also presumed to be that utilized by other microorganisms.) The term "CoA biosynthetic pathway" includes the biosynthetic pathway leading to the synthesis of CoA in microorganisms (e.g., in vivo) as well as the biosynthetic pathway leading to the synthesis of CoA in vitro. The term "Coenzyme A or CoA biosynthetic enzyme" includes any enzyme utilized in the formation of a compound (e.g., intermediate or product) of the CoA biosynthetic pathway, for example, the coaA, panK or coaX gene product which catalyzes the phosphorylation of pantothenate to form 4'-phosphopantothenate, or the coaD gene product which catalyzes the conversion of 4'-phosphopantetheine to dephosphocoenzyme A.

I. Recombinant Microorganisms and Methods for Culturing Microorganisms such that Panto-Compounds are Produced The methodologies of the present invention feature microorganisms, e.g., recombinant microorganisms, preferably including vectors or genes (e.g., wild-type and/or mutated genes) as described herein and/or cultured in a manner which results in the production of a desired product (e.g. a panto-compound or panto-compounds). The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived. Preferably, a "recombinant" microorganism of the present invention has been genetically engineered such that it overexpresses at least one bacterial gene or gene product (e.g., a pantothenate or isoleucine-valine biosynthetic enzyme encoding-gene) as described herein, preferably a biosynthetic enzyme encoding-gene included within a recombinant vector as described herein and/or a biosynthetic enzyme expressed from a recombinant vector. The ordinary skilled will appreciate that a microorganism expressing or overexpressing or gene product produces of overproduces the gene product as a result of expression or overexpression of nucleic acid sequences and/or genes encoding the gene product.

The term "manipulated microorganism" includes a microorganism that has been engineered (e.g., genetically engineered) or modified such that the microorganism has at least one enzyme of the pantothenate biosynthetic pathway and/or at least one enzyme of the isoleucine-valine biosynthetic pathway modified such that pantothenate or other desired panto-compounds are produced. Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression or production of which has been altered or modified such that at least one upstream or downstream precursor, substrate or product of the enzyme is altered or modified, for example, as compared to a corresponding wild-type or naturally occurring enzyme.

The term "overexpressed" or "overexpression" includes expression of a gene product (e.g., a pantothenate biosynthetic enzyme or isoleucine-valine biosynthetic enzyme) at a level greater than that expressed prior to manipulation of the microorganism or in a comparable microorganism which has not been manipulated. In one embodiment, the microorganism can be genetically manipulated (e.g., genetically engineered) to overexpress a level of gene product greater than that expressed prior to manipulation of the microorganism or in a comparable microorganism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

The term "deregulated" or "deregulation" includes the alteration or modification of at least one gene in a microorganism that encodes an enzyme in a biosynthetic pathway, such that the level or activity of the biosynthetic enzyme in the microorganism is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a microorganism arises from the particular phenomenon of microorganisms in which more than one enzyme (e.g., two or three biosynthetic enzymes) are encoded by genes occurring adjacent to one another on a contiguous piece of genetic material termed an "operon".

The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

A particularly preferred "recombinant" microorganism of the present invention has been genetically engineered to overexpress a bacterially-derived gene or gene product. The term "bacterially-derived" or "derived-from", for example bacteria, includes a gene which is naturally found in bacteria or a gene product (e.g., ketopantoate hydroxymethyltransferase, ketopantoate reductase, pantothenate synthetase, aspartate-α-decarboxylate, acetohydroxyacid synthetase, acetohydroxyacid isomeroreductase or dihydroxyacid dehydratase) which is encoded by a bacterial gene (e.g., encoded by panB, panE, pan C, panD, ilvB, ilvN, alsS, ilvC, or ilvD).

The methodologies of the present invention feature recombinant microorganisms which overexpress at least one of ketopantoate hydroxymethyltransferase, ketopantoate reductase, pantothenate synthetase or aspartate-α-decarboxylase. A particularly preferred recombinant microorganism of the present invention has been genetically engineered to overexpress a Bacillus (e.g., Bacillus licheniformis, Bacillus amyloliquefaciens, Bacillus halodurans, Bacillus subtilis, and Bacillus pumilus, etc.) biosynthetic enzyme (e.g., has been engineered to overexpress at least one of B. subtilis ketopantoate reductase (the panE gene product) (e.g., ketopantoate reductase having the amino acid sequence of SEQ ID NO:30 or encoded by the nucleic acid sequence of SEQ ID NO:29), B. subtilis ketopantoate hydroxymethyltransferase (the panB gene product) (e.g., ketopantoate hydroxymethyltransferase having the amino acid sequence of SEQ ID NO:24 or encoded by a nucleic acid molecule having the nucleotide sequence of SEQ ID NO:23), B. subtilis pantothenate synthetase (the panC gene product) (e.g., pantothenate synthetase having the amino acid sequence of SEQ ID NO:26 or encoded by a nucleic acid molecule having the nucleotide sequence of SEQ ID NO:25) and/or B. subtilis aspartate-α-decarboxylase (the panD gene product) (e.g., aspartate-α-decarboxylase having the amino acid sequence of SEQ ID NO:28 or encoded by a nucleic acid molecule having the nucleotide sequence of SEQ ID NO:27).

In an exemplary embodiment, the invention features a microorganism (e.g., a KPAR-O microorganism) that has been transformed with a vector comprising a panE nucleic acid sequence (e.g., a panE nucleic acid seqeunce as set forth in SEQ ID NO:29). In another embodiment, the invention features a microorganism that has been transformed with a vector comprising a panB nucleic acid sequence (e.g., a panB nucleic acid sequence as set forth in SEQ ID NO:23), a vector comprising a panC nucleic acid sequence (e.g., a panC nucleic acid sequence as set forth in SEQ ID NO:25) or a vector comprising a panD nucleic acid sequence (e.g., a panD nucleic acid sequence as set forth in SEQ ID NO:27). In yet another embodiment, the invention features a microorganism having a deregulated panBCD operon (e.g., SEQ ID NO:59).

Other preferred "recombinant" microorganisms of the present invention have a deregulated isoleucine-valine (ilv) pathway. The phrase "microorganism having a deregulated isoleucine-valine (ilv) pathway" includes a microorganism having an alteration or modification in at least one gene encoding an enzyme of the isoleucine-valine (ilv) pathway or having an alteration or modification in an operon including more than one gene encoding an enzyme of the isoleucine-valine (ilv) pathway. A preferred "microorganism having a deregulated isoleucine-valine (ilv) pathway" has been genetically engineered to overexpress a *Bacillus* (e.g., *B. subtilis*) ilv biosynthetic enzyme (e.g., has been engineered to overexpress at least one of acetohydroxyacid synthetase (the ilvBN gene products or the alsS gene product) (e.g., acetohydroxyacid synthetase having subunits having the amino acid sequences of SEQ ID NO:32 and SEQ ID NO:34 or encoded by nucleic acid molecules having the nucleotide sequence of SEQ ID NO:31 and SEQ ID NO:33 or the nucleotide sequence of SEQ ID NO:58 from nucleotides 1-2246 or acetohydroxyacid synthetase encoded by a nucleic acid molecule having the nucleotide sequence of SEQ ID NO:86), acetohydroxyacid isomeroreductase (the ilvC gene product) (e.g., acetohydroxyacid isomeroreductase having the amino acid sequence of SEQ ID NO:36 or encoded by a nucleic acid molecule having the nucleotide sequence of SEQ ID NO:35), dihydroxyacid dehydratase (the ilvD gene product) (e.g., dihydroxyacid dehydratase having the amino acid sequence of SEQ ID NO:38 or encoded by a nucleic acid molecule having the nucleotide sequence of SEQ ID NO:37), and/or has been transformed with a vector comprising an ilvBNC nucleic acid sequence (SEQ ID NO:58, coding regions from nucleotides 1-1725, 1722-2246 and 2263-3291) and/or an ilvD nucleic acid sequence (SEQ ID NO:37).

In another preferred embodiment, a recombinant microorganism is designed or engineered such that a mutant CoaA and/or CoaX biosynthetic enzyme is expressed and at least one pantothenate biosynthetic enzyme and/or at least one isoleucine-valine biosynthetic enzyme is overexpressed or deregulated.

In another preferred embodiment, a microorganism of the present invention overexpresses or is mutated for a gene or biosynthetic enzyme (e.g., a CoA biosynthetic enzyme, pantothenate biosynthetic enzyme or isoleucine-valine biosynthetic enzyme) which is bacterially-derived. The term "bacterially-derived" or "derived-from", for example bacteria, includes a gene product (e.g., ketopantoate hydroxymethyltransferase, ketopantoate reductase, pantothenate synthetase, aspartate-α-decarboxylate, acetohydroxyacid synthetase, acetohydroxyacid isomeroreductase, dihydroxyacid dehydratase or pantothenate kinase) which is encoded by a bacterial gene (e.g., panB, panE, panC, panD, ilvBN (or alsS), ilvC, ilvD, or encoded by coaA or coaX).

Still other preferred recombinant microorganisms of the present invention are mutant microorganisms. As used herein, the term "mutant microorganism" includes a recombinant microorganism that has been genetically engineered to express a mutated gene or protein that is normally or naturally expressed by the microorganism. Preferably, a mutant microorganism expresses a mutated gene or protein such that the microorganism exhibits an altered, modified or different phenotype (e.g., has been engineered to express a mutated CoaA biosynthetic enzyme, for example, pantothenate kinase). In one embodiment, a mutant microorganism is designed or engineered such that it includes a mutant coaX gene, as defined herein. In another embodiment, a recombinant microorganism is designed or engineered such that it includes a mutant coaA gene, as defined herein. In another embodiment, a mutant microorganism is designed or engineered such that a coaX gene has been deleted (i.e., the protein encoded by the coaX gene is not produced). In another embodiment, a mutant microorganism is designed or engineered such that a coaA gene has been deleted (i.e., the protein encoded by the coaA gene is not produced). Preferably, a mutant microorganism has a mutant coaX gene or a mutant coaA gene, or has been engineered to have a coaX gene and/or coaA deleted, such that that the mutant microorganism encodes a "reduced pantothenate kinase activity". In the context of a whole microorganism, a "reduced pantothenate kinase activity" can be determined by measuring or assaying for a decrease in an intermediate or product of the CoA biosynthetic pathway, for example, measuring or assaying for 4'-phosphopantothenate, 4'-phosphopantothenylcysteine, 4'-phosphopantetheine, dephosphocoenzyme A, Coenzyme A, apo-acyl carrier protein (apo-ACP) or holo-acyl carrier protein (ACP) in the microorganism (e.g., in a lysate isolated or derived from the microorganism) or in the medium in which the microorganism is cultured (see e.g., FIG. 16). Alternatively, a "reduced pantothenate kinase activity" can be determined by measuring or assaying for decreased growth of the microorganism. Alternatively, a "reduced pantothenate kinase activity" can be determined by measuring or assaying for an increase in a panto-compound (e.g., pantothenate) in the microorganism or surrounding media, as panto-compounds lie upstream of the CoA biosynthetic pathway, the first step of which is catalyzed by pantothenate kinase. The invention also features recombinant microorganisms that, in addition to having reduced pantothenate kinase activity (e.g., expressing mutant coaA and/or mutant coaX genes) have a deregulated pantothenate biosynthesis pathway and/or a deregulated isoleucine-valine (ilv) biosynthetic pathway.

In one embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism is a microorganism belonging to a genus selected from the group consisting of *Bacillus, Cornyebacterium, Lactobacillus, Lactococci* and *Streptomyces*. In a more preferred embodiment, the recombinant microorganism is of the genus *Bacillus*. In another preferred embodiment, the recombinant microorganism is selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulars, Bacillus coagulans, Bacillus licheniformis, Bacillus megaterium, Bacillus pumilus, Bacillus thuringiensis*, and other Group 1 *Bacillus* species, for example, as characterized by 16S rRNA type (Priest (1993) in *Bacillus subtilis and Other Gram-Positive Bacteria* eds. Sonenshein et al., ASM, Washington, D.C., p. 6). In another preferred embodiment, the recombinant microorganism is *Bacillus brevis* or *Bacillus stearothermophilus*. In another preferred embodiment, the recombinant microorganism is selected from the group consisting of *Bacillus licheniformis, Bacillus amyloliquefaciens, Bacillus halodurans, Bacillus subtilis*, and *Bacillus pumilus*.

In another embodiment, the recombinant microorganism is a Gram negative (excludes basic dye) organism. In a preferred embodiment, the recombinant microorganism is a microorganism belonging to a genus selected from the group consisting of *Salmonella, Escherichia, Klebsiella, Serratia*, and *Proteus*. In a more preferred embodiment, the recombinant microorganism is of the genus *Escherichia*. In an even more preferred embodiment, the recombinant microorganism is *Escherichia coli*. In another embodiment, the recombinant microorganism is *Saccharomyces* (e.g., *S. cerevisiae*).

An important aspect of the present invention involves culturing the recombinant microorganisms described herein, such that a desired compound (e.g., a desired panto-compound) is produced. The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism (e.g., carbon sources or carbon substrate, for example complex carbohydrates such as bean or grain meal, starches, sugars, sugar alcohols, hydrocarbons, oils, fats, fatty acids, organic acids and alcohols; nitrogen sources, for example, vegetable proteins, peptones, peptides and amino acids derived from grains, beans and tubers, proteins, peptides and amino acids derived form animal sources such as meat, milk and animal byproducts such as peptones, meat extracts and casein hydrolysates; inorganic nitrogen sources such as urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., a panto-compound). In one embodiment, microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., panto-compound). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, microorganisms of the present invention can be cultured under controlled temperatures. The term "controlled temperature" includes any temperature which results in production of the desired product (e.g., a panto-compound). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., panto-compound). A variety of such processes have been developed and are well-known in the art.

The phrase "culturing under conditions such that a desired compound (e.g., a panto-compound, for example, pantothenate) is produced" includes maintaining and/or growing microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a panto-compound (e.g., pantothenate, pantoate or β-alanine). Preferably, culturing is continued for a time sufficient to substantially reach maximal production of the panto-compound. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach production yields of panto-compound, for example, cells are cultured such that at least about 15 to 20 g/L of panto-compound are produced, at least about 20 to 25 g/L panto-compound are produced, at least about 25 to 30 g/L panto-compound are produced, at least about 30 to 35 g/L panto-compound are produced, at least about 35 to 40 g/L panto-compound are produced (e.g., at least about 37 g/L panto-compound) or at least about 40 to 50 g/L panto compound are produced. In yet another embodiment, microorganisms are cultured under conditions such that a preferred yield of panto-compound, for example, a yield within a range set forth above, is produced in about 24 hours, in about 36 hours, in about 48 hours, in about 72 hours, or in about 96 hours.

The methodology of the present invention can further include a step of recovering a desired compound (e.g., a panto-compound). The term "recovering" a desired compound (e.g., a panto-compound) includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound (e.g., a panto-compound) can be recovered from culture media by first removing the microorganisms from the culture. Media is then passed through or over a cation exchange resin to remove unwanted cations and then through or over an anion exchange resin to remove unwanted inorganic anions and organic acids having stronger acidities than the panto-compound of interest (e.g., pantothenate). The resulting panto-compound (e.g., pantothenate) can subsequently be converted to a pantothenate salt (e.g., calcium pantothenate) as described herein.

Preferably, a desired compound of the present invention is "extracted", "isolated" or "purified" such that the resulting preparation is substantially free of other components (e.g., free of media components and/or fermentation byproducts). The language "substantially free of other components" includes preparations of desired compound in which the compound is separated (e.g., purified or partially purified) from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound is a panto-compound that has been derivatized to a salt (e.g. a pantothenate salt or pantoate salt), the panto-compound is preferably further free (e.g., substantially free) of chemical contaminants associated with the formation of the salt. When the desired compound is a panto-compound that has been derivatized to an alcohol, the panto-compound is preferably further free (e.g., substantially free) of chemical contaminants associated with the formation of the alcohol.

In an alternative embodiment, the desired panto-compound is not purified from the microorganism, for example, when the microorganism is biologically non-hazardous (e.g., safe). For example, the entire culture (or culture supernatant) can be used as a source of product (e.g., crude product). In one embodiment, the culture (or culture supernatant) supernatant is used without modification. In another embodiment, the culture (or culture supernatant) is concentrated. In yet another embodiment, the culture (or culture supernatant) is dried or lyophilized.

II. Panto-Compound Production Methodologies Featuring Ketopantoate Reductase-Overexpressing Microorganisms One aspect of the invention features methods of producing a panto-compounds that involve culturing a ketopantoate reductase-overexpressing (KPAR-O) microorganism under conditions such that the panto-compound is produced. The term "ketopantoate reductase-overexpressing (KPAR-O) microorganism" includes a microorganism which has been manipulated such that ketopantoate reductase is overexpressed (e.g., a *B. subtilis* ketopantoate reductase protein having the amino acid sequence of SEQ ID NO:30) and/or has been transformed with a vector comprising a panE1 nucleic acid sequence (e.g., a *B. subtilis* panE1 nucleic acid sequence as set forth in SEQ ID NO:29). In one embodiment, the panto-compound is pantothenate. In another embodiment, the panto-compound is pantoate. In another embodiment, the ketopantoate reductase is bacterial-derived. In another embodiemnt, the ketopantoate reductase is derived from *Bacillus* (e.g., is derived from *Bacillus subtilis*). In yet another embodiment, the KPAR-O microorganism is Gram positive. In yet another embodiment, the KPAR-O microorganism is a microorganism belonging to a genus selected from the group consisting of *Bacillus, Cornyebacterium, Lactobacillus, Lactococci* and *Streptomyces*. In a preferred embodiemnt, the KPAR-O microorganism is of the genus *Bacillus*. In a more preferred embodiment, the KPAR-O microorganism is selected from the group consisting of *Bacillus licheniformis, Bacillus amyloliquefaciens, Bacillus halodurans, Bacillus subtilis* and *Bacillus pumilus*. In a particularly preferred embodiement, the KPAR-O microorganism is *Bacillus subtilis*.

In still other embodiments, the KPAR-O microorganism further overexpresses at least one pantothenate biosynthetic enzyme in addition to ketopantoate reductase. In an exemplary embodiment, the KPAR-O microorganism further overexpresses at least one of ketopantoate hydroxymethyltransferase, pantothenate synthetase and aspartate-α-decarboxylase. Also featured are methods of producing panto-compounds, for example, methods that involve culturing a K PAR-O microorganism, which further include the step of recovering the panto-compound.

III. Methods of Producing Panto-Compounds Independent of Precursor Feed Requirements Depending on the biosynthetic enzyme or combination of biosynthetic enzymes manipulated, it may be desirable or necessary to provide (e.g., feed) microorganisms of the present invention at least one pantothenate biosynthetic precursor such that pantothenate or other desired panto-compounds are produced. The term "pantothenate biosynthetic precursor" or "precursor" includes an agent or compound which, when provided to, brought into contact with, or included in the culture medium of a microorganism, serves to enhance or increase pantothenate biosynthesis. In one embodiment, the pantothenate biosynthetic precursor or precursor is aspartate. In another embodiment, the pantothenate biosynthetic precursor or precursor is β-alanine. The amount of aspartate or β-alanine added is preferably an amount that results in a concentration in the culture medium sufficient to enhance productivity of the microorganism (e.g., a concentration sufficient to enhance production of a panto-compound, for example, β-alanine, ketopantoate, pantoate or pantothenate). Pantothenate biosynthetic precursors of the present invention can be added in the form of a concentrated solution or suspension (e.g., in a suitable solvent such as water or buffer) or in the form of a solid (e.g., in the form of a powder). Moreover, pantothenate biosynthetic precursors of the present invention can be added as a single aliquot, continuously or intermittently over a given period of time.

In yet another embodiment, the pantothenate biosynthetic precursor is valine, see e.g., Example III. In yet another embodiment, the pantothenate biosynthetic precursor is α-ketoisovalerate. Preferably, valine or α-ketoisovalerate is added in an amount that results in a concentration in the medium sufficient for production of the desired product (e.g., panto-compound) to occur. Pantothenate biosynthetic precursors are also referred to herein as "supplemental pantothenate biosynthetic substrates".

Providing pantothenate biosynthetic precursors in the pantothenate biosynthetic methodologies of the present invention, can be associated with high costs, for example, when the methodologies are used to produce high yields of panto-compounds. Accordingly, preferred methodologies of the present invention feature microorganisms having at least one biosynthetic enzyme or combination of biosynthetic enzymes (e.g., at least one pantothenate biosynthetic enzyme and/or valine-isoleucine biosynthetic enzyme) manipulated such that pantothenate or other desired panto-compounds are produced in a manner independent of precursor feed. The phrase "a manner independent of precursor feed", for example, when referring to a method for producing a desired compound (e.g., a panto-compound), includes an approach to or a mode of producing the desired compound that does not depend or rely on precursors being provided. (e.g., fed) to the microorganism being utilized to produce the desired compound. For example, microorganisms featured in the methodologies of the present invention can be used to produce panto-compounds in a manner requiring no feeding of the precursors aspartate, β-alanine, valine and/or α-KIV.

Alternative preferred methodologies of the present invention feature microorganisms having at least one biosynthetic enzyme or combination of biosynthetic enzymes manipulated such that pantothenate or other desired panto-compounds are produced in a manner substantially independent of precursor feed. The phrase "a manner substantially independent of precursor feed" includes an approach to or a method of producing the desired compound that depends or relies to a lesser extent on precursors being provided (e.g., fed) to the microorganism being utilized. For example, microorganisms featured in the methodologies of the present invention can be used to produce panto-compounds in a manner requiring feeding of substantially reduced amounts of the precursors aspartate, β-alanine, valine and/or α-KIV. In one embodiment, the invention features methods of producing panto-compounds (e.g., pantothenate) in a manner that requires feeding of less than 5%-10% of the amount of precursor required by a control microorganism (e.g., a microorganism that is dependent, for example is wholly dependent, on precursor feed to efficiently produce the desired compound). In another embodiment, the invention features methods of producing panto-compounds in a manner that requires feeding of less than 15-20% of the amount of precursor required by a control microorganism. In another embodiment, the invention features methods of producing panto-compounds in a manner that requires feeding of less than 25-30%, 35-40%, 45-50% or 55-60% of the amount of precursor required by a control microorganism. As described in Examples I-III herein, particular microorganisms featured in the methodologies of the present invention require, for example, 5 g/L of aspartate, β-alanine, valine or α-KIV (e.g., in test tube or in shake flask cultures). Accordingly, in a preferred embodiment, the present invention features methods of producing panto-compounds (e.g., pantothenate) in a manner requiring feeding of less than 0.25 g/L, 0.5 g/L, 0.75 g/L, l g/L, 1.25 g/L, 1.5 g/L, 1.75 g/L, 2 g/L, 2.25 g/L, 2.5 g/L, 2.75 g/L or 3 g/L.

Preferred methods of producing desired compounds (e.g., panto-compounds) in a manner independent of precursor feed or alternatively, in a manner substantially independent of precursor feed, involve culturing microorganisms which have been manipulated (e.g., designed or engineered, for example, genetically engineered) such that expression of at least one pantothenate biosynthetic enzyme, and/or at least one isoleucine-valine biosynthetic enzyme, is modified. For example, in one embodiment, a microorganism is manipulated (e.g., designed or engineered) such that the production of at least one pantothenate biosynthetic enzyme, and/or at least one isoleucine/valine biosynthetic enzyme is deregulated. In a preferred embodiment, a microorganism is manipulated (e.g., designed or engineered) such that it has a deregulated biosynthetic pathway, for example, a deregulated pantothenate biosynthesis pathway and/or a deregulated isoleucine-valine biosynthetic pathway, as defined herein. In another preferred embodiment, a microorganism is manipulated (e.g., designed or engineered) such that at least one pantothenate biosynthetic enzyme, and/or at least one isoleucine-valine biosynthetic enzyme is overexpressed.

Preferred methods of producing desired compounds (e.g., panto-compounds) in a manner independent of precursor feed or alternatively, in a manner substantially independent of precursor feed, are as follows. In one embodiment, the invention features a method of producing pantothenate in a manner independent of precursor feed comprising culturing an aspartate-α-decarboxylase-overexpressing (AαD-O) microorganism having a deregulated isoleucine-valine (ilv) pathway under conditions such that pantothenate is produced. In another embodiment, the invention features a method of producing pantothenate in a manner independent of precursor feed comprising culturing an aspartate-α-decarboxylase-overexpressing (AαD-O) microorganism having a deregulated pantothenate (pan) pathway and a deregulated isoleucine-valine (ilv) pathway, under conditions such that pantothenate is produced. In another embodiment, the invention features a method of producing pantothenate in a manner independent of aspartate or β-alanine feed comprising culturing an aspartate-α-decarboxylase-overexpressing (AαD-O) microorganism under conditions such that pantothenate is produced. In yet another embodiment, the invention features a method of producing pantothenate in a manner independent of valine or α-ketoisovalerate feed comprising culturing a microorganism having a deregulated isoleucine-valine (ilv) biosynthetic pathway under conditions such that pantothenate is produced.

The term "aspartate-α-decarboxylase-overexpressing (AαD-O) microorganism" includes a microorganism which has been manipulated such that aspartate-α-decarboxylase is overexpressed. A preferred "aspartate-α-decarboxylase-overexpressing (AαD-O) microorganism" has been transformed with a vector comprising a B. subtilis panD nucleic acid sequence (e.g., a panD nucleic acid sequence that encodes an aspartate-α-decarboxylase protein having the amino acid sequence of SEQ ID NO:28, for example, a panD nucleic acid sequence as set forth in SEQ ID NO:27).

The phrase "microorganism having a deregulated isoleucine-valine (ilv) pathway" includes a microorganism having an alteration or modification in at least one gene encoding an enzyme of the isoleucine-valine (ilv) pathway or having an alteration or modification in an operon including more than one gene encoding an enzyme of the isoleucine-valine (ilv) pathway. A preferred "microorganism having a deregulated isoleucine-valine (ilv) pathway" overexpresses acetohydroxyacid synthetase (e.g., acetohydroxyacid synthetase having subunits having the amino acid sequences of SEQ ID NO:32 and SEQ ID NO:34 or acetohydroxyacid synthetase having the amino acid sequence of SEQ ID NO:87), acetohydroxyacid isomeroreductase (having the amino acid sequence of SEQ ID NO:36), or dihydroxyacid dehydratase (having the amino acid sequence of SEQ ID NO:38) and/or has been transformed with a vector comprising ilvB, ilvN, ilvC, ilvBN, ilvBNC or alsS nucleic acid sequences (SEQ ID NO:31, SEQ ID NO:33, SEQ ID NO:35, nucleotides 1-2246 of SEQ ID NO:58, SEQ ID NO:58 having coding regions from nucleotides 1-1725, 1722-2246 and 2263-3291, or SEQ ID NO:86, respectively) and/or an ilvD nucleic acid sequence (SEQ ID NO:37).

IV High Yield Production Methodologies

A particularly preferred embodiment of the present invention is a high yield production method for producing pantothenate comprising culturing a manipulated microorganism under conditions such that pantothenate is produced at a significantly high yield. The phrase "high yield production method", for example, a high yield production method for producing a desired compound (e.g., for producing a panto-compound) includes a method that results in production of the desired compound at a level which is elevated or above what is usual for comparable production methods. Preferably, a high yield production method results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a high yield production method of producing pantothenate that includes culturing a manipulated microorganism under conditions such that pantothenate is produced at a level greater than 2 g/L. In another embodiment, the invention features a high yield production method of producing pantothenate that includes culturing a manipulated microorganism under conditions such that pantothenate is produced at a level greater than 10 g/L. In another embodiment, the invention features a high yield production method of producing pantothenate that includes culturing a manipulated microorganism under conditions such that pantothenate is produced at a level greater than 20 g/L. In yet another embodiment, the invention features a high yield production method of producing pantothenate that includes culturing a manipulated microorganism under conditions such that pantothenate is produced at a level greater than 30 g/L. In yet another embodiment, the invention features a high yield production method of producing pantothenate that includes culturing a manipulated microorganism under conditions such that pantothenate is produced at a level greater than 40 g/L.

The invention further features a high yield production method for producing a desired compound (e.g., for producing a panto-compound) that involves culturing a manipulated microorganism under conditions such that a sufficiently elevated level of compound is produced within a commercially desireable period of time. In an exemplary embodiment, the invention features a high yield production method of producing pantothenate that includes culturing a manipulated microorganism under conditions such that pantothenate is produced at a level greater than 15-20 g/L in 36 hours. In another-embodiment, the invention features a high yield production method of producing pantothenate that includes culturing a manipulated microorganism under conditions such that pantothenate is produced at a level greater than 25-30 g/L in 48 hours. In another embodiment, the invention features a high yield production method of producing pantothenate that includes culturing a manipulated microorganism under conditions such that pantothenate is produced at a level greater than 35-40 g/L in 72 hours, for example, greater that 37 g/L in 72 hours. In another embodiment, the invention features a high yield production method of producing pantothenate that includes culturing a manipulated microorganism under conditions such that pantothenate is produced at a level greater than 30-40 g/L in 60 hours, for example, greater that 30, 35 or 40 g/L in 60 hours. Values and ranges included and/or intermediate within the ranges set forth herein are also intended to be within the scope of the present invention. For example, pantothenate production at levels of at least 31, 32, 33, 34, 35, 36, 37, 38 and 39 g/L in 60 hours are intended to be included within the range of 30-40 g/L in 60 hours. In another example, ranges of 30-35 g/L or 35-40 g/L are intended to be included within the range of 30-40 g/L in 60 hours. Moreover, the skilled artisan will appreciate that culturing a manipulated microorganism to achieve a production level of, for example, "30-40 g/L in 60 hours" includes culturing the microorganism for additional time periods (e.g., time periods longer than 60 hours), optionally resulting in even higher yields of pantothenate being produced.

V. Panto-Compound Production Methodologies Featuring Pantothenate Kinase Mutant Microorganisms The present invention relates to methods of producing pantothenate using microorganisms engineered to produce high yields of pantothenate as well as other panto-compounds. Cells overproducing pantothenate result in high intracellular pantothenate levels that could overcome the feedback inhibition of pantothenate kinase by CoA, leading to overproduction of CoA. Besides consuming pantothenate, increased synthesis of CoA may cause increased feedback inhibition of the PanB, PanD, PanE or PanC reaction, thereby limiting pantothenate production. Accordingly, a reduction in pantothenate kinase activity may lead to a decrease in CoA levels with resulting increases in PanB, PanD, PanE or PanC activity and pantothenate production.

Thus, certain methodologies of the present invention are based, at least in part, on the identification and characterization of the *B. subtilis* coaA gene and the demonstration that the gene is neither essential for *B. subtilis* growth (i.e., deletion of the coaA gene from the chromosome of *B. subtilis* is not a lethal event) nor for pantothenate kinase activity in *B. subtilis*. A second pantothenate kinase-encoding gene has been identified and characterized in *B. subtilis*, and is termed "coaX". This gene complements an *E. coli* mutant that contains a temperature sensitive pantothenate kinase and is not related by homology to any previously known pantothenate kinase gene.

In one aspect, the methodologies of the invention feature recombinant microorganisms that include the coaX gene or that include a mutant coaX gene, having reduced pantothenate kinase activity. In one embodiment, the methodologies feature such recombinant microorganisms further having a deregulated pantothenate biosynthetic pathway. In another embodiment, the methodologies feature such recombinant microorganisms further having a deregulated isoleucine-valine (ilv) pathway. In a preferred embodiment, the microorganisms belong to the genus *Bacillus* (e.g., *B. subtilis*).

The methodologies of the invention also feature recombinant microorganisms (e.g., microorganisms belong to the genus *Bacillus*, for example, *B. subtilis*) that include the coaA gene or that include a mutant coaA gene, optionally including a coaX gene or mutant thereof, having reduced pantothenate kinase activity. In one embodiment, the methodologies feature such recombinant microorganisms further having a deregulated pantothenate biosynthetic pathway or having a deregulated isoleucine-valine (ilv) pathway. Also featured are vectors that include isolated coaX or coaA genes as well as mutant coaX and/or coaA genes. Isolated nucleic acid molecules that include isolated coaX genes or mutant coaX genes are features in addition to isolated CoaX proteins and mutant CoaX proteins.

The above-described nucleic acid molecules (e.g., genes), proteins, vectors, and recombinant microorganisms (e.g., mutant microorganisms), are particularly suited for use in methods of producing panto-compounds and/or methods of enhancing panto-compound production. In one embodiment, the invention features a method for producing a panto-compound (e.g., pantothenate) that includes culturing a pantothenate kinase mutant (e.g., a recombinant microorganism that misexpresses, e.g., is mutated for, pantothenate kinase, as defined herein) under conditions such that panto-compound is produced. In another embodiment, the invention features a method for enhancing production of a panto-compound (e.g., pantothenate) that includes culturing a pantothenate kinase mutant (e.g., a recombinant microorganism that misexpresses, e.g., is mutated for, pantothenate kinase, as defined herein) under conditions such that production of the panto-compound is produced. As used herein, the term "enhancing" (for example, in the context of the phrase "enhancing production") includes increasing the level or rate of production of panto-compound (e.g., pantothenate) as compared to the level or rate of production in a non-mutant microorganism (e.g., a microorganism having a normal pantothenate kinase gene(s) and/or having normal pantothenate production rates and/or levels.

Preferably, the level of panto-compound produced in methodologies featuring the pantothenate kinase mutants of the present invention is increased by at least 5% as compared to the level produced by a non-mutant (e.g., a recombinant microorganism expressing non-mutated pantothenate kinase). Even more preferably, the level of panto-compound is increased 10% as compared to methodologies featuring non-mutants. Even more preferably, panto-compound levels (e.g. pantothenate levels) are increased 20%, 30%, 40%, 50%, 60%, 70%, 80%, 90%, are increased 2-fold, 5-fold, 10-fold, 50-fold, 100-fold or more as compared to methodologies featuring non-mutants.

VI. Additional Mutations Resulting in Enhanced Panto-Compound Production

The methodologies of the present invention further can include, for example in addition to overexpressing or deregulating a pantotllenate biosynthetic enzyme and/or an isoleucine-valine biosynthetic enzyme, or in addition to mutating a pantothenate-kinase encoding gene, deleting or mutating an enzyme that catalyzes the conversion of key pantothenate biosynthesis substrates or precursors to unwanted or undesirable products. For example, mutating the ilvE gene (Kuramitsu et al. (1985) *J. Biochem.* 97:993-999) or a homologue thereof (SEQ ID NO:62 or SEQ ID NO:64), thereby limiting the conversion of α-ketoisovalerate to valine, in addition to mutating a pantothenate kinase encoding enzyme, is predicted to result in even further enhanced or increased production of panto-compound. Alternatively, mutating the ansB gene (Sun and Seflow (1991) *J. Bacteriol* 173:3831-3845) or a homologue thereof (SEQ ID NO:66), thereby limiting the degradation of aspartate, in addition to mutating a pantothenate kinase encoding enzyme, is predicted to result in even further enhanced or increased production of panto-compound. Alternatively, mutating the alsD gene (Renna et al. (1993) *J. Bacteriol.* 175:3863-3875) or a homologue thereof (SEQ ID NO:68), thereby limiting the conversion of acetolactate to acetoin, in addition to mutating a pantothenate kinase encoding enzyme, is predicted to result in even further enhanced or increased production of panto-compound. Alternatively, mutating the avtA gene encoding alanine-valine transaminase or a homologue thereof, thereby limiting the conversion of α-ketoisovalerate to valine, in addition to mutating a pantothenate kinase encoding enzyme, is predicted to result in even further enhanced or increased production of panto-compound. Mutating the avtA gene can include mutating, for example, an avtA gene having the nucleotide sequence of SEQ ID NO:70 (e.g., the *E. coli* avtA gene), or a structural homolog thereof (e.g., a homologue encoding a protein having 30-40%, 40-50%, 50-60%, 60-70%, 70-80%, 80-90%, 90-95% or more identity with the amino acid sequence of SEQ ID NO:71) or a fumctional homologue (e.g., a gene encoding a structurally unrelated protein having alanine-valine transmainase activity. Such mutations can be accomplished using the methodologies as exemplified in the Examples (e.g., Examples XIII, XV, XVI and XVII).

Accordingly, in one embodiment, the invention features a method of producing a panto-compound which includes culturing a microorganism having a mutant pantothenate kinase-encoding gene and which further has a deletion or mutation in an avtA, ilvE, ansB, and/or alsD gene, or homologie thereof. In another embodiment, the invention features a method of producing a panto-compound which includes culturing a microorganism having a mutant pantothenate-kinase encoding gene and a deregulated pantothenate biosynthetic pathway enzyme and which further has a deletion or mutation in an avtA, ilvE, ansB, and/or alsD gene, or homologue thereof. In another embodiment, the invention features a method of producing a panto-compound which includes culturing a microorganism having a mutant pantothenate-kinase encoding gene and a deregulated isoleucine-valine biosynthetic pathway enzyme and which further has a deletion or mutation in an avtA, ilvE, ansB, and/or alsD gene, or homologue thereof.

Mutating the alsD gene can be particularly useful when accomplished in conjunction with overexpression or deregulation of the alsS gene, for example, to prevent carbon (e.g., acetolactate) from being drawn away from the precursor pool utilized for α-KIV production. Accordingly, to maximize the contribution of the als locus to panto-compound production, it is desirable to disrupt the alsD gene in addition to overexpressing the alsS gene. To disrupt the alsD gene, appropriate fragments of the als operon, flanking the alsD gene, are amplified by PCR and cloned to provide homology for creating the disruptions. A drug resistance gene, such as the cat gene, is cloned between the flanking DNA fragments in place of the alsD gene, and the linearized DNA is transformed into a pantothenate production strain such as PA824, selecting for drug-resistance. To overexpress alsS, the alsS coding sequence (e.g., an alsS coding sequence that has been engineered by PCR for expression) is cloned into an expression vector. Vectors which express alsS (or alternatively, vectors which express alsS plus ilvC) are the introduced into panto-compound production strains (e.g., the pantothenate producing strain PA824).

The methodologies of the present invention further can include, for example in addition to overexpressing or deregulating a pantothenate biosynthetic enzyme and/or an isoleucine-valine biosynthetic enzyme, or in addition to mutating a pantothenate-kinase encoding gene, deleting or mutating an enzyme that catalyzes the conversion of desired panto-compounds to unwanted or undesireable downstream products.

VII. Isolated Nucleic Acid Molecules and Genes

Another aspect of the present invention features isolated nucleic acid molecules that encode *Bacillus* proteins (e.g., *B. subtilis* proteins), for example, *Bacillus* pantothenate biosynthetic enzymes (e.g., *B. subtilis* pantothenate biosynthetic enzymes) or *Bacillus* valine-isoleucine biosynthetic enzymes (e.g., *B. subtilis* valine-isoleucine biosynthetic enzymes). Also featured are isolated coaX and/or coaA nucleic acid molecules (e.g., isolated coaX and/or coaA genes) as well as isolated nucleic acid molecules that include such coaX and/or coaA nucleic acid molecules or genes.

The term "nucleic acid molecule" includes DNA molecules (e.g., linear, circular, cDNA or chromosomal DNA) and RNA molecules (e.g., tRNA, rRNA, mRNA) and analogs of the DNA or RNA generated using nucleotide analogs. The nucleic acid molecule can be single-stranded or double-stranded, but preferably is double-stranded DNA. The term "isolated" nucleic acid molecule includes a nucleic acid molecule which is free of sequences which naturally flank the nucleic acid molecule (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an "isolated" nucleic acid molecule, such as a cDNA molecule, can be substantially free of other cellular materials when produced by recombinant techniques, or substantially free of chemical precursors or other chemicals when chemically synthesized.

The term "gene", as used herein, includes a nucleic acid molecule (e.g., a DNA molecule or segment thereof), for example, a protein or RNA-encoding nucleic acid molecule, that in an organism, is separated from another gene or other genes, by intergenic DNA (i.e., intervening or spacer DNA which naturally flanks the gene and/or separates genes in the chromosomal DNA of the organism). A gene may direct synthesis of an enzyme or other protein molecule (e.g., may comprise coding sequences, for example, a contiguous open reading frame (ORF) which encodes a protein) or may itself be functional in the organism. A gene in an organism, may be clustered in an operon, as defined herein, said operon being separated from other genes and/or operons by the intergenic DNA. Individual genes contained within an operon may overlap without intergenic DNA between said individual genes. An "isolated gene", as used herein, includes a gene which is essentially free of sequences which naturally flank the gene in the chromosomal DNA of the organism from which the gene is derived (i.e., is free of adjacent coding sequences which encode a second or distinct protein or RNA molecule, adjacent structural sequences or the like) and optionally includes 5' and 3' regulatory sequences, for example promoter sequences and/or terminator sequences. In one embodiment, an isolated gene includes predominantly coding sequences for a protein (e.g., sequences which encode *Bacillus* proteins). In another embodiment, an isolated gene includes coding sequences for a protein (e.g., for a *Bacillus* protein) and adjacent 5' and/or 3' regulatory sequences from the chromosomal DNA of the organism from which the gene is derived (e.g., adjacent 5' and/or 3' *Bacillus* regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

In one aspect, the present invention features isolated panB nucleic acid sequences or genes, isolated panC nucleic acid sequences or genes, isolated panD nucleic acid sequences or genes, isolated panE nucleic acid sequences or genes, isolated ilvB, ilvN, ilvBN nucleic acid sequences or genes, isolated alsS nucleic acid sequences or genes, isolated ilvC nucleic acid sequences or genes and/or isolated ilvD nucleic acid sequences or genes.

In a preferred embodiment, the nucleic acid or gene is derived from *Bacillus* (e.g., is *Bacillus*-derived). The term "derived from *Bacillus*" or "*Bacillus*-derived" includes a nucleic acid or gene which is naturally found in microorganisms of the genus *Bacillus*. Preferably, the nucleic acid or gene is derived from a microorganism selected from the group consisting of *Bacillus subtilis*, *Bacillus lentimorbus*, *Bacillus lentus*, *Bacillus firmus*, *Bacillus pantothenticus*, *Bacillus amyloliquefaciens*, *Bacillus cereus*, *Bacillus circulans*, *Bacillus coagulans*, *Bacillus licheniformis*, *Bacillus megaterium*, *Bacillus pumilus*, *Bacillus thuringiensis*, and other Group 1 *Bacillus* species, for example, as characterized by 16S rRNA type (Priest, supra). In another preferred embodiment, the nucleic acid or gene is derived from *Bacillus brevis* or *Bacillus stearothermophilus*. In another preferred embodiment, the nucleic acid molecules and/or genes of the present invention are derived from a microorganism selected from the group consisting of *Bacillus licheniformis*, *Bacillus amyloliquefaciens*, *Bacillus halodurans*, *Bacillus subtilis*, and *Bacillus pumilus*. In a particularly preferred embodiment, the nucleic acid or gene is derived from *Bacillus subtilis* (e.g., is *Bacillus subtilis*-derived). The term "derived from *Bacillus subtilis*" or "*Bacillus subtilis*-derived" includes a nucleic acid or gene which is naturally found in *Bacillus subtilis*. In yet another preferred embodiment, the nucleic acid or gene is a *Bacillus* gene homologue (e.g., is derived from a species distinct from *Bacillus* but having significant homology to a *Bacillus* gene of the present invention, for example, a *Bacillus* pan gene or *Bacillus* ilv gene).

Included within the scope of the present invention are bacterial-derived nucleic acid molecules or genes and/or *Bacillus*-derived nucleic acid molecules or genes (e.g., *B. subtilis*-derived nucleic acid molecules or genes), for example, the genes identified by the present inventors, for example, *Bacillus* or *B. subtilis* coaX genes, coaA genes, pan genes and/or ilv genes. Further included within the scope of the present invention are bacterial-derived nucleic acid molecules or genes and/or *Bacillus*-derived nucleic acid molecules or genes (e.g., *B. subtilis*-derived nucleic acid molecules or genes) (e.g., *B. subtilis* nucleic acid molecules or genes) which differ from naturally-occurring bacterial and/or *Bacillus* nucleic acid molecules or genes (e.g., *B. subtilis* nucleic acid molecules or genes), for example, nucleic acid molecules or genes which have nucleic acids that are substituted, inserted or deleted, but which encode proteins substantially similar to the naturally-occurring gene products of the present invention. In one embodiment, an isolated nucleic acid molecule comprises at least one of the nucleotide sequences set forth as SEQ ID NO:23, SEQ ID NO:25, SEQ ID NO:27, SEQ ID NO:29, SEQ ID NO 31, SEQ ID NO:33, SEQ ID NO:86, SEQ ID NO:35 or SEQ ID NO:37. In another preferred embodiment, an isolated nucleic acid molecule comprises at least two, three or four of the nucleotide sequences set forth as SEQ ID NO:23, SEQ ID NO:25, SEQ ID NO:27, SEQ ID NO:29, SEQ ID NO 31, SEQ ID NO:33, SEQ ID NO:88, SEQ ID NO:35 or SEQ ID NO:37. For example, a preferred isolated nucleic acid molecule of the present invention can include the nucleotide sequences of SEQ ID NO:23, SEQ ID NO:25 and SEQ ID NO:27, preferably linked such that the proteins encoded by the nucleotide sequences of SEQ ID NO:23, SEQ ID NO:25 and SEQ ID NO:27 are each produced when the isolated nucleic acid molecule is expressed in a microorganism (e.g., SEQ ID NO:59). In another example, a preferred isolated nucleic acid molecule of the present invention can include the nucleotide sequences of SEQ ID NO:31 and SEQ ID NO:33, preferably linked such that the proteins encoded by the nucleotide sequences of SEQ ID NO:31 and SEQ ID NO:33 are each produced when the isolated nucleic acid molecule is expressed in a microorganism (e.g., nucleotides 1-2246 of SEQ ID NO:58). In another example, a preferred isolated nucleic acid molecule of the present invention can include the nucleotide sequence of SEQ ID NO:86. In another example, a preferred isolated nucleic acid molecule of the present invention can include the nucleotide sequences of SEQ ID NO:31, SEQ ID NO:33 and SEQ ID NO:35, preferably linked such that the proteins encoded by the nucleotide sequences of SEQ ID NO:31, SEQ ID NO:33 and SEQ ID NO:35 are each produced when the isolated nucleic acid molecule is expressed in a microorganism (e.g., SEQ ID NO:58).

In another embodiment, an isolated nucleic acid molecule of the present invention comprises a nucleotide sequence which is at least about 60-65%, preferably at least about 70-75%, more preferable at least about 80-85%, and even more preferably at least about 90-95% or more identical to a nucleotide sequence set forth as SEQ ID NO:23, SEQ ID NO:25, SEQ ID NO:27, SEQ ID NO:29, SEQ ID NO 31, SEQ ID NO:33, SEQ ID NO:88, SEQ ID NO:35 or SEQ ID NO:37. In another embodiment, an isolated nucleic acid molecule hybridizes under stringent conditions to a nucleic acid molecule having a nucleotide sequence set forth as SEQ ID NO:23, SEQ ID NO:25, SEQ ID NO:27, SEQ ID NO:29, SEQ ID NO 31, SEQ ID NO:33, SEQ ID NO:88, SEQ ID NO:35 or SEQ ID NO:37. Such stringent conditions are known to those skilled in the art and can be found in *Current Protocols in Molecular Biology*, John Wiley & Sons, N.Y. (1989), 6.3.1-6.3.6. A preferred, non-limiting example of stringent (e.g. high stringency) hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:23, SEQ ID NO:25, SEQ ID NO:27, SEQ ID NO:29, SEQ ID NO 31, SEQ ID NO:33, SEQ ID NO:88, SEQ ID NO:35 or SEQ ID NO:37 corresponds to a naturally-occurring nucleic acid molecule. As used herein, a "naturally-occurring" nucleic acid molecule refers to an RNA or DNA molecule having a nucleotide sequence that occurs in nature.

A nucleic acid molecule of the present invention (e.g., a nucleic acid molecule having the nucleotide sequence of SEQ ID NO:23, SEQ ID NO:25, SEQ ID NO:27, SEQ ID NO:29, SEQ ID NO 31, SEQ ID NO:33, SEQ ID NO:88, SEQ ID NO:35 or SEQ ID NO:37 can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual 2nd, ed.*, Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the sequence of SEQ ID NO:23, SEQ ID NO:25, SEQ ID NO:27, SEQ ID NO:29, SEQ ID NO 31, SEQ ID NO:33, SEQ ID NO:88, SEQ ID NO:35 or SEQ ID NO:37. A nucleic acid of the invention can be amplified using cDNA, mRNA or alternatively, genomic DNA, as a template and appropriate oligonucleotide primers according to standard PCR amplification techniques. In another preferred embodiment, an isolated nucleic acid molecule of the invention comprises a nucleic acid molecule which is a complement of the nucleotide sequence shown in SEQ ID NO:23, SEQ ID NO:25, SEQ ID NO:27, SEQ ID NO:29, SEQ ID NO:33, SEQ ID NO 31, SEQ ID NO:33, SEQ ID NO:88, SEQ ID NO:35.

Additional panC nucleic acid sequences include those that comprise the nucleotide sequence of SEQ ID NO:25, encode a homologue of the polypeptide having the amino acid sequence set forth in SEQ ID NO:26 (e.g., encode a polypeptide having at least 30%, 40%, 50%, 60%, 70%, 80%, 90%, 95% or more identity to the polypeptide having the amino acid sequence as set forth in SEQ ID NO:26 and a substantially identical activity as said polypeptide), hybridize under stringent conditions to all or a portion of a nucleic acid molecule having the nucleotide sequence of SEQ ID NO:25 or to all or a portion of a nucleic acid molecule that encodes a polypeptide having the amino acid sequence of SEQ ID NO:26, or are complementary to a panc nucleotide sequence as set forth herein.

Additional panD nucleic acid sequences include those that comprise the nucleotide sequence of SEQ ID NO:27, encode a homologue of the polypeptide having the amino acid sequence set forth in SEQ ID NO:28 (e.g., encode a polypeptide having at least 30%, 40%, 50%, 60%, 70%, 80%, 90%, 95% or more identity to the polypeptide having the amino acid sequence as set forth in SEQ ID NO:28 and a substantially identical activity as said polypeptide), hybridize under stringent conditions to all or a portion of a nucleic acid molecule having the nucleotide sequence of SEQ ID NO:27 or to all or a portion of a nucleic acid molecule that encodes a polypeptide having the amino acid sequence of SEQ ID NO:28, or are complementary to a panD nucleotide sequence as set forth herein.

Additional panE nucleic acid sequences include those that comprise the nucleotide sequence of SEQ ID NO:29, encode a homologue of the polypeptide having the amino acid sequence set forth in SEQ ID NO:30 (e.g., encode a polypeptide having at least 30%, 40%, 50%, 60%, 70%, 80%, 90%, 95% or more identity to the polypeptide having the amino acid sequence as set forth in SEQID NO:30 and a substantially identical activity as said polypeptide), hybridize under stringent conditions to all or a portion of a nucleic acid molecule having the nucleotide sequence of SEQ ID NO:29 or to all or a portion of a nucleic acid molecule that encodes a polypeptide having the amino acid sequence of SEQ ID NO:30, or are complementary to a panE nucleotide sequence as set forth herein.

Additional ilvB nucleic acid sequences are those that comprise the nucleotide sequence of SEQ ID NO:31, encode a homologie of the polypeptide having the amino acid sequence set forth in SEQ ID NO:32 (e.g., encode a polypeptide having at least 30%, 40%, 50%, 60%, 70%, 80%, 90%, 95% or more identity to the polypeptide having the amino acid sequence as set forth in SEQ ID NO:32 and a substantially identical activity as said polypeptide), hybridize under stringent conditions to all or a portion of a nucleic acid molecule having the nucleotide sequence of SEQ ID NO:31 or to all or a portion of a nucleic acid molecule that encodes a polypeptide having the amino acid sequence of SEQ ID NO:32, or are complementary to an ilvB nucleotide sequence as set forth herein.

Additional ilvN nucleic acid sequences are those that comprise the nucleotide sequence of SEQ ID NO:33, encode a homologue of the polypeptide having the amino acid sequence set forth in SEQ ID NO:34 (e.g., encode a polypeptide having at least 30%, 40%, 50%, 60%, 70%, 80%, 90%, 95% or more identity to the polypeptide having the amino acid sequence as set forth in SEQ ID NO:34 and a substantially identical activity as said polypeptide), hybridize under stringent conditions to all or a portion of a nucleic acid molecule having the nucleotide sequence of SEQ ID NO:33 or to all or a portion of a nucleic acid molecule that encodes a polypeptide having the amino acid sequence of SEQ ID NO:34, or are complementary to an ilvN nucleotide sequence as set forth herein.

Additional ilvC nucleic acid sequences include those that comprise the nucleotide sequence of SEQ ID NO:35, encode a homologue of the polypeptide having the amino acid sequence set forth in SEQ ID NO:36 (e.g., encode a polypeptide having at least 30%, 40%, 50%, 60%, 70%, 80%, 90%, 95% or more identity to the polypeptide having the amino acid sequence as set forth in SEQ ID NO:36 and a substantially identical activity as said polypeptide), hybridize under stringent conditions to all or a portion of a nucleic acid molecule having the nucleotide sequence of SEQ ID NO:35 or to all or a portion of a nucleic acid molecule that encodes a polypeptide having the amino acid sequence of SEQ ID NO:36, or are complementary to an ilvC nucleotide sequence as set forth herein.

Additional ilvD nucleic acid sequences include those that comprise the nucleotide sequence of SEQ ID NO:37, encode a homologue of the polypeptide having the amino acid sequence set forth in SEQ ID NO:38 (e.g., encode a polypeptide having at least 30%, 40%, 50%, 60%, 70%, 80%, 90%, 95% or more identity to the polypeptide having the amino acid sequence as set forth in SEQ ID NO:38 and a substantially identical activity as said polypeptide), hybridize under stringent conditions to all or a portion of a nucleic acid molecule having the nucleotide sequence of SEQ ID NO:37 or to all or a portion of a nucleic acid molecule that encodes a polypeptide having the amino acid sequence of SEQ ID NO:38, or are complementary to an ilvD nucleotide sequence as set forth herein.

Additional alsS nucleic acid sequences include those that comprise the nucleotide sequence of SEQ ID NO:86, encode a homologue of the polypeptide having the amino acid sequence set forth in SEQ ID NO:87 (e.g., encode a polypeptide having at least 30%, 40%, 50%, 60%, 70%, 80%, 90%, 95% or more identity to the polypeptide having the amino acid sequence as set forth in SEQ ID NO:87 and a substantially identical activity as said polypeptide), hybridize under stringent conditions to all or a portion of a nucleic acid molecule having the nucleotide sequence of SEQ ID NO:86 or to all or a portion of a nucleic acid molecule that encodes a polypeptide having the amino acid sequence of SEQ ID NO:87, or are complementary to an alsS nucleotide sequence as set forth herein.

In another embodiment, an isolated nucleic acid molecule is or includes a coaX gene, or portion or fragment thereof. In one embodiment, an isolated coaX nucleic acid molecule or gene comprises the nucleotide sequence as set forth in SEQ ID NO: 19 (e.g. comprises the *B. subtilis* coaX nucleotide sequence). In another embodiment, an isolated coaX nucleic acid molecule or gene comprises a nucleotide sequence that encodes the amino acid sequence as set forth in SEQ ID NO:9 (e.g., encodes the *B. subtilis* CoaX amino acid sequence). In yet another embodiment, an isolated coaX nucleic acid molecule or gene encodes a homologue of the CoaX protein having the amino acid sequence of SEQ ID NO:9. As used herein, the term "homologue" includes a protein or polypeptide sharing at least about 30-35%, preferably at least about 35-40%, more preferably at least about 40-50%, and even more preferably at least about 60%, 70%, 80%, 90% or more identity with the amino acid sequence of a wild-type protein or polypeptide described herein and having a substantially equivalent functional or biological activity as said wild-type protein or polypeptide. For example, a CoaX homologue shares at least about 30-35%, preferably at least about 35-40%, more preferably at least about 40-50%, and even more preferably at least about 60%, 70%, 80%, 90% or more identity with the protein having the amino acid sequence set forth as SEQ ID NO:9 and has a substantially equivalent functional or biological activity (i.e., is a functional equivalent) of the protein having the amino acid sequence set forth as SEQ ID NO:9 (e.g., has a substantially equivalent pantothenate kinase activity). In a preferred embodiment, an isolated coaX nucleic acid molecule or gene comprises a nucleotide sequence that encodes a polypeptide as set forth in any one of SEQ ID NO:7, SEQ ID NO:8, SEQ ID NO:10, SEQ ID NO: 11, SEQ ID NO: 12, SEQ ID NO:13, SEQ ID NO:14, SEQ ID NO:15, SEQ ID NO:16, SEQ ID NO:17, SEQ ID NO:18, SEQ ID NO:74 or SEQ ID NO:75. In another embodiment, an isolated coaX nucleic acid molecule hybridizes to all or a portion of a nucleic acid molecule having the nucleotide sequence set forth in SEQ ID NO:19 or hybridizes to all or a portion of a nucleic acid molecule having a nucleotide sequence that encodes a polypeptide having the amino acid sequence of any of SEQ ID NOs:7-18, 74 or 75. Such hybridization conditions are known to those skilled in the art and can be found in *Current Protocols ill Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3× SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+ 4(# of G+C bases). For hybrids between 18 and 49 base pairs in length, $T_m$(° C.)=81.5+16.6($\log_{10}$[$Na^+$])+ 0.41(% G+C) −(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or, alternatively, 0.2×SSC, 1% SDS). In another preferred embodiment, an isolated nucleic acid molecule comprises a nucleotide sequence that is complementary to a coaX nucleotide sequence as set forth herein (e.g., is the full complement of the nucleotide sequence set forth as SEQ ID NO: 19).

In another preferred embodiment, an isolated nucleic acid molecule is or includes a coaA gene, for example, a *Bacillus* (e.g., *B. subtilis*) coaA gene, or portion or fragment thereof.

Exemplary isolated coaA nucleic acid molecules and/or genes include (I) an isolated coaA nucleic acid molecule or gene comprising the nucleotide sequence as set forth in any one of SEQ ID NOs:20-22; (2) an isolated coaA nucleic acid molecule or gene comprising a nucleotide sequence that encodes the amino acid sequence as set forth in SEQ ID NO:3; (3) an isolated coaA nucleic acid molecule or gene comprising a nucleotide sequence which encodes a CoaA homologue (e.g., a polypeptide having an amino acid sequence at least about 30-35%, preferably at least about 35-40%, more preferably at least about 40-50%, and even more preferably at least about 60%, 70%, 80%, 90% or more identical to the amino acid sequence set forth as SEQ ID NO:3 and having a substantially equivalent enzymatic activity; (4) an isolated coaA nucleic acid molecule or gene comprising a nucleotide sequence that encodes a polypeptide as set forth in any one of SEQ ID NO: 1, SEQ ID NO:2, SEQ ID NO:4, SEQ ID NO:5 or SEQ ID NO:6; (5) an isolated nucleic acid molecule that hybridizes under stringent conditions to all or a portion of a nucleic acid molecule having the nucleotide sequence set forth in SEQ ID NO:20, SEQ ID NO:21 or SEQ ID NO:22 or hybridizes to all or a portion of a nucleic acid molecule having a nucleotide sequence that encodes a polypeptide having the amino acid sequence of SEQ ID NO:3; and (6) an isolated nucleic acid molecule comprising a nucleotide sequence that is complementary to a coaA nucleotide sequence as set forth herein (e.g., is the full complement of the nucleotide sequence set forth in SEQ ID NO:20, SEQ ID NO:21 or SEQ ID NO:22).

A nucleic acid molecule of the present invention (e.g., a coaX nucleic acid molecule or gene or a coaA nucleic acid molecule or gene), can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the coaX or coaA nucleotide sequences set forth herein, or flanking sequences thereof. A nucleic acid of the invention (e.g., a coaX nucleic acid molecule or gene or a coaA nucleic acid molecule or gene), can be amplified using cDNA, mRNA or alternatively, chromosomal DNA, as a template and appropriate oligonucleotide primers according to standard PCR amplification techniques.

Yet another embodiment of the present invention features mutant coaX and coaA nucleic acid molecules or genes. The phrase "mutant nucleic acid molecule" or "mutant gene" as used herein, includes a nucleic acid molecule or gene having a nucleotide sequence which includes at least one alteration (e.g., substitution, insertion, deletion) such that the polypeptide or protein that may be encoded by said mutant exhibits an activity that differs from the polypeptide or protein encoded by the wild-type nucleic acid molecule or gene. Preferably, a mutant nucleic acid molecule or mutant gene (e.g., a mutant coaA or coaX gene) encodes a polypeptide or protein having a reduced activity (e.g., having a reduced pantothenate kinase activity) as compared to the polypeptide or protein encoded by the wild-type nucleic acid molecule or gene, for example, when assayed under similar conditions (e.g., assayed in microorganisms cultured at the same temperature). A mutant gene also can encode no polypeptide or have a reduced level of production of the wild-type polypeptide.

As used herein, a "reduced activity" or "reduced enzymatic activity" is one that is at least 5% less than that of the polypeptide or protein encoded by the wild-type nucleic acid molecule or gene, preferably at least 5-10% less, more preferably at least 10-25% less and even more preferably at least 25-50%, 50-75% or 75-100% less than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, a "reduced activity" or "reduced enzymatic activity" also includes an activity that has been deleted or "knocked out" (e.g., approximately 100% less activity than that of the polypeptide or protein encoded by the wild-type nucleic acid molecule or gene). Activity can be determined according to any well accepted assay for measuring activity of a particular protein of interest. Activity can be measured or assayed directly, for example, measuring an activity of a protein isolated or purified from a cell. Alternatively, an activity can be measured or assayed within a cell or in an extracellular medium. For example, assaying for a mutant coaA gene or a mutant coaX gene (i.e., said mutant encoding a reduced pantothenate kinase activity) can be accomplished by expressing the mutated gene in a microorganism, for example, a mutant microorganism which expresses pantothenate kinase in a temperature-sensitive manner, assaying the mutant gene for the ability to complement a temperature sensitive (Ts) mutant for pantothenate kinase activity. A coaX mutant gene or coaA mutant gene that encodes a "reduced pantothenate kinase activity" is one that complements the Ts mutant less effectively than, for example, a corresponding wild-type coaX gene or coaA gene.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant nucleic acid or mutant gene (e.g. encoding a mutant polypeptide or protein), as defined herein, is readily distinguishable from a nucleic acid or gene encoding a protein homologue, as described above, in that a mutant nucleic acid or mutant gene encodes a protein or polypeptide having an altered activity, optionally observable as a different or distinct phenotype in a microorganism expressing said mutant gene or nucleic acid or producing said mutant protein or polypeptide (i.e., a mutant microorganism) as compared to a corresponding microorganism expressing the wild-type gene or nucleic acid or producing said mutant protein or polypeptide. By contrast, a protein homologue has an identical or substantially similar activity, optionally phenotypically indiscernable when produced in a microorganism, as compared to a corresponding microorganism expressing the wild-type gene or nucleic acid. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologies and mutants: homologues having, for example, low (e.g., 30-50% sequence identity) sequence identity yet having substantially equivalent functional activities, and mutants, for example sharing 99% sequence identity yet having dramatically different or altered functional activities. Exemplary homologues are set forth in FIG. 20 (i.e., CoaA homologues) and in FIG. 23 (i.e., CoaX homologues). Exemplary mutants are described in Examples XV and XVIII herein.

VIII. Recombinant Nucleic Acid Molecules and Vectors

The present invention-further features recombinant nucleic acid molecules (e.g., recombinant DNA molecules) that include nucleic acid molecules and/or genes described herein (e.g., isolated nucleic acid molecules and/or genes), preferably *Bacillus* genes, more preferably *Bacillus subtilis* genes, even more preferably *Bacillus subtilis* pantothenate kinase genes (e.g., coaX genes or coaA genes), pantothenate biosynthetic genes (e.g., genes encoding pantothenate biosynthetic enzymes, for example, panB genes encoding ketopantoate hydroxymethyltransferase, panE genes encoding ketopantoate reductase, panC genes encoding pantothenate synthetase, and/or panD genes encoding aspartate-α-decarboxylase) and/or isoleucine-valine (ilv) biosynthetic genes (e.g., ilvBN or alsS genes encoding acetohydroxyacid synthetase, ilvC genes encoding acetohydroxyacid isomeroreductase and/or ilvD genes encoding dihydroxyacid dehydratase).

The present invention further features vectors (e.g., recombinant vectors) that include nucleic acid molecules (e.g., isolated or recombinant nucleic acid molecules and/or genes) described herein. In particular, recombinant vectors are featured that include nucleic acid sequences that encode bacterial gene products as described herein, preferably *Bacillus* gene products, more preferably *Bacillus subtilis* gene products, even more preferably *Bacillus subtilis* pantothenate biosynthetic gene products (e.g., pantothenate biosynthetic enzymes, for example, ketopantoate hydroxymethyltransferase, ketopantoate reductase, pantothenate synthetase, and/ or aspartate-α-decarboxylase) and/or isoleucine-valine biosynthetic gene products (e.g., acetohydroxyacid synthetase, acetohydroxyacid isomeroreductase and/or dihydroxyacid dehydratase).

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated nucleic acid molecule or gene of the present invention (e.g., an isolated coaX, coaA, pall or ilv gene) operably linked to regulatory sequences.

The term "recombinant vector" includes a vector (e.g., plasmid, phage, phasmid, virus, cosmid or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a coaX, coaA, pan or ilv gene or recombinant nucleic acid molecule including such coaX, coaA, pan or ilv gene, operably linked to regulatory sequences, for example, promoter sequences, terminator sequences and/or artificial ribosome binding sites (RBSs), as defined herein.

The phrase "operably linked to regulatory sequence(s)" means that the nucleotide sequence of the nucleic acid molecule or gene of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant nucleic acid molecule is included in a recombinant vector, as defined herein, and is introduced into a microorganism).

The term "regulatory sequence" includes nucleic acid sequences which affect (e.g., modulate or regulate) expression of other nucleic acid sequences. In one embodiment, a regulatory sequence is included in a recombinant nucleic acid molecule or recombinant vector in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule or recombinant vector operably linked to a regulatory sequence which accompanies or is adjacent to the gene of interest in the natural organism (e.g., operably linked to "native" regulatory sequences, for example, to the "native" promoter). Alternatively, a gene of interest can be included in a recombinant nucleic acid molecule or recombinant vector operably linked to a regulatory sequence which accompanies or is adjacent to another (e.g., a different) gene in the natural organism. Alternatively, a gene of interest can be included in a recombinant nucleic acid molecule or recombinant vector operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule or recombinant vector of the present invention includes a nucleic acid sequence or gene that encodes at least one bacterial gene product (e.g., a pantothenate biosynthetic enzyme, an isoleucine-valine biosynthetic enzyme, or a CoaA biosynthetic enzyme, for example CoaA or CoaX) operably linked to a promoter or promoter sequence. Preferred promoters of the present invention include *Bacillus* promoters and/or bacteriophage promoters (e.g., bacteriophage which infect *Bacillus*). In one embodiment, a promoter is a *Bacillus* promoter, preferably a strong *Bacillus* promoter (e.g., a promoter associated with a biochemical housekeeping gene in *Bacillus* or a promoter associated with a glycolytic pathway gene in *Bacillus*). In another embodiment, a promoter is a bacteriophage promoter. In a preferred embodiment, the promoter is from the bacteriophage SP01. In a particularly preferred embodiment, a promoter is selected from the group consisting of $P_{15}$, $P_{26}$ or $P_{veg}$, for example, the promoters set forth in SEQ ID NO:39, SEQ ID NO:40 or SEQ ID NO:41. Additional preferred promoters include ref (the translational elongation factor (TEF) promoter) and pyc (the pyruvate carboxylase (PYC) promoter), which promote high level expression in Bacillus (e.g., Bacillus subtilis). Additional preferred promoters, for example, for use in Gram positive microorganisms include, but are not limited to, the amyE promoter or phage SP02 promoters. Additional preferred promoters, for example, for use in Gram negative microorgaisms include, but are not limited to tac, trp, tet, trp-tet, lpp, lac, lpp-lac, lacIq, T7, T5, T3, gal, trc, ara, SP6, $\lambda\text{-}P_R$ or $\lambda\text{-}P_L$.

In another embodiment, a recombinant nucleic acid molecule or recombinant vector of the present invention includes a terminator sequence or terminator sequences (e.g., transcription terminator sequences). The term "terminator sequences" includes regulatory sequences which serve to terminate transcription of a gene. Terminator sequences (or tandem transcription terminators) can further serve to stabilize mRNA (e.g., by adding structure to mRNA), for example, against nucleases.

In yet another embodiment, a recombinant nucleic acid molecule or recombinant vector of the present invention includes sequences which allow for detection of the vector containing said sequences (i.e., detectable and/or selectable markers), for example, sequences that overcome auxotrophic mutations, for example, ura3 or ilvE, fluorescent markers, and/or calorimetric markers (e.g., lacZ/β-galactosidase), and/or antibiotic resistance genes (e.g., amp or tet).

In yet another embodiment, a recombinant nucleic acid molecule or recombinant vector of the present invention includes an artificial ribosome binding site (RBS). The term "artificial ribosome binding site (RBS)" includes a site within an mRNA molecule (e.g., coded within DNA) to which a ribosome binds (e.g., to initiate translation) which differs from a native RBS (e.g., a RBS found in a naturally-occurring gene) by at least one nucleotide. Preferred artificial RBSs include about 5-6, 7-8, 9-10, 11-12, 13-14, 15-16, 17-18, 19-20, 21-22, 23-24, 25-26, 27-28, 29-30 or more nucleotides of which about 1-2, 3-4, 5-6, 7-8, 9-10, 11-12, 13-15 or more differ from the native RBS (e.g., the native RBS of a gene of interest). Preferably, nucleotides which differ are substituted such that they are identical to one or more nucleotides of an ideal RBS (e.g., SEQ ID NO:44, SEQ ID NO:45, SEQ ID NO:46, SEQ ID NO:47 or SEQ ID NO:48), when optimally aligned for comparisons. Artificial RBSs can be used to replace the naturally-occurring or native RBS associated with a particular gene. Artificial RBSs preferably increase translation of a particular gene. Preferred artificial RBSs (e.g., RBSs for increasing the translation of panB, for example, of B. subtilis panB) are depicted in Table 1A (e.g., SEQ ID NO:49 and SEQ ID NO:50).

TABLE 1A

Preferred panB Ribosome Binding Sites

| Sequence | Name | SEQ ID |
|---|---|---|
| -------AGAAAGGAGGTGA | ideal RBS | (SEQ ID NO: 44) |
| CCCTCT-AG-AAGGAGGAGAAAACATG | RBS1 | (SEQ ID NO: 49) |
| CCCTCT-AG--AGGAGGAGAAAACATG | RBS2 | (SEQ ID NO: 50) |
| TAAACAT-G--AGGAGGAGAAAACATG | panB native RBS | (SEQ ID NO: 42) |

Additional preferred artificial RBSs (e.g., RBSs for increasing the translation of panD, for example, of B. subtilis panD) are depicted in Table 1B (e.g., SEQ ID NO:51, SEQ ID NO:52, SEQ ID NO:53 and SEQ ID NO:54).

TABLE 1B

Preferred panD Ribosome Binding Sites

| Sequence | Name | SEQ ID |
|---|---|---|
| CTAGAAAAGGAGGAATTTAAATG | pAN423 RBS | (SEQ ID NO: 88) |
| TTAAGAAAGGAGGTGANNNNATG | ideal RBS | (SEQ ID NO: 45) |
| TTAGAAAGGAGG ATTTAAATATG | new design A | (SEQ ID NO: 51) |
| TTAGAAAGGAGGT TTAATTAATG | new design B | (SEQ ID NO: 52) |
| TTAGAAAGGAGGTGATTTAAATG | new design C1 | (SEQ ID NO: 53) |
| TTAGAAAGGAGGTGTTTAAATG | new design C2 | (SEQ ID NO: 54) |
| TTAGAAAGGAGGTGANNNNNATG | ideal RBS | (SEQ ID NO: 46) |

Additional preferred artificial RBSs (e.g., RBSs for increasing the translation of panD, for example, of B. subtilis panD) are depicted in Table 1C (e.g., SEQ ID NO:55, SEQ ID NO:56 and SEQ ID NO:57). The predicted amino acid sequence at the C-terminus of the PanC protein is shown. The start codon for PanD translation is underlined.

TABLE 1C

Additional Preferred panD Ribosome Binding Sites

| Sequence | Name | SEQ ID |
|---|---|---|
| --- --A GAA AGG AGG TGA NNN NNN N ATG | ideal RBS | (SEQ ID NO: 47) |

TABLE 1C-continued

Additional Preferred panD Ribosome Binding Sites

| | | | | | | | | | | |
|---|---|---|---|---|---|---|---|---|---|---|
| ATT | CGA | GAA | ATG | GAG | AGA | ATA | TAA | T | <u>ATG</u> | native panD RBS (SEQ ID NO: 43) |
| Ile | Arg | Glu | Met | Glu | Arg | Ile | * | | Met | SEQ ID NO: 89 |
| --- | --A | GAA | AGG | AGG | TGA | NNN | NNN | N | <u>ATG</u> | ideal RBS (SEQ ID NO: 47) |
| ATT | CGA | GAA | AGG | AGG | TGA | ATA | TAA | T | <u>ATG</u> | NDI (SEQ ID NO: 55) |
| Ile | Arg | Glu | Arg | Arg | * | | | | Met | SEQ ID NO: 90 |
| ATT | CGA | GAA | AGG | AGG | TGA | ATA | ATA | - | <u>ATG</u> | NDII (SEQ ID NO: 56) |
| Ile | Arg | Glu | Arg | Arg | * | | | | Met | SEQ ID NO: 90 |
| ATT | CGT | AGA | AAG | GAG | GTG | AAT | TAA | T | <u>ATG</u> | NDIII (SEQ ID NO: 57) |
| Ile | Arg | Arg | Lys | Glu | Val | Asn | * | | Met | SEQ ID NO: 91 |
| --- | --- | AGA | AAG | GAG | GTG | ANN | NNN | N | <u>ATG</u> | ideal RBS (SEQ ID NO: 48) |

Accordingly, in one embodiment, a vector of the present invention includes an artificial RBS as set forth in SEQ ID NO:49 or SEQ ID NO:50. In another embodiment, a vector of the present invention includes an artificial RBS as set forth in SEQ ID NO:51, SEQ ID NO:52, SEQ ID NO:53 or SEQ ID NO:54. In yet another embodiment, a vector of the present invention includes an artificial RBS as set forth in SEQ ID NO:55, SEQ ID NO:56 or SEQ ID NO:57.

Figure 3A:
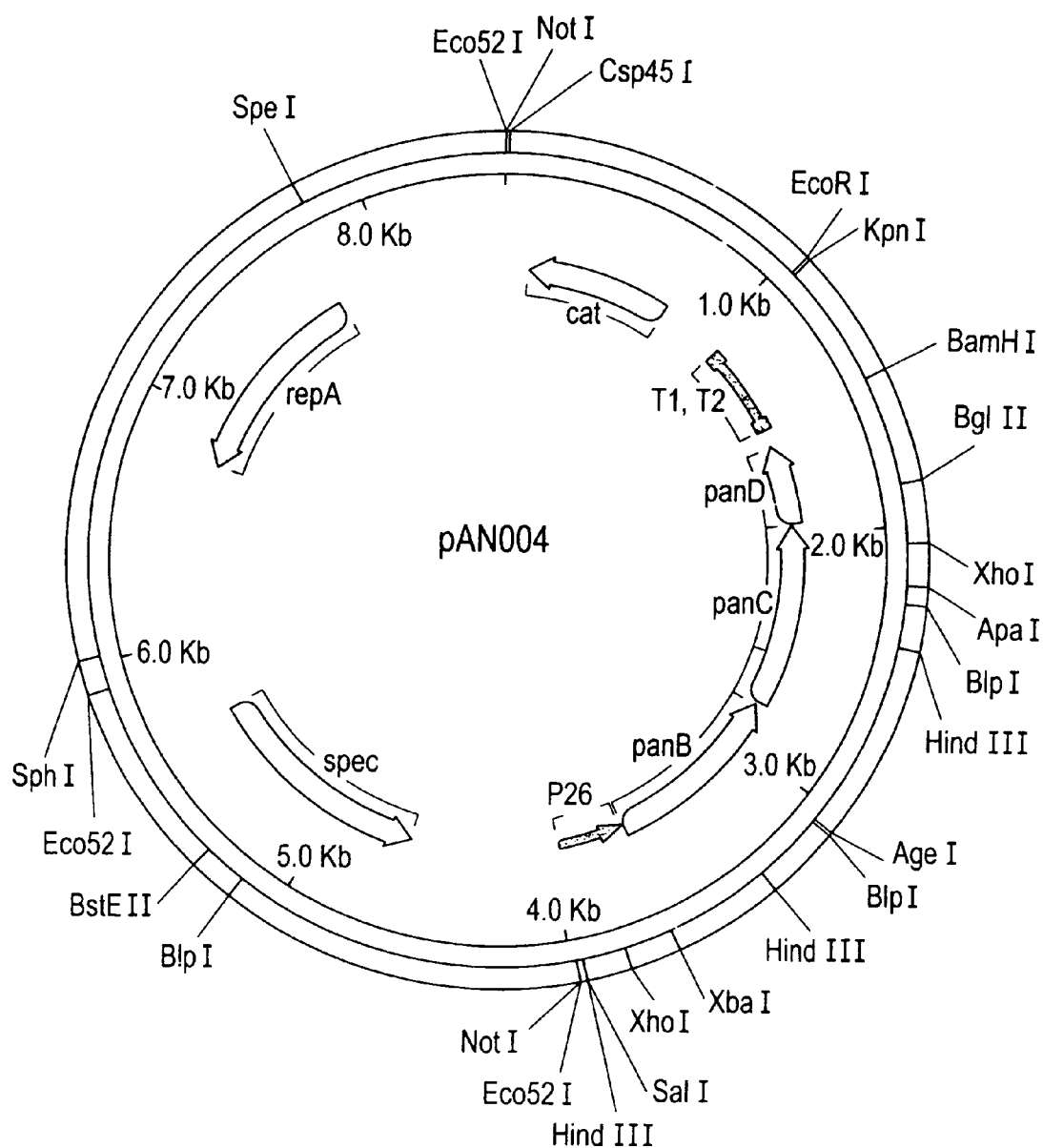
FIG. 3A is a schematic representation of the plasmid pAN004, containing the panBCD operon expressed from $P_{26}$ and RBS1.
Figure 3B:
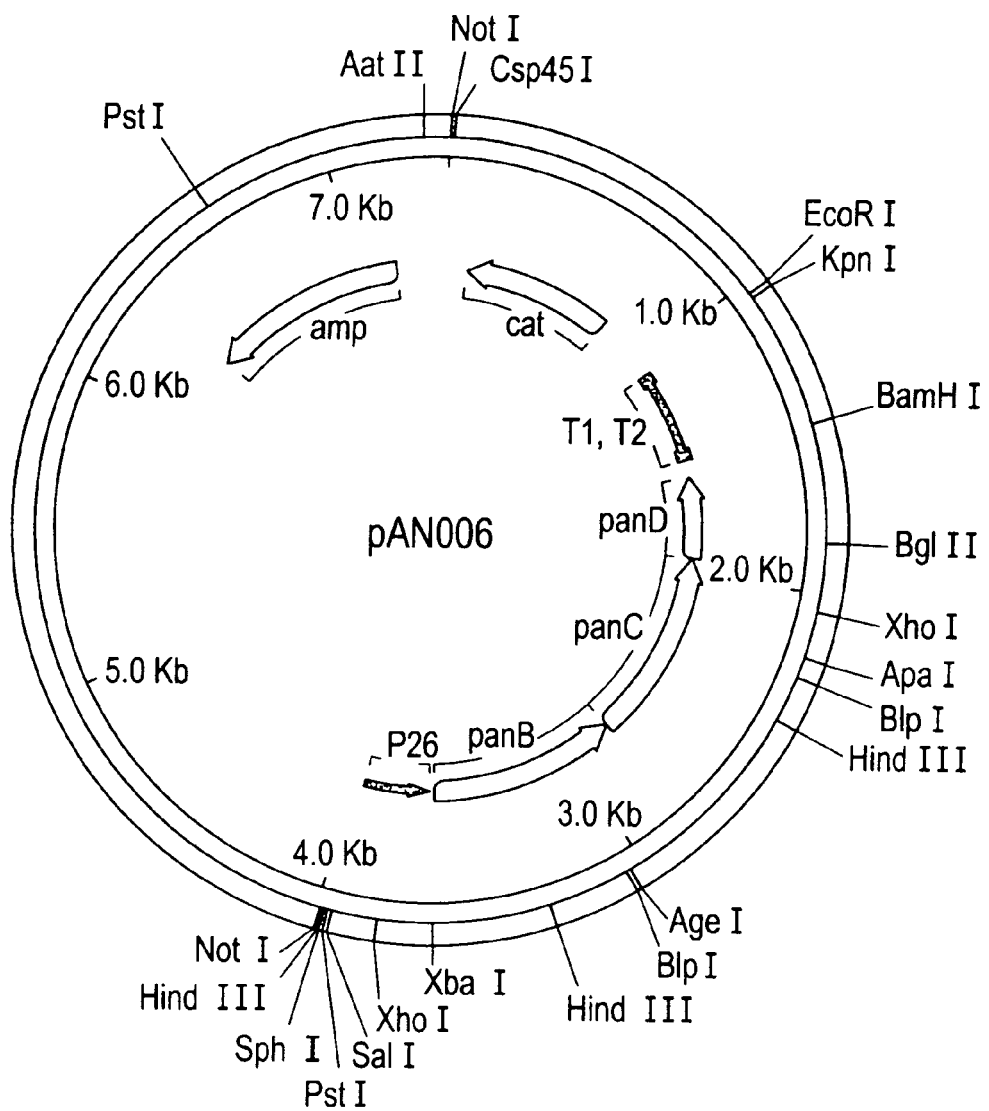
FIG. 3B is a schematic representation of the plasmid pAN006, containing the panBCD operon expressed from $P_{26}$ and RBS2.
Figure 4:
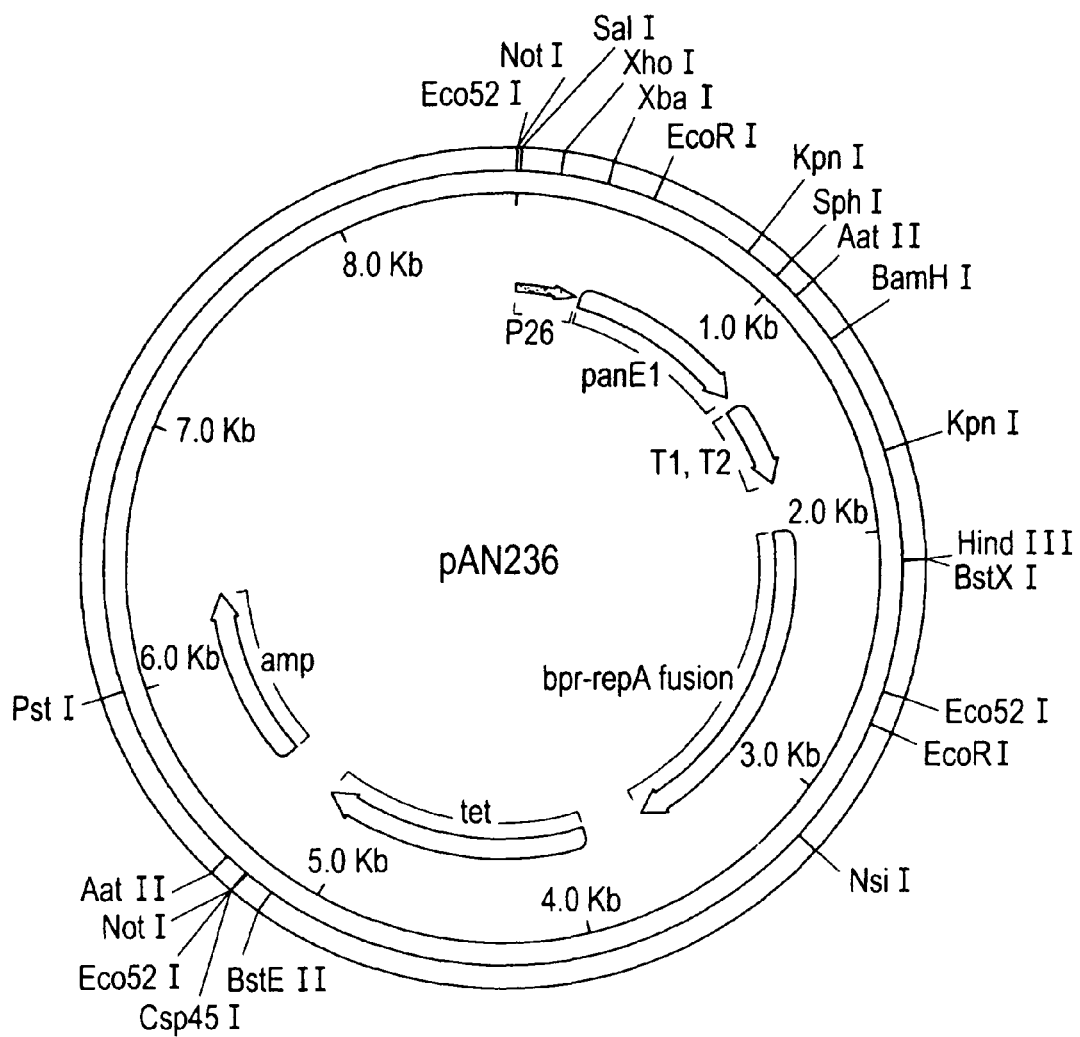
FIG. 4 is a schematic representation of the plasmid pAN236, containing an integratable and amplifiable $P_{26}$-RBS2-panE1 expression cassette.

In another embodiment, a recombinant vector of the present invention includes sequences that enhance replication in bacteria (e.g., replication-enhancing sequences). In one embodiment, replication-enhancing sequences are derived from *E. coli*. In another embodiment, replication-enhancing sequences are derived from pBR322 (e.g., sequences included within the pBR322 derived portion of any of the pAN vectors as set forth in the Figures, i.e., the Not I-Not I sequences from about 5.0 kB to 9.0 kB of the vector depicted in FIG. 3A).

In yet another embodiment, a recombinant vector of the present invention includes antibiotic resistance genes. The term "antibiotic resistance genes" includes sequences which promote or confer resistance to antibiotics on the host organism (e.g., *Bacillus*). In one embodiment, the antibiotic resistance genes are selected from the group consisting of cat (chloramphenicol resistance) genes, tet (tetracycline resistance) genes, erm (erythromycin resistance) genes, neo (neomycin resistance) genes and spec (spectinomycin resistance) genes. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

Preferred vectors of the present invention include, but are not limited to, vectors set forth in FIGS. 2-15, 17, 19, 22, 25 and 26. It will further be appreciated by one of skill in the art that the design of a vector can be tailored depending on such factors as the choice of microorganism to be genetically engineered, the level of expression of gene product desired and the like.

IX. Isolated Proteins

Another aspect of the present invention features isolated proteins (e.g., isolated pantothenate biosynthetic enzymes and/or valine-isoleucine biosynthetic enzymes and/or isolated CoA biosynthetic enzymes, for example isolated CoaA or CoaX). In one embodiment, proteins (e.g., isolated pantothenate biosynthetic enzymes and/or valine-isoleucine biosynthetic enzymes and/or isolated CoA biosynthetic enzymes, for example isolated CoaA or CoaX) are produced by recombinant DNA techniques and can be isolated from microorganisms of the present invention by an appropriate purification scheme using standard protein purification techniques. In another embodiment, proteins are synthesized chemically using standard peptide synthesis techniques.

An "isolated" or "purified" protein (e.g., an isolated or purified biosynthetic enzyme) is substantially free of cellular material or other contaminating proteins from the microorganism from which the protein is derived, or substantially free from chemical precursors or other chemicals when chemically synthesized. In one embodiment, an isolated or purified protein has less than about 30% (by dry weight) of contaminating protein or chemicals, more preferably less than about 20% of contaminating protein or chemicals, still more preferably less than about 10% of contaminating protein or chemicals, and most preferably less than about 5% contaminating protein or chemicals.

In a preferred embodiment, the protein or gene product is derived from *Bacillus* (e.g., is *Bacillus*-derived). The term "derived from *Bacillus*" or "*Bacillus*-derived" includes a protein or gene product which is encoded by a *Bacillus* gene. Preferably, the gene product is derived from a microorganism selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis*, and other Group 1 *Bacillus* species, for example, as characterized by 16S rRNA type (Priest, supra). In another preferred embodiment, the protein or gene product is derived from *Bacillus brevis* or *Bacillus stearothermophilis*. In another preferred embodiment, the protein or gene product is derived from a microorganism selected from the group consisting of *Bacillus licheniformis, Bacillus amyloliquefaciens, Bacillus halodurans, Bacillus subtilis*, and *Bacillus pumilus*. In a particularly preferred embodiment, the protein or gene product is derived from *Bacillus subtilis* (e.g., is *Bacillus subtilis*-derived). The term "derived from *Bacillus subtilis*" or "*Bacillus subtilis*-derived" includes a protein or gene product which is encoded by a *Bacillus subtilis* gene. In yet another preferred embodiment, the protein or gene product is encoded by a *Bacillus* gene homologue (e.g., a gene derived from a species distinct from *Bacillus* but having significant homology to a *Bacillus* gene of the present invention, for example, a *Bacillus* pan gene or *Bacillus* ilv gene).

Included within the scope of the present invention are bacterial-derived proteins or gene products and/or *Bacillus*-derived proteins or gene products (e.g., *B. subtilis*-derived gene products) that are encoded by naturally-occurring bacterial and/or *Bacillus* genes (e.g., *B. subtilis* genes), for example, the genes identified by the present inventors, for example, *Bacillus* or *B. subtilis* coaX genes, coaA genes, pan genes and/or ilv genes. Further included within the scope of the present invention are bacterial-derived proteins or gene products and/or *Bacillus*-derived proteins or gene products (e.g., *B. subtilis*-derived gene products) that are encoded bacterial and/or *Bacillus* genes (e.g., *B. subtilis* genes) which differ from naturally-occurring bacterial and/or *Bacillus* genes (e.g., *B. subtilis* genes), for example, genes which have nucleic acids that are mutated, inserted or deleted, but which encode proteins substantially similar to the naturally-occurring gene products of the present invention. For example, it is well understood that one of skill in the art can mutate (e.g., substitute) nucleic acids which, due to the degeneracy of the genetic code, encode for an identical amino acid as that encoded by the naturally-occurring gene. Moreover, it is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product as compared with a naturally-occurring gene product, each instance of which is intended to be included within the scope of the present invention.

In a preferred embodiment, an isolated protein of the present invention (e.g., an isolated pantothenate biosynthetic enzyme and/or an isolated isoleucine-valine biosynthetic enzyme and/or an isolated CoaA biosynthetic enzymes, for example isolated CoaA or CoaX) has an amino acid sequence shown in SEQ ID NO:3, SEQ ID NO:9, SEQ ID NO:24, SEQ ID NO:26, SEQ ID NO:28, SEQ ID NO:30, SEQ ID NO:32, SEQ ID NO:34, SEQ ID NO:36, SEQ ID NO:38 or SEQ ID NO:87. In other embodiments, an isolated protein of the present invention is a homologue of the at least one of the proteins set forth as SEQ ID NO:3, SEQ ID NO:9, SEQ ID NO:24, SEQ ID NO:26, SEQ ID NO:28, SEQ ID NO:30, SEQ ID NO:32, SEQ ID NO:34, SEQ ID NO:36, SEQ ID NO:38 or SEQ ID NO:87 (e.g., comprises an amino acid sequence at least about 30-40% identical, preferably about 40-50% identical, more preferably about 50-60% identical, and even more preferably about 60-70%, 70-80%, 80-90%, 90-95% or more identical to the amino acid sequence of SEQ ID NO:3, SEQ ID NO:9, SEQ ID NO:24, SEQ ID NO:26, SEQ ID NO:28, SEQ ID NO:30, SEQ ID NO:32, SEQ ID NO:34, SEQ ID NO:36, SEQ ID NO:38 or SEQ ID NO:87, and has an activity that is substantially similar to that of the protein encoded by the amino acid sequence of SEQ ID NO:3, SEQ ID NO:9, SEQ ID NO:24, SEQ ID NO:26, SEQ ID NO:28, SEQ ID NO:30, SEQ ID NO:32, SEQ ID NO:34, SEQ ID NO:36, SEQ ID NO:38 or SEQ ID NO:87, respectively.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total# of positions×100), preferably taking into account the number of gaps and size of said gaps necessary to produce an optimal alignment.

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Research 25(17):3389-3402. When utilizing BLAST and Gapped BLAST programs, the default parameters of the respective programs (e.g., XBLAST and NBLAST) can be used. Another preferred, non-limiting example of a mathematical algorithm utilized for the comparison of sequences is the algorithm of Myers and Miller (1988) Comput Appl Biosci. 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

In another preferred embodiment, the percent homology between two amino acid sequences can be determined using the GAP program in the GCG software package (available at http://www.gcg.com), using either a Blossom 62 matrix or a PAM250 matrix, and a gap weight of 12, 10, 8, 6, or 4 and a length weight of 2, 3, or 4. In yet another preferred embodiment, the percent homology between two nucleic acid sequences can be accomplished using the GAP program in the GCG software package, using a gap weight of 50 and a length weight of 3.

X. Biotransformations and Bioconversions

Another aspect of the present invention includes biotransformation processes which feature recombinant microorganisms (e.g., mutant microorganisms) and/or isolated CoA, pantothenate or isoleucine-valine biosynthetic enzymes described herein. The term "biotransformation process", also referred to herein as "bioconversion processes", includes biological processes which result in the production (e.g., transformation or conversion) of any compound (e.g., intermediate or product) which is upstream of a CoA, pantothenate or isoleucine-valine biosynthetic enzyme to a compound (e.g., substrate, intermediate or product) which is downstream of said CoA, pantothenate or isoleucine-valine biosynthetic enzyme.

In one embodiment, the invention features a biotransformation process for the production of a panto-compound comprising contacting a microorganism which overexpresses at least one pantothenate biosynthetic enzyme with at least one appropriate substrate or precursor under conditions such that said panto-compound is produced and recovering said panto-compound. In a preferred embodiment, the invention features a biotransformation process for the production of pantoate comprising contacting a microorganism which overexpresses ketopantoate reductase (the panE gene product) with an appropriate substrate (e.g., ketopantoate) under conditions such that pantoate is produced and recovering said pantoate.

In another preferred embodiment, the invention features a biotransformation process for the production of pantothenate comprising contacting a microorganism which overexpresses ketopantoate reductase and pantothenate synthetase with appropriate substrates (e.g., ketopantoate and β-alanine) under conditions such that pantothenate is produced and recovering said pantothenate. In yet another preferred embodiment, the invention features a biotransformation process for the production of pantothenate comprising contacting a microorganism which overexpresses ketopantoate hydroxymethyltransferase, ketopantoate reductase and pantothenate synthetase with appropriate substrates (e.g., α-ketoisovalerate and β-alanine) under conditions such that pantothenate is produced and recovering said pantothenate. Preferred recombinant microorganisms for carrying out the above-described biotransformations include pantothenate kinase mutants. Conditions under which pantoate or pantothenate are produced can include any conditions which result in the desired production of pantoate or pantothenate, respectively.

In yet another embodiment, the present invention includes a method of producing β-alanine that includes culturing a microorganism which overexpresses aspartate-α-decarboxylase under conditions such that β-alanine is produced. Preferably, the aspartate-α-decarboxylase-overexpressing microorganism has a mutation in a nucleic acid sequence encoding a pantothenate biosynthetic enzyme selected from the group consisting of ketopantoate hydroxymethyltransferase, ketopantoate reductase and pantothenate synthetase.

The invention further features a method of producing β-alanine that includes contacting a composition comprising aspartate with an isolated *Bacillus* aspartate-α-decarboxylase enzyme under conditions such that β-alanine is produced (e.g., an in vitro synthesis method).

The microorganism(s) and/or enzymes used in the biotransformation reactions are in a form allowing them to perform their intended function (e.g., producing a desired compound). The microorganisms can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall).

Purified or unpurified CoA biosynthetic enzyme(s) (e.g. CoaA and/or CoaX), pantothenate biosynthetic enzyme(s) and/or valine-isoleucine biosynthetic enzyme(s) can also be used in biotransformation reactions. The enzyme can be in a form that allows it to perform its intended function (e.g., obtaining the desired compound). For example, the enzyme can be in free form or immobilized. Purified or unpurified CoA biosynthetic enzyme(s), pantothenate biosynthetic enzyme(s) and/or valine-isoleucine biosynthetic enzyme(s) can be contacted in one or more in vitro reactions with appropriate substrate(s) such that the desired product is produced.

With respect to at least the above-described methodologies (e.g., the production methodologies of the present invention), at least one aspect of the invention features the following: embodiments in which the methods do not use microorganisms of the genus *Corynebacterium* and/or microorganisms of the genus *Escherichia*; embodiments in which the methods do not use microorganisms selected from the group consisting of *Escherichia coli* and *Corynebacterium glutamicum*; embodiments in which the methods do not use gram negative microorganisms; embodiments in which the microorganisms utilized do not include, express or produce nucleic acid molecules, genes or proteins (e.g., biosynthetic enzymes) derived from microorganisms of the genus *Corynebacterium* and/or microorganisms of the genus *Escherichia*; embodiments in which the microorganisms to not include, express or produce nucleic acid molecules, genes or proteins (e.g., biosynthetic enzymes) derived from microorganisms selected from the group consisting of *Escherichia coli* and *Corynebacterium glutamicum*.

XI. Screening Assays

Because CoA is an essential factor in bacteria, proteins (e.g., enzymes) involved in the biosynthesis of CoA provide valuable tools in the search for novel anti-biotics. In particular, the CoaX protein is a valuable target for identifying bacteriocidal compounds because it bears no resemblance in primary sequence to mammalian pantothenate kinase enzymes. Accordingly, the present invention also provides a method (also referred to herein as a "screening assay") for identifying modulators, i.e., candidate or test compounds or agents (e.g., peptides, peptidomimetics, small molecules or other drugs) which bind to CoaX, or have a stimulatory or inhibitory effect on, for example, coaX expression or CoaX activity.

In one embodiment, the invention provides assays for screening candidate or test compounds which are capable of binding to CoaX proteins or a biologically active portion thereof. In another embodiment, the invention provides assays for screening candidate or test compounds which modulate the activity of CoaX proteins or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a microorganism-based assay in which a recombinant microorganism which expresses a CoaX protein or biologically active portion-thereof is contacted with a test compound and the ability of the test compound to modulate CoaX activity is determined.

Determining the ability of the test compound to modulate CoaX activity can be accomplished by monitoring, for example, intracellular phosphopanthoate or CoA concentrations or secreted pantothenate concentrations (as compounds that inhibit CoaX will result in a buildup of pantothenate in the test microorganism). CoaX substrate can be labeled with a radioisotope or enzymatic label such that modulation of CoaX activity can be determined by detecting a conversion of labeled substrate to intermediate or product. For example, CoaX substrates can be labeled with $^{32}P$, $^{14}C$, or $^3H$, either directly or indirectly, and the radioisotope detected by direct counting of radioemission or by scintillation counting. Determining the ability of a compound to modulate CoaX activity can alternatively be determined by detecting the induction of a reporter gene (comprising a CoA-responsive regulatory element operatively linked to a nucleic acid encoding a detectable marker, e.g., luciferase), or detecting a CoA-regulated cellular response.

In yet another embodiment, a screening assay of the present invention is a cell-free assay in which a CoaX protein or biologically active portion thereof is contacted with a test compound in vitro and the ability of the test compound to bind to or modulate the activity of the CoaX protein or biologically active portion thereof is determined. In a preferred embodiment, the assay includes contacting the CoaX protein or biologically active portion thereof with known substrates to form an assay mixture, contacting the assay mixture with a test compound, and determining the ability of the test compound to modulate enzymatic activity of the CoaX on its substrates.

Screening assays can be accomplished in any vessel suitable for containing the microorganisms, proteins, and/or reactants. Examples of such vessels include microtiter plates, test tubes, and micro-centrifuge tubes. In more than one embodiment of the above assay methods of the present invention, it may be desirable to immobilize either CoaX protein or a recombinant microorganism expressing CoaX protein to facilitate separation of products and/or substrates, as well as to accommodate automation of the assay. For example, glutathione-S-transferase/CoaX fusion proteins can be adsorbed onto glutathione sepharose beads (Sigma Chemical, St. Louis, Mo.) or glutathione derivatized microtiter plates. Other techniques for immobilizing proteins on matrices (e.g., biotin-conjugation and streptavidin immobilization or antibody conjugation) can also be used in the screening assays of the invention.

In another embodiment, modulators of CoaX expression are identified in a method wherein a cell is contacted with a candidate compound and the expression of coaX mRNA or CoaX polypeptide in the cell is determined. The level of expression in the presence of the candidate compound is compared to the level of expression in the absence of the candidate compound (or to a suitable control, for example, an appropriate buffer control or standard). The candidate compound can then be identified as a modulator of coaX mRNA or CoaX polypeptide expression based on this comparison.

This invention further pertains to novel agents identified by the above-described screening assays. Accordingly, it is within the scope of this invention to further use an agent identified as described herein in an appropriate animal model. For example, an CoaX modulating agent identified as described herein (e.g., an anti-bactericidal compound) can be used in an infectious animal model to determine the efficacy, toxicity, or side effects of treatment with such an agent.

This invention is further illustrated by the following examples which should not be construed as limiting. The contents of all references, patents and published patent applications cited throughout this application are incorporated herein by reference.

EXAMPLES

General Methodology

Strains. *Bacillus subtilis* strains of the present invention are generally derived from either of two strains. The first is variously named "168", "1A1", or "RL-1". The genotype is trpC2. This strain was derived from the wild type "Marburg" strain by mutagenesis and has been the basis of much of the molecular biology work done on *B. subtilis*. The second strain is PY79, a prototrophic derivative of 168 that was made Trp$^+$ by transduction from the wild type strain W23.

Media. Standard minimal medium for *B. subtilis* is comprised of 1× Spizizen salts and 0.5% glucose. Standard solid "rich medium" is Tryptone Blood Agar Broth (Difco), and standard liquid "rich medium" is VY, a mixture of veal infusion broth and yeast extract. For testing production of pantothenate in liquid test tube cultures, an enriched form of VY, called "Special VY" or "SVY" is used. For batch fermentations, SVYG and PFMG are used. The compositions of these media are given below.

VY, a rich liquid medium: 25 g Difco Veal Infusion Broth, 5 g Difco Yeast Extract, 1 L water (autoclave).

TBAB, a rich solid medium: 33 g Difco Tryptone Blood Agar Broth, 1 L water (autoclave).

MIN, a minimal medium: 100 ml 10× Spizizen salts; 10 ml 50% glucose; 2 ml 10% arginine HCl*; 10 ml 0.8% tryptophan**; water to 1 liter. (*In some cases, arginine is omitted or replace by sodium glutamate at 0.04% final concentration. In general, *B. subtilis* grows faster in minimal medium when certain amino acids, such as arginine, glutamine, glutamate, or proline, are added as an auxiliary nitrogen source.) (**For strains that are tryptophan auxotrophs, tryptophan is routinely added to most minimal media.)

10× Spizizen Salts: 174 g $K_2HPO_4.3H_2O$; 20 g $(NH_4)_2SO_4$; 60 g $KH_2PO_4$; 10 g $Na_3Citrate-2H_2O$; 2 g $MgSO_4.7H_2O$; water to 993 mls; then add 3.5 ml $FeCl_3$ solution and 3.5 ml Trace Elements solution.

$FeCl_3$ Solution: 4 g $FeCl_3.6H_2O$; 197 g $Na_3Citrate\ 2H_2O$; water to 1 liter (filter sterilize)

Trace Elements Solution: 0.15 g $Na_2MoO_4.2H_2O$; 2.5 g $H_3BO_3$; 0.7 g $CoCl_2.6H_2O$; 0.25 g $CuSO_4.5H_2O$; 1.6 g $MnCl_2.4H_2O$; 0.3 g $ZnSO_4.7H_2O$; water to 1 liter (filter sterilize).

SVY, Special VY, a supplemented* rich medium for testing pantothenate production in test tube cultures: 25 g Difco Veal Infusion Broth; 5 g Difco yeast extract; 5 g sodium glutamate; 2.7 g ammonium sulfate; 740 ml water (autoclave); add 200 ml 1 M potassium phosphate, pH 7.0; 60 ml 50% glucose. (*For testing pantothenate production in liquid SVY test tube cultures, Na α-ketoisovalerate and/or β-alanine can be added to a concentration of 5 g/L from filter-sterilized stocks.)

PFMG, a yeast extract based medium used infermentors: 20 g Amberex 1003™ yeast extract; 5 g sodium glutamate, 2 g ammonium sulfate; 5 g tryptophan; 10 g $KH_2PO4$; 20 g $K_2HPO_4.3H_2O$; 1 g $MgCl_2.6H_2O$; 0.1 g $CaCl_2.2H_2O$; 1 g sodium citrate; 0.01 g $FeSO_4.7H_2O$; 1 ml trace elements solution; 20 g glucose; add water to 1 L. Glucose or other sugars are fed as needed. Feed solutions can contain minerals, defined or food grade nutrients.

PF, a chemically defined pantothenate free medium for testing pantothenate auxotrophy: 100 ml 10× Spizizen Salts; 100 ml 1× Difco Pantothenate Assay Medium; 10 ml 50% glucose; water to 1 liter.

For pantothenate auxotrophs, 1 mM Na pantothenate is added to both minimal and rich media, since there is generally not enough pantothenate in rich media to support *B. subtilis* pan mutants. Amino acids are at 100 mg per liter, when used. Selection for antibiotic resistance is done with 5 mg/L chloramphenicol, 100 mg/L spectinomycin HCl, 15 mg/L tetracycline HCl, or 1 mg/L erythromycin plus 25 mg/L lincomycin.

Pantothenate Assays: Biological assay. The indicator organism, *Lactobacillus plantarum*, requires: pantothenate for growth, and responds to low concentrations (µg/L). Thus, using serial dilutions, a wide range of concentrations can be assayed. Commercially available medium (e.g., Pantothenate Assay Medium (PAM), Difco), can be used. However, Difco PAM supplemented with pantothenate does not support growth to the same level as obtainable using a fresh-mixed version of Pantothenate Assay Medium (FM-PAM), made up of the individual components as specified by Difco, which is accordingly, routinely used instead of the commercial product.

Before assaying *B. subtilis* culture supernatants, the *B. subtilis* cells must be either removed or killed. *B. subtilis* culture supernatants give approximately the same pantothenate titer when the supernatants are autoclaved as when they are sterile filtered. Accordingly, routine procedures involve autoclaving samples for 5 minutes prior to the biological assay.

Pantothenate Assays: HPLC assay. Pantothenic acid production is measured by HPLC with a detector wavelength of 197 nm and a reference at 450 nm. The procedure is a modification of one recommended by Hewlett-Packard for water soluble vitamins. Samples of culture broth are diluted into an equal volume of 60% acetonitrile (ACN), centrifuged and filtered. Typically a further 10-fold dilution before analysis brings the final dilution to 20-fold. Higher concentrations of product are diluted further. Compounds are separated on a C18 Phenomenex 5µ Aqua 250×4.6 mm column with 5% acetonitrile (ACN) in 50 mM Na phosphate buffer at pH 2.5. An ACN gradient from 5% to 95% washes the column between every sample. The area of the pantothenate peak is proportional to the concentration between 5 to 1000 mg/L. Other panto-compounds are also separated and quantitated by this method.

Amino Acid Analysis: HPLC assay. Amino acids present in the fermentation medium and throughout the fermentation are measured by HPLC with a detector wavelength of 338 nm and a reference at 390 nm. The procedure is a modification of one recommended by Hewlett-Packard for amino acid analysis. Samples of culture broth are prepared identically as for the panto-compound analysis. Compounds are separated on a C18 Hypersil 5µ ODS 200×2.1 mm column. Solvent A is 20 mM Na acetate buffer at pH 7.2. Solvent B contains 40% ACN and 40% methanol. A gradient from 100% Solvent A to 100% Solvent B separates amino acids and washes the column between every sample.

Batch Fermentations. Pantothenate producing strains are grown in stirred tank fermentors, for example, in CF3000 Chemap 14 liter vessels with 10 liter working volumes. Computer control and data collection is by commercial software, for example, B. Braun Biotech MFCS software. Fermentations can be batch processes but are preferably sugar-limited, fed batch processes. Some media components (e.g. of SVYG and PMFG) are added to the fermentor and sterilized in place. Portions of the media are sterilized separately and added to the fermentors aseptically. This procedure is well known to those familiar with the art. Additional nitrogen sources in feeds are sterilized separately and added to the carbon source after cooling.

The initial sugar in the medium is consumed in approximately 6 hours. Afterwards, glucose or other sugars are fed with the possible addition of minerals, and defined or food grade nutrients. Alternatively, feeds are scheduled based on a consensus profile of nutritional requirements from samples taken from earlier fermentations.

After inoculation, agitation is set at a relatively low speed, e.g. 200 rpm. When the dissolved oxygen (pO2) falls to 30%, computer control automatically adjusts the agitation to maintain a dissolved oxygen concentration between 25 and 30% pO2.

Example I

Enhanced Production of a Panto-Compound Using Bacteria Overexpressing panBCD Gene Products This Example describes the cloning of the *B. subtilis* panBCD operon and the generation of microorganisms overexpressing the panBCD gene products.

To clone the *B. subtilis* panBCD operon, a plasmid library of *B. subtilis* GP275 (a derivative of 168) genomic DNA was transformed in *E. coli* BM4062 (birA$^{ts}$), and temperature resistant clones were selected at 42° C. By comparison of restriction maps to the genome sequence, one particular clone was deduced to contain the *B. subtilis* birA gene and the adjacent panBCD genes. This plasmid was named pAN201.

To overexpress the panBCD operon and produce pantothenate, the native promoter of the panBCD operon was replaced by either of two strong, constitutive promoters derived from the *B. subtilis* bacteriophage SP 01. These two promoters are named $P_{26}$ and $P_{15}$. In addition, either of two artificial ribosome binding sites (RBSs) were used to replace the native panB RBS. These two artificial RBSs (set forth as SEQ ID NO:49 and SEQ ID NO:50) were predicted to increase translation of panBCD; their sequences are shown in Table 1A. Three such engineered panBCD expression cassettes were built into circular plasmids capable of replicating in *E. coli*. Other features of the plasmids include a strong rho-independent transcription terminator from the *E. coli* ribosomal RNA transcription unit, called $T_1T_2$, a Gram-positive chloramphenicol resistance gene (cat), derived from pC194, and a pair of NotI restriction sites at the junctions between the *E. coli* replicon and the segment intended for integration into *B. subtilis*. Three plasmids of this series, pAN004, pAN005, and pAN006 were constructed. pAN004 contains the $P_{26}$ promoter, RBS 1, and a low copy *E. coli* replicon. pAN005 contains the $P_{15}$ promoter, which in our experience is not as strong as $P_{26}$, RBS1, and the low copy replicon. pAN006 contains the $P_{26}$ promoter, RBS2, and a medium copy replicon.

The three panBCD expression cassettes contained in the above-mentioned three plasmids were all ligated to a DNA fragment consisting of sequences that naturally occur immediately upstream from the native panB gene and integrated in single copy by homologous recombination into the panBCD locus of *B. subtilis* strains RL-1 and PY79, replacing the wild-type operon. This was accomplished in two steps. First a deletion-substitution that replaced about two thirds of the panB coding region with a Gram-positive spectinomycin resistance gene (spec) was integrated at panb to yield Spec$^-$, pantothenate auxotrophs. These intermediate strains were than transformed with the panBCD expression cassettes of pAN004, pAN005, and pAN006 after ligating them to a DNA fragment containing chromosomal sequences just upstream of panB. Selection of the incoming cassette was for pantothenate prototrophy. The resulting strains were named PA221, PA222 and PA223 (from RL-1), and PA235, PA232 and PA233 (from PY79), respectively. An example of a plasmid that contains the joined upstream sequence that is in the integrated strain in PA221 is pAN240 (see FIG. 2). The nucleotide sequence of pAN240 is set forth as SEQ ID NO:76.

Polymerase chain reaction using appropriate primers was used to verify the correct chromosomal structures of these engineered strains. When extracts of strain PA221 were examined by SDS-PAGE, two proteins were found to be overexpressed. One protein had an apparent molecular weight of 29,000 and the other protein appeared to be 39,000 daltons. The 29,000 dalton bands is presumably PanB (predicted molecular weight of 29,761). The larger protein band presumably represents PanC (predicted size 31,960 daltons).

The ability of these strains to produce pantothenate in test tube cultures was assesed as follows. Each strain was grown in SVY medium supplemented with 5 g/L α-ketoisovalerate (α-KIV) and 5 g/L β-alanine, to ensure that these precursors were not limiting. Culture supernatants were autoclaved and assayed using the bioassay. Relative to the parent strains, RL-1 and PY79, the engineered strains produced about 8- to 30-fold more pantothenate, attaining 1 g/L pantothenate in some cases.

TABLE 2

Production of pantothenate by engineered *B. subtilis* strains in liquid test tube cultures grown in SVY medium with 5 g/L α-KIV and 5 g/L β-alanine.

| Expt. | Strain | Promoter | RBS at panB | [pantothenate] mg/L |
|---|---|---|---|---|
| 1 | RL-1 | Native | Native | 30 |
|   | PA221 | $P_{26}$ | RBS1 | 990 |
|   |       |          |      | 790 |
|   | PA222 | $P_{15}$ | RBS1 | 250 |
|   |       |          |      | 250 |
|   | PA223 | $P_{26}$ | RBS2 | 790 |
|   |       |          |      | 790 |
| 2 | PY79 | Native | Native | 40 |
|   | PA235 | $P_{26}$ | RBS1 | 930 |
|   |       |          |      | 860 |
|   | PA221 | $P_{26}$ | RBS1 | 1100 |
|   |       |          |      | 1030 |

The $P_{26}$ promoter was about 3- to 4-fold more effective than the $P_{15}$ promoter, while RBS1 and RBS2 were roughly equivalent. Plasmids such as pAN004, pAN005, pAN006 can also be recombined as circles into the *B. subtilis* wild type panBCD locus by Campbell-type (single crossover) integration, selecting for chloramphenicol resistance at 5 mg/L. Strains obtained in this fashion produce about the same amount of pantothenate as strains PA221, PA222, and PA223, respectively. pAN004 containing the $P_{26}$ promoter, RBS 1 and a low copy *E. coli* replicon, is depicted schematically in FIG. 3A. The nucleotide sequence of plasmid pAN004 is set forth as SEQ ID NO:93. pAN006 containing the $P_{26}$ promoter, RBS2 and a medium copy *E. coli* replicon, is depicted schematically in FIG. 3B. The nucleotide sequence of plasmid pAN006 is set forth as SEQ ID NO:94. The nucleotide sequence of panBCD is set forth as SEQ ID NO:59 and the predicted amino acid sequences of PanB, PanC and PanD are set forth as SEQ ID NO:24, SEQ ID NO:26 and SEQ ID NO:28, respectively. Methods for manipulating *Bacilli* are described, for example, in Harwood, C. R. and Cutting, S. M. (editors), Molecular Biological Methods for *Bacillus* (1990) John Wiley & Sons, Ltd., Chichester, England, the content of which is incorporated herein by reference.

Example II

Enhanced Production of a Panto-Compound Using Bacteria Overexpressing the panE1 Gene Product—Ketopantoate Reductase This Example describes the cloning of the *B. subtilis* panE1 gene and the generation of microorganisms overexpressing the panE1 gene product.

Pan⁻ *B. subtilis* strains (e.g., *B. subtilis* mutants blocked in the synthesis of pantothenic acid) had previously been isolated, one of which was reported to be affected in ketopantoate reductase activity (Baigori et al. (1991) *J. Bacteriol.* 173:4240-4242). However, the mutations in these strains were incorrectly mapped to the purE-tre interval of the *B. subtilis* genetic map which does not contain the panE or panBCD genes. Furthermore as shown below, a panE mutant does not have a Pan⁻ phenotype as the ilvC gene product can substitute for the panE gene product in *B. subtilis* as in other bacterial strains such as *E. coli*. More recently, the *S. typhimuruim* panE gene has been located and determined to be allelic to apbA, a gene required for anaerobic purine biosynthesis (Frodyma et al. (1998) *J. Biol. Chem.* 273:5572-5576). *E. coli* carries a highly homologous gene at the same map location. Identification of the panE genes in *E. coli* and *S. typhimurium* was complicated by the fact that the ilvC gene product, acetohydroxy acid isomeroreductase, is also capable of carrying out the ketopantoate reductase reaction. As a result, pantothenate auxotrophy is not obtained unless both panE and ilvC are mutated.

To identify the *B. subtilis* panE1 gene, the *B. subtilis* genome was searched using the protein sequence of *E. coli* or *S. typhimurium* ApbA (PanE), and two open reading frames were identified having homology to ApbA, named ylbQ and ykpB. These genes were renamed panE1 and panE2, due to their proposed function in pantothenate biosynthesis. Both panE1 and panE2 were cloned as PCR products generated from RL-1 genomic DNA as a template. Both genes were disrupted by either a spectinomycin resistance gene (spec) or a chloramphenicol resistance gene (cat). The interrupted genes were each integrated by double crossover into PY79 to give PA240 (ΔpanE1::spec) and PA241 (ΔPanE2::cat). Neither of these strains were pantothenate auxotrophs when tested on pantothenate-free (PF) plates, although PA240 containing ΔPanE1::spec grew slightly more slowly on TBAB without added pantothenate than with a 1 mM pantothenate supplement. By comparison, a ΔPanB::spec strain does not produce single colonies on TBAB, presumably because *B. subtilis* has no active uptake system for pantothenate.

It was hypothesized that the *B. subtilis* gene, ilvC, could function for panE as had been shown for *E. coli*. Accordingly, the panE1 and panE2 disruptions were introduced into a strain, CU550, which is reported to be trpC2 ilvC4 leuC124. Both the single panE1 and the double panE1, panE2 disruptants were pantothenate auxotrophs on PF medium.

TABLE 3

Phenotypes of various panE1 and panE2 mutants on rich and defined media.

| | | Growth*: | |
|---|---|---|---|
| Strain | Medium | −pan | +pan |
| PY79 | TBAB | +++ | +++ |
|      | PF   | ++  | ++  |
| PA240 | TBAB spec | + | +++ |
|       | PF        | ++ | ++ |

TABLE 3-continued

Phenotypes of various panE1 and panE2 mutants on rich and defined media.

| Strain | Medium | Growth*: -pan | Growth*: +pan |
|---|---|---|---|
| PA241 | TBAB cam | +++ | +++ |
|  | PF | ++ | ++ |
| CU550 | TBAB | +++ | +++ |
|  | PF | ++ | ++ |
| PA256 | TBAB spec | − | +++ |
|  | PF | − | ++ |
| PA258 | TBAB spec, cam | − | +++ |
|  | PF | − | ++ |

*Each "+" represents about 1 mm of colony diameter after overnight at 37° C.

Thus, mutating both panE1 and ilvC results in pantothenate auxotrophy, while mutating only panE1 does not, similar to what has been reported for E. coli and S. typhimurium.

Next, the quantitative effect of panE1 and panE2 knockouts in a pantothenate overproducing strain (PA235 described herein) was examined. The panE1 and panE2 disruptions were introduced into PA235, either singly or together to produce PA245 (ΔpanE1::spec), PA248 (ΔPanE2::cat) and PA244 (ΔpanE1::cat, ΔpanE2::spec). The effect of each mutation on pantothenate production was then tested in liquid test tube cultures.

TABLE 4

Pantothenate production by PA235 derivatives containing panE1 and panE2 disruptions.

| Strain | [pan] mg/L | % of PA235 |
|---|---|---|
| PA235 | 990 | (100) |
| PA235 | 940 | 95 |
| PA245 | 59 | 6 |
| PA245 | 82 | 8 |
| PA248 | 1060 | 106 |
| PA248 | 1030 | 104 |
| PA244 | 25 | 3 |
| PA244 | 50 | 5 |

Thus, deletion analysis indicated that the panE1 gene contributes to over 90% of the pantothenate production, while deletion of panE2 did not have a significant effect on pantothenate production. It is therefore concluded that panE1 accounts for most, but not necessarily all, of the ketopantoate reductase activity in B. subtilis. The rest of the ketopantoate reductase activity is predicted to be supplied by ilvC.

Having identified panE1 as an important gene for pantothenate production, increased panE1 expression was tested to determine whether it could enhance pantothenate production in strains such as PA221 or PA235. The panE1 coding sequence was installed downstream of the $P_{26}$ promoter and RBS2 in a vector, pOTP61, designed to integrate and amplify at either the bpr locus (a non-essential protease gene) or at the locus of the cloned insert. The resulting plasmid, pAN236 (FIG. 4) was transformed into PA221, selecting for resistance to tetracycline at 15 mg/L. The nucleotide sequence of pAN236 is set forth as SEQ ID NO:77. One transformant, named PA236 was chosen for further study.

PA236 was shown to overexpress a protein of about 31,000 daltons, which is close to the expected molecular weight of 33,290 daltons for panE1 protein. Briefly, whole cell extracts were prepared from PY79, RL-1, PA221, PA221/pOTP61 and PA236 (2 samples). Cell extracts were separated by gel electrophoresis and the gels were coomassie stained to visualize proteins. In cells engineered to overexpress panE (PA236-1 and PA236-2), a band was visible having an approximate molecular weight of ~31,000 daltons (as compared to molecular weight markers). Moreover, PA221 and PA236 expressed increased levels of a ~29,000 dalton band, corresponding to the panB gene product, and a ~39,000 dalton band, presumably corresponding the panC gene product. Furthermore, E. coli transformed with pAN006 (FIG. 3B) expressed bands correlating to the panB and panC gene products and E. coli transfected with PAN236 expressed a ~31,000 dalton band corresponding to the panE gene product.

Next, PA236 was compared to PA221 carrying the empty vector pOTP61 for pantothenate production in liquid test tube cultures supplemented with 5 g/L β-alanine and 5 g/L α-KIV.

TABLE 5

Effect of overexpression of panE1 and panE2 on pantothenate production by engineered strains in liquid test tube cultures.

| Strain | Additional Plasmid | Gene Overexpressed | [Pantothenate] mg/L |
|---|---|---|---|
| PA221 | pOTP61 | none | 1,000 |
|  |  |  | 940 |
| PA236 | pAN236 | panE1 | 2,030 |
|  |  |  | 2,050 |
| PA238 | pAN238 | panE2 | 530 |
|  |  |  | 680 |

Overexpression of panE1 caused a two-fold increase in pantothenate production when compared to the parent strain (e.g., to slightly over 2 g/L) whereas overexpression of panE2 resulted in a strain that produced about 35% less pantothenate than the parent strain. The panE1 nucleotide sequence and predicted amino acid sequence are set forth as SEQ ID NO:29 and SEQ ID NO:30.

Example III

Enhanced Production of a Panto-Compound by Culturing Bacteria Overexpressing panE1 or panBCD in the Presence of Valine The ability of valine to function as a media supplement (e.g., as a substitute for α-KIV) in strains engineered to overexpress the panBCD operon and panE1 was evaluated. Valine is closely related to α-KIV by transamination, is less expensive than A-KIV, and is commercially available in kilogram quantities. Valine was substituted for α-KIV in the standard liquid test tube cultures in SVY medium. The concentration of valine was varied from 5 to 50 g/L. Although valine at 5 g/L was slightly less effective than α-KIV in promoting pantothenate production, valine at 10 or 20 g/L equaled or surpassed 5 g/L α-KIV in promoting pantothenate production.

Examples IV-X

Generation of Microorganisms Capable of Producing Pantothenate in a Precursor-Independent Manner B. subtilis strains such as PA221 and PA235 (engineered to overexpress panBCD) and PA236 (engineered to overexpress panBCD and panE1) need to be fed α-ketoisovalerate (α-KIV) (or valine) and aspartate (or β-alanine) to achieve maximal pantothenate production, as both these precursors are limiting for pantothenate synthesis. Accordingly, manipulated microorganisms were designed to eliminate the need to feed limiting precursors of pantothenate biosynthesis in the production of pantothenate. These strains are also useful in the production of various pantothenate biosynthetic pathway intermediates.

Example IV

Figure 5:
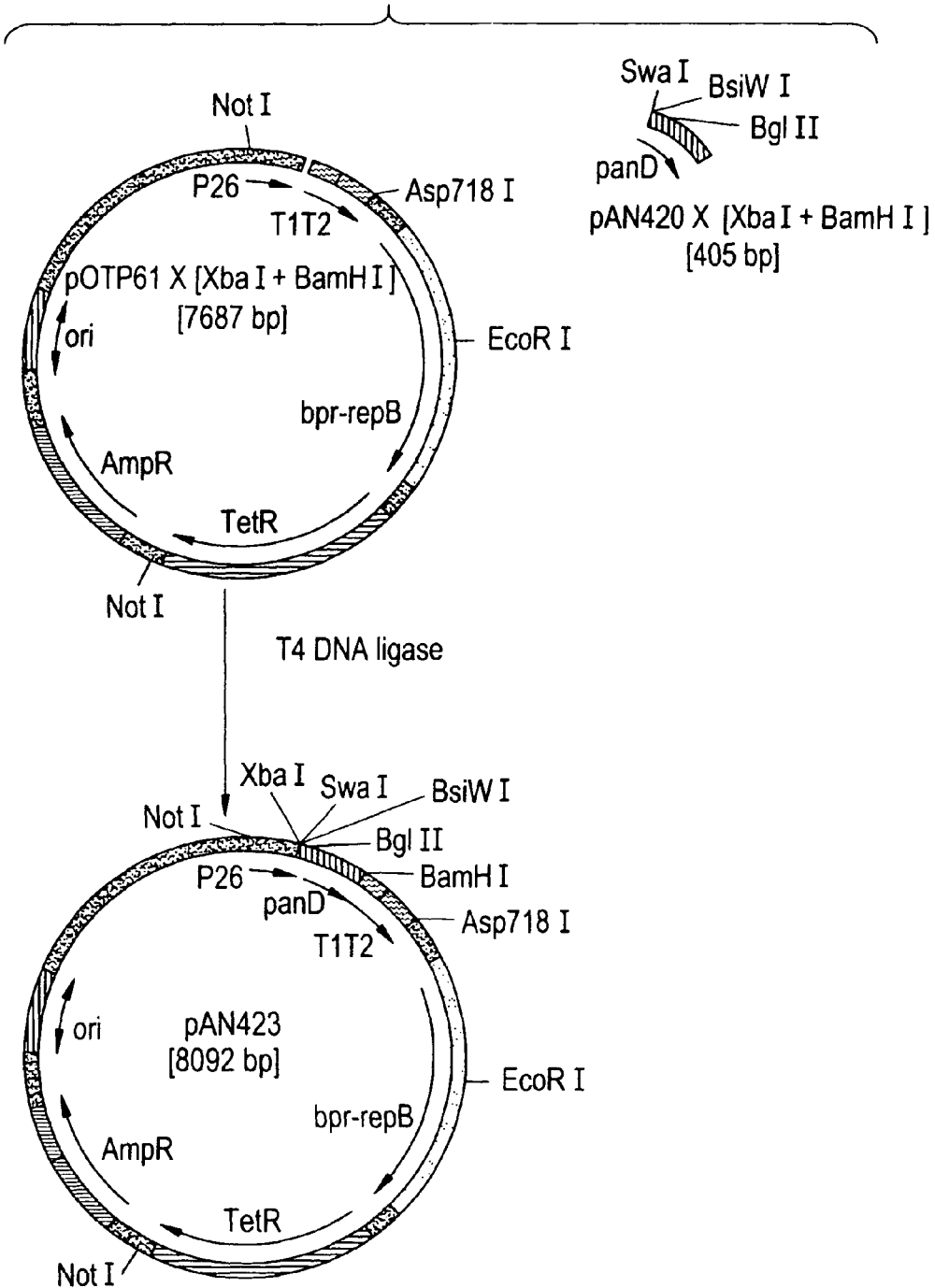
FIG. 5 is a schematic representation of the construction of plasmid pAN423.

Generation of Microorganisms Capable of Producing Pantothenate in an Aspartate- (or β-Alanine) Independent Manner The panD gene was cloned into *B. subtilis* expression vector pOTP61 to construct pAN423 (FIG. 5). The nucleotide sequence of pAN423 is set forth as SEQ ID NO:78. The NotI restriction fragment containing panD was isolated from pAN423, self ligated and used to transform PA221. Transformants resistant to Tet[15], Tet[30], and Tet[60] were isolated and saved for further analysis.

Six of the pAN423 transformants plus two control transformants were grown in SVY containing 5 g/l α-KIV with and without 10 g/l aspartate and then assayed for pantothenate production (Table 6).

TABLE 6

Effect of overproducing PanD on pantothenate production with and without added aspartate.

| Culture* (PA221 transformants) | Asp (10 g/L) | TetR** (µg/ml) | OD$_{550}$ | [pan] (mg/L) |
|---|---|---|---|---|
| pOTP61-1 | − | 60 | 8.0 | 76 |
| pOTP61-2 | − | 60 | 7.7 | 91 |
| 423#1-1 | − | 15 | 8.5 | 180 |
| 423#1-2 | − | 15 | 8.0 | 150 |
| 423#1-3 | − | 30 | 8.3 | 220 |
| 423#1-4 | − | 30 | 8.5 | 280 |
| 423#1-5 | − | 60 | 8.9 | 580 |
| 423#1-6 | − | 60 | 8.8 | 280 |
| pOTP61-1 | + | 60 | 7.5 | 380 |
| pOTP61-2 | + | 60 | 6.9 | 560 |
| 423#1-1 | + | 15 | 8.5 | 1200 |
| 423#1-2 | + | 15 | 8.6 | 1000 |
| 423#1-3 | + | 30 | 8.8 | 1200 |
| 423#1-4 | + | 30 | 9.0 | 1200 |
| 423#1-5 | + | 60 | 9.0 | 1200 |
| 423#1-6 | + | 60 | 9.0 | 1200 |

*Test tubes cultures were grown in SVY + α-KIV (5 g/L) with Asp (10 g/L) where indicated.
**TetR = Approximate Tet-resistance of transformant The pAN423 transformants produced at least twice the amount of pantothenate as the controls (i.e., to a level at or near that which was obtained in earlier experiments by the addition of β-alanine to the culture medium). The data also show that in the absence of added aspartate, transformants containing additional copies of the panD gene expression cassette produce more pantothenate than the control transformants. One of the transformants, 423#1-5, produced about five times as much pantothenate as the controls. These results indicated that increased levels of PanD protein "pull" the conversion of available aspartate towards β-alanine, and that increasing panD gene expression can result in enhancement of pantothenate production both in the presence and absence of added aspartate.

Transformant 423#1-5 was re-named strain PA401 and studied further in shake flask fermentations. The shake flask medium was SVY with maltose instead of SVY with glucose. Results of shake flask experiments agreed well with test tube experiments during the first 24 hours. In shake flask experiments without the addition of β-alanine, PA401 produced approximately 1.5 g/l of pantothenate in 24 hours. Addition of β-alanine to the culture medium did not further improve pantothenate titers (Table 7), indicating that with this strain and these fermentation conditions, β-alanine is not limiting pantothenate production. In fact, when no β-alanine is fed, one can observe that PA401 is secreting β-alanine in significant amounts into the medium.

TABLE 7

Shake flask cultures with strain PA401 (panD) with and without β-alanine.

| Initial | | 24 hours | | | |
|---|---|---|---|---|---|
| β-ala | Amino acids (g/l) | | | | Pantothenate |
| Added | β-ala | Val | pH | OD$_{600}$ | (g/l) |
| 0 | 0.7 | 1.5 | 7.5 | 13.7 | 1.5 |
| 5 g/l | 7.1 | 1.4 | 7.6 | 12.4 | 1.5 |

Each value represents the average of duplicate 250 ml baffled flasks containing 50 ml of medium, incubated at 37° C. with shaking (200 rpm).
Base Medium: SVY with 10 g/l α-KIV, 30 g/l maltose
2% Inoculum: SVY with Tet[15] grown 24 hours.

Example V

Engineering the panD gene for Further Increased Synthesis of Aspartate Decarboxylase and Enhanced Production of Pantothenate This Example describes the generation of improved ribosome binding sites (RBSs) in the panD gene to increase the translation of panD mRNA.
Increasing the Translation of the panD Gene mRNA by Generation of Synthetic panD RBSs The RBS (SEQ ID NO:88) used to express panD in pAN423 is a synthetic RBS and has been used to successfully produce other proteins in *B. subtilis* at a high level. However, it contains six mismatches when aligned to the "ideal" *B. subtilis* RBS (SEQ ID NO:45) (e.g., an RBS having a sequence which is complementary to the 16S RNA sequence within the *B. subtilis* ribosome). (See e.g., Table 1B, mismatches in bold). Two new RBSs were designed to more closely mimic the ideal RBS. These synthetic RBSs, named new design A (NDA) and new design B (NDB) (also referred to herein as RBS3 and RBS4), are set forth as SEQ ID NO:51 and SEQ ID NO:52 and are aligned with the ideal RBS in Table 1B.

Figure 6:
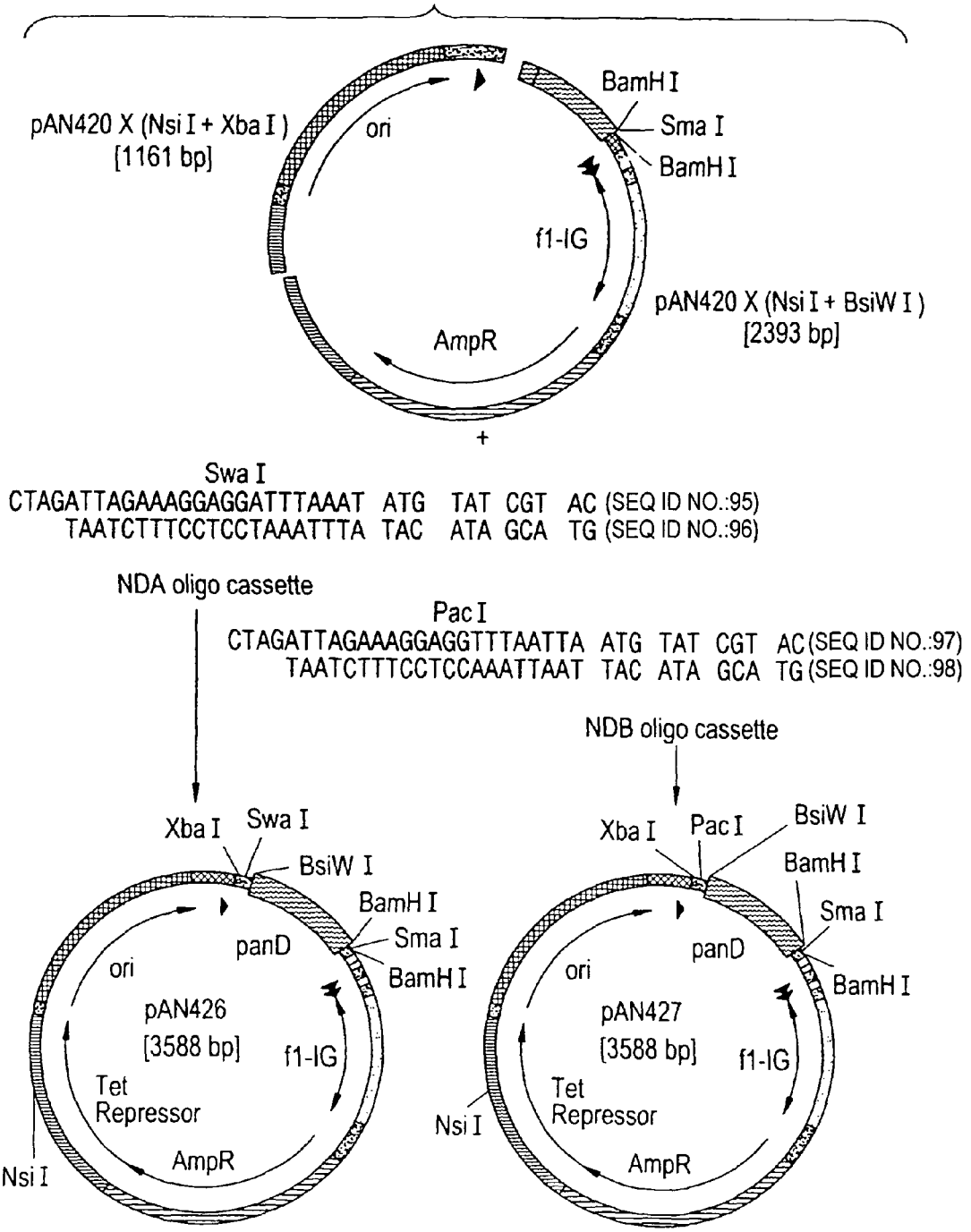
FIG. 6 is a schematic representation of the construction of plasmids pAN426 and pAN427.
Figure 7:
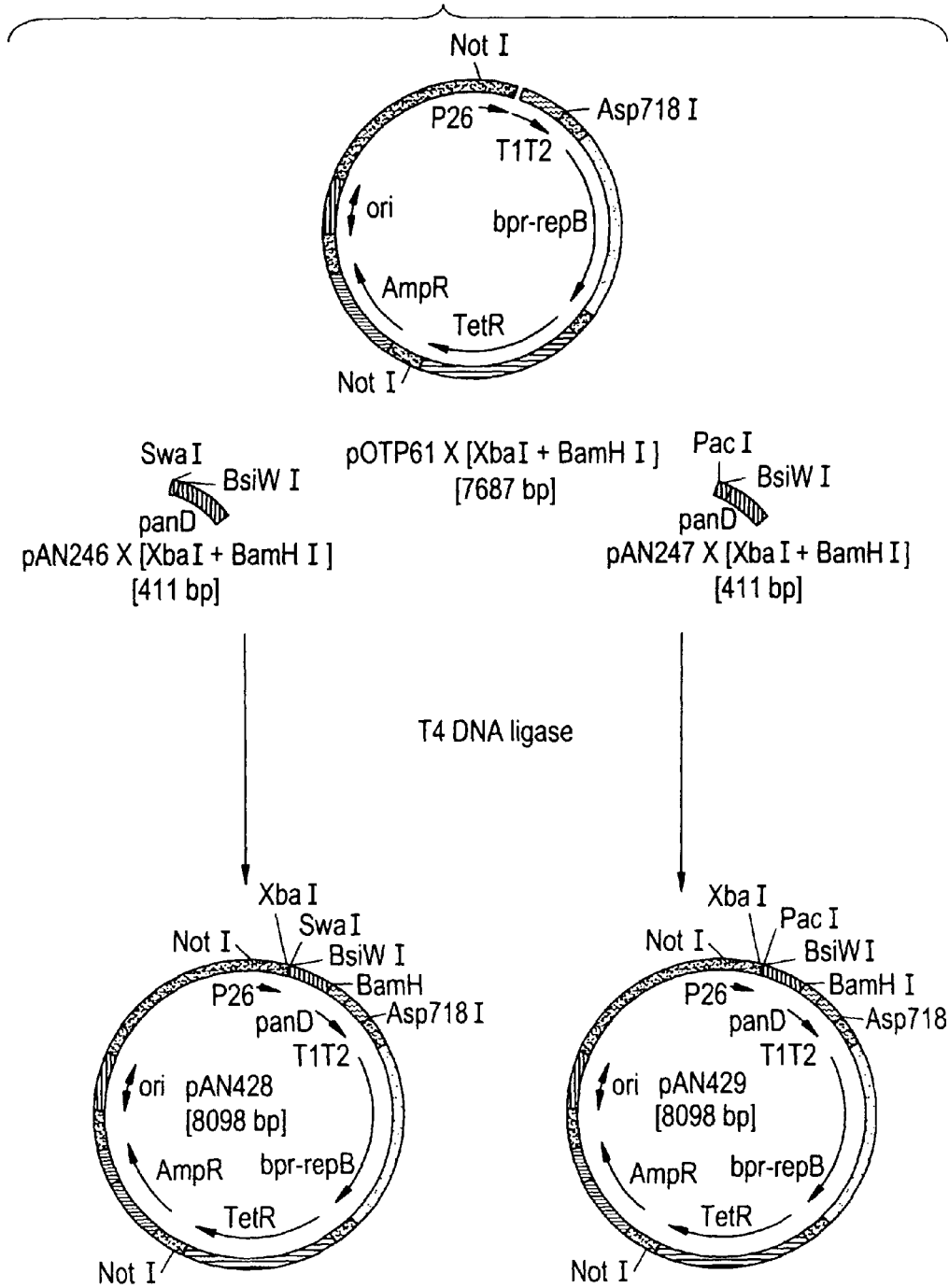
FIG. 7 is a schematic representation of the construction of plasmids pAN428 and pAN429.

Oligonucleotides corresponding to the top and bottom strands of each new RBS were synthesized, annealed, then used to replace the RBS in pAN420, generating plasmids pAN426 and pAN427. These constructions are illustrated in FIG. 6. The presence of the NDA and NDB RBS in pAN426 and pAN427 was confirmed by DNA sequence analysis. Next, the panD genes from pAN426 and pAN427 were transferred to *B. subtilis* expression vector pOTP61 as shown in FIG. 7, creating pAN428 and pAN429. The nucleotide sequence of pAN429 is set forth as SEQ ID NO:79.

NotI restriction fragments lacking the *E. coli* vector sequences were isolated from pAN428 and pAN429, self-ligated, and used to transform strain PA221 to resistance to Tet[15]. Four isolates resistant to Tet[60] were picked from each transformation and assayed for pantothenate and β-alanine production along with PA221 transformed with the empty vector (pOTP61) and PA221 transformed with pAN423 (strain PA401) (see Table 8).

TABLE 8

Panthothenate production by test tube cultures of PA221 transformed with pAN428 and pAN429

| Plasmid | Medium Supplements | OD$_{550}$ | Pan g/l | β-Ala g/l |
|---|---|---|---|---|
| pOTP61 | α-KIV$^5$ | 10 | UND | 0.04 |
| pAN423 | α-KIV$^5$ | 10 | 0.4 | 0.04 |
| pAN428-1* | α-KIV$^5$ | 12 | 0.6 | 0.04 |
| pAN428-2 | α-KIV$^5$ | 11 | 0.5 | 0.03 |
| pAN428-3 | α-KIV$^5$ | 11 | 0.3 | 0.03 |
| pAN428-4 | α-KIV$^5$ | 10 | 0.1 | UND |
| pAN429-1 | α-KIV$^5$ | 12 | 0.6 | 0.04 |
| pAN429-2 | α-KIV$^5$ | 11 | 0.5 | 0.04 |
| pAN429-3 | α-KIV$^5$ | 11 | 0.6 | 0.05 |
| pAN429-4# | α-KIV$^5$ | 12 | 0.8 | 0.10 |
| pOTP61 | α-KIV$^5$ + Asp$^{10}$ | 11 | 0.5 | 0.08 |
| pAN423 | α-KIV$^5$ + Asp$^{10}$ | 12 | 0.9 | 1.32 |
| pAN428-1* | α-KIV$^5$ + Asp$^{10}$ | 12 | 0.8 | 1.97 |
| pAN428-2 | α-KIV$^5$ + Asp$^{10}$ | 12 | 0.8 | 1.51 |
| pAN428-3 | α-KIV$^5$ + Asp$^{10}$ | 12 | 0.9 | 1.02 |
| pAN428-4 | α-KIV$^5$ + Asp$^{10}$ | 11 | 0.8 | 0.30 |
| pAN429-1 | α-KIV$^5$ + Asp$^{10}$ | 12 | 0.8 | 1.78 |
| pAN429-2 | α-KIV$^5$ + Asp$^{10}$ | 12 | 0.8 | 1.66 |
| pAN429-3 | α-KIV$^5$ + Asp$^{10}$ | 12 | 0.8 | 1.78 |
| pAN429-4# | α-KIV$^5$ + Asp$^{10}$ | 13 | 0.8 | 2.28 |

UND: Below the limits of detection.
*Renamed PA402
Renamed PA403

When grown in medium supplemented with α-KIV at 5 g/l (α-KIV$^5$), the pAN428-1 transformant and all four of the pAN429 transformants produced more pantothenate than did PA401, suggesting that these transformants contain higher levels of aspartate decarboxylase activity. When grown in medium supplemented with α-KIV$^5$ and Asp$^{10}$ none of the pAN428 or pAN429 transformants produced more pantothenate than PA401. However, the pAN428-1 transformant and all four of the pAN429 transformants produced significantly more β-alanine than did PA401. It is possible that the excess β-alanine produced from added aspartate causes inhibition of pantothenate production. Alternatively, β-alanine may accumulate because pantoate is limiting in these strains.

The strains that produced the highest level of β-alanine, the pAN428-1 and pAN429-4 transformants, were renamed PA402 and PA403, respectively. These two strains were grown in SVY medium supplemented with various intermediates and reassayed for pantothenate and β-alanine production. PA221 and PA401 were included as controls. The results of the assays are presented in Table 9.

TABLE 9

Pantothenate production of PA402 and PA403 in test tube cultures.

| Strain | Medium Supplements | OD$_{550}$ | Pan g/l | β-Ala g/l | Val g/l |
|---|---|---|---|---|---|
| PA221 | α-KIV$^5$ | 7.9 | UND | UND | 0.9 |
| PA401 | α-KIV$^5$ | 8.7 | 0.3 | 0.04 | 0.9 |
| PA402 | α-KIV$^5$ | 8.5 | 0.5 | 0.04 | 0.9 |
| PA403 | α-KIV$^5$ | 9.4 | 0.7 | 0.07 | 0.9 |
| PA221 | α-KIV$^5$ + Asp$^{10}$ | 9.8 | 0.4 | 0.11 | 0.8 |
| PA401 | α-KIV$^5$ + Asp$^{10}$ | 9.1 | 0.8 | 1.15 | 0.8 |
| PA402 | α-KIV$^5$ + Asp$^{10}$ | 9.4 | 0.8 | 2.02 | 0.8 |
| PA403 | α-KIV$^5$ + Asp$^{10}$ | 9.7 | 0.7 | 2.40 | 0.8 |
| PA221 | Pantoate$^5$ | 8.9 | UND | UND | 0.2 |
| PA401 | Pantoate$^5$ | 8.7 | 0.3 | 0.02 | 0.2 |
| PA402 | Pantoate$^5$ | 10.6 | 0.5 | 0.02 | 0.2 |
| PA403 | Pantoate$^5$ | 10.5 | 0.7 | 0.02 | 0.2 |
| PA221 | Pantoate$^5$ + Asp$^{10}$ | 9.5 | 0.4 | 0.06 | 0.2 |
| PA401 | Pantoate$^5$ + Asp$^{10}$ | 9.2 | 2.2 | 0.62 | 0.2 |
| PA402 | Pantoate$^5$ + Asp$^{10}$ | 9.1 | 2.8 | 1.17 | 0.2 |
| PA403 | Pantoate$^5$ + Asp$^{10}$ | 10.2 | 2.9 | 1.58 | 0.2 |

UND: Below the limits of detection.

When grown in medium supplemented with either α-KIV$^5$ or Pantoate$^5$, PA402 and PA403 produced significantly more pantothenate than did PA401. As before, even though PA402 and PA403 produced significantly more β-alanine than PA401 when grown in medium supplemented with α-KIV$^5$ and Asp$^{10}$, they did not produce a proportional increase in pantothenate. However, when grown in medium supplemented with Pantoate$^5$ plus Asp$^{10}$, both PA402 and PA403 produced significantly more pantothenate than PA401, about a 30% increase.

It can be concluded from these experiments that the improved NDA and NDB panD ribosome binding sites, engineered into pAN428 and pAN429, respectively, lead to increased levels of aspartate decarboxylase activity.

Increasing the Translation of the panD Gene mRNA by Generation of Synthetic panD RBSs within the panBCD Operon The native *B. subtilis* panD gene ribosome binding site (RBS) (SEQ ID NO:43), which is found in the P$_{26}$panBCD operon cassette present in PA221 (and in other engineered pantothenate production strains described herein), is shown in Table 1C aligned with the ideal ribosome binding site (SEQ ID NO:47). The alignment shows mismatches between the native *B. subtilis* panD gene RBS, which is located within the coding sequence for PanC, and the the ideal RBS. Three new RBSs (within the P26 panBCD operon cassette) were generated to increase translation of the panD gene mRNA and to yield increased synthesis of aspartate decarboxylase. These synthetic RBSs (termed NDI, NDII, and NDIII, also referred to herein as RBS5, RBS6 and RBS7, respectively) are set forth as SEQ ID NO:55, SEQ ID NO:56 and SEQ ID NO:57, respectively) and are included in Table 1C. It should be noted that although changes in the panD RBS within the panBCD operon also changes the C-terminal amino acid sequence of the PanC protein encoded by that operon, an alignment of known and suspected PanC protein amino acid sequences showed that the sequence of the last nine amino acids of the *B. subtilis* PanC protein could be altered without affecting any conserved amino acid residues indicating that such changes should not reduce pantothenate synthetase activity or expression. The new RBSs were synthesized and incorporated into the P$_{26}$panBCD operon expression cassette as follows.

Figure 8:
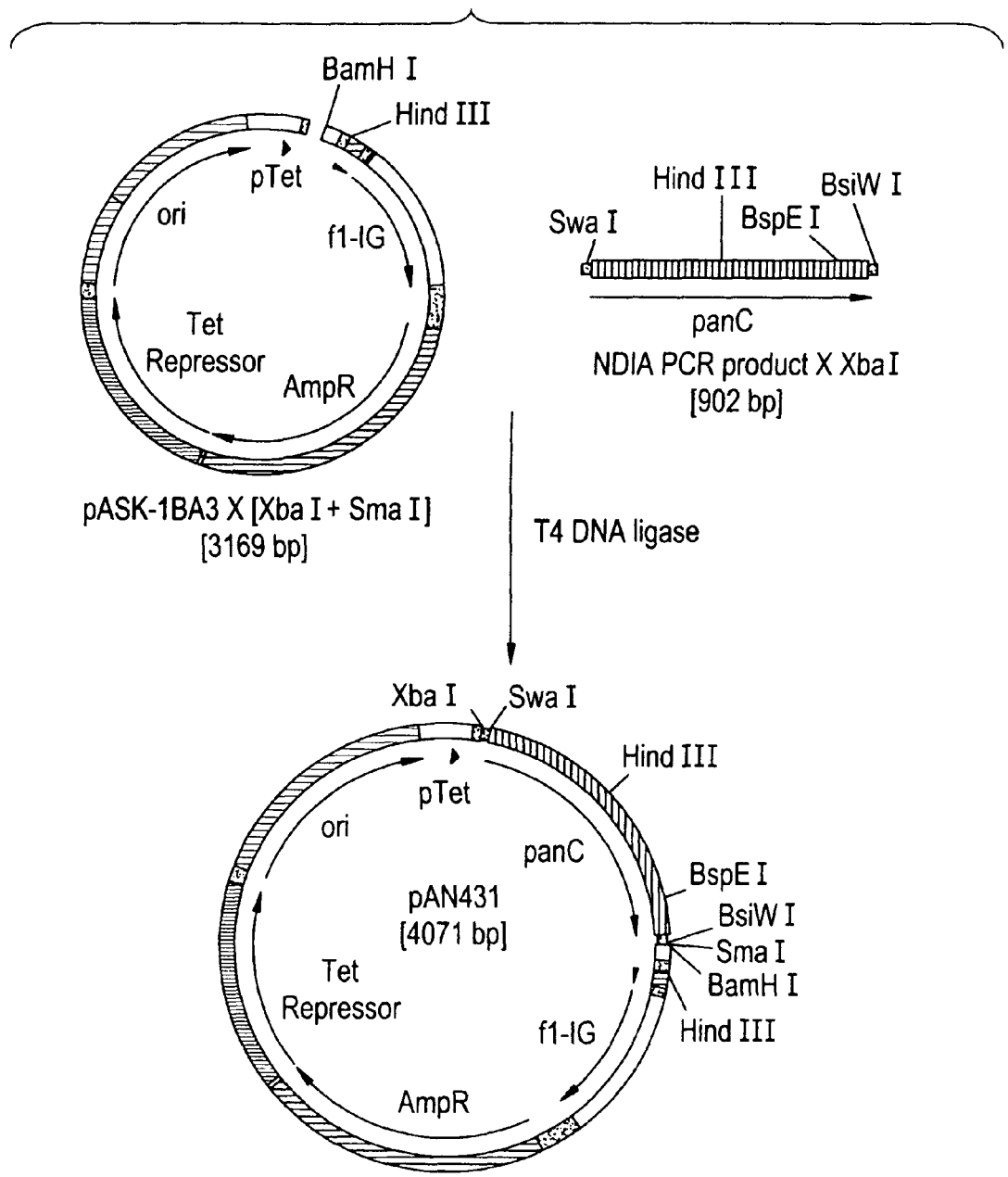
FIG. 8 is a schematic representation of the construction of plasmid pAN431.

First, PCR primers were designed to contain the following elements: (1) a nucleic acid sequence encoding the first five amino acids of PanD up to and including a unique BsiWI restriction site that had been previously introduced into panD by PCR; (2) a stop codon for panC, (3) at least one synthetic RBS; and (4) 30-39 bp of nucleic acid sequence having 100% identity with panC upstream of the panD RBS. The primers were named TP102, TP103, and TP104 and contain the NDI, NDII, and NDIII ribosome binding sites, respectively. These three primers were used in conjunction with the 5' primer TP101, which hybridizes near the start codon of panC, in three independent PCR reactions to generate the NDI, NDII, and NDIII PCR products. The PCR products were purified, digested with XbaI, then cloned into plasmid vector pASK- 1BA3 which had been digested with XbaI and SmaI. The resulting plasmids were named pAN431, pAN432, and pAN433. The construction of pAN431 is illustrated in FIG. 8 and is representative of all three plasmid constructions. The presence of the desired synthetic panD gene RBS in each new plasmid was confirmed by DNA sequencing.

Figure 9:
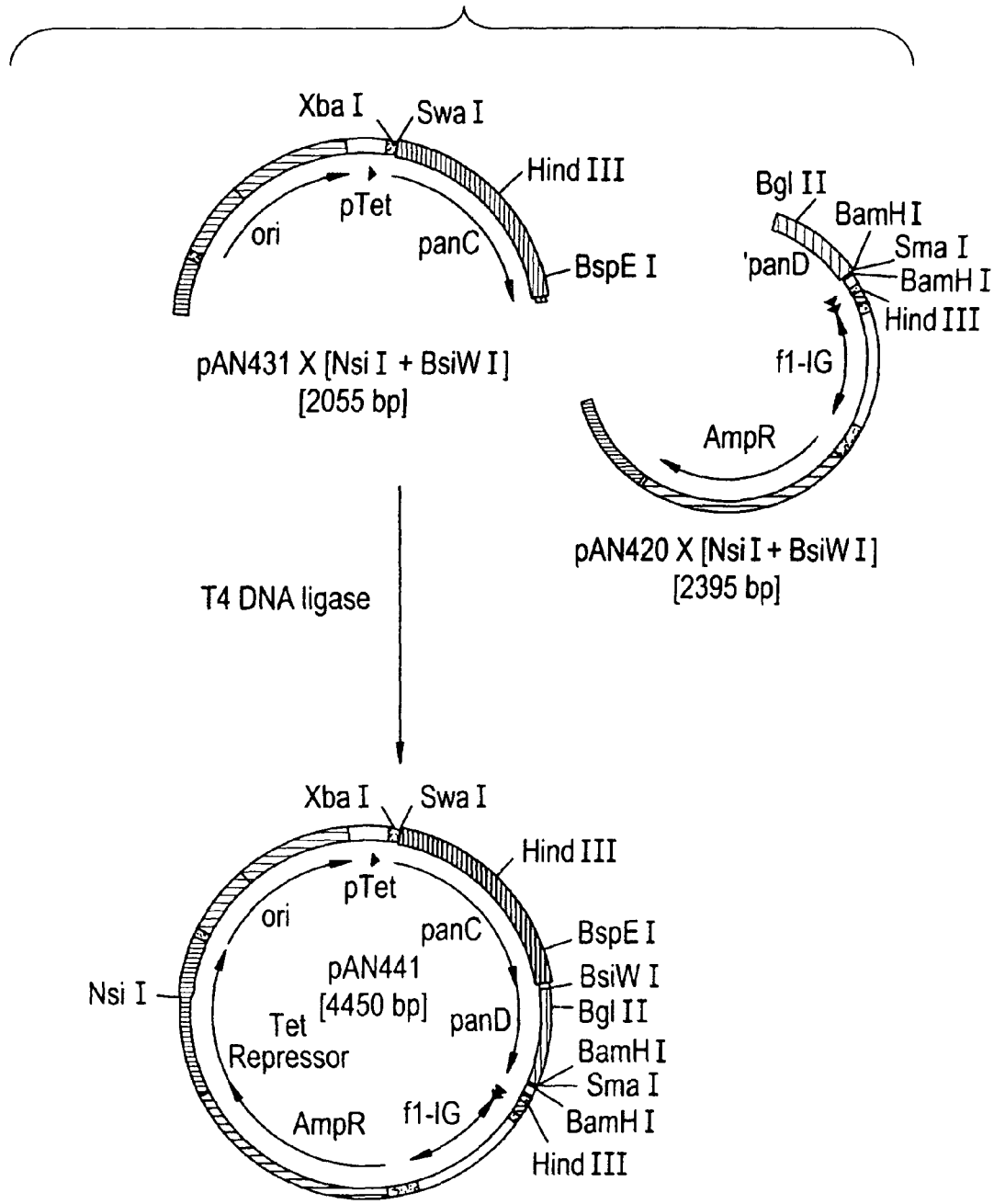
FIG. 9 is a schematic representation of the construction of plasmid pAN441.

Next, the modified panC genes containing the new panD RBSs were joined with the panD gene utilizing the unique BsiWI restriction site. This was accomplished by isolating the appropriate NsiI-BsiWI restriction fragments from pAN431, pAN432, and pAN433 and ligating them with a 2395 bp NsiI-BsiWI restriction fragment from pAN420, which supplied the BsiWI-modified panD gene. These constructions resulted in plasmids pAN441, pAN442, and pAN443, respectively. A representative construction (pAN441) is illustrated in FIG. 9. The nucleotide sequence of pAN443 is set forth as SEQ ID NO:80.

Figure 10:
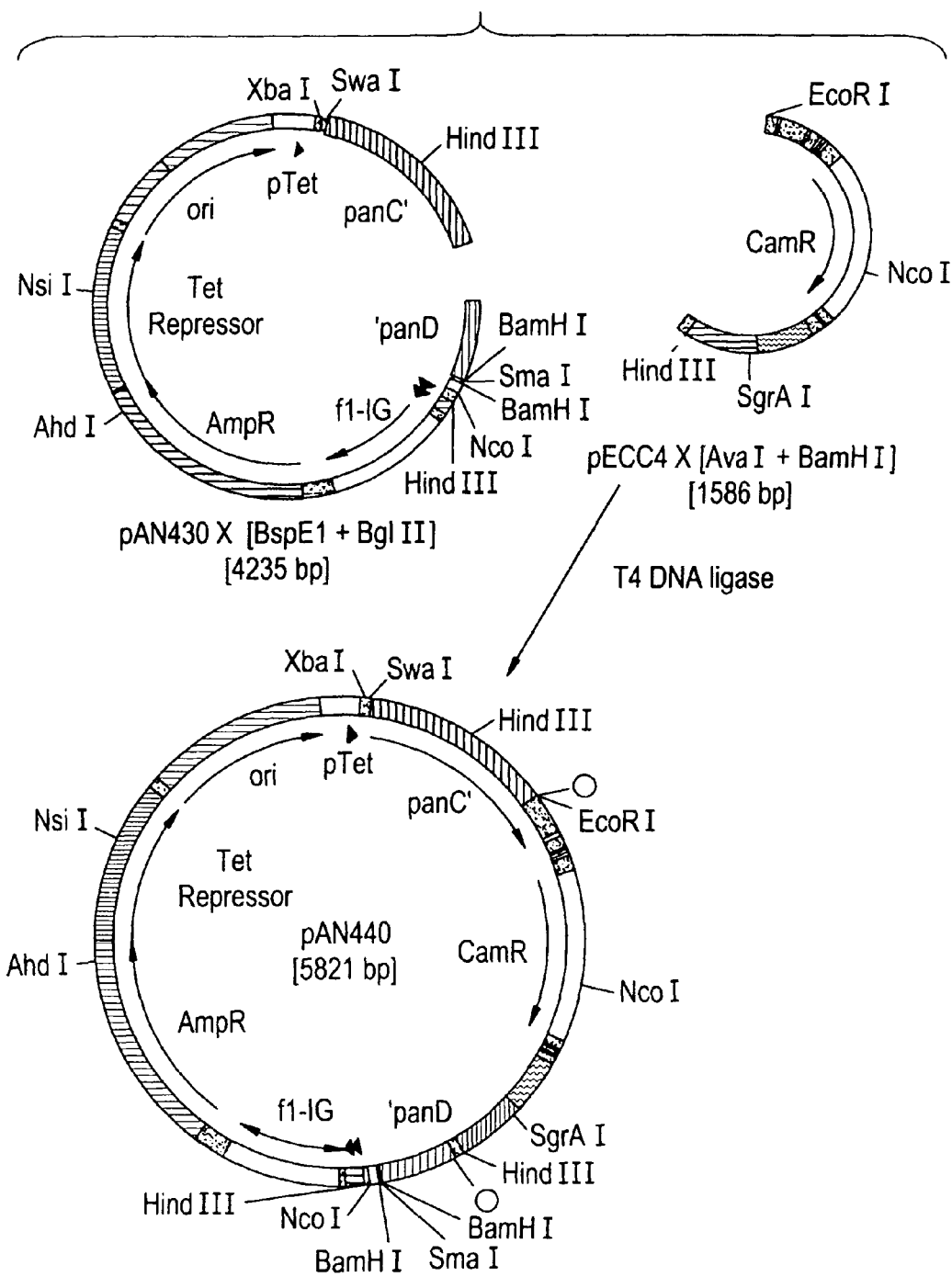
FIG. 10 is a schematic representation of the construction of plasmid pAN440.

The new panD gene RBSs were then substituted into the $P_{26}$panBCD operon expression cassette as follows. First, a deletion-insertion mutation which removes the region of panC containing the panD RBS was created. This was constructed by digesting pAN430 with a mixture of BspE1 and BglII and recovering the 4235 bp fragment which is now missing the 3' end of panC and the 5' end of panD. This fragment was ligated with an AvaI-BamHI restriction fragment from plasmid pECC4, which contains the chloramphenicol acetyl transferase (cat) gene. The 5' extension produced by AvaI digestion is compatible with that produced by BspE1 while the BglII and BamHI extensions are also compatible. The resulting plasmid was named pAN440, and its construction is illustrated in FIG. 10.

The resulting deletion-insertion mutation was crossed into the $P_{26}$ panBCD operon via homologous recombination by transforming PA221 with linearized pAN440 and selecting for resistance to chloramphenicol on $Cam^5$ plates containing 1 mM pantothenate. Several transformants were tested, and were all found to require 1 mM pantothenate for growth, as expected. Two of these transformants were renamed PA408A and PA408B and were assayed for pantothenate production. Neither strain synthesized measurable quantities of pantothenate, even when grown in medium containing pantoate and β-alanine at 5 g/l, indicating that the strains are deficient in pantothenate synthetase activity. Next, the new panD RBSs were crossed into the $P_{26}$ panBCD operon by transforming PA408 with linearized pAN441, pAN442, and pAN443 plasmid DNA and selecting for growth on TBAB plates without pantothenate supplementation. A transformation with linearized pAN430 (including the native panD RBS) was included as a control and was expected to give rise to transformants identical to PA221 described herein. Four isolates from each transformation were assayed for pantothenate and β-alanine production in SVY medium supplemented with various intermediates (Tables 10 and 11).

TABLE 10

Pantothenate production of PA410-PA413 in test tube cultures.

| Strain | RBS | Medium Supplements | $OD_{550}$ | Pan g/l | β-Ala g/l |
|---|---|---|---|---|---|
| PA221 | native | Pantoate[5] | 11 | UND | UND |
| PA410-1 | native | Pantoate[5] | 12 | UND | UND |
| PA410-2 | | Pantoate[5] | 12 | UND | UND |
| PA410-3 | | Pantoate[5] | 12 | UND | UND |
| PA410-4 | | Pantoate[5] | 12 | UND | UND |
| PA411-1 | NDI | Pantoate[5] | 12 | 0.23 | UND |
| PA411-2 | | Pantoate[5] | 12 | 0.20 | UND |
| PA411-3 | | Pantoate[5] | 12 | 0.19 | UND |
| PA411-4 | | Pantoate[5] | 12 | UND | UND |
| PA412-1 | NDII | Pantoate[5] | 12 | UND | UND |
| PA412-2 | | Pantoate[5] | 11 | UND | UND |
| PA412-3 | | Pantoate[5] | 13 | 0.18 | UND |
| PA412-4 | | Pantoate[5] | 12 | 0.18 | UND |
| PA413-1 | NDIII | Pantoate[5] | 12 | 0.18 | UND |
| PA413-2 | | Pantoate[5] | 12 | 0.17 | UND |
| PA413-3 | | Pantoate[5] | 12 | 0.16 | UND |
| PA413-4 | | Pantoate[5] | 12 | 0.17 | UND |

UND: Below the limits of detection.

TABLE 11

Pantothenate production of PA410-PA413 in test tube cultures.

| Strain | RBS | Medium Supplements | $OD_{550}$ | Pan g/l | β-Ala g/l |
|---|---|---|---|---|---|
| PA221 | native | Pantoate[5] + Asp[10] | 11 | 0.3 | UND |
| PA410-1 | native | Pantoate[5] + Asp[10] | 12 | 0.4 | UND |
| PA410-2 | | Pantoate[5] + Asp[10] | 12 | 0.4 | UND |
| PA410-3 | | Pantoate[5] + Asp[10] | 12 | 0.4 | UND |
| PA410-4 | | Pantoate[5] + Asp[10] | 12 | 0.4 | UND |
| PA411-1 | NDI | Pantoate[5] + Asp[10] | 13 | 1.7 | 0.4 |
| PA411-2 | | Pantoate[5] + Asp[10] | 13 | 1.7 | 0.4 |
| PA411-3 | | Pantoate[5] + Asp[10] | 13 | 1.8 | 0.3 |
| PA411-4 | | Pantoate[5] + Asp[10] | 13 | 0.4 | UND |
| PA412-1 | NDII | Pantoate[5] + Asp[10] | 13 | 0.4 | UND |
| PA412-2 | | Pantoate[5] + Asp[10] | 12 | 0.4 | UND |
| PA412-3 | | Pantoate[5] + Asp[10] | 12 | 1.6 | 0.3 |
| PA412-4 | | Pantoate[5] + Asp[10] | 12 | 1.5 | 0.2 |
| PA413-1 | NDIII | Pantoate[5] + Asp[10] | 13 | 1.6 | 0.3 |
| PA413-2 | | Pantoate[5] + Asp[10] | 13 | 1.6 | 0.4 |
| PA413-3 | | Pantoate[5] + Asp[10] | 13 | 1.7 | 0.4 |
| PA413-4 | | Pantoate[5] + Asp[10] | 13 | 1.7 | 0.4 |

UND: Below the limits of detection.

As expected from previous experiments using PA221, none of the transformants that contained the native panD RBS produced measurable quantities of pantothenate when grown in medium supplemented with pantoate. However, nine of the twelve transformants expected to contain modified panD RBSs produced significant quantities of pantothenate (160-230 mg/l) under these conditions, indicating that they possess elevated levels of aspartate decarboxylase activity. When grown in medium supplemented with both pantoate and aspartate, these same nine transformants produced approximately four times more pantothenate than those with the native panD RBS. In addition, these nine transformants accumulated measurable quantities of β-alanine (230-410 mg/l). All transformants produced roughly equivalent quantities of pantothenate when grown in medium containing pantoate and β-alanine, demonstrating that each contains a functional pantothenate synthetase.

These data demonstrate that the synthetic panD RBSs are about four times more effective than the native panD RBS in directing translation of the panD gene mRNA and evidence the utility of such synthetic RBSs in enhancing pantothenate production. Additional approaches to increasing pantothenate production can include, for example, increasing the half-life of the panD gene mRNA, increasing the strength of the promoter for panD transcription and/or increasing the stability of the PanD protein.

Example VI

Construction of Strains Containing an Integrated $P_{26}$ panE1 Cassette without an Antibiotic Resistance Gene Example II describes the identification of the *B. subtilis* panE1 gene that encodes the enzyme responsible for the majority of the ketopantoate reductase activity in *B. subtilis*. PA236 (containing the pAN236 plasmid) produced about twice as much pantothenate (2 g/l) as its parent strain, PA221 (1 g/l) in 24 hour SVY test tube cultures. PA236 was presumed to contain an amplified (~3 copies) integrated pAN236 plasmid based on selection for tetracycline resistance (the tetR gene product being encoded on the pAN236 plasmid in addition to the $P_{26}$ panE1 cassette). Also useful in the methodologies of the present invention are strains that contain a single integrated unamplifiable copy of $P_{26}$ panE1 at the panE1 locus, for example, without an antibiotic resistance gene in the strain. Such a strain was generated as follows.

Figure 11:
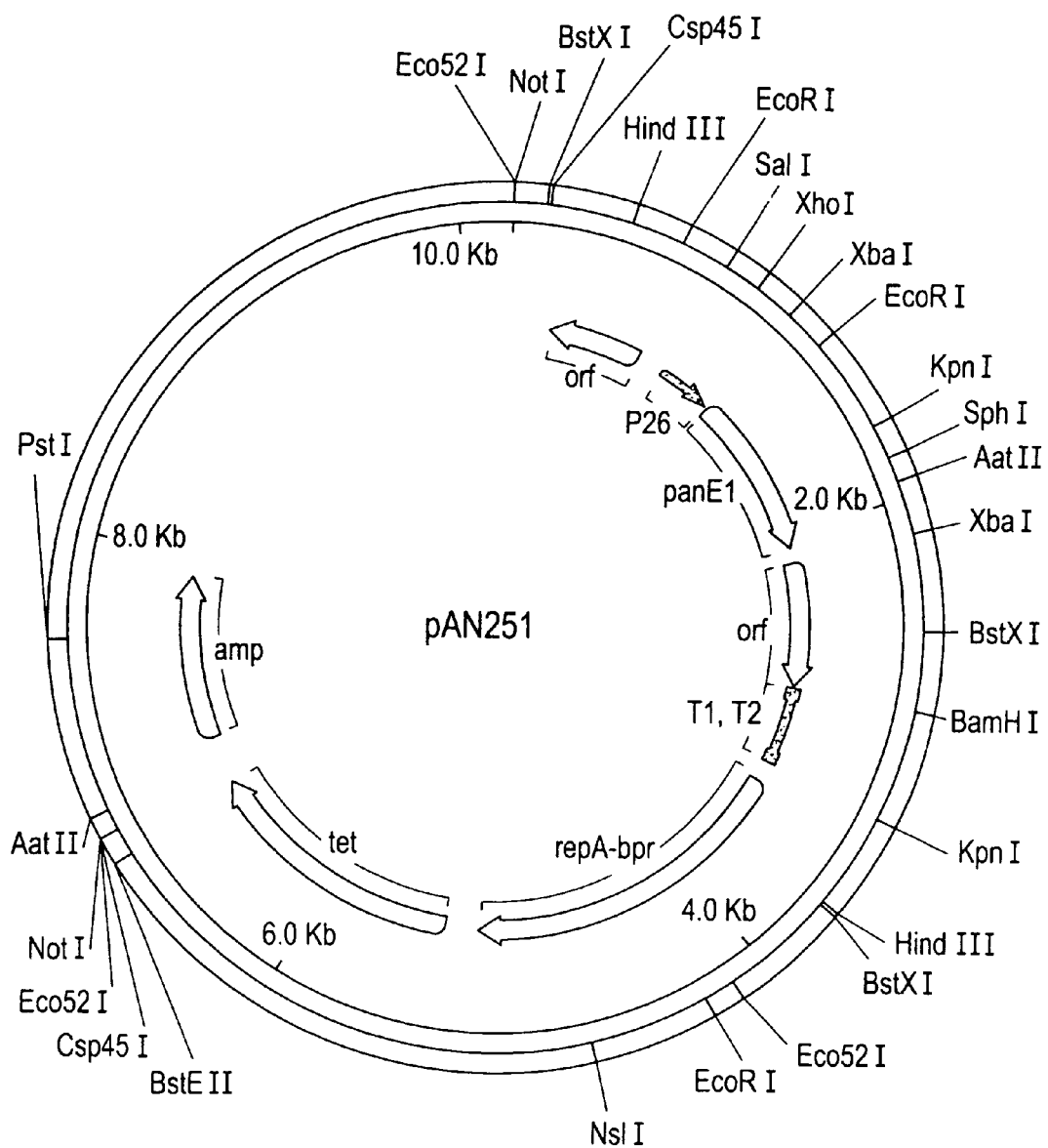
FIG. 11 is a schematic representation of the plasmid pAN251 designed to integrate a single copy of a $P_{26}$-panE1 cassette at the panE1 locus by double crossover.

A plasmid named pAN251 was derived from pAN236 by inserting additional chromosomal sequences just upstream and just downstream from the $P_{26}$ panE1 cassette. These additional sequences, which provide homology to allow integration of the $P_{26}$ panE1 cassette at panE1 by double crossover, were obtained by PCR from chromosomal DNA as a template. pAN251 is shown in FIG. 11. The nucleotide sequence of pAN251 is set forth as SEQ ID NO:81.

Next, a strain was constructed which allowed selection for the incoming $P_{26}$ panE1 cassette. The strain included the following three components: (1) $P_{26}$ panBCD; (2) ΔPanE1; and (3) ilvC, since both panE1 and ilvC must be mutated to have a Pan⁻ phenotype. The starting strain was CU550 (trpC2, ilvC4, leuC124). The $P_{26}$ panBCD cassette from PA221 chromosomal DNA was introduced in two steps to create strain PA290. Next, ΔPanE1::spec was transformed into PA290, using chromosomal DNA from strain PA240, to give strain PA294 (trpC2, ilvC4, leuC124, $P_{26}$ panBCD, ΔPanE1::spec), which is a strict pantothenate auxotroph. Finally, PA294 was transformed with plasmid pAN251, selecting for pantothenate prototrophy, to give strain PA303. This strain was expected to have the genotype trpC2, ilvC4, leuC124, $P_{26}$ panBCD, $P_{26}$ panE1. PA303 was checked for the correct chromosomal structure at the panE1 locus by PCR using primers that flank the $P_{26}$ insertion just upstream of panE1. The PCR product from PA303 was of the expected size, with a concomitant loss of the PCR product from the wild type panE1 gene, consistent with having obtained the desired double crossover event. Furthermore, PA303 was tetracycline sensitive, which is also consistent with the desired double crossover event, as opposed to a Campbell-type single crossover of the plasmids into the chromosome. The trp, ilv, and leu auxotrophies from the parent strain were all maintained in PA303.

In 24 hour liquid SVY test tube cultures, PA303 produced almost the same level of pantothenate as positive control PA236, and about twice as much as PA221, which does not contain engineered panE1 as indicated in Table 12.

TABLE 12

Pantothenate production by 24 hr. test tube cultures of PA303 and controls grown in SVY plus 5 g/l α-KIV and 5 g/l β-alanine.

| Strain | $OD_{600}$ | [pan] g/l |
|---|---|---|
| PA221-1 | 10.9 | 0.85 |
| PA221-2 | 10.5 | 0.85 |
| PA236-1 | 9.5 | 1.74 |
| PA236-2 | 9.3 | 1.70 |
| PA303-1 | 10.8 | 1.66 |
| PA303-2 | 10.7 | 1.61 |

Example VII

Generation of Microorganisms Capable of Producing Pantothenate in an α-KIV (or Valine) Independent Manner α-ketoisovalerate (α-KIV) is a rate limiting intermediate for pantothenate production in certain strains deregulated for pantothenate synthesis. Addition of either α-KIV or valine at 5 g/l increases pantothenate production about 5-fold in test tube cultures with strains such as PA221. In order to alleviate the need to feed either α-KIV or valine, strains were engineered that have an increased capacity to synthesize α-KIV.

α-KIV is produced in *B. subtilis* from pyruvate by the sequential action of three enzymes encoded by four genes, ilvB and ilvN, ilvC, and ilvD. In a wild type *B. subtilis*, three of the genes (ilvB, ilvN, and ilvC) are the first three genes of the large ilv-leu operon. The fourth gene necessary for α-KIV synthesis, ilvD, is located by itself elsewhere on the chromosome. The *B. subtilis* ilv-leu operon is thought to be regulated only by leucine levels. Feeding of exogenous leucine reduces transcription of the ilv-leu operon by about 13-fold, probably by an attenuation mechanism (Grandoni et al. (1992) *J. Bacteriol.* 174: 3212-3219). The only known feedback regulation in the ilv-leu pathway is the inhibition of the leuA gene product by leucine.

Figure 12:
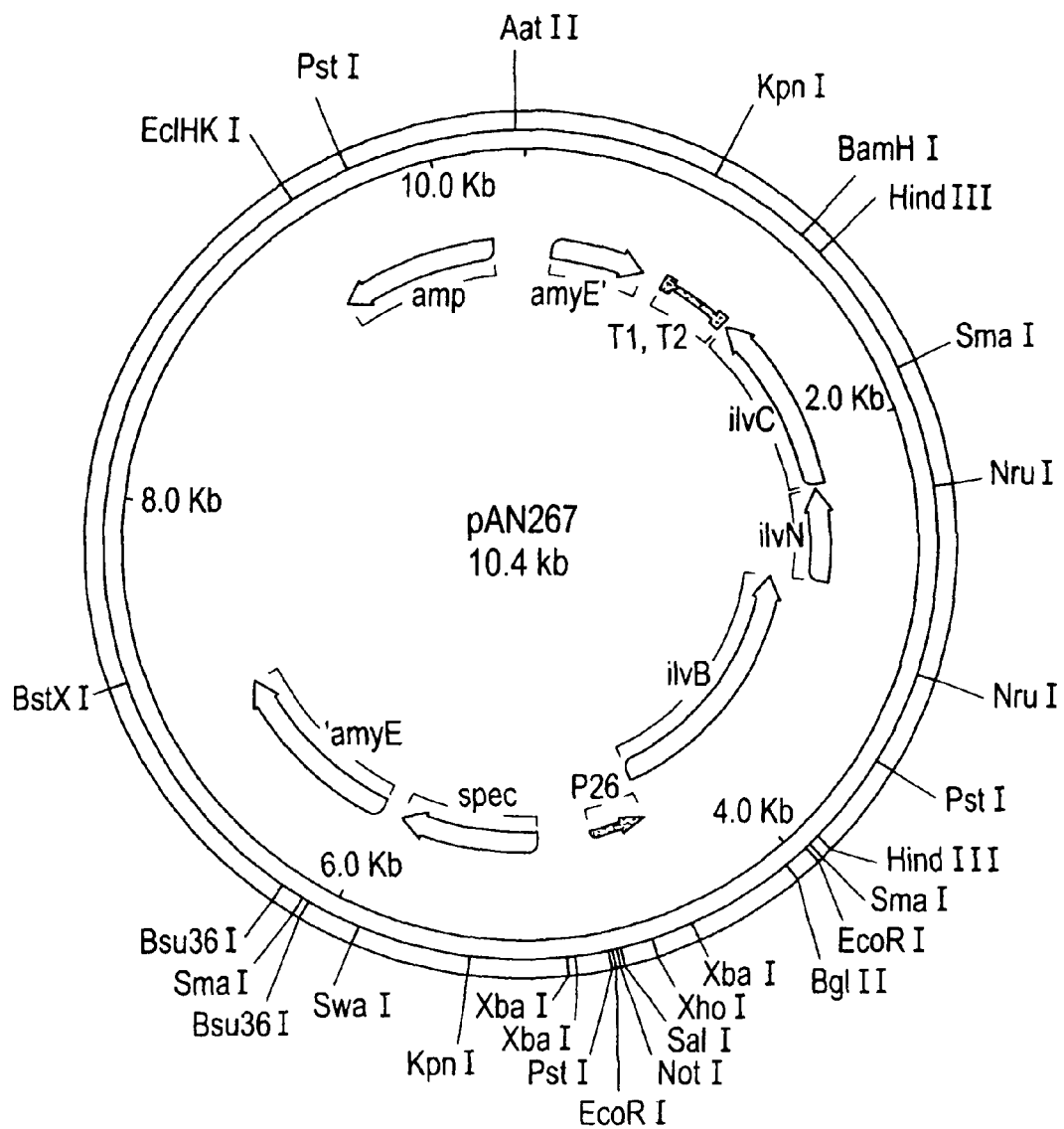
FIG. 12 is a schematic representation of the plasmid pAN267 designed to integrate a single copy of a $P_{26}$-ilvBNC cassette at the amyE locus.
Figure 13:
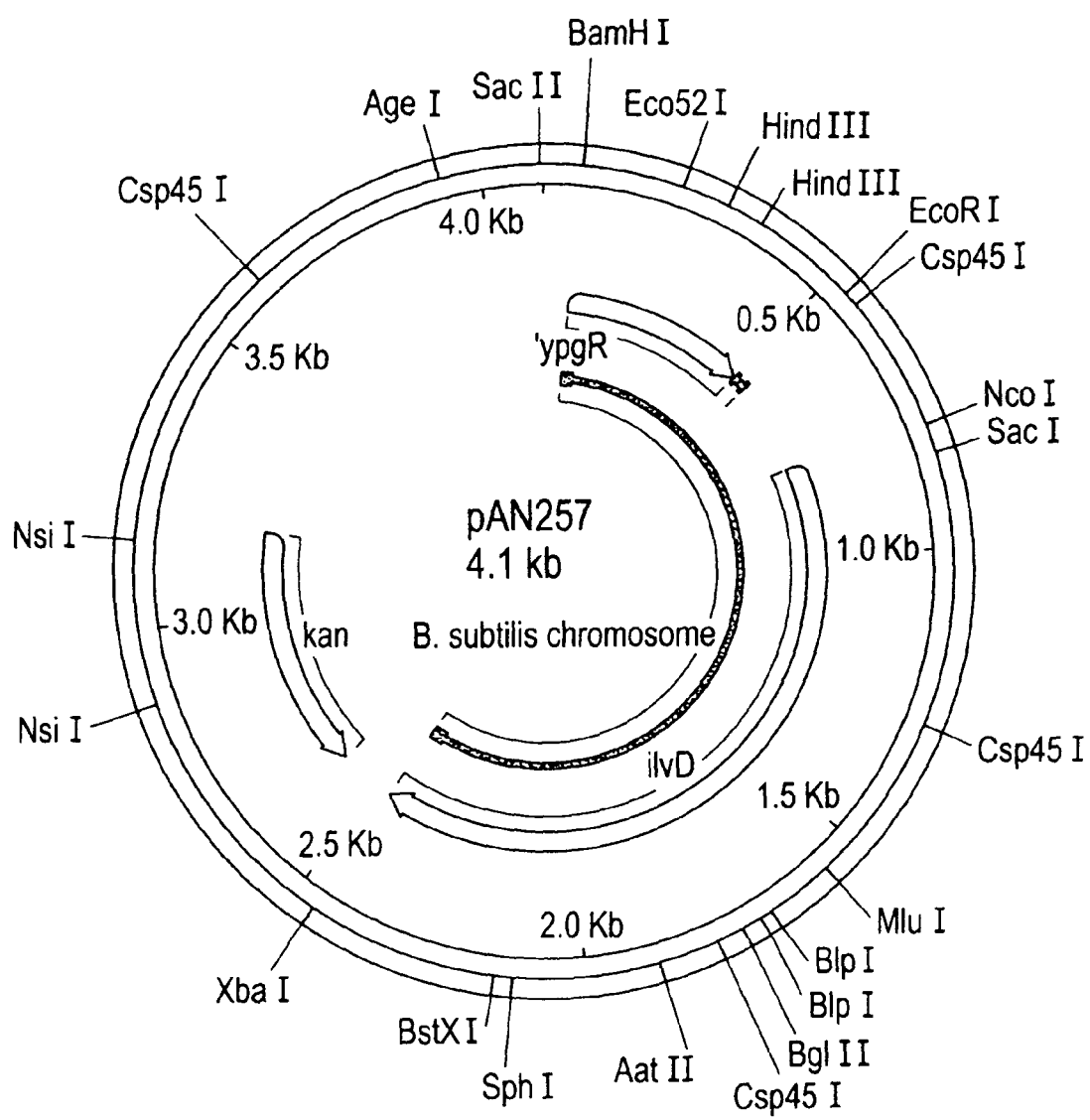
FIG. 13 is a schematic representation of the plasmid pAN257, a clone of *Bacillus subtilis* ilvD in a low copy vector.

As a first step to deregulate the synthesis of α-KIV, a copy of the ilvBNC region from the wild type *B. subtilis* ilv-leu operon was isolated by PCR, and installed adjacent to the $P_{26}$ promoter and RBS2 on a vector, pOLL8, that was designed to integrate a single $P_{26}$ expression cassette by double recombination at the amyE locus. The amyE gene encodes a nonessential α-amylase, and is a useful locus for installing expression cassettes. The resulting plasmid, pAN267, is illustrated in FIG. 12. The nucleotide sequence of pAN267 is set forth as SEQ ID NO:82. pAN267 readily gave stable transformants by double crossover at the amyE locus of *B. subtilis* strains, as described in detail below.

Construction of Pantothenate Overproducing Strains that are Leucine Prototrophs Initially, a *B. subtilis* strain containing ilvC4 and ΔPanE1 was used to introduce a single copy of $P_{26}$ panE1 into the chromosome without using an antibiotic resistance gene. The double mutant was required to select for the incoming $P_{26}$ panE1 cassette because a ΔPanE1 mutation alone does not result in pantothenate auxotrophy. A strain named CU550 was obtained containing ilvC4 to be used as a basis for this type of strain construction. However, CU550 also contains a closely linked leuC124 mutation, so all strains derived from CU550 required leucine. Having shown that the combination of $P_{26}$ panBCD and $P_{26}$ panE1 was favorable for pantothenate production, the next step was to reassemble this combination of two cassettes in a leucine prototroph.

Accordingly, the two cassettes were combined in two different strain backgrounds, RL-1 and PY79. To introduce chromosomal $P_{26}$ panE1 into the PY79 and RL-1 strain backgrounds without using an antibiotic resistance gene, a strategy was used that did not rely on ilvC4. (The strategy took advantage of the observation that the ΔPanE1 mutation causes a pantothenate bradytrophy, manifested by relatively small colonies on TBAB (rich) plates). First, ΔpanB::cat and ΔPanE::spec were introduced into both strain backgrounds. Next, the resulting strains were transformed simultaneously with DNA from two strains, PA221 ($P_{26}$ panBCD) and PA303 ($P_{26}$ panE1), selecting for Pan$^+$ on TBAB plates. Colonies of two distinct sizes grew on the selective plates, with the larger size comprising about 2% of the colonies. The larger colonies were presumed to represented co-transformants that received both $P_{26}$ panBCD and $P_{26}$ panE1, and that the smaller colonies had received only $P_{26}$ panBCD. Consistent with this prediction, the larger colonies had lost both Cam$^r$ and Spec$^r$, while the smaller colonies had lost only the cat gene, and retained the spec gene. Furthermore, a representative derivative of PY79 named PA327, and a representative derivative of RL-1, named PA328, both produced the elevated levels of pantothenate in test tube cultures which was about 1.6 to 1.7 g/l (Table 13).

TABLE 13

Pantothenate production of PA327, PA328, and controls from 24 hr test tube cultures grown in SVY plus 5 g/l α-KIV and β-alanine.

| Strain | Background | $P_{26}$ panE1 copy number | [pan] g/l |
|---|---|---|---|
| PA221-1 | RL-1 | 0 | 0.92 |
| PA221-2 | RL-1 | 0 | 0.95 |
| PA236-1 | RL-1 | amplified (~3) | 1.60 |
| PA236-2 | RL-1 | amplified (~3) | 1.73 |
| PA327-1 | PY79 | 1 | 1.66 |
| PA327-2 | PY79 | 1 | 1.65 |
| PA328-1 | RL-1 | 1 | 1.61 |
| PA328-2 | RL-1 | 1 | 1.91 |

Thus, PA327 and PA328 were concluded to contain both $P_{26}$ panBCD and $P_{26}$ panE1, and were used for further constructions as described below. PCR analysis confirmed the presence of the two cassettes.

Installation of a Stable P26 ilvBNC Cassette into Two Lineages of Pantothenate Overproducing Strains Having constructed PA327 and PA328, derivatives of PY79 and RL-1 that contain P26 panBCD and P26 panE1, and that are Leu$^+$, the next step was to introduce stable copies of P26 ilvBNC. This was accomplished by transforming PA327 and PA328 with plasmid pAN267, selecting for Spec$^r$. Screening by PCR showed that about 85% of the obtained transformants contain P26 ilvBNC integrated at amyE by double crossover. One transformant of PA327, named PA340, and one transformant of PA328, named PA342, were chosen for further study.

In test tube cultures grown in SVY medium plus 5 g/l β-alanine but without added α-KIV, both PA340 and PA342 gave the expected increase in pantothenate production over that of PA327 and PA328, to about 1.3 to 2 g/l (Table 14).

TABLE 14

Pantothenate and valine production by PA340 and PA342, both containing $P_{26}$ ilvBNC in 24 hr test tube cultures grown in SVY with 5 g/l β-alanine and with or without 5 g/l α-KIV

| | | $OD_{600}$ | | [pan] g/l | | [val] g/l | |
|---|---|---|---|---|---|---|---|
| Strain | Background | −α-KIV | +α-KIV | −α-KIV | +α-KIV | −α-KIV | +α-KIV |
| PA340-1 | PY79 | 11.8 | 7.1 | 2.02 | 2.10 | 0.38 | 0.90 |
| PA340-2 | PY79 | 10.3 | 7.5 | 1.97 | 2.03 | 0.40 | 0.91 |
| PA342-1 | RL-1 | 10.2 | 8.0 | 1.29 | 1.89 | 0.27 | 0.78 |
| PA342-2 | RL-1 | 9.6 | 9.2 | 1.34 | 2.04 | 0.21 | 0.79 |

The two new strains also gave a slight increase in valine secretion, indicating that the ilvBNC genes had been deregulated. However, when the same strains were grown with 5 g/l α-KIV added, a further increase in pantothenate production occurred from PA342, suggesting that α-KIV was still rate limiting in this strain background. Similar results, only with more growth and hence higher pantothenate levels, were seen in shake flask cultures (Table 15).

TABLE 15

Pantothenate and valine production by PA340 and PA342, both containing $P_{26}$ ilvBNC in 24 hour shake flask cultures grown in SVY with 5 g/l β-alanine and with or without 5 g/l α-KIV.

| | | $OD_{600}$ | | [pan] g/l | | [val] g/l | |
|---|---|---|---|---|---|---|---|
| Strain | Background | −α-KIV | +α-KIV | −α-KIV | +α-KIV | −α-KIV | +α-KIV |
| PA327 | PY79 | 21 | 22 | 0.6 | 3.0 | 0.5 | 1.3 |
| PA340-1 | PY79 | 20 | 20 | 3.5 | 4.1 | 1.0 | 1.9 |
| PA340-2 | PY79 | 22 | 19 | 3.0 | 2.1 | 0.8 | 1.4 |
| PA328 | RL-1 | 20 | 16 | 1.4 | 2.7 | 0.6 | 1.3 |
| PA342-1 | RL-1 | 17 | 16 | 3.3 | 3.6 | 0.9 | 1.6 |
| PA342-2 | RL-1 | 18 | 18 | 3.1 | 4.2 | 0.8 | 1.4 |

Example VIII

Increasing panD Copy Number in Strains Engineered to Overproduce panE1 and the ilvBNC Gene Products Enhances Pantothenate Production Experiments where β-alanine was fed to cultures of engineered *B. subtilis* strains consistently showed that β-alanine was a rate limiting intermediate in pantothenate synthesis. The effect of adding additional copies of panD on pantothenate production in PA340 and PA342 was examined. Strains PA340 and PA342 were transformed with chromosomal DNA isolated from PA401 with selection on plates containing 15 μg/ml of tetracycline (Tet[15] plates). Transformants derived from each parent were patched onto Tet60 plates to identify those which were likely to contain multiple copies of the expression cassette. Twelve transformants from each transformation which grew on Tet[60] were streaked for single colonies on this medium and then assayed in SVY medium test tube cultures for pantothenate production. One transformant from each group was found to produce greater than 300 mg/l pantothenate in 24 hours. These two transformants were saved and named PA404 (PA340 strain background) and PA405 (PA342 strain background). Both strains were resistant to spectinomycin, indicating that the $P_{26}$ ilvBNC expression cassette was still present at amyE. PCR analysis of chromosomal DNA isolated from each strain confirmed that the deregulated panE1 gene had also been retained.

Next, PA404 and PA405 were evaluated in shake flask cultures which were grown in SVY medium containing maltose as the carbon source and supplemented with various intermediates. The cultures were grown for 24 and 48 hours and then assayed for pantothenate, β-alanine, and valine production. The results of this experiment are presented in Table 16. Analogous shake flask culture data for the parent strains (PA340 and PA342) are included in the tables for comparison.

TABLE 16

Pantothenate production by PA404 and PA405 in shake flask cultures after 24 hours

| Strain | Medium Supplements | $OD_{600}$ | Pan g/l | β-Ala g/l | Val g/l |
|---|---|---|---|---|---|
| PA340 | none | 20 | 0.4 | <0.1 | 1.0 |
| PA404 | none | 22 | 1.8 | <0.1 | 0.7 |
| PA342 | none | 19 | 0.3 | 0.2 | 0.7 |
| PA405 | none | 19 | 1.4 | 0.4 | 0.5 |
| PA340 | β-alanine[5] | 18 | 3.6 | 3.2 | 0.6 |
| PA404 | β-alanine[5] | 18 | 2.8 | 5.1 | 0.7 |
| PA342* | β-alanine[5] | 17 | 3.3 | 3.3 | 0.5 |
| PA405* | β-alanine[5] | 19 | 1.3 | 6.5 | 0.6 |

Values are the average of duplicate flasks except where indicated by *.

In the absence of any medium supplementation, PA404 and PA405 made four to five times more pantothenate in 24 hours compared to their isogenic parent strains (Table 16). The supply of β-alanine was clearly limiting in the parent strains PA340 and PA342. Addition of amplified P26 panD greatly increased the supply of β-alanine.

Example IX

Deregulation of the *B. subtilis* ilvD Gene Enhances Pantothenate Production

To deregulate expression of the ilvD gene, standard procedures (described above) were used to integrate the constitutive $P_{26}$ promoter and an artificial ribosome binding site, RBS2, just upstream of the ilvD coding region. The ilvD gene maps by itself, unlinked to the ilvBNC operon. First, a 2.4 kb region of the RL-1 chromosome that contains the ilvD coding region and 730 bp of upstream sequence was cloned by PCR into a low copy (about 15 per *E. coli* cell) vector called pOK12, to give plasmid pAN257, shown in FIG. 13.

Figure 14:
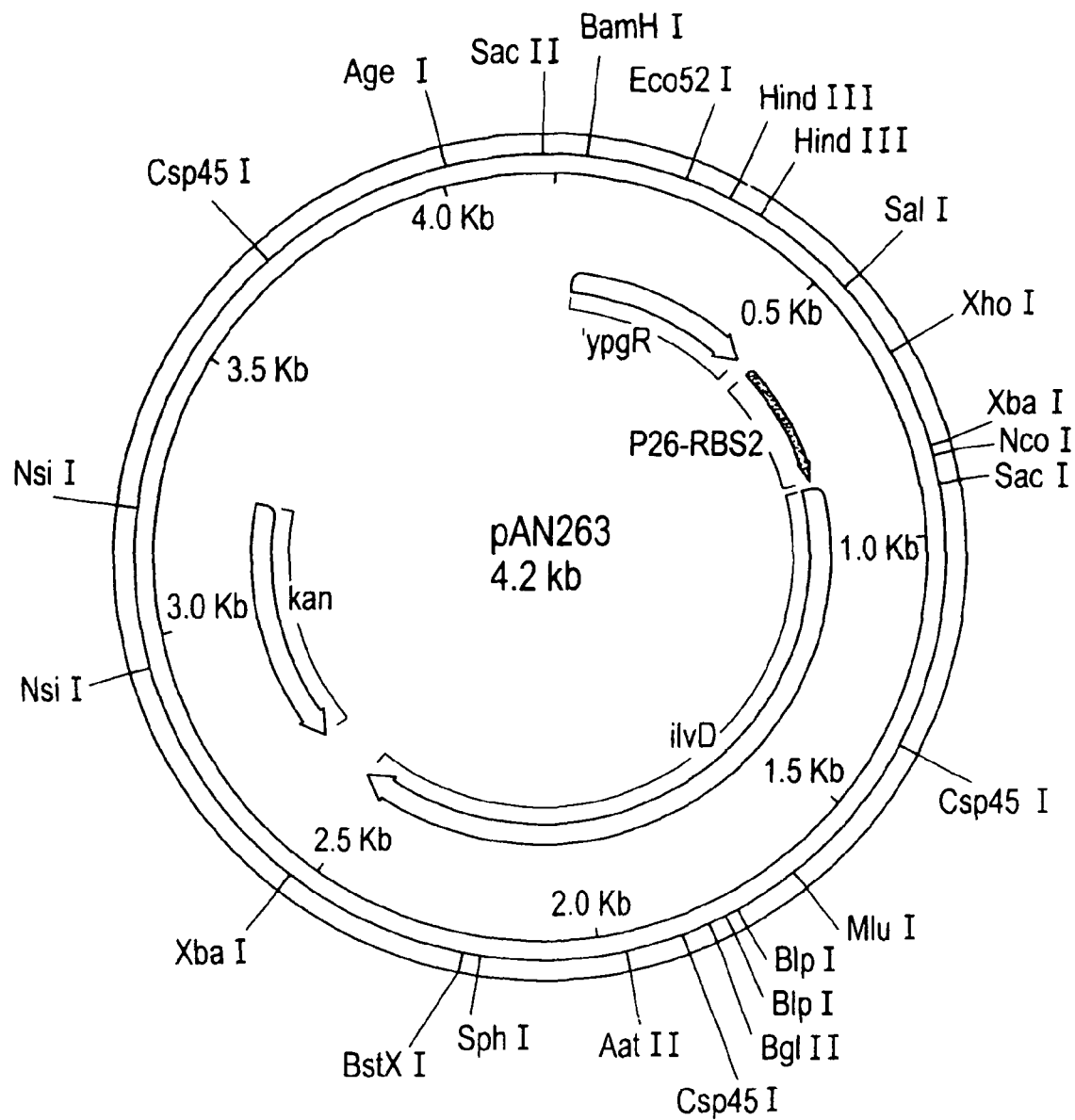
FIG. 14 is a schematic representation of the plasmid pAN263, designed to integrate a single copy of a $P_{26}$-ilvD cassette at the ilvD locus.
Figure 15:
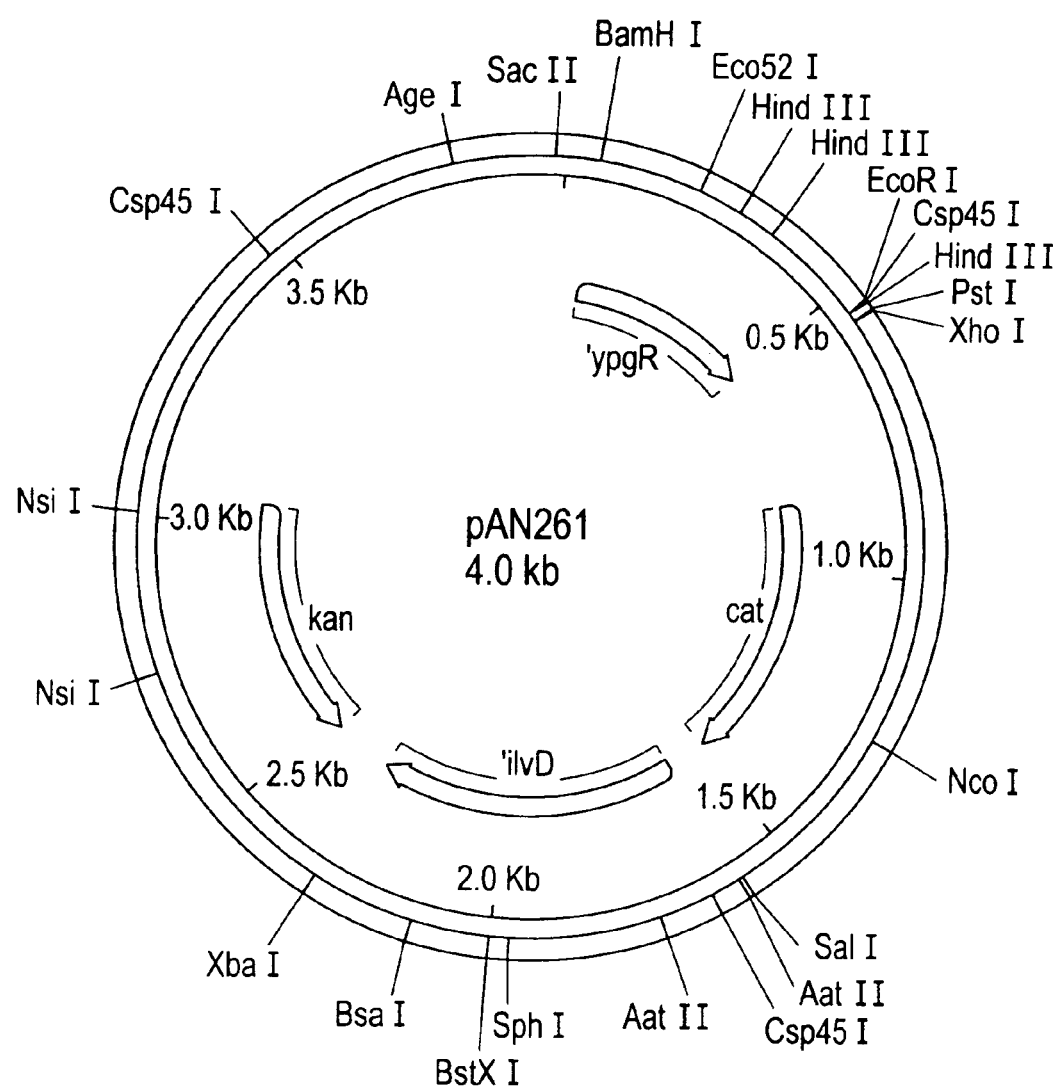
FIG. 15 is a schematic representation of the plasmid pAN261, designed to disrupt the *Bacillus subtilis* ilvD gene with the cat gene.

Taking advantage of a natural EcoRI site just upstream of the native ilvD gene promoter, and a natural NcoI site at the ilvD start codon, an artificial sequence containing $P_{26}$ and RBS2 was inserted into pAN257 to give pAN263 (FIG. 14). The nucleotide sequence of pAN263 is set forth as SEQ ID NO:83. In parallel with this construction, the cat gene was also inserted into pAN257, between the same upstream EcoRI site and a BglII site in the middle of the ilvD coding region, to give pAN261, which is deleted for a large portion of the ilvD gene (FIG. 15). Using pAN261 and pAN263, the $P_{26}$ ilvD cassette could then be installed in the *B. subtilis* chromosome in two steps. In the first step, pAN261 is introduced by transformation, selecting for chloramphenicol resistance, and then confirming an Ilv⁻ phenotype. In the second step, pAN263 is introduced, selecting for Ilv⁺, checking for chloramphenicol sensitivity, and confirming correct local structure by PCR.

pAN261 was first transformed into strain RL-1 (highly competent) to give strain PA343 (ΔilvD::cat), and then chromosomal DNA from PA343 was used to transform PA340 and PA342 to Ilv⁻ auxotrophy, yielding strains named PA348 and PA349, respectively. Chromosomal DNA is inherently more efficient than monomeric plasmid in transforming *B. subtilis*. Similarly, pAN263 DNA was transformed into PA343 (moderately competent) to give strain PA345 ($P_{26}$ ilvD), and then PA345 chromosomal DNA was used to transform PA348 and PA349 to Ilv⁺ prototrophy, yielding strains PA374 and PA354, respectively.

As predicted, PA374 and PA354 gave further increases in pantothenate production, to about 2.5 to 2.9 g/l, in test tube cultures grown in SVY plus 5 g/l β-alanine (Table 17).

TABLE 17

Pantothenate and valine production by PA374 and PA354, containing $P_{26}$ ilvD, and controls, in 24 hr test tube cultures grown in SVY with 5 g/l β-alanine and with or without 5 g/l α-KIV.

| Strain | Background | ilvD status | $OD_{600}$ α-KIV − | $OD_{600}$ α-KIV + | [pan] g/l α-KIV − | [pan] g/l α-KIV + | [val] g/l α-KIV − | [val] g/l α-KIV + |
|---|---|---|---|---|---|---|---|---|
| PA340 | PY79 | w.t. | 9.2 | 9.0 | 2.14 | 2.23 | 0.38 | 0.90 |
| PA348 | PY79 | ilvD::cat | 11.7 | 10.0 | 0.19 | 2.23 | 0.19 | 0.91 |
| PA374-1 | PY79 | $P_{26}$ ilvD | 9.1 | 7.3 | 2.93 | 2.40 | 0.58 | 0.87 |
| PA374-2 | PY79 | $P_{26}$ ilvD | 8.2 | 7.7 | 2.99 | 2.36 | 0.60 | 0.95 |
| PA342 | RL-1 | w.t. | 10.2 | 8.0 | 1.29 | 1.89 | 0.27 | 0.78 |
| PA349 | RL-1 | ilvD::cat | 8.1 | 7.7 | 0.17 | 1.87 | 0.22 | 0.88 |
| PA354-1 | RL-1 | $P_{26}$ ilvD | 9.6 | 9.6 | 2.57 | 2.03 | 0.65 | 1.23 |
| PA354-2 | RL-1 | $P_{26}$ ilvD | 7.5 | 8.2 | 2.48 | 2.24 | 0.64 | 0.97 |

In the absence of added β-alanine, strains PA374 and PA354 produced only about 0.2 g/l pantothenate in test tube cultures, indicating that PanD activity is significantly rate limiting.

To alleviate this limitation, the amplifiable $P_{26}$ panD cassette from strain PA401 was installed. PA401 chromosomal DNA was transformed into PA374 and PA354, selecting for Tet^r at 15 mg/l, to yield strains PA377 and PA365, respectively. After transformants were obtained, the strains were streaked on plates containing 30 and 60 mg/l tetracycline to reamplify the copy number of the $P_{26}$ panD cassette integrated at the bpr locus. In test tube cultures grown in SVY without α-KIV or β-alanine, a substantial improvement in pantothenate titers over those of PA374 and PA354 was obtained (Tables 18 and 19).

TABLE 18

Pantothenate production by PA365, containing amplified $P_{26}$ panD, and controls, in 24 and 36 hr test tube cultures grown in SVY-glucose without β-alanine or α-KIV.

| | | $OD_{600}$ | | [pan] g/l | |
|---|---|---|---|---|---|
| Strain | Relevant genotype | 24 hrs. | 36 hrs | 24 hrs. | 36 hrs. |
| PA342-1-1 | w.t. ilvD | 11.7 | 8.8 | b.d. | 0.27 |
| PA342-1-2 | w.t. ilvD | 12.8 | 8.8 | b.d. | 0.26 |
| PA354-1-1 | $P_{26}$ ilvD | n.d. | 11.0 | n.d. | 0.19 |
| PA354-1-2 | $P_{26}$ ilvD | n.d. | 8.4 | n.d. | 0.20 |
| PA365-1 | $P_{26}$ ilvD, $P_{26}$ panD | 9.8 | 10.0 | 1.01 | 2.07 |
| PA365-2 | $P_{26}$ ilvD, $P_{26}$ panD | 9.9 | 10.4 | 0.96 | 2.09 | n.d. = not determined;
b.d. = below detection

TABLE 19

Pantothenate production by PA377, containing amplified $P_{26}$ panD, and controls, in 27 hr test tube cultures grown in SVY-glucose or SVY-maltose, without α-KIV, and with or without β-alanine.

| Strain | Relevant genotype | −β-ala Glucose | +β-ala Glucose | −β-ala Maltose | +β-ala Maltose |
|---|---|---|---|---|---|
| | | $OD_{600}$ | | | |
| PA374-1 | $P_{26}$ ilvD | 9.4 | 9.8 | 7.0 | 6.4 |
| PA374-2 | $P_{26}$ ilvD | 9.2 | 9.6 | 6.6 | 6.3 |
| PA377-1 | $P_{26}$ ilvD, $P_{26}$ panD | 10.0 | 7.6 | 7.2 | 6.1 |
| PA377-2 | $P_{26}$ ilvD, $P_{26}$ panD | 10.5 | 7.8 | 9.4 | 5.4 |
| | | [pan] g/l | | | |
| PA374-1 | $P_{26}$ ilvD | 0.04 | 2.76 | 0.14 | 1.31 |
| PA374-2 | $P_{26}$ ilvD | 0.10 | 2.65 | 0.15 | 1.33 |
| PA377-1 | $P_{26}$ ilvD, $P_{26}$ panD | 1.25 | 2.76 | 1.26 | 1.10 |
| PA377-2 | $P_{26}$ ilvD, $P_{26}$ panD | 1.25 | 2.35 | 1.31 | 1.26 |

In SVY with glucose, an increase in pantothenate production can still be achieved by feeding 5 g/l β-alanine suggesting that increasing panD expression further might increase pantothenate production. In SVY with maltose, no further increase in pantothenate was obtained by feeding β-alanine suggesting that β-alanine and/or aspartate synthesis is suppressed by glucose. Strains PA377 and PA365 have been evaluated in 10 liter fermentors, where they typically produce above 20 g/l pantothenate in 48 hours without supplemental β-alanine and α-KIV or valine, described in detail below.

Example X 10 liter Fermentations of Pantothenate-Producing Microbes

Engineering of the $P_{26}$ ilvBNC and $P_{26}$ ilvD cassettes to give strains PA342 and PA354 allowed the production of 22 and 26 g/l of pantothenate, respectively, without the addition of valine or α-KIV to the fermentation medium (Table 20). At 48 hours, both strains had secreted about 0.5 g/l of valine into the medium.

TABLE 20

10-liter fermentations of five pantothenate overproducing strains.

| Strain | Medium | Feed 40% Glucose plus | OD 600 48 hr | Valine 48 hours g/l | β-ala 48 hr g/l | Pantothenate g/L 36 hr | 48 hr | 72 hr |
|---|---|---|---|---|---|---|---|---|
| PA 236 | SVYG | 50 g/l β-ala 25 g/l α-KIV | 108 | added | added | 16 | 19 | 21 |
| PA 342 | SVYG | 50 g/l β-ala | 92 | 0.5 | added | 17 | 22 | — |
| PA 354 | SVYG | 50 g/l β-ala | 90 | 0.5 | added | 19 | 26 | — |
| PA 365 | SVYG | 25 g/l YE | 77 | 0.85 | 0.4 | 18 | 21 | 27 |
| PA 377 | SVYG | 25 g/l YE | 85 | 1.5 | 0.5 | 18 | 22 | 31 |
| PA 377 | PFMG | 25 g/l YE | 96 | 0.8 | 0.4 | 19 | 25 | 29 |
| PA 377 | PFMG | — | 71 | 0.7 | 0.1 | 16 | 21 | — |

Pantothenate Synthesis in Fermentors

With the addition of the $P_{26}$ panD cassette to strains PA354 and PA374 to create strains PA365 and PA377, neither β-alanine nor α-KIV needed to be added to the fermentors. Strain PA365 produced 21 g/l pantothenate in 48 hours and 27 g/l in 72 hours with no precursors added to the medium (Table 20). PA377 was somewhat better, producing 18 g/l of pantothenate in 36 hours, 22 g/l in 48 hours, and 31 g/l in 72 hours). Valine was measured at 0.85 and 1.5 g/l for strains PA365 and PA377, respectively, at 48 hours in SVYG medium. Strain PA377 maintained valine between 1-1.5 g/l throughout most of the fermentation and α-alanine between 0.2 and 0.5 g/l.

Strain PA377 was further evaluated in 10-liter fermentors in yeast extract based PFMG medium. Pantothenate yields in PFMG and SVYG medium were similar. In PFMG, PA377 produced 19 g/l of pantothenate in 36 hours, 25 g/l in 48 hours, and 29 g/l in 72 hours. In SVYG, PA377 produced 18 g/L pantothenate in 36 hours, 22 g/L in 48 hours and 31 g/L in 72 hours (Table 20).

Example XI

Converting Strain PA377 to a Tryptophan Prototroph

PA377 (Trp$^-$) was transformed to Trp$^+$ using chromosomal DNA from PY79 to give strain PA824. After re-amplification of the $P_{26}$PanD casette, PA824 was compared to PA377 for pantothenate production in test tube cultures grown in SVY glucose with or without 5 g/L β-alanine (Table 21).

TABLE 21

Trp$^+$ derivatives of PA377: Pantothenate production in 48 hour test tube cultures grown in SVY glucose, ±β-alanine

| Strain | trpC donor | $OD_{600}$ −β-alanine | +β-alanine | [pan] g/L −β-alanine | +β-alanine |
|---|---|---|---|---|---|
| PA377-1 | RL-1 | 8 | 8 | 1.5 | 3.4 |
| PA377-2 | RL-1 | 8 | 9 | 1.6 | 3.6 |
| PA824-1 | PY79 | 12 | 10 | 0.7 | 3.7 |
| PA824-2 | PY79 | 11 | 11 | 1.9 | 4.9 |

The Trp+ strains grew to slightly higher densities than PA377. In the absence of exogenous β-alanine, all of the strains produced similar levels of pantothenate, while with the addition of β-alanine, the Trp+ derivatives produced somewhat more pantothenate.

Fermentor Studies with PA824

PA824 was evaluated in CF3000 Chemap 14 liter vessels with 10 liter working volumes. Formulations for two of the media used in the fermentors are given in Tables 22 and 23.

TABLE 22

Formulation for PFMG-5 medium

| | MATERIAL | g/L (final [ ]) |
|---|---|---|
| | BATCH | |
| 1 | Amberex 1003 | 10 |
| 2 | Na Glutamate | 5 |

TABLE 22-continued

Formulation for PFMG-5 medium

| | | |
|---|---|---|
| 3 | (NH$_4$)$_2$SO$_4$ | 8 |
| 4 | MAZU DF 37C | 2.5 |
| | Added After Sterilization and Cool Down | |
| 1 | KH$_2$PO$_4$ | 10 |
| 2 | K$_2$HPO$_4$•3H$_2$O | 20 |
| 1 | Glucose | 20 |
| 2 | MgCl$_2$•6H$_2$O | 1 |
| 3 | CaCl$_2$•2H$_2$O | 0.1 |
| 1 | Sodium Citrate | 1 |
| 2 | FeSO$_4$•7H$_2$O | 0.01 |
| 3 | SM-1000X | 1.0 ml |
| | H$_2$O | qs to 6000 ml |

FEED

| | MATERIAL | g/L |
|---|---|---|
| 1 | Glucose | 600 |
| 2 | CaCl$_2$•2H$_2$O | 0.6 |
| | H$_2$O | qs to 3000 ml |

TABLE 23

Formulation for SVY-4 medium

| | MATERIAL | g/L (final [ ]) |
|---|---|---|
| | BATCH | |
| 1 | Veal Infusion | 25 |
| 2 | Yeast Extract | 5 |
| 3 | Na Glutamate | 5 |
| 4 | (NH$_4$)$_2$SO$_4$ | 4 |
| 5 | MAZU DF 37C | 2.5 |
| | Added After Sterilization and Cool Down | |
| 1 | KH$_2$PO$_4$ | 10 |
| 2 | K$_2$HPO$_4$•3H$_2$O | 20 |
| 1 | Glucose | 20 |
| 2 | MgCl$_2$•6H$_2$O | 1 |
| 3 | CaCl$_2$•2H$_2$O | 0.1 |
| 1 | Sodium Citrate | 1 |
| 2 | FeSO$_4$•7H$_2$O | 0.01 |
| 3 | SM-1000X | 1.0 ml |
| | H$_2$O | qs to 6000 ml |

FEED

| | MATERIAL | g/L |
|---|---|---|
| 1 | Glucose | 600 |
| 2 | CaCl$_2$•2H$_2$O | 0.6 |
| | H$_2$O | qs to 3000 ml |

All fermentations were glucose limited fed batch processes. Immediately after inoculation, agitation was set at 200 rpm. The initial batched 2% glucose was consumed during exponential growth. Afterwards, glucose concentrations were maintained between 0.2 and 1.0 g/L by continuous feeding of a 60% glucose solution. The variable rate feed pump was computer controlled and linked to the dissolved oxygen concentration [pO$_2$] in the tank by an algorithm. When the [pO$_2$] fell to 30%, computer control began to automatically adjust the agitation rate to maintain a dissolved oxygen concentration between 25 and 30% [pO$_2$]. Computer control and data recording were by Braun MFCS software.

In one study, PA284 was grown in fermentors at two temperatures (40° C. and 43° C.) in the medium described in Table 22. Results of two experiments demonstrated that the highest pantothenate titers at early time points were produced at 43° C. The cell mass approached 150 optical density units at OD$_{600}$ and 56 hours at 43° C., and the pantothenate titers were 21 g/L, 28 g/L and 36 g/L at 36, 48 and 72 hours respectively. In the parallel fermentation at 40° C., the cell mass approached 120 optical density units at OD$_{600}$ and 56 hours, and the pantothenate titers were 18 g/L, 26 g/L and 37 g/L at 36, 48 and 72 hours, respectively.

In another study, PA824 was grown in a fermentor at 43° C. in the medium described in Table 23. The cell mass exceeded 160 optical density units at OD$_{600}$ and 36 hours, and the pantothenate titers were 23 g/L, 34 g/L, 37 g/L and 40 g/L at 24, 36, 48 and 60 hours, respectively. In other fermentations, increasing the amount of trace elements in the glucose feed (e.g., increasing the concentration of SM from 1× to 2×) resulted in even higher titers of pantothenate.

Example XII

Identification and Characterization of the B. subtilis coaA Gene Product

Figure 18:
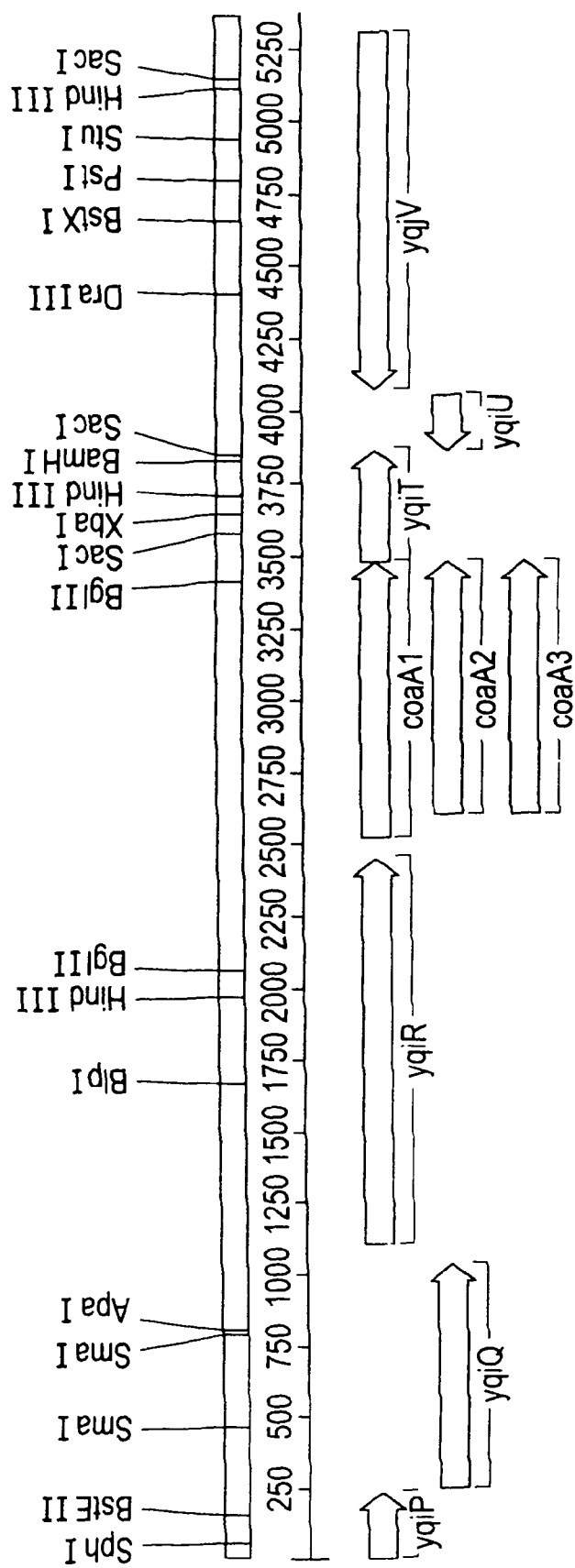
FIG. 18 is a schematic representation of the structure of the *Bacillus subtilis* genome in the region of the coaA gene. The scale is in base pairs and the significant open reading frames are shown by open arrows.

The annotated version of the B. subtilis genome sequence available on the "Subtilist" web site contains no gene labeled as coaA. However a homology search using the protein sequence of E. coli pantothenate kinase as a query sequence gave a good match with B. subtilis gene yqjS, which is annotated as "unknown; similar to pantothenate kinase." This gene appears to be the penultimate gene in an operon containing five open reading frames (FIG. 18). Two of the open reading frames encode proteins which are similar to D-serine dehydratase and to "ketoacyl reductase"; the other two have no known homologies. For the open reading frame corresponding to coaA, there are three possible start codons; each having a possible ribosome-binding site (RBS) associated with it. The three potential coaA ORFs were named coaA1, coaA2, and coaA3, from longest to shortest.

Figure 19:
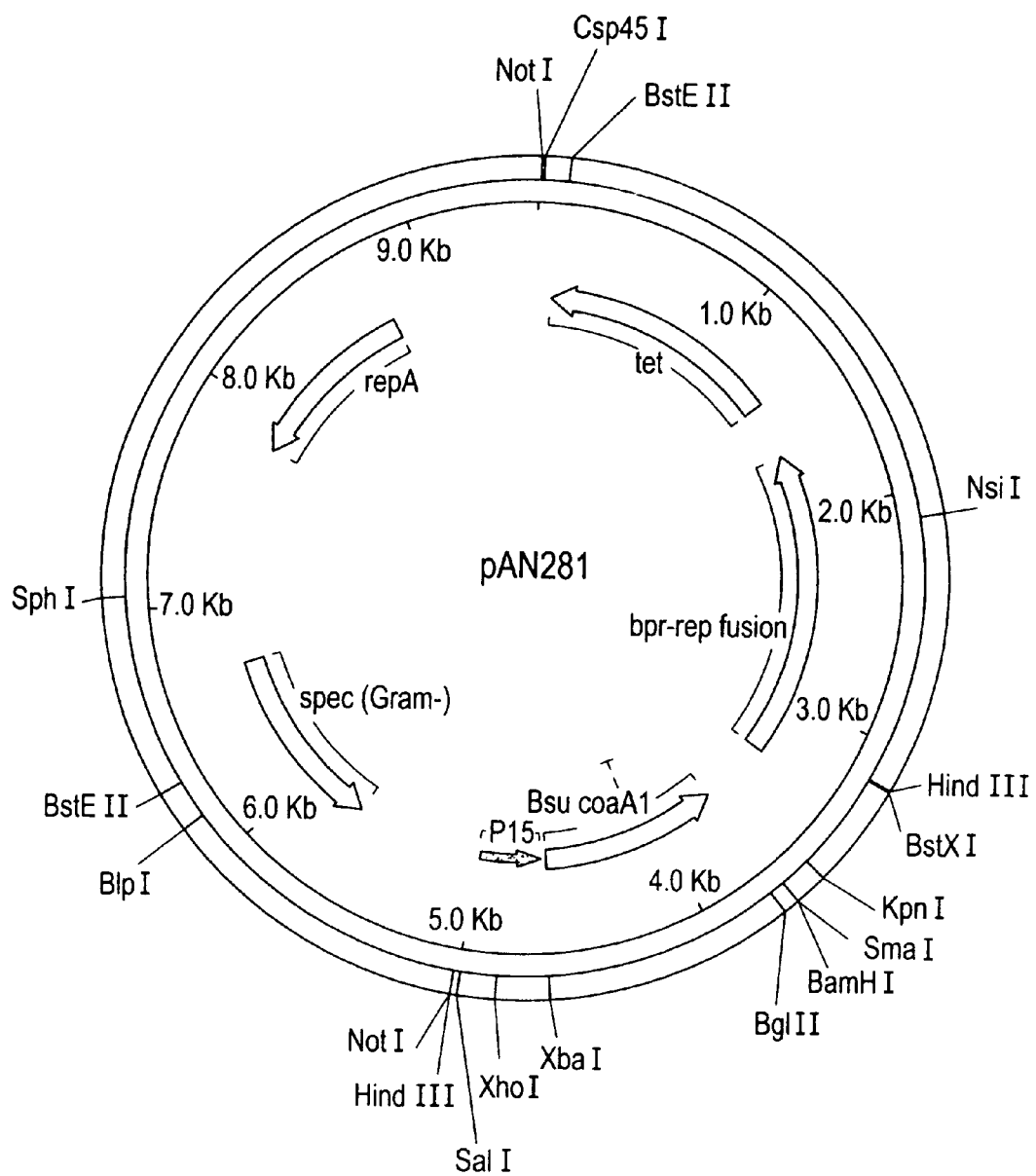
FIG. 19 is a schematic representation of the plasmid pAN281, a plasmid for expressing *Bacillus subtilis* coaA after integration at the bpr locus.

All three potential coaA open reading frames were cloned along with their respective RBSs by PCR followed by ligation into expression plasmid pAN229. pAN229 is a low copy vector in E. coli that provides expression from the SP01 phage P$_{15}$ promoter and can integrate by single crossover at bpr with tetracycline selection. A representative resulting plasmid, pAN281, is shown in FIG. 19.

To determine if the cloned putative coaA ORFs actually encode a pantothenate kinase activity, several isolates of all three plasmids were transformed into the E. coli strain YH 1, that contains the coaA15(Ts) allele. Transformants were streaked to plates incubated at 30° and 43° C. to test for complementation of the temperature sensitive allele. All isolates of all three coaA variants, except for one isolate of pAN282, complemented well at 43° C., indicating that all three plasmid constructs encode an active pantothenate kinase. Accordingly, it can be concluded that the B. subtilis yqjS open reading frame codes for an active pantothenate kinase.

Example XIII

Deletion of the coaA Gene from the B. subtilis Genome

The coaA gene of B. subtilis (yqjS) was deleted from the chromosome of a B. subtilis strain by conventional means. The majority of the coaA coding sequence was deleted from a plasmid clone and replaced by a chloramphenicol resistance gene (cat), while leaving approximately 1 kb of upstream and downstream sequence to allow homologous recombination within the chromosome, to give plasmid pAN296 (see FIG.

17). pAN296 was then used to transform a *B. subtilis* strain (PY79), selecting for chloramphenicol resistance. The majority of transformants result from a double crossover event that effectively substitutes the cat gene for the coaA gene. The transformed strain containing the coaA deletion—cat insertion grew normally due the presence of a second *B. subtilis* pantothenate kinase encoding gene described herein.

Example XIV

Identification and Characterization of a Second *B. Subtilis* Gene Encoding Pantothenate Kinase Activity As described in detail in the instant specification, in order to maximize pantothenate production, it is necessary to restrict the flow of pantothenate toward Coenzyme A (CoA), for example, by reducing the activity of pantothenate kinase, the first enzyme in the pathway from pantothenate to CoA. After finding that deletion of the coaA gene from the chromosome of *B. subtilis* is not a lethal event (see Example XIII), it was concluded that *B. subtilis* must contain a second gene that encodes an active pantothenate kinase, since pantothenate kinase is an essential enzyme activity.

A second pantothenate kinase-encoding gene was identified by complementing the *E. coli* strain YH1 (coaA15(Ts)) with a *B. subtilis* gene bank and selecting for transformants that were able to grow at 43° C. Found among the transformants were two families of plasmids that had overlapping restriction maps within each family, but not between the families. As expected, the restriction map of one family was identical to that predicted from the *B. subtilis* genome sequence for the homologue of the *E. coli* coaA gene (which we named coaA also, see above) and surrounding sequences. The other family had a restriction map that was completely non-overlapping with the first.

DNA sequencing of the ends of the cloned inserts from the second family showed that the clones came from a region of the *B. subtilis* chromosome that includes the 3' end of the ftsH gene, the 5' end of the sul gene, and all of the yacB, yacC, yacD, cysK, pabB, pabA and pabC genes. None of the open reading frames of these cloned inserts showed homology to any known pantothenate kinase sequences, either prokaryotic or eukaryotic.

Figure 21:
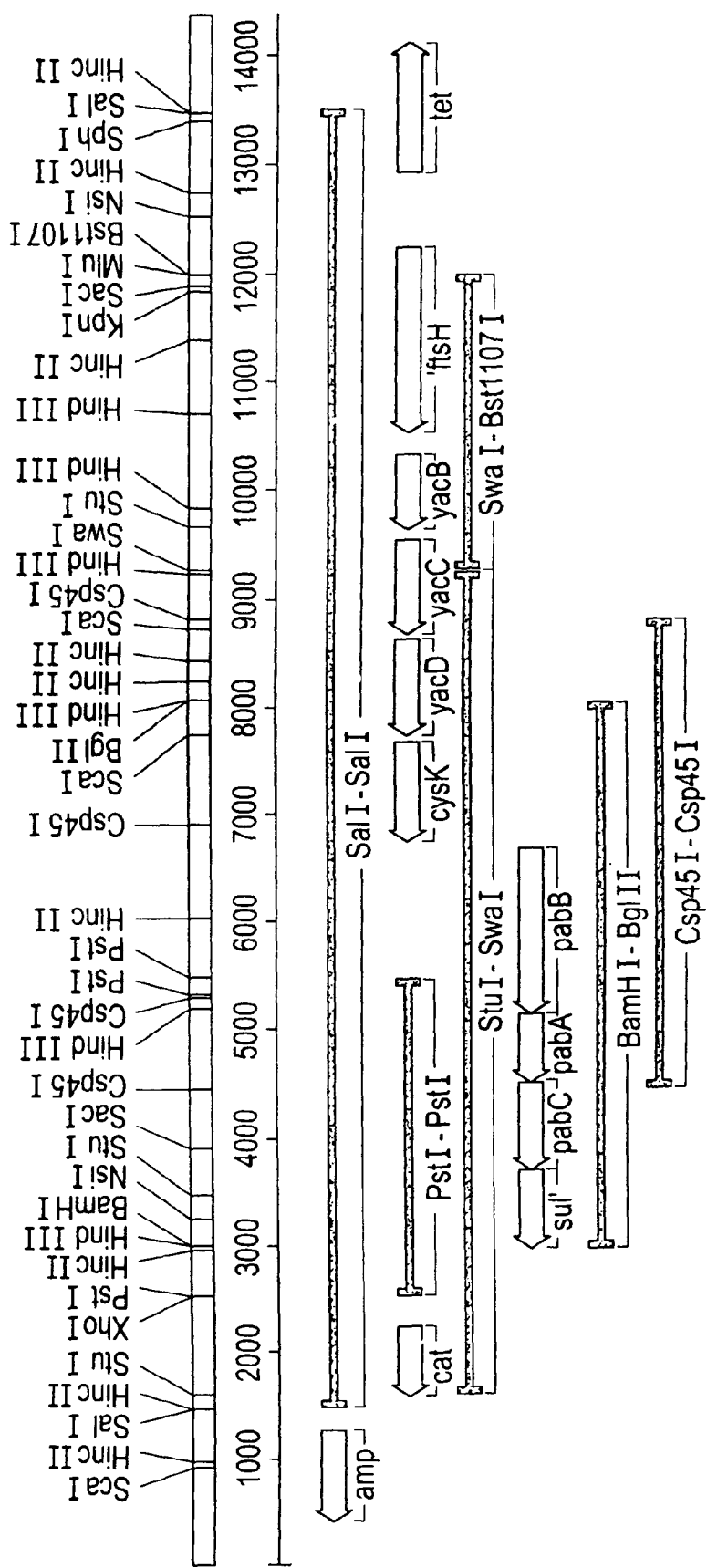
FIG. 21 is a schematic representation of the structure of the *Bacillus subtilis* genome in the region of the coaX (yacB) gene. The scale is in base pairs, the significant open reading frames are shown by open arrows and certain predicted restriction fragments are indicated by thick bars.
Figure 22:
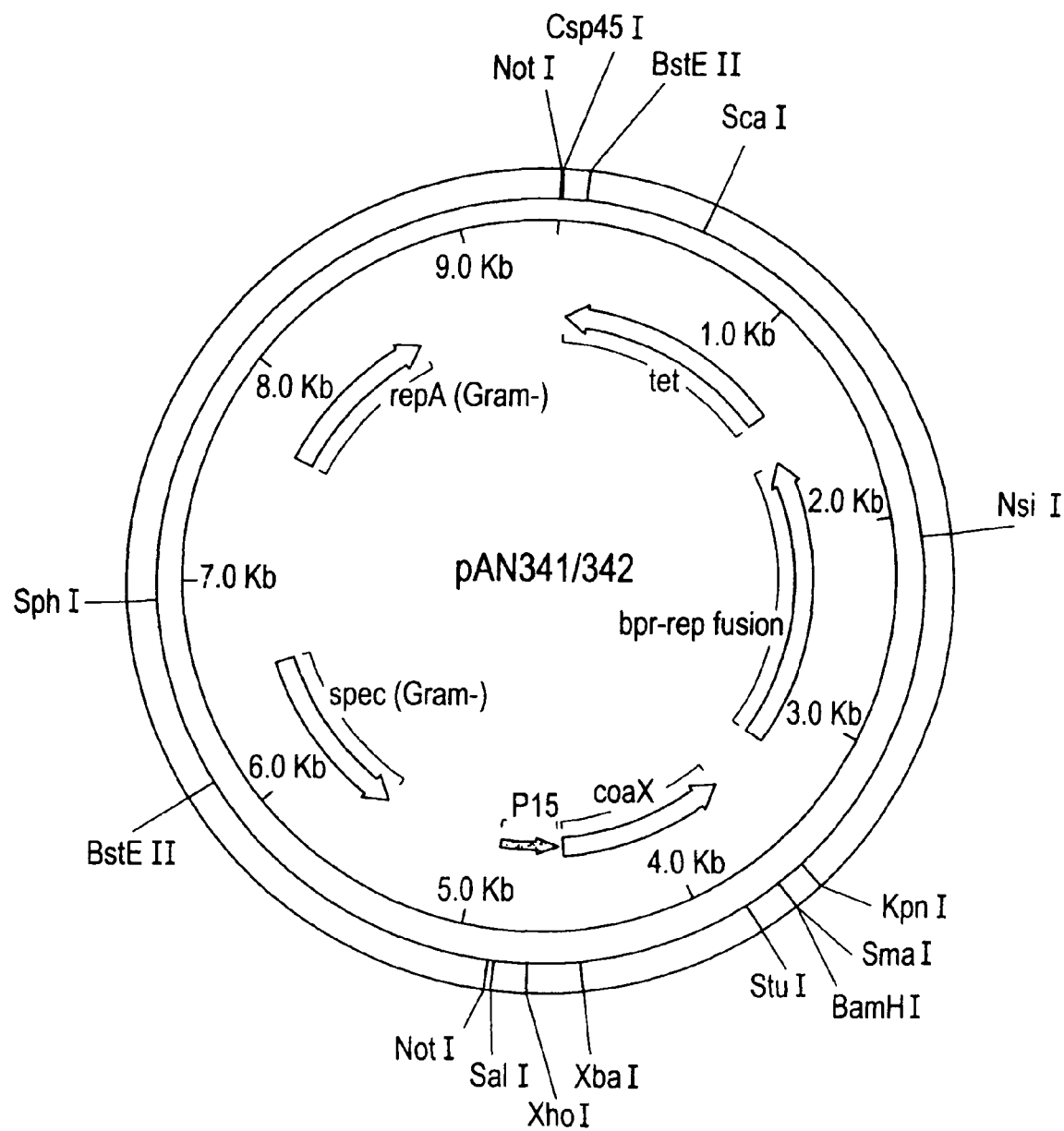
FIG. 22 is a schematic representation of the structure of pAN341 and pAN342, two independent PCR-derived clones of *B. subtilis* yacB (remaned herein as coaX).

Several deletions were created through the *B. subtilis* genomic sequences in the cloned inserts. Each deletion was tested for complementation of the *E. coli* temperature sensitive pantothenate kinase. In particular, a deletion that removed all DNA between a Stu I site in the cloning vector and a Swa I site in the yacC gene, leaves yacB as the only intact open reading frame in the cloned insert (see FIG. 21). This deleted plasmid still complemented the *E. coli* pantothenate kinase mutant. However, another deletion that removed DNA from the Swa I site in yacC through a Bst1107I site in the (already truncated) ftsH gene, could not complement the *E. coli* pantothenate kinase mutant. From these results, it was concluded that the yacB open reading frame was responsible for the complementation activity. To confirm that yacB is a pantothenate kinase gene, the yacB ORF plus 112 base pairs of downstream flanking sequence was amplified by PCR in two independent reactions and cloned downstream of a constitutive promote to give plasmids pAN341 and pAN342 (FIG. 22). Both pAN341 and pAN342 complemented the defect in YH1 at 44° C., while a control plasmid, which has the same backbone, but expresses panBCD instead of yacB did not. This confirmed that the yacB open reading frame was responsible for the complementation of YH1.

As such, a novel gene that encodes pantothenate kinase activity in *B. subtilis* has been discovered that is not related by homology to any previously known pantothenate kinase gene. This gene has been renamed coaX, as a second, alternative gene that encodes an enzyme that catalyzes the first step in the pathway from pantothenate to CoaA. Deletion of coaX by methods described above for deleting coaA, in conjunction with reduction in the activity of the CoaA enzyme, provides a means to reduce pantothenate kinase activity to the desired level.

Several homologues of the *B. subtilis* coaX gene were identified by homology searching of various publically available databases using the published yacB (coaX) open reading frame sequence and predicted amino acid sequence (as set forth in SEQ ID NOs:84 and 85 respectively). In two cases (*Mycobacterium tuberculosis* and *Streptomyces coelicolor*) the homologous coaX genes are adjacent to, or almost adjacent to, pantothenate biosynthetic genes, consistent with these homologs having a role in pantothenate metabolism. The CoaX proteins show no homology to the CoaA family of pantothenate kinases, nor to the eukaryotic family of pantothenate kinases exemplified by PanK of *Saccharomyces cerevisiae*.

Alignment of the amino acid sequences of several bacterial CoaX homologs with the amino acid sequence predicted from translating the *B. subtilis* yacB ORF described in the published *B. subtilis* genome sequence revealed that the CoaX proteins from other bacteria contained additional amino acid residues at their carboxy-terminal ends. Moreover, these extensions beyond the end of the predicted amino acid for the *B. subtilis* gene product contained two relatively well conserved segments of sequence.

Translation of nucleotide sequences just downstream from the stop codon of the *B. subtilis* yacB ORF in a different reading frame revealed the existence of amino acid sequences very similar to the carboxy-terminal extensions of the other bacterial CoaX proteins. It is thus believed that an error exists in the published DNA sequence of the *B. subtilis* yacB ORF sequence that causes a frame shift leading to an artifactual downstream amino acid sequence and premature termination.

The PCR-generated sequences of *B. subtilis* CoaX in pAN341 and pAN342 (described above) contain enough downstream flanking sequence to encode the putative carboxy-terminal extension described above, which is consistent with the result that the clones were functional in the complementation assay. However when the 3' PCR primer was positioned to include only the shorter yacB ORF predicted from the published sequence, but not to include the putative carboxy-terminal extension, then the resulting plasmids, pAN329 and pAN330 (similar in structure to pAN341 and pAN342; see FIG. 22), did not complement the defect in YH1. This result supports the notion that the published yacB coding sequence contains a frame-shift error, and that the carboxy-terminal end of CoaX is necessary for pantothenate kinase activity. The predicted correct nucleotide sequence for *B. subtilis* coaX is set forth as SEQ ID NO: 19 and the translated amino acid sequence is set forth as SEQ ID NO:9. A multiple sequence alignment of the CoaX amino acid sequences of *B. subtilis* and 11 homologues thereof is set forth in FIG. 23.

Example XV

Generation of Mutant coaA Genes Encoding Pantothenate Kinase having Reduced or Temperature Sensitive Activities This Example describes strategies for modifying the coaA gene (i.e., by introducing point mutations) to reduce the activity of pantothenate kinase after coaX is deleted from the genome.

Cloning and Sequencing of the Temperature Sensitive Allele of the E. coli coaA Gene.

Two E. coli strains, each exhibiting a different mutant CoaA phenotype, were obtained from the E. coli Genetic Stock Center. Strain DV62 contains the coaA15(Ts) allele, and DV79 contains the coaA16(Fr) mutation. DV62 is temperature sensitive at 43° C. and produces a pantothenate kinase that is temperature sensitive. DV79 was obtained by reversion of DV62 to temperature resistance, and it produces a temperature stable, feedback resistant pantothenate kinase activity. Since the DNA sequences of these alleles are not available in the literature, the coaA genes from the two mutant strains were cloned by PCR and sequenced, in addition to a coaA gene from a strain that is wild type at the coaA locus, MM294. The PCR primer at the 5' end was designed to include the start codon plus four bases upstream, and added an arbitrarily chosen ribosome binding site (RBS). The three PCR generated fragments were each ligated between the XbaI and BamHI sites of pAN229 to give pAN284 (from coaA15(Ts)), pAN285 (from wild type coaA), and pAN286 (from coaA16(Fr)). pAN229 is a low copy E. coli vector that provides expression from the $P_{15}$ promoter and that can integrate by single crossover at bpr in B. subtilis with tetracycline selection.

All three plasmids were transformed into the E. coli strain YH1 for complementation testing. All three plasmids complemented the temperature sensitive coaA mutation in E. coli YH1. It is presumed that the coaA15(Ts) gene in pAN284 is probably significantly overexpressed relative to the normal chromosomal gene, such that the overproduction compensates for the temperature sensitive defect. Complementation of a defect by overproduction is a well-documented phenomenon in E. coli.

The coaA coding regions from pAN284, 285, and 286 were subcloned into pGEM7 to give pAN306, 307, and 308, respectively, for DNA sequencing. As expected, the DNA sequence of the insert in pAN307 (from wild type coaA) matched the coaA sequence from the E. coli genome database (GenBank™). The sequence from pAN306 contains a single base change that causes a S176L substitution (i.e., a Ser→Leu substitution in the amino acid sequence set forth as SEQ ID NO:2). Interestingly, the DNA sequence of the pAN308 insert, derived from the feedback resistant strain, was identical to that derived from its temperature sensitive parent (represented in pAN306). This is in accord with the genetic data that indicates that the reversion of the temperature sensitive mutation occurred at a second site unlinked to the coaA gene.

The S176L mutation, predicted to cause the temperature sensitive defect in E. coli pantothenate kinase, changed a serine residue that is conserved in all known or suspected bacterial coaA encoded pantothenate kinases, including that of B. subtilis (see SEQ ID NO:3 and refer to alignment). Based on this, a serine to leucine change at the homologous residue in the B. subtilis pantothenate kinase is predicted to result in either a temperature sensitive enzyme or one which is less active. Accordingly, to produce a mutant B. subtilis coaA gene, this specific change was introduced into the B. subtilis coaA gene. The mutant version is installed in the chromosome of a B. subtilis strain deleted for coaX, for example, and the recombinant microorganism is checked for temperature sensitivity (e.g., reduced growth at 43° C.). The mutation is then installed into a pantothenate overproducing strain, preferably a strain deleted for the above mentioned coaX gene by standard methods to give strains favorable for pantothenate production in B. subtilis, i.e., a strain that has reduced pantothenate kinase activity under typical fermentation conditions.

Additional coaA Point Mutations Resulting in Reduced Pantothenate Kinase Activity Of course it is expected that many other point mutations or combinations of more than one point mutation in B. subtilis coaA will also lead to reduced activity. Appropriate mutations can be generated by mutagenic polymerase chain reaction and in vitro recombination, and identified by screening for alleles that poorly complement the E. coli coaA15(Ts) mutant. An example of such a mutation of this type is a tyrosine to histidine substitution at amino acid 181 of B. subtilis coaA, generated by mutagenic polymerase chain reaction (see SEQ ID NO:3 and first line of the alignment of FIG. 24).

Isolate pAN282A was derived from the middle-sized B. subtilis coaA open reading frame described in Example XII. pAN282A complemented the E. coli coaA15(Ts) mutant very poorly, but nonetheless at a level that was detectable above background. As was done for the E. coli coaA clones, the open reading frame from pAN282A was subcloned into pGEM7 to give pAN303. The DNA sequence of the insert in pAN303 showed a single base change that led to a tyrosine to histidine amino acid change at the tyrosine corresponding to Y181 of SEQ ID NO:3. This tyrosine residue is conserved in all bacterial coaA genes/homologues present in GenBank (FIG. 24). This tyrosine residue and the serine that is altered in the E. coli temperature sensitive pantothenate kinase described above are separated by only three amino acid residues in a region which is highly conserved in bacterial pantothenate kinases whereas the DNA sequence of a second isolate of the middle-sized open reading frame, from pAN282B, was identical to the wild type sequence from the B. subtilis genome sequencing project. The single base change found in pAN303 probably occurred during PCR amplification of the coaA gene. If this variant of coaA2 has sufficient residual biological activity in B. subtilis, it may be useful in the future for providing reduced pantothenate kinase activity.

Figure 25:
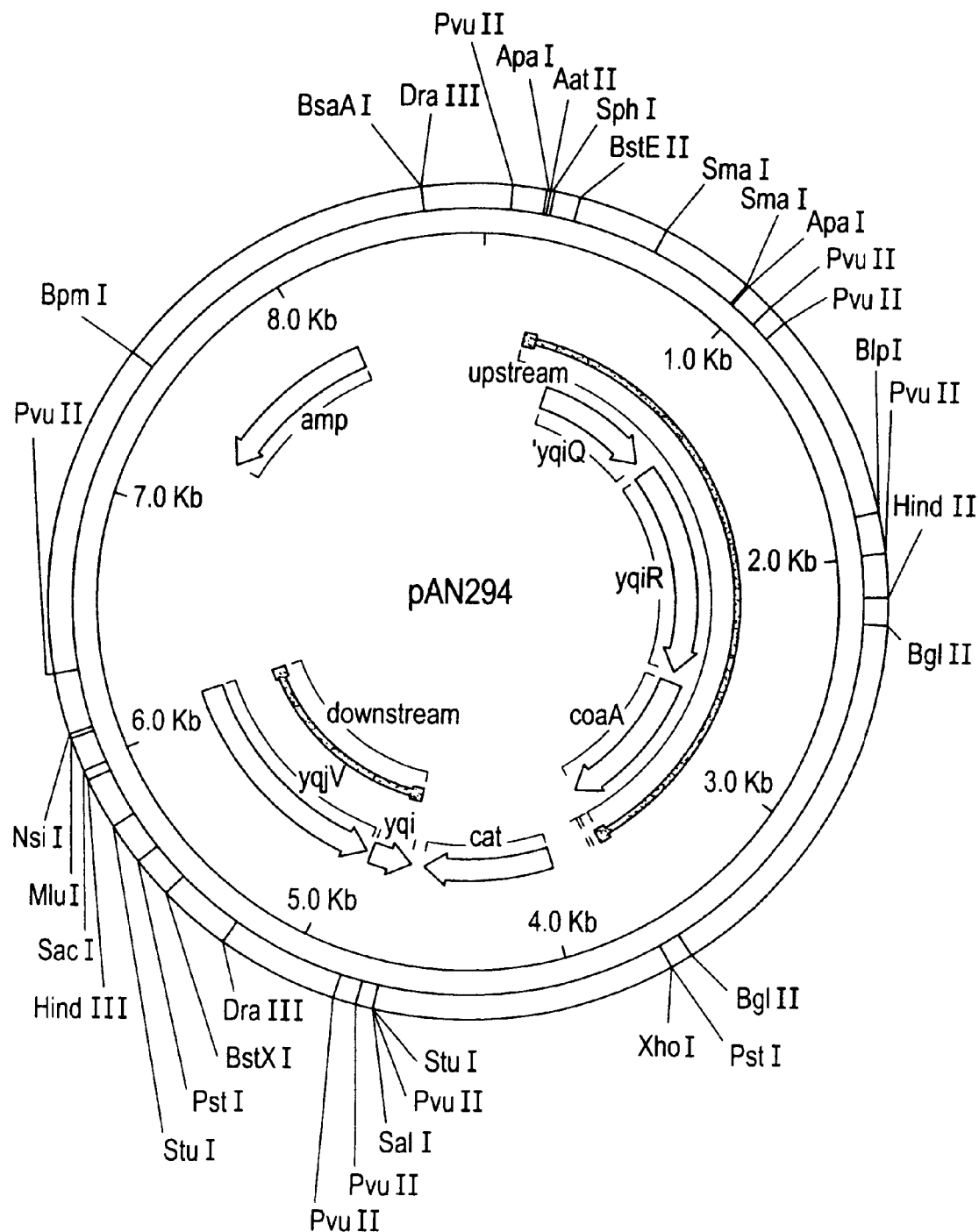
FIG. 25 is a schematic representation of the structure of pAN294, a plasmid for integrating mutagenized *B. subtilis* coaA at its native locus.

A preferred plasmid that can serve as a basis for mutagenizing the coaA open reading frame is pAN294 (see e.g., FIG. 25 and Example XII). Briefly, mutagenic PCR is performed using pAN294 as a template and variants of coaA having reduced pantothenate kinase activity are screened as described above. Alternatively, mutations such as the one isolated in pAN282A can be installed into pAN294. The desired mutation is then introduced into the chromosome of a B. subtilis strain by transformation with the appropriate pAN294 derivative and selected for chloramphenicol resistance at 5 mg/L. Among the resulting transformants will be isolates that contain the desired mutation.

In a similar fashion, mutations that reduce the activity of the CoaX enzyme can be generated and identified, and such mutations used for optimizing pantothenate production by reducing CoA production as described above.

Example XVI

Deleting the Second Pantothenate Kinase Gene, coaX Gene from B. subtilis

With the knowledge gained above concerning the existence and nature of coaX, one can create a deletion of the coaX open reading frame from the B. subtilis chromosome that will remove the encoded activity, and that will not adversely affect the expression of the genes downstream from coaX. In such a deleted strain, the coaA gene will be the only gene that encodes pantothenate kinase.

Figure 26:
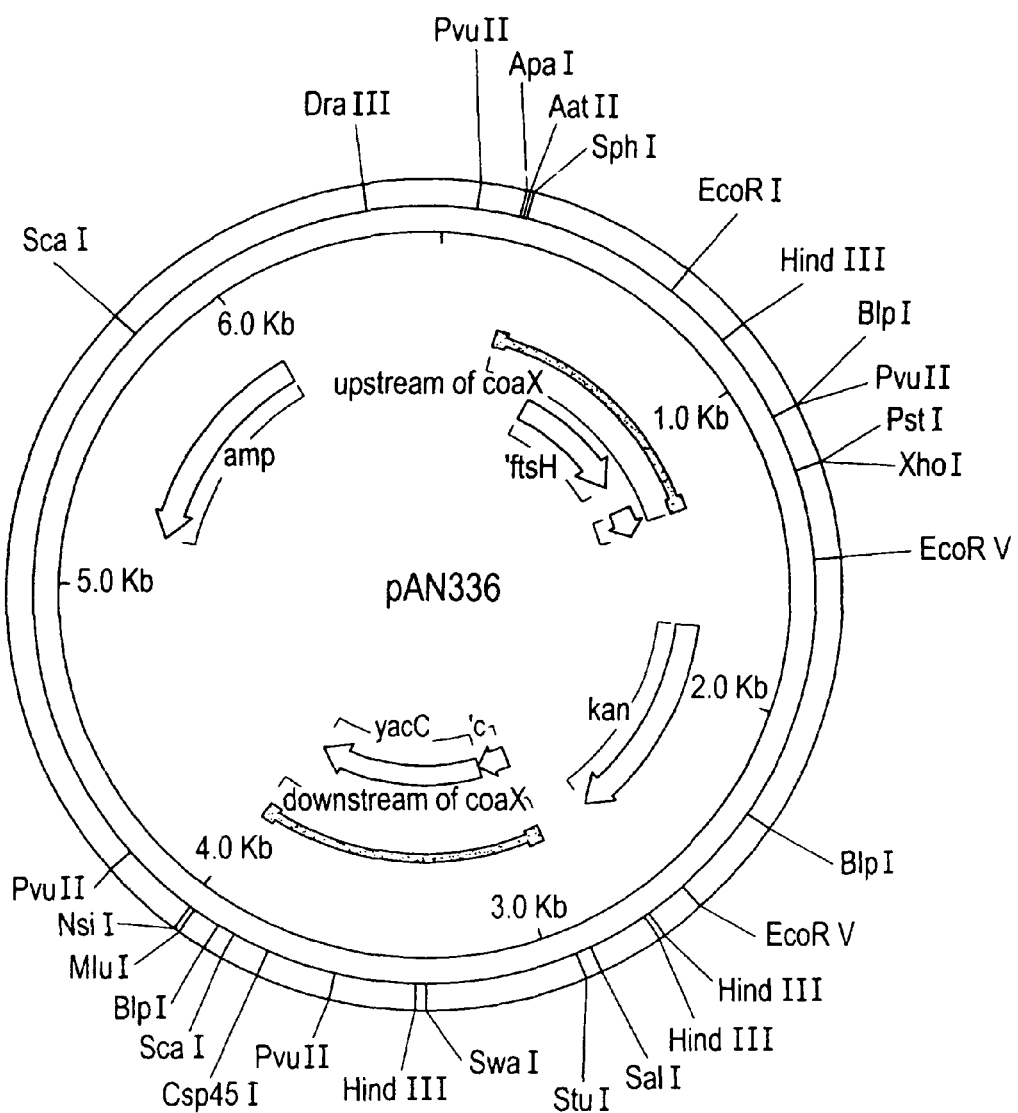
FIG. 26 is a schematic representation of the structure of pAN336, a plasmid designed to delete *B. subtilis* coaX from its chromosomal locus and replace it with a kanamycin resistance gene.

To delete the coaX gene from B. subtilis, plasmid pAN336 (SEQ ID NO:92), which contains upstream and downstream homology for double crossover, was constructed with a kanamycin resistance gene replacing most of the coaX ORF (FIG. 26). Strain PY79 was transformed to kanamycin resistance by pAN336, and an isolate confirmed to have resulted from a double crossover by PCR was named PA876. As predicted, deletion of coaX by itself is not lethal for *B. subtilis*. Furthermore, chromosomal DNA from PA876 would not transform competent PA861 (PY79 ΔcoaA::cat) to kanamycin resistance. These results indicate that it is the combination of ΔcoaA::cat and ΔcoaX::kan that is lethal for *B. subtilis*, confirming that *B. subtilis* contains two unlinked genes that encode pantothenate kanase, coaA and coaX, and that either gene alone is capable of supplying sufficient pantothenate kinase for a normal rate of growth.

Example XVII

Construction of a Plasmid Designed to Allow Directed Mutagenesis of the *B. subtilis* coaA Gene In order to easily introduce mutated coaA genes into the *B. subtilis* chromosome, it was necessary to install an antibiotic resistance gene adjacent to the coaA gene. This was accomplished by joining together in the vector pGEM5 three DNA fragments: (1) a 3.4 kb DNA sequence containing 2.5 kb of genomic sequence upstream from coaA and the coaA open reading frame(s); (2) a 1.1 kb DNA sequence containing a chloramphenicol resistance gene (cat); and (3) a 1.4 kb DNA sequence comprising a region downstream from the operon that contains coaA. The resulting plasmid, named pAN294, effectively replaces the open reading frame yqjT (the open reading frame just downstream from coaA) with the cat gene, with enough homology flanking both sides of the cat gene to allow double recombination into the *B. subtilis* chromosome (FIG. 25). pAN294 was transformed into *B. subtilis* strain PY79, selecting for chloramphenicol resistance at 5 mg/l to give strains PA836 and PA837, which are presumably identical. PA836 and 837 were checked by diagnostic PCR to show that the cat gene had integrated by double crossover, as opposed to single crossover. PA836 and PA837 grow normally, leading to the conclusion that the open reading frame yqjT is not essential (i.e., the yqjT open reading frame could be deleted from strains PA836 and PA837 with no significant effect on growth or pantothenate production). Thus, variant alleles (i.e., mutations) of the coaA gane can be introduced into pAN294 and the resulting plasmids can be used to introduce the variant alleles into the chromosome of, for example, a *B. subtilis* strain.

Example XVIII

Generation of Mutant coaX Genes Encoding Pantothenate Kinase having Reduced or Temperature Sensitive Activities Mutant coaX genes are generated by introducing point mutations into the gene and testing the resulting mutants for the ability to complement the *E. coli* YH1 strain as described in Example XII. Preferred mutations in the coaX gene seqeunces are those that encode a substitution of a residue conserved among CoaX sequences from a variety of bacterial sources (e.g., a conserved residue set forth in FIG. 23). Alternatively, random mutations in the coaX gene sequence are generated by mutagenic PCR and in vitro recombination and identified by screening for alleles that poorly complement the *E. coli* coaA15(Ts) mutant.

Mutants so generated (i.e., mutants having reduced coaX activity) can be further engineered such that the endogenous coaA gene is deleted (as described in Example XIII). CoaX reduced-activity mutants can also be further engineered to contain reduced-activity CoaA gene products as described in Example XV.

Example XIX

Enhanced Production of Panto-Compounds Using Bacteria Having Deletions in One or More Pantothenate Biosynthetic Enzymes If the desired panto-compound is not pantothenate, then an appropriate deletion of one or more of the pantothenate biosynthetic genes from a pantothenate overproducing strain will provide a strain that produces said desired panto-compound. In this example, the desired panto-compound is pantoate. Starting with, for example, strain PA236, PA313 or PA824 either one or both of the panC and panD genes is deleted. In another example, ketopantoate is the desired panto-compound. Starting with, for example strain PA244, PA245 or PA824 one, two or all of the ilvC, panE1, panC and panD genes are deleted from the starting strain. If β-alanine is the desired panto-compound, then panB and panC can be deleted, preferably in a fashion that leaves an in frame fusion of a small portion of the 5' end of panB with a small portion of the 3' end of panC, from the strain PA221, PA235, PA245, or PA313. In all of the above-mentioned examples, the panto-compound producing strain will be a pantothenate auxotroph. Accordingly, the growth medium requires sufficient pantothenate for adequate growth. Vectors designed to overexpress panD as described above are then transformed into the above strains to further enhance β-alanine production.

The above-mentioned deletions are accomplished by methods well-known to those skilled in the art, for example, by insertion of an antibiotic resistance gene and removing sufficient sequence from the target gene(s) to inactivate said target gene(s). Alternatively, removal of targeted sequences is accomplished without simultaneous introduction of an antibiotic resistance gene in said target gene and then introduced by congression (co-transformation with any other appropriate selectable DNA sequence) followed by screening for the loss of function of said target gene by replica plating.

TABLE 24

Strains (and corresponding phenotypes) for panto-compound production

| Name | Phenotype | Drug resist. | panBCD locus | panE locus | ilvD locus | amyE locus | bpr locus | Parent |
|---|---|---|---|---|---|---|---|---|
| PA221 | Trp- | | P26panBCD | | | | | |
| PA222 | | | $P_{15}$panBCD | | | | | RL-1 |
| PA235 | | | P26panBCD | | | | | |
| PA236 | | | $P_{26}$panBCD | $P_{26}$panE1 | | | | PA221 |
| PA327 | Trp- | | P26panBCD | P26panE1 | | | | PA221 |

TABLE 24-continued

Strains (and corresponding phenotypes) for panto-compound production

| Name | Phenotype | Drug resist. | panBCD locus | panE locus | ilvD locus | amyE locus | bpr locus | Parent |
|---|---|---|---|---|---|---|---|---|
| PA328 | Trp- | | P26panBCD | P26panE1 | | | | PA235 |
| PA340 | Trp- | Spc | P26panBCD | P26panE1 | | P26ilvBNC | | PA327 |
| PA342 | Trp- | Spc | P26panBCD | P26panE1 | | P26ilvBNC | | PA328 |
| PA354 | Trp- | Spc | P26panBCD | P26panE1 | P26ilvD | P26ilvBNC | | PA342 |
| PA365 | Trp- | Spc, Tet | P26panBCD | P26panE1 | P26ilvD | P26ilvBNC | P26panD423 | PA354 |
| PA374 | Trp- | Spc | P26panBCD | P26panE1 | P26ilvD | P26ilvBNC | | PA340 |
| PA377 | Trp- | Spc, Tet | P26panBCD | P26panE1 | P26ilvD | P26ilvBNC | P26panD423 | PA374 |
| PA401 | Trp- | | P26panBCD | | | | P26panD423 | PA221 |
| PA402 | Trp- | | P26panBCD | | | | P26panD428 | PA221 |
| PA403 | Trp- | | P26panBCD | | | | P26panD429 | PA221 |
| PA404 | Trp- | Spc, Tet | P26panBCD | P26panE1 | | P26ilvBNC | P26panD423 | PA340 |
| PA405 | Trp- | Spc, Tet | P26panBCD | P26panE1 | | P26ilvBNC | P26panD423 | PA342 |
| PA651 | Trp- | Spc | P26panBC*D | P26panE1 | P26ilvD | P26ilvBNC | | PA374 |
| PA284 | | Spc, Tet | P26'panBCD | P26panE1 | P26ilvD | P26ilvBNC | P26panD423 | PA377 |

Equivalents Those skilled in the art will recognize, or be able to ascertain using no more than routine experimentation, many equivalents to the specific embodiments of the invention described herein. Such equivalents are intended to be encompassed by the following claims.

What is claimed is:

1. A method of producing pantoate and/or pantothenate, comprising culturing a microorganism under conditions such that pantoate and/or pantothenate is produced, wherein the microorganism comprises a recombinant vector comprising a panE1 gene and an artificial ribosome binding site (RBS) comprising the nucleotide sequence set forth in SEQ ID NO: 50 operably linked to the panE1 gene, wherein the panE1 gene comprises:
    (a) the nucleotide sequence of SEQ ID NO: 29;
    (b) a nucleotide sequence encoding the polypeptide sequence of SEQ ID NO: 30; or
    (c) a nucleotide sequence encoding a polypeptide sequence having at least 95% or greater amino acid sequence identity to the polypeptide sequence of SEQ ID NO: 30 and having ketopantoate reductase activity.

2. A method for producing greater than 2 grams/liter pantothenate comprising:
    (a) obtaining a microorganism comprising a recombinant vector comprising a panD gene or a panBCD operon, and a panE1 gene, and
    (b) culturing said microorganism in the absence of added β-alanine under conditions to produce pantothenate, wherein the pantothenate produced is at a level greater than 2 grams/liter,
    wherein the panD gene comprises:
    (aa) the nucleotide sequence of SEQ ID NO: 27;
    (bb) a nucleotide sequence encoding the polypeptide sequence of SEQ ID NO: 28; or
    (cc) a nucleotide sequence encoding a polypeptide sequence having at least 95% or greater amino acid sequence identity to the polypeptide sequence of SEQ ID NO: 28 and having aspartate 1-decarboxylase activity,
    wherein the panBCD operon comprises:
    (aaa) the nucleotide sequences of SEQ ID NO: 23, 25, and 27;
    (bbb) a nucleotide sequence encoding the polypeptide sequences of SEQ ID NO: 24, 26, and 28; or
    (ccc) a nucleotide sequence encoding a polypeptide sequence having at least 95% or greater amino acid sequence identity to the polypeptide sequence of SEQ ID NO: 24 and having ketopantoate hydroxymethyltransferase activity, a polypeptide sequence having at least 95% or greater amino acid sequence identity to the polypeptide sequence of SEQ ID NO: 26 and having pantothenate synthetase activity, and a polypeptide sequence having at least 95% or greater amino acid sequence identity to the polypeptide sequence of SEQ ID NO: 28 and having aspartate 1-decarboxylase activity,
    wherein the panE1 gene comprises:
    (aaaa) the nucleotide sequence of SEQ ID NO: 29;
    (bbbb) a nucleotide sequence encoding the polypeptide sequence of SEQ ID NO: 30; or
    (cccc) a nucleotide sequence encoding a polypeptide sequence having at least 95% or greater amino acid sequence identity to the polypeptide sequence of SEQ ID NO: 30 and having ketopantoate reductase activity,
    and wherein the recombinant vector comprises:
    (i) the panD gene, the panE1 gene, and an artificial ribosome binding site (RBS) comprising the nucleotide sequence set forth in SEQ ID NO: 50 operably linked to at least one of the panD gene and the panE1 gene; or
    (ii) the panBCD operon, the panE1 gene, and an artificial ribosome binding site (RBS) comprising the nucleotide sequence set forth in SEQ ID NO: 50 operably linked to at least one of the panBCD operon and the panE1 gene.

3. A method for producing pantoate and/or pantothenate comprising:
    (a) transforming a microorganism with a vector to produce a recombinant microorganism, wherein said vector comprises:
        a nucleotide sequence encoding a polypeptide with 95% or greater amino acid sequence identity to SEQ ID NO: 30, wherein said polypeptide has ketopantoate reductase activity,
        a constitutively active promoter set forth in SEQ ID NO: 40, operably linked to the nucleotide sequence encoding the polypeptide, and
        an artificial ribosome binding site (RBS) comprising the nucleotide sequence set forth in SEQ ID NO: 50 operably linked to the nucleotide sequence encoding the polypeptide;
    (b) growing said recombinant microorganism in an appropriate culture medium and under conditions suitable for the production of said pantoate and/or pantothenate; and
    (c) recovering said pantoate and/or pantothenate from said culture medium.

4. A method for producing pantoate and/or pantothenate comprising:
    (a) transforming a microorganism with a first vector, wherein said first vector comprises:
        a nucleotide sequence encoding a polypeptide with 95% or greater amino acid sequence identity to SEQ ID NO: 30, wherein said polypeptide has ketopantoate reductase activity,
        a constitutively active promoter set forth in SEQ ID NO: 40 operably linked to the nucleotide sequence encoding the polypeptide,
        an artificial ribosome binding site (RBS) comprising the nucleotide sequence set forth in SEQ ID NO: 50 operably linked to the nucleotide sequence encoding the polypeptide;
    (b) further transforming said microorganism with a second vector to produce a recombinant microorganism, wherein said second vector comprises:
        an operon comprising a nucleotide sequence encoding a polypeptide sequence having at least 95% or greater amino acid sequence identity to the polypeptide sequence of SEQ ID NO: 24 and having ketopantoate hydroxymethyltransferase activity; a nucleotide sequence encoding a polypeptide sequence having at least 95% or greater amino acid sequence identity to the polypeptide sequence of SEQ ID NO: 26 and having pantothenate synthetase activity; and a nucleotide sequence encoding a polypeptide sequence having at least 95% or greater amino acid sequence identity to the polypeptide sequence of SEQ ID NO: 28 and having aspartate 1-decarboxylase activity,
        a constitutively active promoter set forth in SEQ ID NO: 40 operably linked to the operon, and
        an artificial ribosome binding site (RBS) comprising the nucleotide sequence set forth in SEQ ID NO: 50 operably linked to the operon;
    (c) growing said recombinant microorganism in an appropriate culture medium and under conditions suitable for the production of said pantoate and/or pantothenate; and
    (d) recovering said pantoate and/or pantothenate from said culture medium.

5. The method of claim 4, wherein said recombinant microorganism is further transformed with a vector comprising the nucleotide sequence set forth in SEQ ID NO: 78.

6. The method of claim 5, wherein said recombinant microorganism is further transformed with a vector comprising the nucleotide sequence set forth in SEQ ID NO: 82.

7. The method of claim 6, wherein said recombinant microorganism is further transformed with a polynucleotide sequence encoding the polypeptide sequence of SEQ ID NO: 38 or a polypeptide with 95% or greater amino acid sequence identity to SEQ ID NO: 38 and having dihydroxyacid dehydratase activity.

8. The method of any one of claims 3-7, wherein said appropriate culture medium contains valine.

9. A method of producing pantoate and/or pantothenate, comprising culturing a microorganism under conditions such that pantoate and/or pantothenate is produced, wherein said microorganism comprises a recombinant vector integrated into a panE1 locus of the microorganism, wherein the recombinant vector comprises a constitutively active promoter and an artificial ribosome binding site (RBS) comprising the nucleotide sequence set forth in SEQ ID NO: 50 operably linked to the panE1 locus, and wherein said recombinant vector enhances expression of a panE1 gene as compared to a wild-type microorganism, and wherein the panE1 gene comprises:
(a) the nucleotide sequence of SEQ ID NO: 29;
(b) a polynucleotide sequence encoding the polypeptide sequence of SEQ ID NO: 30; or
(c) a polynucleotide sequence encoding a polypeptide with at least 95% or greater amino acid sequence identity to SEQ ID NO: 30 and having ketopantoate reductase activity.

10. The method of claim 1 or 9, wherein the microorganism further comprises a recombinant vector comprising at least one pantothenate biosynthetic enzyme encoded by a nucleic acid comprising a nucleotide sequence selected from the group consisting of:
(a) the nucleotide sequence of SEQ ID NO: 23, 25, or 27;
(b) a nucleotide sequence encoding the polypeptide sequence of SEQ ID NO: 24, 26, or 28;
(c) a nucleotide sequence encoding a polypeptide sequence having at least 95% or greater amino acid sequence identity to the polypeptide sequence of SEQ ID NO: 24 and having ketopantoate hydroxymethyltransferase activity;
(d) a nucleotide sequence encoding a polypeptide sequence having at least 95% or greater amino acid sequence identity to the polypeptide sequence of SEQ ID NO: 26 and having pantothenate synthetase activity; and
(e) a nucleotide sequence encoding a polypeptide sequence having at least 95% or greater amino acid sequence identity to the polypeptide sequence of SEQ ID NO: 28 and having aspartate 1-decarboxylase activity.

11. A method for producing pantoate and/or pantothenate, comprising: culturing a microorganism under conditions such that pantoate and/or pantothenate is produced, wherein the microorganism comprises a recombinant vector comprising:
a nucleotide sequence encoding a polypeptide with 95% or greater amino acid sequence identity to SEQ ID NO: 30, wherein said polypeptide has ketopantoate reductase activity, a constitutively active promoter operably linked to the nucleotide sequence encoding the polypeptide, and
an artificial ribosome binding site (RBS) comprising the nucleotide sequence set forth in SEQ ID NO: 50 operably linked to the nucleotide sequence encoding the polypeptide.

12. A method for producing pantoate and/or pantothenate, comprising: culturing a microorganism under conditions such that pantoate and/or pantothenate is produced, wherein the microorganism comprises a recombinant vector comprising:
a nucleotide sequence encoding a polypeptide with 95% or greater amino acid sequence identity to SEQ ID NO: 30, wherein said polypeptide has ketopantoate reductase activity,
a constitutively active promoter operably linked to the nucleotide sequence encoding the polypeptide, and
an artificial ribosome binding site (RBS) comprising the nucleotide sequence set forth in SEQ ID NO: 50 operably linked to the nucleotide sequence encoding the polypeptide; and
a recombinant vector comprising:
an operon comprising a nucleotide sequence encoding a polypeptide sequence having at least 95% or greater amino acid sequence identity to the polypeptide sequence of SEQ ID NO: 24 and having ketopantoate hydroxymethyltransferase activity; a nucleotide sequence encoding a polypeptide sequence having at least 95% or greater amino acid sequence identity to the polypeptide sequence of SEQ ID NO: 26 and having pantothenate synthetase activity; and a nucleotide sequence encoding a polypeptide sequence having at least 95% or greater amino acid sequence identity to the polypeptide sequence of SEQ ID NO: 28 and having aspartate 1-decarboxylase activity,
a constitutively active promoter operably linked to said operon, and
an artificial ribosome binding site (RBS) comprising the nucleotide sequence set forth in SEQ ID NO: 50 operably linked to said operon.

13. A method of producing pantoate and/or pantothenate comprising culturing a microorganism in the absence of added β-alanine under conditions such that pantoate and/or pantothenate is produced, wherein the microorganism comprises a recombinant vector comprising a panE1 gene and an artificial ribosome binding site (RBS) comprising the nucleotide sequence set forth in SEQ ID NO: 50 operably linked to the panE1 gene, wherein the panE1 gene comprises:
(a) the nucleotide sequence of SEQ ID NO: 29;
(b) a nucleotide sequence encoding the polypeptide sequence of SEQ ID NO: 30; or
(c) a nucleotide sequence encoding a polypeptide sequence having at least 95% or greater amino acid sequence identity to the polypeptide sequence of SEQ ID NO: 30 and having ketopantoate reductase activity.

* * * * *